United States Patent [19]

Ogawa et al.

[11] Patent Number: 5,811,439
[45] Date of Patent: Sep. 22, 1998

[54] THIAZOLIDINEDIONE DERIVATIVES, METHOD FOR PREPARING THE DERIVATIVES AND PHARMACEUTICAL COMPOSITIONS CONTAINING SAME

[75] Inventors: Masashi Ogawa, Inagi; Tadashi Morita, Hamura; Norihiro Iibuchi, Hamura; Hideyuki Tsutsui, Hamura, all of Japan

[73] Assignee: Senga Pharmaceutical Laboratory Inc., Tokyo, Japan

[21] Appl. No.: 768,937

[22] Filed: Dec. 18, 1996

[30] Foreign Application Priority Data

Dec. 22, 1995 [JP] Japan ................................ 7-349564

[51] Int. Cl.$^6$ ........................ C07D 417/06; A61K 31/425
[52] U.S. Cl. ............................... 514/369; 548/181
[58] Field of Search ............................. 548/181; 514/369

[56] References Cited

U.S. PATENT DOCUMENTS 5,143,927  9/1992  Boschelli et al. ...................... 514/369
5,599,826  2/1997  Mertens ................................. 514/364

FOREIGN PATENT DOCUMENTS 0 587 377   3/1994   European Pat. Off. .
WO 96/26207  8/1996   WIPO .

OTHER PUBLICATIONS

Chemical Abstracts, vol. 73, No. 5, Aug. 3, 1970, AN–25236b.
Chemical Abstracts, vol. 75, No. 15, Oct. 11, 1971, AN–98387c.
Chemical Abstracts, vol. 113, No. 5, Jul. 30, 1990, AN–40530f.
Chemical Abstracts, vol. 116, No. 13, Mar. 30, 1992, AN–128752c.

*Primary Examiner*—Robert Gerstl
*Attorney, Agent, or Firm*—Oblon, Spivak, McClelland, Maier & Neustadt, P.C.

[57] ABSTRACT

A thiazolidinedione derivative represented by the following general formula (I):

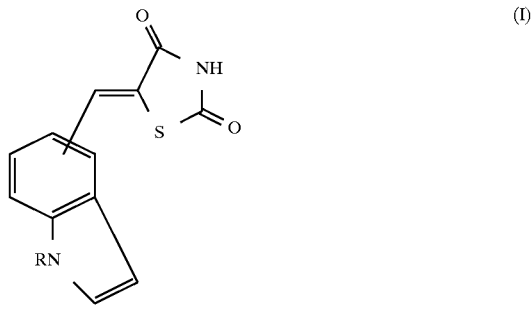

[wherein the dotted line represents a single bond or a double bond, the thiazolidinedione ring residue is linked to either of 2-, 3-, 4-, 5- and 6-positions on the indole ring and R represents a group selected from the group consisting of hydrogen atom and alkyl, alkenyl, alkynyl, phenyl, aralkyl, heterocycloalkyl, arylsulfonyl and arylaminocarbonyl groups] or a pharmaceutically acceptable salt thereof exhibits excellent effects of reducing the blood sugar level and of reducing the lipid concentration in blood and is accordingly useful as a therapeutic agent for treating diabates mellitus. These derivatives and pharmaceutically acceptable salt thereof are almost free of any side effect.

11 Claims, No Drawings

THIAZOLIDINEDIONE DERIVATIVES, METHOD FOR PREPARING THE DERIVATIVES AND PHARMACEUTICAL COMPOSITIONS CONTAINING SAME

BACKGROUND OF THE INVENTION

The present invention relates to a novel thiazolidinedione derivative or a pharmaceutically acceptable salt thereof having an effect of reducing the blood sugar level and the lipid concentration in blood as well as a method for preparing the derivative or salt and a pharmaceutical composition containing the same.

It has been known that the diabates mellitus may be divided into several types of symptoms, but the disease has been roughly divided into insulin-dependent diabates mellitus (type I diabates mellitus) and insulin-independent diabates mellitus (type II diabates mellitus). The former may be treated by the insulin-supplementing treatment, but insulin does not show its effect when it is administered to a patient suffering from the diabates mellitus of the latter type. In other words, the latter is a disease resistant to the action of insulin because of, for instance, the abnormality of receptors and carriers for transporting sugar, present in the peripheral tissues.

This tendency would be very conspicuous in particular when the patient is also fleshy and it has been suggested that the resistance to insulin would not only lead to an increase in the blood sugar level, but also be involved in the progress of complications.

The insulin-independent diabates mellitus has presently been treated mainly by a combination of exercise therapy, alimentary therapy and an oral administration of an agent for reducing the blood sugar level and when the symptom becomes severer, insulin-containing pharmaceuticals have been used. There have clinically been used sulfonyl urea-containing and biguanide-containing pharmaceuticals, as drugs showing an effect of reducing the blood sugar level and orally administered.

However, the biguanide-containing drug has not been used at all because of side effects such as lactic acid acidosis.

On the other hand, the use of the sulfonyl urea-containing drug requires careful management because it has a strong blood sugar level-reducing effect, but often becomes a cause of severe hypoglycemia and induces resistance to drugs.

For this reason, there have recently been developed novel orally administered drugs for reducing the blood sugar level free of side effects, which may be used instead of the foregoing sulfonyl urea-containing drug. Among these, drugs which can reduce the resistance to insulin in the peripheral tissues and show the effect of reducing the blood sugar level have attracted special interest recently.

However, most of these drugs have been insufficient in the efficacies, have side effects and there has not yet been developed any satisfactory drug. Therefore, it has been urgent to develop a drug having a higher efficacy and almost free of side effect.

SUMMARY OF THE INVENTION

Accordingly, it is an object of the present invention to provide a novel thiazolidinedione derivative or a pharmaceutically acceptable salt thereof having an effect of reducing the blood sugar level and an effect of reducing the lipid concentration in blood.

It is another object of the present invention to provide a method for preparing such a novel thiazolidinedione derivative or a salt thereof.

A further object of the present invention is to provide a pharmaceutical composition containing the novel thiazolidinedione derivative or salt thereof.

The inventors of this invention have conducted various studies to accomplish the foregoing objects, i.e., to develop a drug for treating diabates mellitus which is excellent in the effects of reducing the blood sugar level and of reducing the lipid concentration in blood and which is almost free of side effect, have found out thiazolidinedione derivatives whose activities can considerably be enhanced by introducing a thiazolidinedione ring residue into either of 2-, 3-, 4-, 5- and 6-positions on an indole ring and thus have completed the present invention.

According to the present invention, the foregoing objects can effectively be achieved by providing a thiazolidinedione derivative represented by the following general formula (I) or a pharmaceutically acceptable salt thereof:

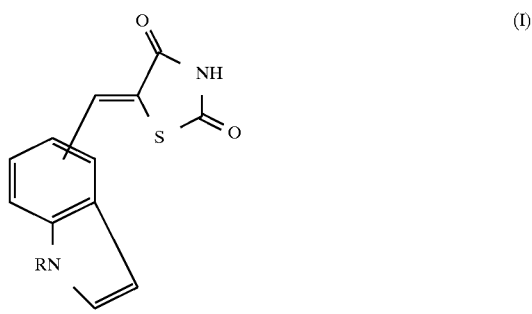

(I)

wherein the dotted line represents a single bond or a double bond, the thiazolidinedione residue is linked to either of 2-, 3-, 4-, 5- and 6-positions on the indole ring and R represents a group selected from the group consisting of a hydrogen atom, and alkyl, alkenyl, alkynyl, phenyl, aralkyl, heterocycloalkyl, arylsulfonyl and arylaminocarbonyl groups; a pharmaceutical composition comprising, as an effective component, a thiazolidinedione derivative represented by the foregoing general formula (I) or a pharmaceutically acceptable salt thereof; and a method for preparing a thiazolidinedione derivative represented by the foregoing general formula (I) which comprises the steps of condensing an indole carbaldehyde derivative represented by the following general formula (II) with 2,4-thiazolidinedione and optionally subjecting the resulting condensate to a reducing reaction:

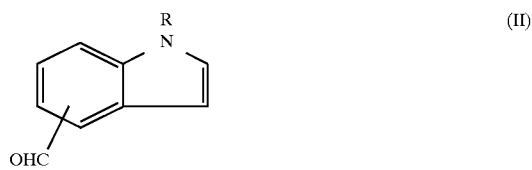

(II)

wherein the aldehyde group is linked to either of 2-, 3-, 4-, 5- and 6-positions on the indole ring and R represents a group selected from the group consisting of a hydrogen atom, and alkyl, alkenyl, alkynyl, phenyl, aralkyl, heterocycloalkyl, arylsulfonyl and arylaminocarbonyl groups.

The compounds represented by Formula (I) correspond to those represented by the following general formula (III):

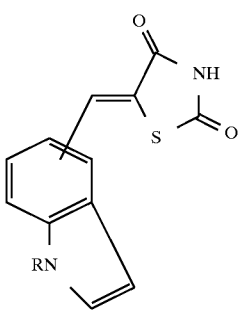

(III)

wherein the thiazolidinedione ring residue is linked to either of 2-,3-, 4-, 5- and 6-positions on the indole ring and R represents a group selected from the group consisting of a hydrogen atom, and alkyl, alkenyl, alkynyl, phenyl, aralkyl, heterocycloalkyl, arylsulfonyl and arylaminocarbonyl groups, when the dotted line in the formula represents a double bond; and those represented by the following general formula (IV):

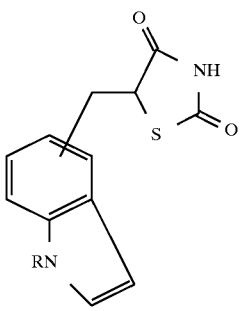

(IV)

wherein each symbol is the same as that defined above, when the dotted line in the formula represents a single bond. Among the compounds represented by Formula (I), preferred are those in which the dotted line represents a single-bond.

DESCRIPTION OF THE PREFERRED EMBODIMENTS

The alkyl groups are those except for aralkyl and heterocycloalkyl groups and preferably include linear alkyl groups having 1 to 10 carbon atoms, cycloalkyl groups having 3 to 10 carbon atoms, branched unsubstituted alkyl groups having 3 to 10 carbon atoms or alkyl groups which may be substituted with an alkoxycarbonyl or carboxyl group; the alkenyl groups may be linear, branched or cyclic alkenyl groups having 5 to 11 carbon atoms; the alkynyl groups may be linear or branched ones having 4 carbon atoms; the phenyl group may be substituted with an amino or cyano group; the aryl or heterocyclic group which constitutes the aralkyl, heterocycloalkyl, arylsulfonyl or arylaminocarbonyl group may be one selected from the group consisting of phenyl, naphthyl, pyridyl, thienyl, quinolyl, tetrahydroquinolyl, oxazolyl, thiazolyl, pyrrolidinyl and benzdioxanyl groups, which may be unsubstituted groups or may have a substituent selected from halogen atoms and alkyl having 1 to 2 carbon atoms, trihalomethyl, methoxy, benzyloxy, methylenedioxy, cyano, carboxyl, methoxycarbonyl, hydroxy, amino, dialkylamino, phenyl and nitro groups, provided that if the foregoing aryl or heterocyclic groups each has at least two such substituents, they may be the same or different; the alkylene groups constituting the aralkyl or heterocycloalkyl groups are represented by the formula: $(CH_2)_n$ (n is an integer ranging from 1 to 3), in which a hydrogen atom may be substituted with a halogen atom or an alkyl, hydroxy, alkoxy, benzyloxy, phenyl, azido, amino or dialkylamino group or in which two hydrogen atoms linked to the same carbon atom may be substituted with an oxygen atom.

Examples of alkyl groups are methyl, n-hexyl, cyclohexylmethyl, 2-ethylbutyl, 2-methoxycarbonylethyl, 2-carboxyethyl, cyclohexyl and pinanyl groups.

Examples of alkenyl groups include 3-methyl-2-butenyl, 4-methyl-3-pentenyl, 1,5-dimethyl-4-hexenyl, limonenyl, pinenyl and pinenylmethyl groups.

Examples of alkynyl groups include 2-butynyl group.

Examples of aralkyl groups are benzyl, benzoyl, phenylacetyl, 4-ethylbenzyl, 2-fluorobenzyl, 3-fluorobenzyl, 4-fluorobenzyl, 2,3-difluorobenzyl, 2,4-difluorobenzyl, 2,5-difluorobenzyl, 2,6-difluorobenzyl, 3,4-difluorobenzyl, 3,5-difluorobenzyl, 2-trifluoromethylbenzyl, 3-trifluoromethylbenzyl, 4-trifluoromethylbenzyl, 2,4-ditrifluoromethylbenzyl, 4-fluorophenethyl, 2-methoxybenzyl, 3-methoxybenzyl, 4-methoxybenzyl, 3,4-dimethoxybenzyl, 3,5-dimethoxybenzyl, 2,5-dimethoxybenzyl, 3-cyanobenzyl, 4-cyanobenzyl, 4-chlorobenzyl, 4-benzyloxybenzyl, piperonyl, 3-methylbenzyl, α-methylbenzyl, β-naphthylmethyl, phenethyl, 2-phenylbenzyl, 3-phenylpropyl, 4-methoxycarbonylbenzyl, 4-carboxybenzyl, 2-bromobenzyl, 4-nitrobenzyl, 4-aminobenzyl, 4-dimethylaminobenzyl, 3,5-ditrifluoromethylbenzyl, 2,4-dimethoxybenzyl, 4-hydroxybenzyl, benzhydryl, β-hydroxyphenethyl, β-benzyloxyphenethyl, β-fluorophenethyl, β-chlorophenethyl, β-methoxyphenethyl, β-aminophenethyl, β-dimethylaminophenethyl and phenacyl groups.

Examples of heterocycloalkyl groups are 2-picoryl, 4-picoryl, (5-methyl-2-phenyloxazol,4-yl)methyl, 3,4-methylenedioxybenzyl, 2-thienylmethyl, 2-(thien-2-yl)ethyl, (2-methylthiazol-4-yl)methyl, 2-(4-methylthiazol-5-yl)ethyl, (quinol-2-yl)methyl, 1,2,3,4-tetrahydroquinol-2-yl) methyl, (1,4-benzdioxan-2-yl)methyl and 2-(pyrrolidin-1-yl)ethyl.

Examples of arylsulfonyl groups are benzenesulfonyl, p-toluenesulfonyl, 4-fluorobenzenesulfonyl and 3-trifluoromethylbenzenesulfonyl groups.

Examples of arylaminocarbonyl groups include m-tolylcarbamoyl group.

The salts of the compounds represented by Formula (I):

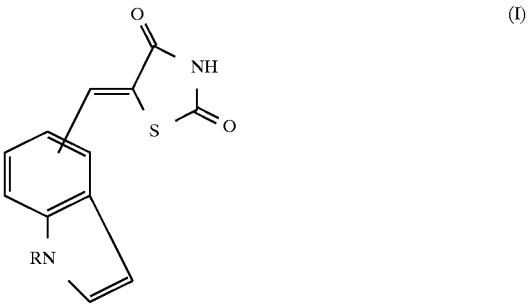

(I)

(wherein each symbol is the same as that defined above) according to the present invention may be acid-addition salts or base-addition salts with pharmaceutically acceptable acid or base compounds. Examples of such acid-addition salts are salts with acids such as hydrochloric acid, sulfuric acid, phosphoric acid, oxalic acid, maleic acid, fumaric acid, malic acid, tartaric acid, citric acid, benzoic acid, acetic acid, p-toluenesulfonic acid and ethanesulfonic acid. Examples of base-addition salts include salts with alkali metal and alkaline earth metals such as sodium, potassium, magnesium and calcium; and organic salts with, for instance, amines such as ammonia, methylamine, dimethylamine, piperidine, cyclohexylamine and triethylamine.

The thiazolidinedione derivatives of the present invention can be prepared through the following several steps:

lowing two methods, when Compound (VI) is used in the preparation methods.

The first method comprises the steps of reacting an indolecarboxylate with a compound (VI) and then reducing and oxidizing the reaction product. More specifically, an indole carboxylate (V) is reacted with a compound (VI) in the presence of a base to give a product (VII), provided that if the compound (VI) is styrene oxide, it is reacted with the

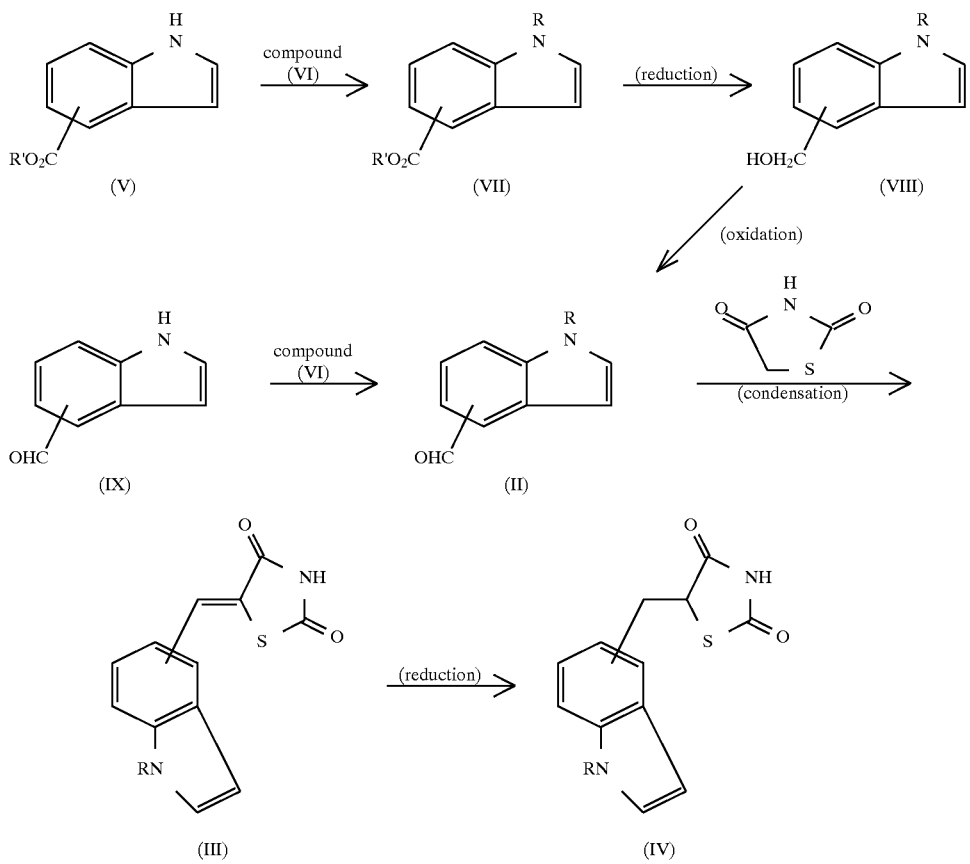

In the foregoing reaction scheme, Compound (VI) may arbitrarily be used and if it is used, the compound may be one capable of forming the R portion through substitution, addition or condensation, for instance, a compound represented by the formula: RX (wherein R represents a group selected from the group consisting of alkyl, alkenyl, alkynyl, phenyl, aralkyl, heterocycloalkyl and arylsulfonyl groups and X represents a halogen atom such as a chlorine or bromine atom or a methanesulfonate residue), a styreneoxide, an acryl ester or an aryl isocyanate. Moreover, R' represents a lower alkyl group such as a methyl or ethyl group.

If Compound (VI) is not used, an indole carboxylate (V) may be directly subjected to a reducing reaction to give a product (VIII), followed by oxidation of the product (VIII) into an indole carbaldehyde (II) and a condensation reaction of the compound (II) with 2,4-thiazolidinedione to give a thiazolidinedione derivative (III), or a thiazolidinedione derivative (III) may be prepared through a direct condensation reaction of an indole carbaldehyde (IX) with 2,4-thiazolidinedione.

In the foregoing preparation methods, the indole carbaldehyde derivatives (II) used as ingredients for preparing the thiazolidinedione derivatives may be produced by the folindole carboxylate (V) in the presence of a base and then the resulting product is esterified to give a reaction product (VII) wherein the R portion is a 2-hydroxy-2-phenylethyl group.

The reaction is preferably carried out in an appropriate solvent. Such a solvent is not restricted to a specific one and examples thereof are ethers such as diethyl ether, tetrahydrofuran and dioxane; alkyl ketones such as acetone, methyl ethyl ketone and methyl isobutyl ketone; alcohols such as methanol, ethanol and propanol; aprotic polar solvents such as N,N-dimethylformamide, N,N-dimethylacetamide, acetonitrile, dimethylsulfoxide and hexamethylphosphoric acid triamide; water, acetic acid and formic acid, which may be used alone or in any combination. Examples of bases usable herein are sodium methoxide, sodium ethoxide, potassium carbonate, sodium carbonate, sodium hydride and sodium acetate. Regarding the rate of these reactants, the compound (VI) is used in an amount ranging from 1 to 20 mole equivalents and preferably 1 to 5 mole equivalents per mole of the starting compound (V). The reaction temperature may range from −30° C. to the boiling point of the solvent used, preferably −10° C. to 100° C. The reaction time may be in the range of from 0.1 to 96 hours, preferably 0.5 to 24 hours. Then the resulting reaction product (VII) is reduced using a suspension of a reducing agent such as lithium aluminum hydride or borane-dimethyl sulfide complex in a tetrahydrofuran solution to give a compound (VIII). The reaction may be carried out at a temperature ranging from −30° C. to the boiling point of the solvent used for a time ranging from 0.1 to 48 hours, preferably 0.5 to 6 hours. Furthermore, the compound (VIII) is oxidized in, for instance, a solution of-manganese dioxide in dichloromethane or a solution obtained by dissolving triethylamine in dimethylsulfoxide and then adding a sulfur trioxide-pyridine complex to the solution to give an indole carbaldehyde derivative (II). The reaction temperature may be in the range of from −30° C. to the boiling point of the solvent used, preferably −10° C. to 80° C., while the reaction time may fall within the range of from 0.1 to 48 hours, preferably 0.5 to 6 hours.

The second method comprises the step of reacting an indole carbaldehyde (IX) with a compound (VI) in the presence of a base to give an indole carbaldehyde derivative (II). In this respect, however, when the compound (VI) is an acrylic acid ester, it may be reacted with an indole carbaldehyde (IX) in the presence of a base, followed by esterification of the resulting product to give an indole carbaldehyde derivative (II) whose R portion is a 2-alkoxycarbonylethyl group. In addition, when the compound (VI) is an aryl isocyanate, it may be reacted with an indole carbaldehyde (IX) in the presence of a base to give an indole carbaldehyde derivative (II) whose R portion is an arylcarbamoyl group.

The reaction is preferably carried out in an appropriate solvent, such a solvent is not restricted to any specific one so far as they do not take part in the reaction and examples thereof include ethers such as diethyl ether, tetrahydrofuran and dioxane; alkyl ketones such as acetone, methyl ethyl ketone and methyl isobutyl ketone; alcohols such as methanol, ethanol and propanol; aprotic polar solvents such as N,N-dimethylformamide, N,N-dimethylacetamide, acetonitrile, dimethylsulfoxide and hexamethylphosphoric acid-triamide; water, acetic acid and formic acid, which may be used alone or in any combination. Examples of bases usable in the reaction are sodium methoxide, sodium ethoxide, potassium carbonate, sodium carbonate, sodium hydride and sodium acetate. Regarding the rate of these reactants, the compound (VI) is used in an amount ranging from 1 to 20 mole equivalents and preferably 1 to 5 mole equivalents per mole of the starting compound (IX). The reaction temperature may range from −30° C. to the boiling point of the solvent used, preferably −10° C. to 100° C. The reaction time may be in the range of from 0.1 to 96 hours, preferably 0.5 to 24 hours.

The R portions of the indole carbaldehyde derivatives (II) prepared by the foregoing first and second methods may be converted into other groups according to the following methods. For instance, when the indole carbaldehyde derivative (II) has a 2-hydroxy-2-phenylethyl group as such an R portion, the hydroxy group of the R portion may be changed to a benzyloxy group with benzyl halide or to a methoxy group with a methyl halide by the usual methods or to an azido group by once converting it into a methanesulfonyloxy group with a methanesulfonyl halide and then reacting the product with sodium azide.

The condensation of the resulting indole carbaldehyde derivative (II) with 2,4-thiazolidinedione is carried out in a solvent in the presence of a base. The solvent usable in the condensation may be, for instance, alcohols such as methanol, ethanol, propanol, isopropanol and 2-methoxyethanol; aromatic hydrocarbons such as benzene, toluene and xylene; ethers such as ethyl ether, isopropyl ether, dioxane and tetrahydrofuran; N,N-dimethylformamide, acetonitrile, dimethylsulfoxide and acetic acid. Examples of such bases are sodium methoxide, sodium ethoxide, potassium carbonate, sodium carbonate, sodium hydride, sodium acetate, piperidine, piperazine, pyrrolidine, morpholine, diethylamine, diisopropylamine and triethylamine. The amount of 2,4-thiazolidinedione to be used ranges from 1 to 20 mole equivalents and preferably 1 to 5 mole equivalents per mole of the indole carbaldehyde derivative. The amount of the base to be used suitably ranges from 0.01 to 5 mole equivalents, preferably 0.02 to 2 mole equivalents per mole of the indole carbaldehyde derivative. The reaction temperature may range from 0° C. to the boiling point of the solvent used, preferably 10° C. to 100°C. The reaction time may be in the range of from 0.1 to 96 hours, preferably 0.5 to 24 hours.

The thiazolidinedione derivatives (III) thus prepared have, in themselves, an effect as therapeutic agents for treating diabetes mellitus, but they may further be subjected to a reducing reaction after isolation thereof as intermediates or without any isolation to give thiazolidinedione derivatives (IV). This reducing reaction may be carried out in an inert solvent by the methods known per se such as the catalytic reduction carried out in the presence of a catalyst. Such a solvent used in the reduction is not restricted to any specific one inasmuch as they are not involved in the reaction and examples thereof are ethyl acetate, methanol, ethanol, tetrahydrofuran, 1,4-dioxane, N,N-dimethylformamide and acetic acid, which may be used alone or in any combination. Catalysts usable in the catalytic reduction may be, for instance, palladium/carbon and platinum. The hydrogen gas pressure suitably ranges from ordinary pressure to 100 atm, preferably ordinary pressure to 10 atm, the reaction temperature may fall within the range of from 0° to 100° C., preferably 10° to 60° C. The reaction time may range from 0.1 to 72 hours, preferably 0.5 to 5 hours. Alternatively, if using magnesium metal, the reduction is carried out in an inert gas atmosphere such as argon or nitrogen gas atmosphere and, if necessary, in the presence of iodine as a catalyst. In this case, the reaction temperature may range from 0° to 100° C., preferably 10° to 60° C., while the reaction time may range from 0.5 to 72 hours, preferably 1 to 4 hours.

If the R portion of the thiazolidinedione derivative (III) as the starting compound used in this reducing reaction has a group susceptible to reduction, the reducing reaction provides a thiazolidinedione derivative (IV) as a reduced product whose R portion is simultaneously reduced. For instance, nitro and azide groups are reduced into amino groups, a cyclohexenyl group is reduced into a cyclohexyl group and a quinolyl group is reduced into a tetrahydroquinolyl group. Moreover, the R portion of the thiazolidinedione derivative (IV) may be changed after the reducing reaction. For instance, when an amino or hydroxy group is present in the R portion, such an amino group can be converted into a dimethylamino group by the usual method using formalin and sodium cyanohydroborate; and such a hydroxy group may be converted into a fluoro group using diethylaminosulfur trifluoride, or may be once converted into a methanesulfonyloxy group with a methanesulfonyl halide, followed by converting the latter into a chloro group through a reaction with lithium chloride.

The compounds of the present invention obtained according to the foregoing methods may be isolated or purified by the means for separation and/or purification commonly employed such as column chromatography, recrystallization and distillation under reduced pressure.

The compounds and pharmaceutically acceptable salts thereof according to the present invention show an effect of reducing the blood sugar level and do not cause severe hypoglycemia and therefore, can be used for treating mammals including human beings suffering from diabates mellitus, by themselves or in the form of a mixture with, for instance, conventionally known pharmaceutically acceptable carriers, vehicles and extenders. Moreover, they can be used as blood sugar level-reducing agents through elimination or relaxation of insulin-resistance.

When the compounds and pharmaceutically acceptable salts thereof according to the present invention are used in pharmaceutical compositions, the composition may have various dosage forms such as orally administered drugs, injectable liquids, suppositories, ointments and pastes. These dosage forms may be prepared by the methods known to and commonly used by those skilled in the art.

When preparing solid pharmaceuticals for oral use, tablets, coating tablets, granules, powders, capsules or the like may be produced by adding a vehicle and optionally a binder, a disintegrator, a lubricant, a coloring agent, a corrigent (e.g., taste-improving and/or odor-improving agents) to the compound of the present invention and then processed by the usual method. Such additives may be those commonly used in this field. More specifically, examples of vehicles are lactose, sucrose, glucose, starch, calcium carbonate, kaolin, microcrystalline cellulose and silicate; examples of binders include water, ethanol, propanol, simple syrup, glucose solution, starch solution, gelatin solution, carboxymethyl cellulose, hydroxypropyl cellulose, hydroxypropyl starch, methyl cellulose, ethyl cellulose, shellac, calcium phosphate and polyvinyl pyrrolidone; examples of disintegrators are dried starch, sodium alginate, agar powder, sodium hydrogen carbonate, calcium carbonate, sodium laurylsulfate, stearic acid monoglyceride and lactose; examples of lubricants are purified talc, stearates, borax and polyethylene glycol; and examples of taste-improving agents are sucrose, bitter orange peel, citric acid and tartaric acid.

When preparing liquid pharmaceuticals for oral use, liquid drugs for internal use, syrups, elixirs or the like may be prepared by adding, for instance, a corrigent (e.g., taste-improving and/or odor-improving agents), a buffering agent and/or a stabilizer to the compound of the present invention and then processed by the usual methods. In this case, the taste-improving agent may be the same as those listed above, examples of buffering-agents are sodium citrate and examples of stabilizers are tragacanth, gum arabic and gelatin.

When preparing injections, the compound of the present invention may be admixed with, for instance, a pH-adjusting agent, a buffering agent, a stabilizer, an isotonicity and a local anesthetic and then the resulting mixture may be processed by the usual methods to give injections administered through subcutaneous, intramuscular and intravenous routes. In this case, examples of pH-adjusting agents and buffering agents are sodium citrate, sodium acetate and sodium phosphate. Examples of stabilizers are sodium pyrosulfite, EDTA, thioglycollic acid and thiolactic acid. Examples of local anesthetics are procaine hydrochloride and lidocaine hydrochloride. Examples of isotonicities are sodium chloride and glucose.

When preparing suppositories, the compound of the present invention may be blended with a base commonly used and optionally a stabilizer, a humectant, a preservative or the like, followed by mixing and formed into suppositories according to the usual methods. Examples of bases are liquid paraffin, white soft paraffin, white beeswax, octyl-dodecyl alcohol and paraffins. Examples of preservatives are methyl p-oxybenzoate, ethyl p-oxybenzoate and propyl p-oxybenzoate.

Plasters may be prepared by applying, for instance, the foregoing ointments, creams, gels and pastes onto the commonly used supports according to the usual methods. Examples of such supports suitably used herein are woven and nonwoven fabrics of, for instance, cotton, staple fibers and chemical fibers; films such as soft polyvinyl chloride, polyethylene and polyurethane films; or foamed sheets.

The amount of the compound of the present invention to be incorporated into the foregoing unit dose varies depending on the symptoms of patients to which these drugs are administered or the dosage forms, but generally and desirably ranges from about 1 to 1000 mg for orally administered drugs; about 0.1 to 500 mg for injections; and about 5 to 1000 mg for suppository per unit dose. Moreover, the daily dose of the drug in the foregoing dosage form varies depending on various factors such as the symptom, body weight, age and sex of a particular patient and cannot be sweepingly determined, but generally and desirably ranges from about 0.1 to 5000 mg/day, preferably about 1 to 1000 mg/day for adult and the drug may preferably be administered to a patient once a day or in portions about 2 to 4 times a day.

The present invention will hereinafter be described in more detail with reference to the following Examples, but the present invention is not restricted to these specific Examples. In the following Examples, symbols "Bn", "Ph", "Me" and "Et" represent a benzyl group, a phenyl group, a methyl group and an ethyl group respectively.

EXAMPLE 1

Synthesis of 1-benzylindole-4-carbaldehyde

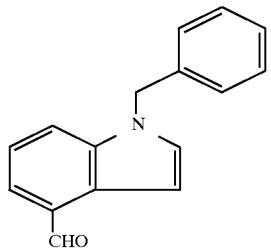

Sodium hydride (95%; 0.37 g) was suspended in 10 ml of dimethylformamide and cooled to a temperature ranging from 0° to 5° C. with stirring, under an argon gas atmosphere. To the resulting mixed liquid, there was dropwise added a solution of 2.00 g of indole-4-carbaldehyde in 5 ml of dimethylformamide over 15 minutes. After completion of the dropwise addition, the mixture was stirred at a temperature ranging from 0° to 5° C. for 30 minutes. To the reaction solution, there was added a solution of 2.47 g of benzyl bromide in 5 ml of dimethylformamide, followed by stirring at room temperature for 2 hours. The reaction solution was poured into 200 ml of a 10% ammonium chloride aqueous solution, followed by extraction with ethyl acetate (200 ml×2). After washing the extract with a saturated common salt solution, it was dried over anhydrous sodium sulfate, followed by evaporation of the solvent under reduced pressure to give 3.18 g of 1-benzylindole-4-carbaldehyde as brown crystals. The yield thereof was found to be 98%.

NMR (CDCl$_3$) δ: 5.35 (2H,s), 7.0~7.1 (2H,m), 7.2~7.4 (6H,m), 7.51 (1H,d,J=8.0 Hz), 7.60 (1H,d,J=8.0 Hz), 10.21 (1H,s)

EXAMPLE 2

Synthesis of 5-(1-benzylindol-4-yl)methylene-2,4-thiazolidinedione

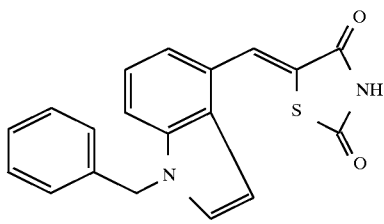

To 60 ml of ethanol, there were dissolved 3.00 g of 1-benzylindole-4-carbaldehyde prepared in Example 1 and 0.22 g of piperidine, followed by addition of 2.99 g of 2,4-thiazolidinedione to the resulting solution and heating the mixture under reflux for 24 hours. To the reaction solution, there was added 120 ml of diethyl ether and the mixture was stirred at 0° C. for one hour. The crystals precipitated were filtered off and washed with a diethyl ether/ethanol (2:1) mixed solvent. The crystals were dried under reduced pressure to give 3.24 g of 5-(1-benzylindol-4-yl)methylene-2,4-thiazolidinedione as yellow crystals. The yield thereof was found to be 76%.

IR(KBr)cm$^{-1}$: 1740, 1680, 1580, 1320, 1270; NMR (DMSO-d$_6$) δ: 5.49 (2H,s), 6.80 (1H,d,J=3.0 Hz), 7.1~7.4 (7H,m), 7.61 (1H,d,J=8.0 Hz), 7.70 (1H,d,J=3.0 Hz), 8.16 (1H,s), 12.60 (1H,bs)

EXAMPLE 3

Synthesis of 5-(1-benzylindol-4-yl)methyl-2,4-thiazolidinedione

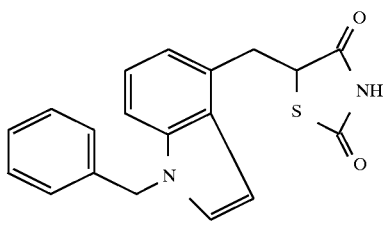

To metal magnesium, there was added methanol in an amount sufficient for immersing the magnesium metal and then a small amount of iodine powder was added thereto, under an argon gas atmosphere. The mixture was allowed to stand till foaming was initiated and then stirred till the color of the iodine disappeared. To the mixed liquid, there were added 3.00 g of 5-(1-benzylindol-4-yl)methylene-2,4-thiazolidinedione prepared in Example 2 and 210 ml of methanol, followed by stirring at room temperature and addition of 4.36 g of magnesium powder over 2 hours. After the addition of the magnesium powder, the resulting mixture was stirred at room temperature for 2 hours. The reaction solution was poured into 2 l of a 20% ammonium chloride aqueous solution, followed by extraction with dichloromethane (1 l×3). The resulting extract was washed with a 10% citric acid aqueous solution and a saturated common salt solution in this order, followed by drying the extract over anhydrous sodium sulfate and evaporation of the solvent under reduced pressure to give 2.24 g of 5-(1-benzylindol-4-yl)methyl-2,4-thiazolidinedione as yellow crystals. The yield thereof was found to be 74%.

IR(KBr) cm$^{-1}$: 1750, 1670, 1300, 1160, 750; NMR (DMSO-d$_6$) δ: 3.2~3.5 (1H,m), 3.6~3.8 (1H,m), 4.9~5.1 (1H,m), 5.40 (2H,s), 6.60 (1H,d,J=3.0 Hz), 6.8~7.4 (8H,m), 7.50 (1H,d,J=3.0 Hz), 12.08 (1H,bs)

EXAMPLE 4

Synthesis of 1-(4-picolyl)indole-4-carbaldehyde

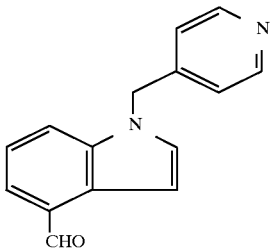

To a mixture of 2.00 g of indole-4-carbaldehyde and 9.52 g of potassium carbonate, there was added 40 ml of dimethylformamide and then the resulting mixture was stirred. To the mixed liquid, there was added 4.52 g of 4-picolyl chloride hydrochloride and the mixture was stirred at 60° C. for 24 hours. The reaction solution was poured into 400 ml of a 10% ammonium chloride aqueous solution followed by extraction with ethyl acetate (400 ml×2). After washing the extract with a saturated common salt solution, it was dried over anhydrous sodium sulfate and evaporation of the solvent under reduced pressure gave 6.09 g of a residue. The residue was purified by silica gel chromatography (hexane: ethyl acetate=1:3) to give 1.88 g of 1-(4-picolyl)indole-4-carbaldehyde as colorless crystals. The yield thereof was found to be 58%.

NMR (CDCl$_3$) δ: 5.40 (2H,s), 6.90 (2H,d,J=3.0 Hz), 7.2~7.5 (4H,m) 7.65 (1H,d,J=8.0 Hz), 8.50 (2H,d,J=3.0 Hz), 10.25 (1H,s)

EXAMPLE 5

Synthesis of 5-[1-(4-picolyl)indol-4-yl]methylene-2,4-thiazolidinedione

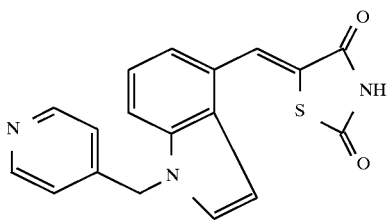

The same procedures used in Example 2 were repeated using 1.80 g of 1-(4-picolyl)indole-4-carbaldehyde prepared in Example 4 to give 2.19 g of 5-[1-(4-picolyl)indol-4-yl]methylene-2,4-thiazolidinedione as yellow crystals. The yield thereof was found to be 86%.

IR (KBr) cm$^{-1}$: 1730, 1690, 1600, 1590, 1330, 1290; NMR (DMSO-d$_6$) δ: 5.59 (2H,s), 6.8~7.8 (7H,m), 8.16 (1H,s), 8.4~8.6 (2H,m), 12.60 (1H,bs)

EXAMPLE 6

Synthesis of 5-[1-(4-picolyl)indol-4-yl]methyl-2,4-thiazolidinedione

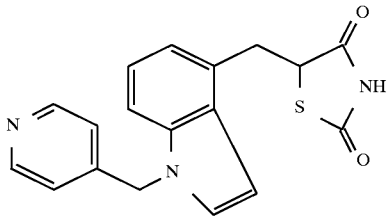

To a mixture of 2.00 g of 5-[1-(4-picolyl)indol-4-yl] methylene-2,4-thiazolidinedione prepared in Example 5 and 2.00 g of a 10% palladium/carbon, there was added 200 ml of tetrahydrofuran and then hydrogen gas was introduced into the reaction vessel. The hydrogen gas pressure was adjusted to 6 atm and the reaction mixture was stirred at room temperature for 24 hours. The reaction solution was filtered, followed by evaporation of the solvent under reduced pressure to give 1. 94 g of 5-[1-(4-picolyl)indol-4-yl]methyl-2,4-thiazolidinedione as yellow crystals. The yield thereof was found to be 97%.

IR (KBr) cm$^{-1}$: 1740, 1700, 1600, 1310, 1180, 750; NMR (DMSO-$d_6$) δ: 3.35 (1H,dd,J=10.4 Hz, 14.1 Hz), 3.72 (1H, dd,J=14.1 Hz,4.0 Hz), 5.00 (1H,dd,J=4.0 Hz,10.4 Hz), 5.49 (2H,s), 6.65 (1H,d,J=3.3 Hz), 6.8~7.4 (5H,m), 7.54 (1H,d, J=3.3 Hz), 8.48 (2H,d,J=5.1 Hz)

EXAMPLE 7

Synthesis of 1-(4-methoxycarbonylbenzyl)indole-4-carbaldehyde

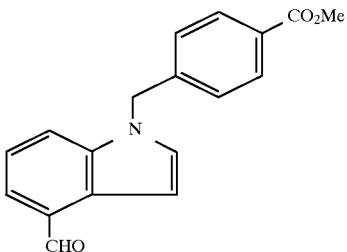

To a mixture of 2.00 g of indole-4-carbaldehyde and 9.52 g of potassium carbonate, there was added 40 ml of acetonitrile and then the resulting mixture was stirred. To the mixed liquid, there was added 6.31 g of methyl 4-bromomethylbenzoate and the mixture was stirred at 60° C. for 24 hours. The reaction solution was filtered, followed by evaporation of the solvent under reduced pressure to give 7.76 g of a residue. The residue was purified by silica gel chromatography (hexane: ethyl acetate=4:1) to give 2.82 g of 1-(4-methoxycarbonylbenzyl) indole-4-carbaldehyde as colorless crystals. The yield thereof was found to be 70%. NMR (CDCl$_3$) δ: 3.89 (3H,s), 5.45 (2H,s), 7.0~7.5 (7H,m), 7.97 (2H,d,J=8.0 Hz), 10.25 (1H,s)

EXAMPLE 8

Synthesis of 5-[1-(4-methoxycarbonylbenzyl)indol-4-yl]methylene-2,4-thiazolidinedione

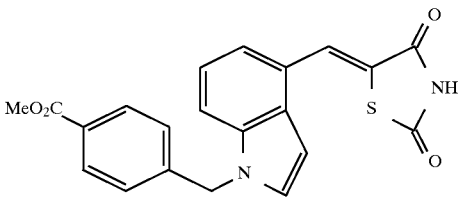

The same procedures used in Example 2 were repeated using 2.80 g of 1-(4-methoxycarbonylbenzyl)indole-4-carbaldehyde prepared in Example 7 to give 3.21 g of 5-[1-(4-methoxycarbonylbenzyl)indol-4-yl]methylene-2,4-thiazolidinedione as yellow crystals. The yield thereof was found to be 86%.

IR (KBr) cm$^{-1}$: 1740, 1720, 1690, 1590, 1340, 1280; NMR (DMSO-$d_6$) δ: 3.81 (3H,s), 5.60 (2H,s), 6.83 (1H,d, J=3.0 Hz), 7.1~7.4 (4H,m), 7.5~7.6 (1H,m ), 7.74 (1H,d,J= 3.0 Hz), 7.90 (2H,d,J=8.0 Hz), 8.16 (1H,s), 12.60 (1H,bs)

EXAMPLE 9

Synthesis of 5-[1-(4-methoxycarbonylbenzyl)indol-4-yl]methyl-2,4-thiazolidinedione

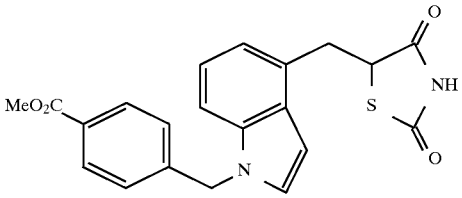

The same procedures used in Example 6 were repeated using 3.00 g of 5-[1-(4-methoxycarbonylbenzyl)indol-4-yl] methylene-2,4-thiazolidinedione prepared in Example 8 to give 3.00 g of 5-[1-(4-methoxycarbonylbenzyl)indol-4-yl] methyl-2,4-thiazolidinedione as colorless crystals. The yield thereof was found to be 99%. IR (KBr) cm$^{-1}$: 1740, 1700, 1300, 750; NMR (DMSO-$d_6$) δ: 3.33 (1H,dd,J=10.3 Hz,14.3 Hz), 3.70 (1H,dd,J=14.3 Hz, 4.0 Hz), 3.82 (3 H,s) 4.99 (1H,dd,J=4.0 Hz, 10.3 Hz), 5.52 (2H,s), 6.63 (1H,d,J=3.3 Hz), 6.91 (1H,d,J=7.7 Hz), 7.06 (1H,dd,J=7.7 Hz,J=7.7 Hz), 7.2~7.4 (3H,m), 7.54 (1H,d,J=3.3 Hz), 7.90 (2H,d,J=8.1 Hz)

EXAMPLE 10

Synthesis of 5-[1-(4-carboxybenzyl) indol-4-yl]-methyl-2,4-thiazolidinedione

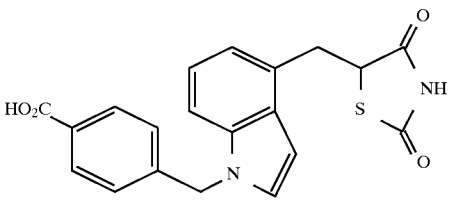

To a mixture of 2.00 g of 5-[1-(4-methoxycarbonylbenzyl)indol-4-yl]methyl-2,4- thiazolidinedione prepared in Example 9 and 0.43 g of lithium hydroxide monohydrate, there were, in order, added 40 ml of tetrahydrofuran, 40 ml of water and 20 ml of methanol and the resulting mixture was stirred at 60° C. for 2 hours. After concentrating the reaction solution to about 40 ml, the concentrate was neutralized with a 10% citric acid aqueous solution, followed by extraction with dichloromethane (100 ml×3). The extract was washed with a saturated common salt solution, dried over anhydrous sodium sulfate, followed by evaporation of the solvent under reduced pressure to give 1.54 g of 5-[1-(4-carbonylbenzyl)indol-4-yl]methyl-2,4-thiazolidinedione as pale yellow crystals. The yield thereof was found to be 80%.

IR (KBr) cm$^{-1}$: 1750, 1700, 1300, 750; NMR (DMSO-d$_6$) δ: 3.33 (1H,dd,J=10.4 Hz,14.4 Hz), 3.71 (1H,dd,J=14.4 Hz, 4.2 Hz), 5.00 (1H,dd,J=4.2 Hz,10.4 Hz), 5.51 (2H,S), 6.62 (1H,d,J=2.9 Hz), 6.91 (1H,d,J=7.7 Hz ), 7.06 (1H dd,J=7.7 Hz,J=7.7 Hz,), 7.2~7.4 (3H,m), 7.56 (1H,d,J=2.9 Hz), 7.89 (2H, J=8.0 Hz)

EXAMPLE 11

Synthesis of 1-phenylacetylindole-4-carbaldehyde

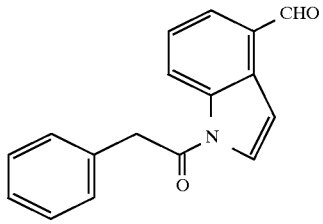

Sodium hydride (95%; 418 mg) was suspended in dimethylformamide under an argon gas atmosphere. A solution of 2.00 g of indole-4-carbaldehyde in 10 ml of dimethylformamide was dropwise added to the suspension with ice-cooling and stirring. After stirring at room temperature for 15 minutes, the mixture was again ice-cooled and a solution of 2.56 g of phenylacetyl chloride in 10 ml of dimethylformamide was dropwise added thereto. After stirring at room temperature for one day, the reaction mixture was poured into 400 ml of a 10% ammonium chloride aqueous solution followed by extraction with ethyl acetate (200 ml×2). The resulting organic phase was washed with a saturated common salt solution, dried over anhydrous sodium sulfate, followed by evaporation of the solvent under reduced pressure. The resulting crude product was purified by silica gel column chromatography (hexane:ethyl acetate= 10:1) to thus give 1.41 g of 1-phenylacetylindole-4-carbaldehyde as a yellow oily substance. The yield thereof was found to be 39%.

NMR (CDCl$_3$) δ: 4.25 (2H,s), 7.1~7.5 (7H,m), 7.6~7.8 (2H,m), 8.7~8.8 (1H,m), 10.20 (1H,s)

EXAMPLE 12

Synthesis of 5-(1-phenylacetylindol-4-yl)methylene-2,4-thiazolidinedione

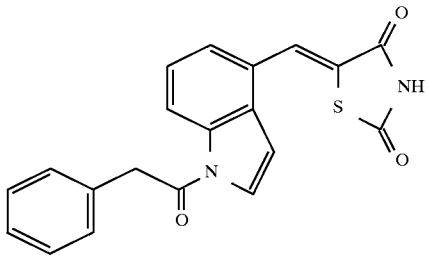

The same procedures used in Example 2 were repeated using 1.40 g of 1-phenylacetylindole-4-carbaldehyde prepared in Example 11 to give 1. 75 g of 5-(1-phenylacetylindol-4-yl)methylene-2,4-thiazolidinedione as yellow crystals. The yield thereof was found to be 91%. IR (KBr) cm$^{-1}$: 1740, 1720, 1690, 1340, 1300; NMR (DMSO-d$_6$) δ: 4.48 (2H,s), 7.1~7.2 (1H,m), 7.2~7.5 (7H,m) ,8.08 (1H,s), 8.2~8.3 (1H,m), 8.4~8.5 (1H,m)

EXAMPLE 13

Synthesis of 5-(1-phenylacetylindol-4-yl)methyl-2,4-thiazolidinedione

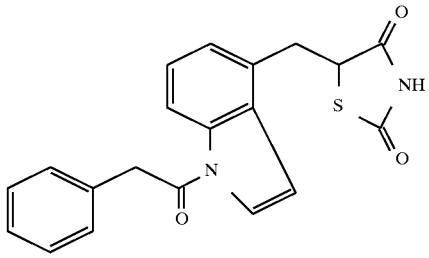

The same procedures used in Example 6 were repeated using 1.70 g of 5-(1-phenylacetylindol-4-yl)methylene-2,4-thiazolidinedione prepared in Example 12 to give 1.53 g of 5-(1-phenylacetylindol-4-yl)methyl-2,4-thiazolidinedione as a yellow amorphous substance. The yield thereof was found to be 90%.

IR (KBr) cm$^{-1}$: 1750, 1690, 1430, 1350, 1150; NMR (DMSO-d$_6$) δ: 3.43 (1H,dd,J=13.9,9.1), 3.65 (1H,dd,J=9.3 Hz, 4.4 Hz), 4.43 (2H,s), 4.99 (1H,dd,J=9.1 Hz, 4.4 Hz), 6.92 (1H,d,J=3.8 Hz), 7.15 (1H,d,J=7.3 Hz), 7.2~7.5 (7H, m), 8.08 (1H,d,J=3.8 Hz), 8.26 (1H,d,J=8.4 Hz), 12.07 (1H,bs)

EXAMPLE 14

Synthesis of 1-benzoylindole-4-carbaldehyde

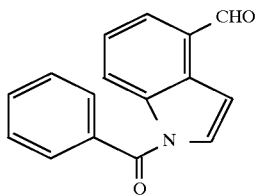

The same procedures used in Example 11 were repeated except for using 725 mg of indole-4-carbaldehyde and 773 mg of benzoyl chloride instead of phenylacetyl chloride to give 260 mg of 1-benzoylindole- 4-carbaldehyde as colorless crystals. The yield thereof was found to be 21%.

NMR (CDCl$_3$) δ: 7.4~7.9 (9H,m), 8.71 (1H,d,J=8.0 Hz), 10.26 (1H,s)

EXAMPLE 15

Synthesis of 5-(1-benzoylindol-4-yl)methylene-2,4-thiazolidinedione

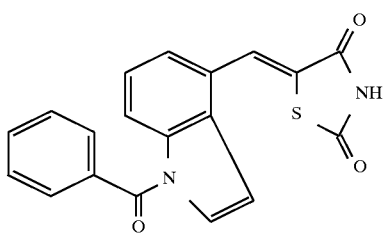

The same procedures used in Example 2 were repeated except for using 249 mg of 1-benzoylindole-4-carbaldehyde prepared in Example 14 to give 210 mg of 5-(1-benzoylindol-4-yl)methylene-2,4-thiazolidinedione as yellow crystals. The yield thereof was found to be 60%.

IR (KBr) cm$^{-1}$: 1750, 1700, 1680, 1330; NMR (DMSO-d$_6$) δ: 7.09 (1H,d,J=4.0 Hz), 7.4~7.9 (8H,m), 8.11 (1H,s), 8.37 (1H,d,J=7.7 Hz), 12.68 (1H,bs)

EXAMPLE 16

Synthesis of 5-(1-benzoylindol-4-yl)methyl-2,4-thiazolidinedione

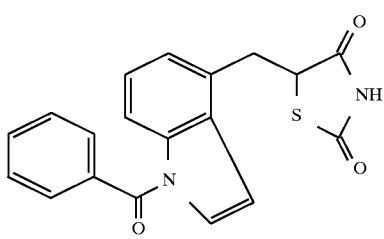

The same procedures used in Example 6 were repeated except for using 177 mg of 5-(1-benzoylindol-4-yl)methylene-2,4-thiazolidinedione prepared in Example 15 to give 169 mg of 5-(1-benzoylindol-4-yl)methyl-2,4-thiazolidinedione as colorless crystals. The yield thereof was found to be 95%.

IR (KBr) cm$^{-1}$: 1760, 1700, 1430, 1340; NMR (DMSO-d$_6$) δ: 3.45 (1H,dd,J=14.2 Hz, 9.6 Hz), 3.68 (1H,dd,J=14.2 Hz, 4.4 Hz), 4.99 (1H,dd,J=9.6 Hz, 4.4 Hz), 6.8~7.0 (2H,m), 7.21 (1H,d,J=7.3 Hz), 7.33 (1H,d,J=8.0 Hz), 7.4~7.8 (5H, m), 8.20 (1H,d,J=8.4 Hz), 12.09 (1H,bs)

EXAMPLE 17

Synthesis of 1-benzenesulfonylindole-4-carbaldehyde

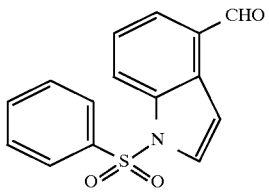

Indole-4-carbaldehyde (580 mg) was dissolved in 8 ml of dimethylformamide, then 176 mg of sodium hydride (content 60%) was added to the resulting solution with ice-cooling, followed by stirring for one hour, addition of 777 mg of benzenesulfonyl chloride and stirring for one hour. To the reaction solution, there were added 50 ml of ethyl acetate and 50 ml of a saturated sodium hydrogen carbonate aqueous solution followed by stirring for 30 minutes. After separation of phases, the aqueous phase was further extracted with 50 ml of ethyl acetate. The combined organic phase was washed with 50 ml of saturated common salt solution, dried over anhydrous sodium sulfate, followed by evaporation of the solvent under reduced pressure to give a crude product. The crude product was subjected to silica gel chromatography (eluent: hexane/ethyl acetate=9/1) to give 842 mg of 1-benzenesulfonylindole-4-carbaldehyde as pale brown crystals. The yield thereof was found to be 74%.

NMR (CDCl$_3$) δ: 7.3~7.6 (5H,m), 7.72 (1H,dd,J=7.0 Hz, 1.1 Hz), 7.76 (1H,d,J=3.3 Hz), 7.8~7.9 (2H,m), 8.28 (1H, d,J=7.9 Hz), 10.16 (1H,s)

EXAMPLE 18

Synthesis of 5-[1-(benzenesulfonyl)indol-4-yl]-methylene-2,4-thiazolidinedione

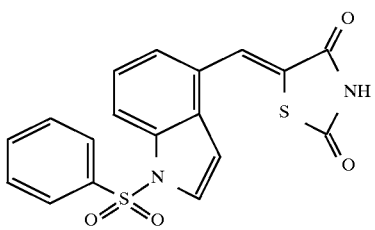

The same procedures used in Example 2 were repeated except for using 770 mg of 1-benzenesulfonylindole-4-carbaldehyde prepared in Example 17 to give 716 mg of 5-[1-(benzenesulfonyl)indol-4-yl]-methylene- 2,4-thiazolidinedione as pale yellow crystals. The yield thereof was found to be 69%.

IR (KBr) cm$^{-1}$: 1740, 1680, 1270, 1170; NMR (DMSO-d$_6$) δ: 7.20 (1H,d,J=3.7 Hz), 7.40 (1H,d, J=7.7 Hz), 7.5~7.8 (4H,m), 7.9~8.2 (5H,m), 12.64 (1H,bs)

EXAMPLE 19

Synthesis of 5-[1-(benzenesulfonyl)indol-4-yl]-methyl-2,4-thiazolidinedione

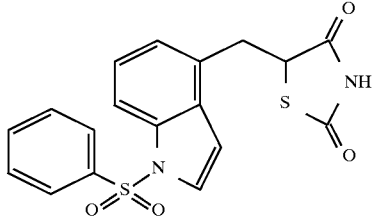

The same procedures used in Example 6 were repeated except for using 405 mg of 5-[1-(benzenesulfonyl)indol-4-yl]-methylene-2,4-thiazolidinedione prepared in Example 18 to give 367 mg of 5-[1-(benzenesulfonyl)indol-4-yl]-methyl-2,4-thiazolidinedione as colorless crystals. The yield thereof was found to be 90%.

IR (KBr) cm$^{-1}$: 1760, 1670, 1360, 1130; NMR (DMSO-d$_6$) δ: 3.38 (1H,dd,J=14.0 Hz, 9.9 Hz), 3.60 (1H,d,J=14.0 Hz, 4.4Hz), 4.95 (1H,dd,J=9.9 Hz, 4.4 Hz), 7.00 (1H,d,J=3.7 Hz), 7.14 (1H,d,J=7.5 Hz), 7.31 (1H,dd,J=7.5 Hz, 7.5 Hz), 7.5~7.8 (3H,m), 7.8~7.9 (2H,m), 7.9~8.0 (2H,m), 12.07 (1H,bs)

EXAMPLE 20

Synthesis of 5-[1-(4-fluorobenzenesulfonyl)indol-4-yl]methylene-2,4-thiazolidinedione

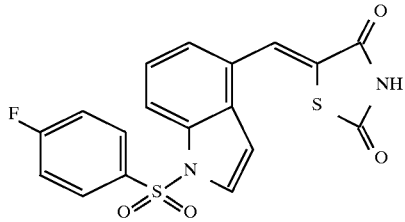

The same procedures used in Example 17 and Example 2 were repeated except for using 725 mg of indole-4-carbaldehyde and 1.07 g of 4-fluorobenzenesulfonyl chloride instead of the benzenesulfonyl chloride used therein to thus give 497 mg of 5-[1-(4-fluorobenzenesulfonyl) indol-4-yl]-methylene-2,4-thiazolidinedione as pale yellow crystals. The yield thereof was found to be 25%.

IR (KBr) cm$^{-1}$: 1740, 1690, 1590, 1140; NMR (DMSO-d$_6$) δ: 7.23 (1H,d,J=4.0 Hz), 7.3~7.6 (4H,m), 7.99 (1H,d,J=3.6 Hz), 8.05 (1H,s), 8.1~8.3 (3H,m)

EXAMPLE 21

Synthesis of 5-[1-(4-fluorobenzenesulfonyl)indol-4-yl]-methyl-2,4-thiazolidinedione

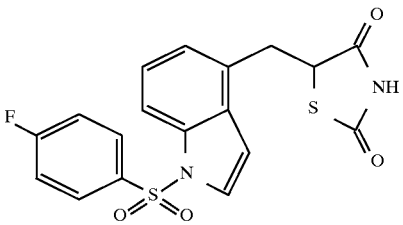

The same procedures used in Example 6 were repeated except for using 486 mg of 5-[1-(4-fluorobenzenesulfonyl)indol-4 -yl]-methylene-2,4-thiazolidinedione prepared in Example 20 to thus give 405 mg of 5-[1-(4-fluorobenzenesulfonyl)indol-4-yl]-methyl-2,4-thiazolidinedione as colorless crystals. The yield thereof was found to be 83%.

IR (KBr) cm$^{-1}$: 1760, 1700, 1590, 1370; NMR (DMSO-d$_6$) δ: 3.38 (1H,dd,J=14.6 Hz, 9.5 Hz), 3.61 (1H,dd,J=14.6 Hz, 4.4 Hz), 4.95 (1H,dd,J=9.5 Hz, 4.4 Hz), 7.02 (1H,d,J=4.0 Hz), 7.15 (1H,d,J=7.3 Hz), 7.2~7.5 (3H,m), 7.84 (1H,s), 7.87 (1H,d,J=4.0 Hz), 8.0~8.2 (2H,m), 12.05 (1H,bs)

EXAMPLE 22

Synthesis of 1-(p-toluenesulfonyl)indole-4-carbaldehyde

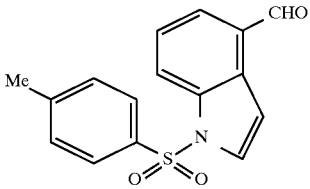

The same procedures used in Example 17 were repeated except for using 1.09 g of indole-4-carbaldehyde and 1.05 g of p-toluenesulfonyl chloride instead of the benzenesulfonyl chloride used therein to thus give 1.79 g of 1-(p-toluenesulfonyl)indole-4-carbaldehyde as brown crystals. The yield thereof was found to be 80%.

NMR (CDCl$_3$) 2.32 (3H,s), 7.22 (2H,d,J=8.6 Hz), 7.4~7.6 (2H,m), 7.6~7.8 (4H,m), 8.26 (1H,d,J=7.1 Hz), 10.17 (1H,s)

EXAMPLE 23

Synthesis of 5-[1-(p-toluenesulfonyl)indol-4-yl]-methylene-2,4-thiazolidinedione The same procedures used in Example 2 were repeated except for using 1.79 g of 1-(p-toluenesulfonyl)indole-4- carbaldehyde prepared in Example 22 to give 1.46 g of 5-[1-(p-toluenesulfonyl)indol-4-yl]methylene-2,4-thiazolidinedione as yellow crystals. The yield was found to be 61%.

IR (KBr) cm$^{-1}$: 1740, 1680, 1270, 1170; NMR (DMSO-d$_6$) δ: 2.32 (3H,s), 7.19 (1H,d,J=3.7 Hz), 7.3~7.4 (3H,m), 7.51 (1H,dd,J=7.9 Hz,7.9 Hz), 7.91 (2H,d,J=8.3 Hz), 7.97 (1H,d,J=3.6 Hz), 8.04 (1H,s ), 8.06 (1H,d,J=7.9 Hz), 12.66 (1H,bs)

EXAMPLE 24

Synthesis of 5-[1-(p-toluenesulfonyl)indol-4-yl]-methyl-2,4-thiazolidinedione

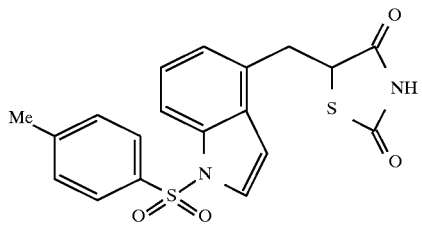

The same procedures used in Example 6 were repeated except for using 1.42 g of 5-[1-(p-toluenesulfonyl)indol-4-yl]methylene-2,4-thiazolidinedione prepared in Example 23 to give 1.27 g of 5-[1-(p-toluenesulfonyl)indol-4-yl]methyl-2,4-thiazolidinedione as colorless crystals. The yield was found to be 89%.

IR (KBr) cm$^{-1}$: 1760, 1680, 1360, 1160; NMR (DMSO-d$_6$) δ: 2.31 (3H,s), 3.32 (1H,dd,J=14.3 Hz, 9.5 Hz), 3.61 (1H,dd, J=14.3 Hz, 4.6 Hz) 4.95 (1H,dd,J=9.5 Hz , 4.6 Hz), 6.98 (1H,d,J=3.6 Hz), 7.13 (1H,d,J=7.3 Hz), 7.2~7.5 (3H, m), 7.7~7.9 (4H,m), 12.05 (1H,bs)

EXAMPLE 25

Synthesis of 1-[3-(trifluoromethyl)benzenesulfonyl]-indole-4-carbaldehyde

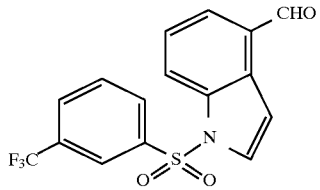

The same procedures used in Example 17 were repeated except for using 580 mg of indole-4-carbaldehyde and 1.08 g of 3-trifluorobenzenesulfonyl chloride instead of the benzenesulfonyl chloride used therein to give 866 mg of 1-[3-(trifluoromethyl)-benzenesulfonyl]indole-4-carbaldehyde as pale brown crystals. The yield was found to be 61%.

NMR (CDCl$_3$) δ: 7.5~7.7 (3H,m), 7.7~7.9 (3H,m), 8.03 (1H,d,J=7.7 Hz), 8.16 (1H,s), 8.28 (1H,d,J=8.4 Hz), 10.18 (1H,s)

EXAMPLE 26

Synthesis of 5-{1-[3-(trifluoromethyl)benzenesulfonyl]indol-4-yl }methylene-2,4-thiazolidinedione

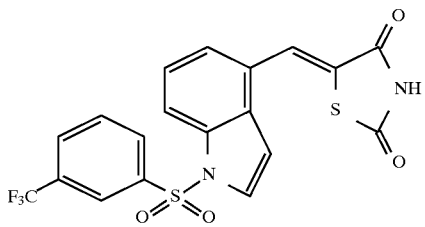

The same procedures used in Example 2 were repeated except for using 841 mg of 1-[3-(trifluoromethyl)benzenesulfonyl]indole-4-carbaldehyde prepared in Example 25 to give 632 mg of 5-{1-[3-(trifluoromethyl)benzenesulfonyl]indol-4-yl}methylene-2,4-thiazolidinedione as yellow crystals. The yield was found to be 59%.

IR (KBr) cm$^{-1}$: 1740, 1690, 1330, 1150; NMR (DMSO-d$_6$) δ: 7.26 (1H,d,J=3.7 Hz), 7.42 (1H,d,J=7.7 Hz), 7.55 (1H,dd,J=7.7 Hz, 7.7Hz), 7.86 (1H,dd,J=8.2 Hz,8.2 Hz), 8.05 (1H,s), 8.1~8.2 (2H,m), 8.3~8.4 (2H,m), 12.65 (1H,bs)

EXAMPLE 27

Synthesis of 5-{1-[3-(trifluoromethyl)benzene-sulfonyl]indol-4-yl}methyl-2,4-thiazolidinedione

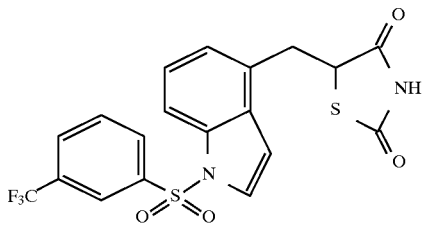

The same procedures used in Example 6 were repeated except for using 506 mg of 5-{1-[3-(trifluoromethyl)benzenesulfonyl]indol-4-yl}methylene-2,4-thiazolidinedione prepared in Example 26 to give 397 mg of 5-{1-[3-(trifluoromethyl)benzenesulfonyl]indol-4-yl}methyl-2,4-thiazolidinedione as colorless crystals. The yield was found to be 78%.

IR (KBr) cm$^{-1}$: 1750, 1700, 1320, 1140; NMR (DMSO-d$_6$) δ: 3.32 (1H,dd,J=14.2 Hz, 9.5 Hz), 3.60 (1H,dd,J=14.2 Hz, 4.4 Hz), 4.94 (1H,dd,J=9.5 Hz, 4.4 Hz)

EXAMPLE 28

Synthesis of methyl 1-[(5-methyl-2-phenyloxazol-4-yl)methyl]indole-4-carboxylate

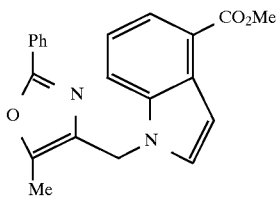

Methyl indole-4-carboxylate (700 mg) was dissolved in 7 ml of dimethylformamide, then 160 mg of sodium hydride (content 60%) was added to the resulting solution at room temperature and the mixture was stirred for 30 minutes. After adding 830 mg of 4-chloromethyl-5-methyl-2-phenyloxazole to the mixture and stirring them for 2 hours, the reaction solution was added to 70 ml of water and extracted with ethyl acetate (50 ml×2). The resulting organic phase was washed with, in order, water (50 ml×2) and 50 ml of a saturated common salt aqueous solution and dried over anhydrous sodium sulfate. After evaporation of the solvent under reduced pressure, the residue was crystallized in 50 ml of hexane to thus give 1.18 g of methyl 1-[(5-methyl-2-phenyloxazol-4-yl)methyl]indole-4-carboxylate as pale brown crystals. The yield thereof was found to be 85%.

NMR (CDCl$_3$) δ: 2.08 (3H,s), 3.98 (3H,s), 5.27 (2H,s), 7.17 (1H,d,J=2.9 Hz,0.8 Hz), 7.2~7.5 (5H,m), 7.65 (1H,d, J=8.0 Hz), 7.8~8.0 (3H,m)

EXAMPLE 29

Synthesis of 4-hydroxymethyl-1-[(5-methyl-2-phenyloxazol-4-yl)methyl]indole

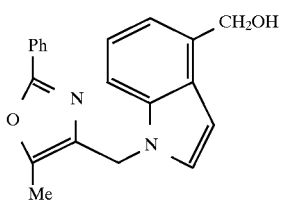

To a suspension of 114 mg of lithium aluminum hydride in 5 ml of tetrahydrofuran, there was dropwise added a solution obtained by dissolving, in 5 ml of tetrahydrofuran, 1.04 g of methyl 1-[(5-methyl-2-phenyloxazol-4-yl)methyl] indole-4-carboxylate prepared in Example 28 over 30 minutes, with ice-cooling and under an argon gas atmosphere. After stirring the reaction solution for one hour, there were, in order, added 0.11 ml of water, 0.11 ml of a 15% aqueous sodium hydroxide solution and 0.33 ml of water to the reaction solution, followed by stirring the mixture for 2 hours. The insolubles were filtered off, the resulting filtrate was concentrated and the residue was dried under reduced pressure to give 949 mg of 4-hydroxymethyl-1-[(5-methyl-2-phenyloxazol-4-yl)methyl]indole as colorless crystals. The yield thereof was found to be 99%.

NMR (CDCl$_3$) δ: 1.80 (1H,bs), 2.11 (3H,s), 4.97 (2H,s), 5.21 (2H,s), 6.64 (1H,d,J=3.3 Hz), 7.1~7,5 (7H,m), 7.8~8.0 (2H,m)

EXAMPLE 30

Synthesis of 1-[(5-methyl-2-phenyloxazol-4-yl)-methyl]indole-4-carbaldehyde

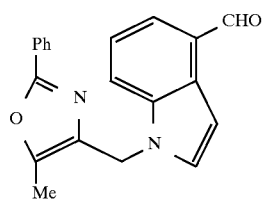

There were dissolved, in 14 ml of dimethylsulfoxide, 700 mg of 4-hydroxymethyl-1-[(5-methyl-2-phenyloxazol-4-yl) methyl]indole prepared in Example 29 and 890 mg of triethylamine, followed by addition of 700 mg of sulfur trioxide-pyridine complex to the solution and stirring for 30 minutes. The reaction solution was added to 100 ml of a 10% ammonium chloride aqueous solution, followed by extraction with ethyl acetate (50 ml×3). The resulting organic phase was washed, in turn, with water (50 ml×2) and 50 ml of a saturated common salt solution and dried over anhydrous sodium sulfate. After removal of the solvent through distillation under reduced pressure, the resulting residue was crystallized in 50 ml of ether to thus give 640 mg of 1-[(5-methyl-2-phenyloxazol-4-yl)methyl]indole-4-carbaldehyde as pale yellow crystals. The yield thereof was found to be 84%.

NMR (CDCl$_3$) δ: 2.13 (3H,s), 5.28 (2H,s), 7.3~7.5 (6H, m), 7.64 (1H,dd,J=7.4 Hz, 1.1 Hz), 7.75 (1H,d,J=8.4 Hz), 7.9~8.0 (2H,m), 10.24 (1H,s)

EXAMPLE 31

Synthesis of 5-{1-[(5-methyl-2-phenyloxazol-4-yl) methyl]indol-4-yl}methylene-2,4-thiazolidine-dione

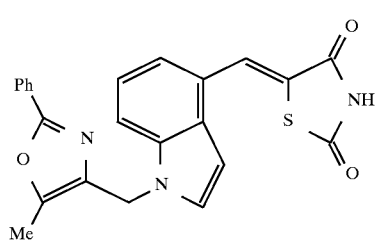

The same procedures used in Example 2 were repeated except for using 569 mg of 1-[(5-methyl-2-phenyloxazol-4-yl)methyl]indole-4-carbaldehyde prepared in Example 30 to thus form 681 mg of 5-{1-[(5-methyl-2-phenyloxazol-4-yl) methyl]indol-4-yl}methylene-2,4-thiazolidinedione as yellow crystals. The yield thereof was found to be 91%.

IR (KBr) cm$^{-1}$: 1740, 1680, 1320, 1280; NMR (DMSO-d$_6$) δ: 2.42 (3H,s), 5.40 (2H,s), 6.78 (1H,d,J=3.3 Hz), 7.2~7.9 (9H,m), 8.12 (1H,s), 12.58 (1H,bs)

EXAMPLE 32

Synthesis of 5-{1-[(5-methyl-2-phenyloxazol-4-yl)methyl]indol-4-yl}methyl-2,4-thiazolidinedione

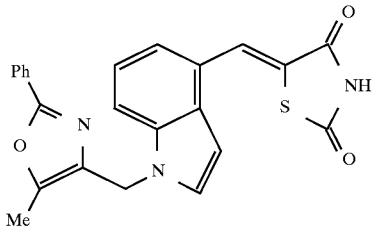

The same procedures used in Example 6 were repeated except for using 300 mg of 5-{1-[(5-methyl-2-phenyloxazol-4-yl)methyl)indol-4-yl}methylene-2,4-thiazolidinedione prepared in Example 31 to thus form 216 mg of 5-{1-[(5-methyl-2-phenyloxazol-4-yl)methyl]indol-4-yl}methyl-2,4-thiazolidinedione as pale yellow crystals. The yield thereof was found to be 72%.

IR (KBr) cm$^{-1}$: 1750, 1700, 1450, 1300; NMR (DMSO-d$_6$) δ: 2.37 (3H,s), 3.30 (1H,dd,J=14.3 Hz, 10.2 Hz), 3.68 (1H,dd,J=14.3 Hz, 4.0 Hz), 4.97 (1H,dd,J=10.2 Hz, 4.0 Hz), 5.32 (2H,s), 6.56 (1H,d,J=3.3 Hz), 6.90 (1H,d,J=7.0 Hz), 7.11 (1H,dd,J=7.9 Hz,7.0 Hz), 7.4~7.6 (5H,m), 7.8~8.0 (2H,m)

EXAMPLE 33

Synthesis of methyl 1-(4-ethylbenzoyl)indole-4-carboxylate

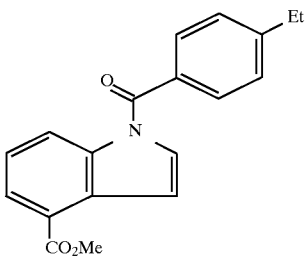

Sodium hydride (95%; 0.30 g) was suspended in 10 ml of dimethylformamide and the suspension was stirred while cooling the same at a temperature ranging from 0° to 5° C. To this mixed liquid, there was dropwise added a solution of 2.00 g of methyl indole-4-carboxylate in 5 ml of dimethylformamide over 15 minutes. After the completion of the dropwise addition, the reaction solution was stirred at a temperature ranging from 0° to 5° C. for 30 minutes. To the reaction solution, there was added a solution of 2.09 g of 4-ethylbenzoyl chloride in 5 ml of dimethylformamide, followed by stirring at room temperature for 2 hours. The reaction solution was poured into 200 ml of a 10% ammonium chloride aqueous solution, followed by extraction with ethyl acetate (200 ml×2). The extract was washed with a saturated common salt solution, dried over anhydrous sodium sulfate and the solvent was removed through distillation under reduced pressure to thus give 3.51 g of a residue. The residue was purified by silica gel chromatography (hexane:ethyl acetate=11:1) to give 2.18 g of methyl 1-(4-ethylbenzoyl)indole-4-carboxylate as colorless crystals. The yield thereof was found to be 62%.

NMR (CDCl$_3$) δ: 1.30 (3H,t,J=7.6 Hz), 2.75 (2H,q,J=7.6 Hz), 3.98 (3H,s), 7.3~7.5 (4H,m), 7.68 (2H,d,J=8.1 Hz), 8.04 (1H,d,J=7.8 Hz), 8.64 (1H,d,J=8.3 Hz)

EXAMPLE 34

Synthesis of 1-(4-ethylbenzyl)-4-(hydroxymethyl)-indole

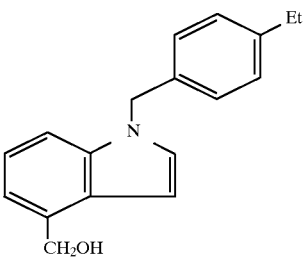

To 2.00 g of methyl 1-(4-ethylbenzoyl)indole-4-carboxylate prepared in Example 33, there was added 10 ml of tetrahydrofuran and the resulting mixture was stirred. To the mixture, there was immediately added borane-dimethylsulfide complex (2.0M tetrahydrofuran solution; 20 ml), followed by heating the resulting mixture under reflux for 2 hours. The reaction solution was cooled to a temperature ranging from 0°to 5° C., 30 ml of methanol was carefully added thereto and the resulting mixture was stirred for one hour. The solvent was removed through distillation under reduced pressure, the resulting residue was dissolved in ethyl acetate (150 ml), the solution was washed with, in order, a 10% aqueous solution of hydrochloric acid (100 ml×1) and a saturated common salt solution (100 ml×3) and dried over anhydrous sodium sulfate. The solvent was removed through distillation under reduced pressure to give 1.38 g of a residue. It was purified by silica gel chromatography (hexane:ethyl acetate=4:1) to give 1.00 g of 1-(4-ethylbenzyl)-4-(hydroxymethyl)indole as a colorless oily substance. The yield thereof was found to be 58%.

NMR (CDCl$_3$) δ: 1.21 (3H,t,J=7.6 Hz), 2.61 (2H,q,J=7.6 Hz), 4.96 (2H,s), 5.28 (2H,s), 7.0~7.3 (9H,m)

EXAMPLE 35

Synthesis of 1-(4-ethylbenzyl)indole-4-carbaldehyde

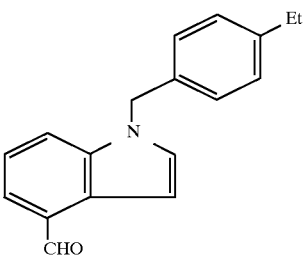

To a mixture of 1.00 g of 1-(4-ethylbenzyl)-4-(hydroxymethyl) indole prepared in Example 34 and 2.31 g of activated manganese dioxide (~85%), there was added 30 ml of dichloromethane and the resulting mixture was stirred at room temperature for 4 hours. The reaction solution was filtered, followed by washing with dichloromethane (50 ml×2). The solvent was distilled off, under reduced pressure, from the resulting filtrate to give 0.92 g of 1-(4-ethylbenzyl) indole-4-carbaldehyde as a yellow oily substance. The yield thereof was found to be 93%.

NMR (CDCl$_3$) δ: 1.19 (3H,t,J=7.6 Hz), 2.61 (2H,q,J=7.6 Hz), 5.34 (2H,s), 7.01 (2H,d,J=8.2 Hz), 7.13 (2H,d,J=8.2 Hz), 7.2~7.4 (3H,m), 7.5~7.7 (2H,m), 10.25 (1H,s)

EXAMPLE 36

Synthesis of 5-[1-(4-ethylbenzyl)indol-4-yl]-methylene-2,4-thiazolidinedione

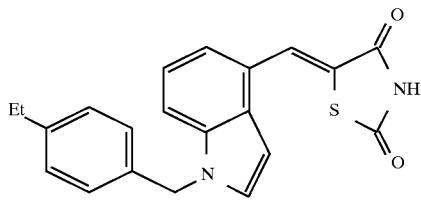

The same procedures used in Example 2 were repeated except for using 0.90 g of 1-(4-ethylbenzyl)indole-4-carbaldehyde prepared in Example 35 to give 0.93 g of 5-[1-(4-ethylbenzyl)indol-4-yl]methylene-2,4-thiazolidinedione as yellow crystals. The yield thereof was found to be 75%.

IR (KBr) cm$^{-1}$: 1740, 1690, 1590, 1330, 1300; NMR (DMSO-d$_6$) δ: 1.11 (3H,t,J=7.7 Hz), 2.53 (2H,q,J=7.7 Hz), 5.43 (2H,s), 6.78 (1H,d,J=2.9 Hz), 7.0~7.3 (6H, m), 7.5~7.8 (2H,m), 8.13 (1H,s), 12.60 (1H,bs)

EXAMPLE 37

Synthesis of 5-[1-(4-ethylbenzyl)indol-4-yl]-methyl-2,4-thiazolidinedione

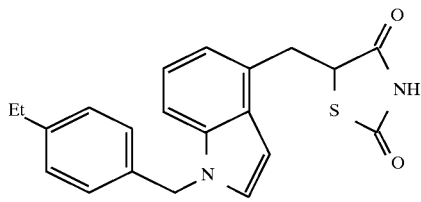

The same procedures used in Example 6 were repeated except for using 0.90 g of 5-[1-(4-ethylbenzyl)indol-4-yl] methylene-2,4-thiazolidinedione prepared in Example 36 to give 0.86 g of 5-[1-(4-ethylbenzyl)indol-4-yl]methyl-2,4-thiazolidinedione as colorless crystals. The yield thereof was found to be 95%.

IR (KBr) cm$^{-1}$: 1750, 1680, 1330, 1300, 750; NMR (DMSO-d$_6$) δ: 1.12 (3H,t,J=7.7 Hz), 2.53 (2H,q,J=7.7 Hz), 3.33 (1H,dd,J=10.2 Hz, 14.0 Hz), 3.70 (1H,dd,J=14.0 Hz, 4.0 Hz), 4.93 (1H,dd,J=4.0 Hz, 10.2 Hz), 5.36 (2H,s), 6.56 (1H,d,J=2.9 Hz), 6.88 (1H,d,J=7.0 Hz), 7.0~7.3 (5H,m), 7.37 (1H,d,J=7.0 Hz), 7.50 (1H,d,J=2.9 Hz)

EXAMPLE 38

Synthesis of 1-(2-methoxycarbonylethyl)indole-4-carbaldehyde

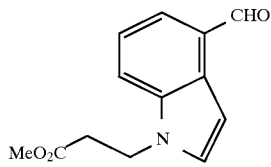

Sodium hydride (95%; 383 mg) was suspended in 10 ml of dimethylformamide under an argon gas atmosphere. To the suspension, there was dropwise added a solution of 2.00 g of indole-4-carbaldehyde in 10 ml of dimethylformamide with ice-cooling and stirring. After stirring the reaction mixture at room temperature for 25 minutes, it was again ice-cooled followed by dropwise addition of a solution of 1.33 g of methyl acrylate in 10 ml of dimethylformamide and stirring at room temperature for 19 hours. The reaction system was poured into 400 ml of a 10% ammonium chloride solution, followed by addition of a 2% HCl aqueous solution till the system became acidic and extraction with ethyl acetate (200 ml×2). After drying the extract over anhydrous magnesium sulfate, the solvent was removed by distillation under reduced pressure and the resulting crude product was purified by silica gel column chromatography (hexane:ethyl acetate=2:1) to thus give 3.68 g of a pale yellow oily substance. This was dissolved in 40 ml of dimethylformamide, followed by addition of 2.70 g of methyl iodide and 2.58 g of potassium carbonate and stirring the mixture at room temperature for 1.5 hour. The mixture was poured into 400 ml of a 10% ammonium chloride aqueous solution and extracted with ethyl acetate (200 ml×2). After drying the resulting extract over anhydrous sodium sulfate, the solvent was removed by distillation under reduced pressure and the resulting crude product was purified by silica gel column chromatography to give 848 mg of 1-(2-methoxycarbonylethyl)indole-4-carbaldehyde as a yellow oily substance. The yield thereof was found to be 27%.

NMR (CDCl$_3$) δ: 2.82 (2H,t,J=6.8 Hz), 3.64 (3H,s), 4.50 (2H,t,J=6.8 Hz), 7.2~7.4 (3H,m), 7.6~7.7 (2H,m), 10.22 (1H,s)

EXAMPLE 39

Synthesis of 5-[1-(2-methoxycarbonylethyl)indol-4-yl]methylene-2,4-thiazolidinedione

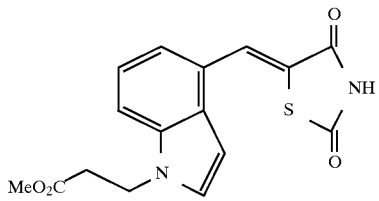

The same procedures used in Example 2 were repeated except for using 820 mg of 1-(2-methoxycarbonylethyl) indole-4-carbaldehyde prepared in Example 38 tp give 327 mg of 5-[1-(2-methoxycarbonylethyl) indol-4-yl] methylene-2,4-thiazolidinedione as orange yellow crystals. The yield thereof was found to be 28%.

IR (KBr) cm$^{-1}$: 1730, 1690, 1590, 1330, 620; NMR (DMSO-d$_6$) δ: 2.87 (2H,t,J=6.6 Hz), 3.57 (3H,s), 4.49 (2H,t,J=6.6 Hz), 6.7~6.8 (1H,m), 7.2~7.4 (2H,m), 7.5~7.6 (1H,m 7.67 (1H,d,J=8.1 Hz), 8.11 (1H,s), 12.58 (1H,bs)

EXAMPLE 40

Synthesis of 5-[1-(2-methoxycarbonylethyl)indol-4-yl]methyl-2,4-thiazolidinedione

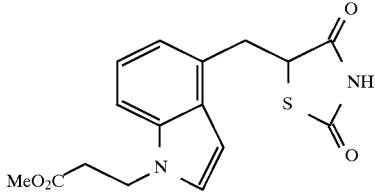

The same procedures used in Example 6 were repeated except for using 300 mg of 5-[1-(2-methoxycarbonylethyl) indol-4-yl]methylene-2,4-thiazolidinedione prepared in Example 39 to give 235 mg of 5-[1-(2-methoxycarbonylethyl)indol-4-yl]methyl-2,4-thiazolidinedione as colorless crystals. The yield thereof was found to be 78%.

IR (KBr) cm$^{-1}$: 1750, 1710, 1440, 1330, 1160; NMR (DMSO-d$_6$) δ: 2.84 (2H,t,J=6.8 Hz), 3.2~3.4 (1H,m), 3.56 (3H,s), 3.68 (1H,dd,J=14.3 Hz, 4.0 Hz), 4.42 (2H,t,J=6.8 Hz), 4.98 (1H,dd,J=10.1Hz, 4.0 Hz), 6.51 (1H,d,J=3.3 Hz), 6.89 (1H,d,J=7.0 Hz), 7.09 (1H,t,d=7.7 Hz), 7.3~7.4 (2H,m)

EXAMPLE 41

Synthesis of 5-[1-(2-carboxyethyl)indol-4-yl]-methyl-2,4-thiazolidinedione

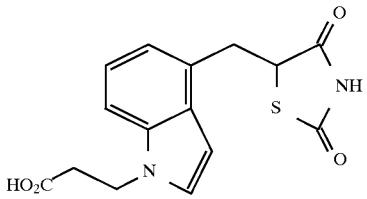

The same procedures used in Example 10 were repeated except for using 220 mg of 5-[1-(2-methoxycarbonylethyl) indol-4-yl]methyl-2,4-thiazolidinedione prepared in Example 40 to give 182 mg of 5-[1-(2-carboxyethyl)indol-4-yl]methyl-2,4-thiazolidinedione as colorless crystals. The yield thereof was found to be 87%.

IR (KBr) cm$^{-1}$: 1750, 1690, 1440, 1330, 1160, 750; NMR (DMSO-d$_6$) δ: 2.75 (2H,t,J=6.6 Hz), 3.2~3.4 (1H,m), 3.68 (1H,dd,J=14.1 Hz, 4.2 Hz), 4.39 (2H,t,J=6.6 Hz), 4.98 (1H,dd,J=10.4 Hz, 4.2 Hz), 6.50 (1H,d,J=3. 3 Hz), 6.89 (1H,d,J=7.3 Hz), 7.09 (1H,t,J=7.7 Hz), 7.3~7.4 (2H,m), 12.10 (1H, bs), 12.26 (1H, bs)

EXAMPLE 42

Synthesis of 1-(m-tolylcarbamoyl)indole-4-carbaldehyde

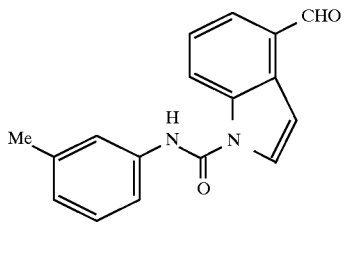

Indole-4-carbaldehyde (435 mg) was dissolved in 8 ml of dimethylformamide at room temperature under an argon gas atmosphere, then 126 mg of sodium hydride (content 60%) was added to the resulting solution and the mixture was stirred for 30 minutes, then 439 mg of m-tolylisocyanate was added thereto and the resulting mixture was stirred for one hour. The reaction solution was added to 50 ml of water followed by extraction with ethyl acetate (50 ml×2). The resulting organic phase was washed with water (50 ml×2), dried over anhydrous sodium sulfate and the solvent was removed by distillation under reduced pressure to give a crude product. This was subjected to silica gel chromatography (eluent: hexane/ethyl acetate=4/1) to give 736 mg of 1-(m-tolylcarbamoyl)indole-4-carbaldehyde as pale yellow crystals. The yield thereof was found to be 88%.

NMR (CDCl$_3$) δ: 2.37 (3H,s), 7.01 (1H,d,J=7.3 Hz), 7.2~7.5 (4H,m), 7.59 (1H,bs), 7.67 (1H,d,J=3.7 Hz), 7.72 (1H,dd, J=7.3 Hz, 1.0 Hz), 8.50 (1H,d,J=8.4 Hz), 10.21 (1H, s)

EXAMPLE 43

Synthesis of 5-[1-(m-tolylcarbamoyl)indol-4-yl]-methylene-2,4-thiazolidinedione

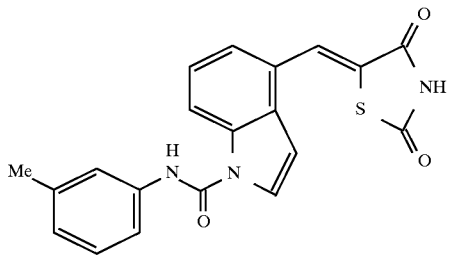

The same procedures used in Example 2 were repeated except for using 578 mg of 1-(m-tolylcarbamoyl)indole-4-carbaldehyde prepared in Example 42 to thus give 614 mg of 5-[1-(m-tolylcarbamoyl)indol-4-yl]methylene-2,4-thiazolidinedione as yellow crystals. The yield thereof was found to be 78%.

IR (KBr) cm$^{-1}$: 1730, 1700, 1680, 1550, 1320; NMR (DMSO-d$_6$) δ: 2.34 (3H,s), 6.98 (1H,d,J=7.3 Hz), 7.11 (1H,d,J=3.6 Hz), 7.2~7.5 (5H,m), 8.14 (1H,s), 8.19 (1H,d, J=3.6 Hz), 8.34 (1H,d, J=7.7 Hz), 10.11 (1H,s), 12.17 (1H,bs)

EXAMPLE 44

Synthesis of 5-[1-(m-tolylcarbamoyl)indol-4-yl]-methyl-2,4-thiazolidinedione

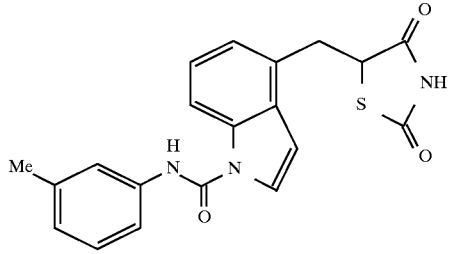

The same procedures used in Example 6 were repeated except for using 374 mg of 5-[1-(m-tolylcarbamoyl)indol-4-yl]methylene-2,4-thiazolidinedione prepared in Example 43 to thus give 360 mg of 5-[1-(m-tolylcarbamoyl)indol-4-yl]methyl-2,4-thiazolidinedione as a colorless amorphous substance. The yield thereof was found to be 95%.

IR (KBr) cm$^{-1}$: 1750, 1690, 1540, 1330; NMR (DMSO-$d_6$) δ: 2.33 (3H,s), 3.41 (1H,dd,J=14.2 Hz, 9.6 Hz), 3.68 (1H,dd,J=14.2 Hz, 4.4 Hz), 5.00 (1H,dd,J=9.6 Hz, 4.4 Hz), 6.8~7.0 (2H,m), 7.11 (1H,d,J=7.0 Hz), 7.2~7.3 (2H,m), 7.4~7.5 (2H,m), 8.03 (1H,d,J=4.0 Hz), 8.12 (1H,d,J=8.3 Hz), 9.99 (1H,s), 12.08 (1H,bs)

EXAMPLE 45

Synthesis of 1-(2-fluorobenzyl)indole-4-carbaldehyde

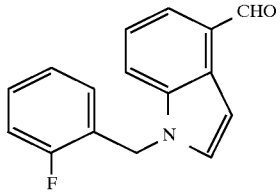

The same procedures used in Example 1 were repeated except for using 725 mg of indole-4-carbaldehyde and 2-fluorobenzyl bromide instead of the benzyl bromide used in Example 1 to give 1.22 g of 1-(2-fluorobenzyl)indole-4-carbaldehyde as yellow crystals. The yield thereof was found to be 96%.

NMR (CDC1$_3$) δ: 5.43 (1H,s), 6.84 (1H,ddd,J=7.3 Hz, 7.3 Hz, 1.4 Hz), 6.9~7.2 (2H,m), 7.2~7.4 (4H,m), 7.5~7.7 (2H,m), 10.25 (1H,s)

EXAMPLE 46

Synthesis of 5-[1-(2-fluorobenzyl)indol-4-yl]-methylene-2,4-thiazolidinedione

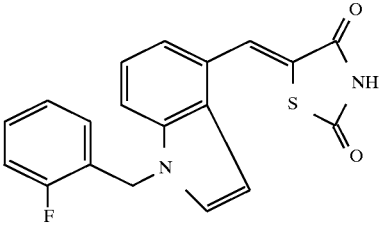

The same procedures used in Example 2 were repeated except for using 1.19 g of 1-(2-fluorobenzyl)indole-4-carbaldehyde prepared in Example 45 to give 1.38 g of 5-[1-(2-fluorobenzyl)indol-4-yl]methylene-2,4-thiazolidinedione as yellow crystals. The yield thereof was found to be 84%.

IR (KBr) cm$^{-1}$: 1730, 1680, 1590, 1320; NMR (DMSO-$d_6$) δ: 5.55 (2H,s), 6.80 (1H,d,J=3.3 Hz), 7.0~7.4 (6H,m), 7.5~7.7 (2H,m), 8.13 (1H,s), 12.60 (1H,bs)

EXAMPLE 47

Synthesis of 5-[1-(2-fluorobenzyl)indol-4-yl]-methyl-2,4-thiazolidinedione

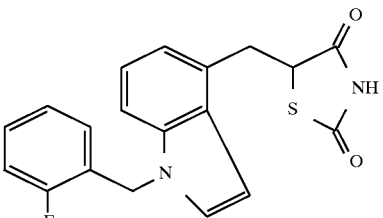

The same procedures used in Example 6 were repeated except for using 1.33 g of 5-[1-(2-fluorobenzyl)indol-4-yl]methylene-2,4-thiazolidinedione prepared in Example 46 to give 1.17 g of 5-[1-(2-fluorobenzyl)indol-4-yl]methyl-2,4-thiazolidinedione as colorless crystals. The yield thereof was found to be 87%.

IR (KBr) cm$^{-1}$: 1750, 1670, 1490, 1300; NMR (DMSO-$d_6$) δ: 3.31 (1H,dd,J=14.2 Hz, 10.2 Hz), 3.69 (1H,dd, J=14.2 Hz, 4.0 Hz), 4.99 (1H,dd,J=10.2 Hz, 4.0 Hz), 5.47 (1H,s), 6.59 (1H,d,J=3.3 Hz), 6.90 (1H,d,J=7.3 Hz), 7.0~7.4 (6H, m), 7.46 (1H,d,J=3.3 Hz), 12.06 (1H,bs)

EXAMPLE 48

Synthesis of 1-(3-fluorobenzyl)indole-4-carbaldehyde

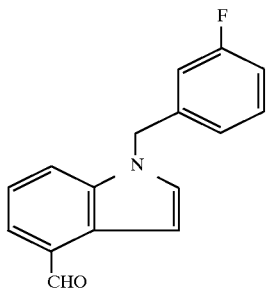

The same procedures used in Example 7 were repeated except for using 3.90 g of 3-fluorobenzyl bromide in place of the methyl 4-bromomethylbenzoate used in Example 7 to give 2.88 g of 1-(3-fluorobenzyl)indole-4-carbaldehyde as colorless crystals. The yield thereof was found to be 83%.

NMR (CDCl$_3$) δ: 5.38 (2H,s), 6.7~7.0 (3H,m), 7.2 ~7.7 (6H,m), 10.26 (1H,s)

EXAMPLE 49

Synthesis of 5-[1-(3-fluorobenzyl)indol-4-yl]-methylene-2,4-thiazolidinedione

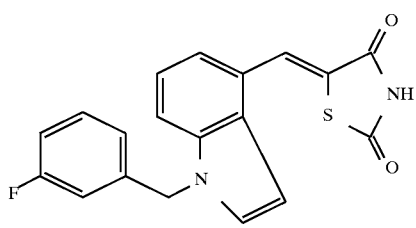

The same procedures used in Example 2 were repeated except for using 2.50 g of 1-(3-fluorobenzyl)indole-4-carbaldehyde prepared in Example 48 to give 2.00 g of 5-[1-(3-fluorobenzyl)indol-4-yl]methylene-2,4-thiazolidinedione as yellow crystals. The yield thereof was found to be 57%.

IR (KBr) cm$^{-1}$: 1740, 1690, 1330, 1290; NMR (DMSO-d$_6$) δ: 5.52 (2H,s), 6.82 (1H,d,J=3.3 Hz), 6.9~7.5 (6H,m), 7.65 (1H,d,J=7.3 Hz), 7.73 (1H,d, J=3.3 Hz), 8.14 (1H,s), 12.60 (1H,bs)

EXAMPLE 50

Synthesis of 5-[1-(3-fluorobenzyl)indol-4-yl]-methyl-2,4-thiazolidinedione

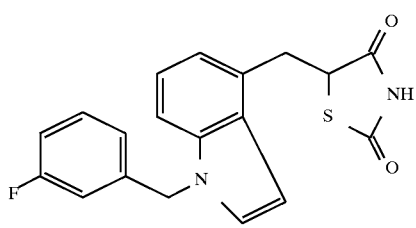

The same procedures used in Example 6 were repeated except for using 1.50 g of 5-[1-(3-fluorobenzyl)indol-4-yl]methylene-2,4-thiazolidinedione prepared in Example 49 to give 1.37 g of 5-[1-(3-fluorobenzyl)indol-4-yl]methyl-2,4-thiazolidinedione as colorless crystals. The yield thereof was found to be 91%.

IR (KBr) cm$^{-1}$: 1750, 1690, 1670, 750; NMR (DMSO-d$_6$) δ: 3.2~3.4 (1H,m), 3.6~3.8 (1H,m), 4.9~5.1 (1H,m), 5.42 (2H,s), 6.60 (1H,d,J=3.2 Hz), 6.8~7.2 (7H,m), 7.2~7.5 (2H, m), 7.53 (1H,d,J=3.2 Hz), 12.10 (1H,bs)

EXAMPLE 51

Synthesis of 5-[1-(4-fluorobenzyl)indol-4-yl]-methylene-2,4-thiazolidinedione

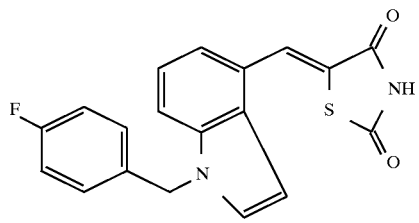

There were dissolved, in 20 ml of acetonitrile, 2.00 g of indole-4-carbaldehyde and 5.20 g of 4-fluorobenzyl bromide, followed by addition of 9.52 g of potassium carbonate and stirring for 16 hours while heating the reaction mixture to 52° C. The reaction solution was cooled down to room temperature, followed by removal of potassium carbonate through filtration and removal of the solvent through evaporation under reduced pressure. The resulting crude product was purified by silica gel chromatography (hexane:ethyl acetate=10:1) to give a yellow oily substance. The substance was dissolved in 40 ml of ethanol, followed by addition, to the solution, of 240 mg of piperidine and 3.4 g of 2,4-thiazolidinedione and reflux of the mixture with heating over 22 hours. The reaction mixture was cooled in an ice bath followed by addition of 80 ml of diethyl ether, stirring at that temperature for one hour, then separation of the precipitated yellow crystals through filtration and washing with diethyl ether to give 3.95 g of 5-[1-(4-fluorobenzyl) indol-4-yl]methylene-2,4-thiazolidinedione as yellow crystals. The yield thereof was found to be 81%.

IR (KBr) cm$^{-1}$: 1730, 1690, 1510, 1330, 1290; NMR (DMSO-d$_6$) δ: 5.48 (2H,s), 6.80 (1H,d,J=2.9 Hz), 7.0~7.3 (6H, m), 7.5~7.7 (2H,m), 8.14 (1H,s), 12.59 (1H,bs)

EXAMPLE 52

Synthesis of 5-[1-(4-fluorobenzyl)indol-4-yl]-methyl-2,4-thiazolidinedione

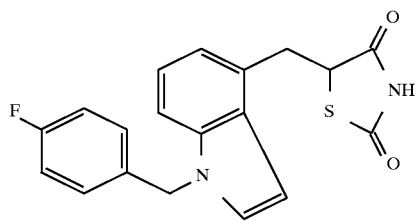

The same procedures used in Example 3 were repeated except for using 3.90 g of 5-[1-(4-fluorobenzyl)indol-4-yl] methylene- 2,4-thiazolidinedione prepared in Example 51 to give 2.43 g of 5-[1-(4-fluorobenzyl)indol-4-yl]methyl-2,4- thiazolidinedione as yellow crystals. The yield thereof was found to be 62%.

IR (KBr) cm$^{-1}$: 1750, 1670, 1510, 1210, 750; NMR (DMSO-d$_6$) δ: 3.3~3.4 (1H,m), 3.6~3.8 (1H,m), 4.99 (1H, dd,J=10.3 Hz, 4.4 Hz), 5.40 (2H,s), 6.59 (1H,d,J=2.9 Hz), 6.89 (1H,d,J=7.3 Hz), 7.0~7.4 (6H,m), 7.52 (1H,d,J=2.9 Hz), 12.09 (1H,bs)

EXAMPLE 53

Synthesis of 1-(2,3-difluorobenzyl)indole-4-carbaldehyde

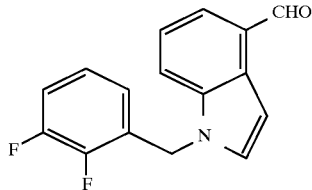

The same procedures used in Example 1 were repeated except for using 580 mg of indole-4-carbaldehyde and 911 mg of 2,3-difluorobenzyl bromide in place of the benzyl bromide used in Example 1 to give 841 mg of 1-(2,3-difluorobenzyl)indole-4-carbaldehyde as pale brown crystals. The yield thereof was found to be 76%.

NMR (CDCl$_3$) δ: 5.46 (2H,s), 6.59 (1H,dd,J=7.0 Hz, 7.0 Hz), 6.8~7.2 (2H,m), 7.2~7.4 (3H,m), 7.59 (1H,d,J=8.1 Hz), 7.65 (1H,dd,J=7.3 Hz, 1.1 Hz), 10.25 (1H,s)

EXAMPLE 54

Synthesis of 5-[1-(2,3-difluorobenzyl)indol-4-yl]-methylene-2,4-thiazolidinedione

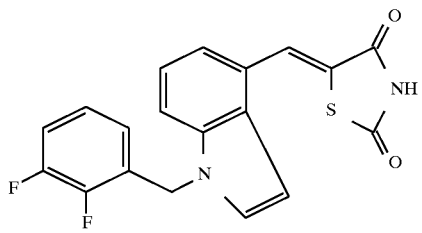

The same procedures used in Example 2 were repeated except for using 794 mg of 1-(2,3-difluorobenzyl)indole-4-carbaldehyde to give 822 mg of 5-[1-(2,3-difluorobenzyl)indol-4-yl]methylene-2,4-thiazolidinedione as yellow crystals. The yield thereof was found to be 76%.

IR (KBr) cm$^{-1}$: 1740, 1700, 1680, 1490, 1290; NMR (DMSO-d$_6$) δ: 5.62 (2H,s), 6.7~6.9 (2H,m), 7.0~7.4 (4H, m), 7.5~7.7 (2H,m), 8.13 (1H,s), 12.59 (1H,bs)

EXAMPLE 55

Synthesis of 5-[1-(2,3-difluorobenzyl)indol-4-yl]-methyl-2,4-thiazolidinedione

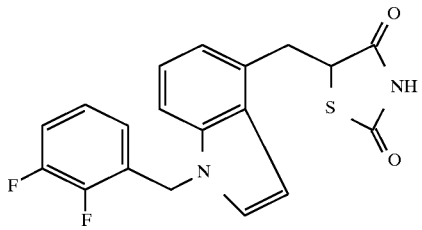

The same procedures used in Example 6 were repeated except for using 775 mg of 5-[1-(2,3-difluorobenzyl)indol-4-yl]methylene-2,4-thiazolidinedione prepared in Example 54 to give 670 mg of 5-[1-(2,3-difluorobenzyl)indol-4-yl] methyl-2,4-thiazolidinedione as colorless crystals. The yield thereof was found to be 86%.

IR (KBr) cm$^{-1}$: 1750, 1670, 1490, 1300; NMR (DMSO-d$_6$) δ: 3.32 (1H,dd,J=14.2 Hz, 10.2 Hz), 3.69 (H,dd,J=14.2 Hz, 4.4 Hz), 4.99 (1H,dd,J=10.2 Hz, 4.4 Hz), 5.54 (2H,s), 6.61 (1H,d,J=3.3 Hz), 6.7~7.0 (2H,m), 7.0~7.2 (2H,m), 7.3~7.4 (2H,m), 7.48 (1H,d,J=3.3 Hz), 12.06 (1H,bs)

EXAMPLE 56

Synthesis of 1-(2,4-difluorobenzyl)indole-4-carbaldehyde

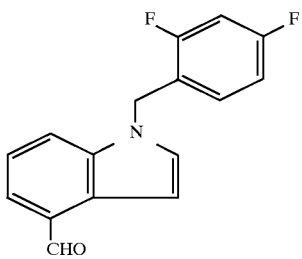

The same procedures used in Example 7 were repeated except for using 5.70 g of 2,4-difluorobenzyl bromide instead of the methyl 4-bromomethylbenzoate used in Example 7 to give 2.74 g of 1-(2,4-difluorobenzyl)indole-4-carbaldehyde as a yellow oily substance. The yield thereof was found to be 73%.

NMR (CDCl$_3$) δ: 5.37 (2H,s), 6.6~7.0 (3H,m), 7.2~7.4 (3H,m), 7.5~7.7 (2H,m), 10.24 (1H,s)

EXAMPLE 57

Synthesis of 5-[1-(2,4-difluorobenzyl)indol-4-yl]-methylene-2,4-thiazolidinedione

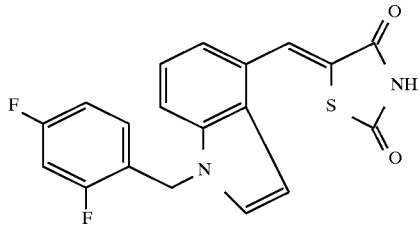

The same procedures used in Example 2 were repeated except for using 2.70 g of 1-(2,4-difluorobenzyl)indole-4-carbaldehyde prepared in Example 56 to give 2.92 g of 5-[1-(2,4-difluorobenzyl)indol-4-yl]methylene-2,4-thiazolidinedione as yellow crystals. The yield thereof was found to be 79%.

IR (KBr) cm$^{-1}$: 1730, 1690, 1590, 1500, 1330, 1290, 750; NMR (DMSO-d$_6$) δ: 5.50 (2H,s), 6.7~6.9 (1H,m), 6.9~7.5 (5H, m), 7.5~7.8 (2H,m), 8.14 (1H,s), 12.60 (1H,bs)

EXAMPLE 58

Synthesis of 5-[1-(2,4-difluorobenzyl)indol-4-yl]-methyl-2,4-thiazolidinedione

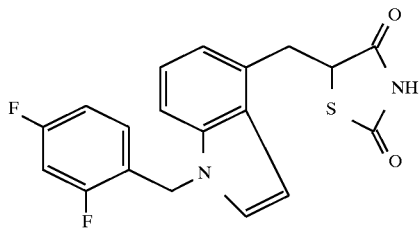

The same procedures used in Example 6 were repeated except for using 2.80 g of 5-[1-(2,4-difluorobenzyl)indol-4-yl]methylene-2,4-thiazolidinedione prepared in Example 57 to give 2.38 g of 5-[1-(2,4-difluorobenzyl)indol-4-yl]methyl-2,4-thiazolidinedione as colorless crystals. The yield thereof was found to be 85%.

IR (KBr) cm$^{-1}$: 1750, 1680, 1500, 1330, 1160, 1140, 750; NMR (DMSO-d$_6$) δ: 3.30 (1H,dd,J=10.6 Hz, 14.3 Hz), 3.69 (1H,dd,J=14.3 Hz, 4.0 Hz), 4.97 (1H,dd,J=4.0 Hz, 10.6 Hz), 5.44 (2H,s), 6.59 (1H,d,J=3.3 Hz), 6.8~7.4 (6H,m), 7.46 (1H,d,J=3.3 Hz)

EXAMPLE 59

Synthesis of 5-[1-(4-methoxybenzyl)indol-4-yl]-methylene-2,4-thiazolidinedione

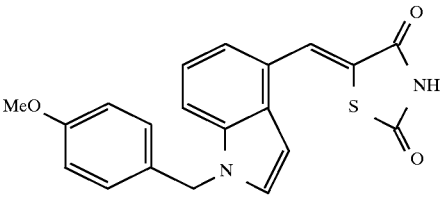

Sodium hydride (60%; 579 mg) was suspended in 10 ml of dimethylformamide under an argon gas atmosphere. To the suspension, there was dropwise added a solution of 2.00 g of indole-4-carbaldehyde in 10 ml of dimethylformamide with ice-cooling and stirring. After stirring at room temperature for 20 minutes, the reaction system was again ice-cooled, followed by dropwise addition of a solution of 2.26 g of 4-methoxybenzyl chloride in 10 ml of dimethylformamide and stirring at room temperature for one hour. The reaction system was poured into 200 ml of a 10% ammonium chloride aqueous solution, followed by extraction with ethyl acetate (150 ml×2). The resulting organic phase was washed with a saturated common salt solution, dried over anhydrous magnesium sulfate and the solvent was removed through evaporation under reduced pressure. The resulting crude product was purified by silica gel column chromatography (hexane:ethyl acetate=5:1) to give 3.76 g of pale yellow crystals. The crystals were dissolved in 60 ml of ethyl alcohol, followed by addition of 242 mg of piperidine and 3.36 g of 2,4-thiazolidinedione and heating under reflux for 17 hours. Then the mixture was ice-cooled, followed by addition of 120 ml of diethyl ether and stirring at that temperature for one hour. The crystals separated were filtered off and washed with diethyl ether to give 4.67 g of 5-[1-(4-methoxybenzyl)indol-4-yl]methylene-2,4-thiazolidinedione as yellow crystals. The yield thereof was found to be 93%.

IR (KBr) cm$^{-1}$: 1740, 1680, 1510, 1330, 1290; NMR (DMSO-d$_6$): 3.69 (3H,s), 5.40 (2H,s), 6.77 (1H,d,J=2.9 Hz), 6.86 (2H,d,J=8.8 Hz), 7.2~7.3 (4H,m), 7.6~7.7 (2H,m), 8.12 (1H,s), 12.57 (1H,bs)

EXAMPLE 60

Synthesis of 5-[1-(4-methoxybenzyl)indol-4-yl]-methyl-2,4-thiazolidinedione

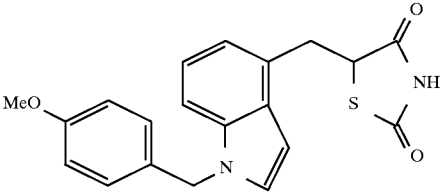

The same procedures used in Example 6 were repeated except for using 4.60 g of 5-[1-(4-methoxybenzyl)indol-4-yl]methylene-2,4-thiazolidinedione prepared in Example 59 to give 4.28 g of 5-[1-(4-methoxybenzyl)indol-4-yl]methyl-2,4-thiazolidinedione as colorless crystals. The yield thereof was found to be 93%.

IR (KBr) cm$^{-1}$: 1750, 1700, 1510, 1250, 750; NMR (DMSO-d$_6$) δ: 3.30 (1H,dd,J=14.3 Hz, 10.6 Hz), 3.69 (1H, dd, J=14.3 Hz, 4.0 Hz), 3.69 (3H,s), 4.98 (1H,dd,J=10.6 Hz, 4.0 Hz), 5.32 (2H,s), 6.55 (1H,d,J=3.3 Hz), 6.85 (2H,d,J=8.6 Hz), 6. 88 (1H,d,J=8.1 Hz), 7.05 (1H,t,J=8.1 Hz), 7.18 (2H,d,J=8.6 Hz), 7.38 (1H,d,J=8.1 Hz), 7.49 (1H,d,J=3.3 Hz), 12.06 (1H,bs)

EXAMPLE 61

Synthesis of 5-[1-(2,5-difluorobenzyl)indol-4-yl]-methylene-2,4-thiazolidinedione

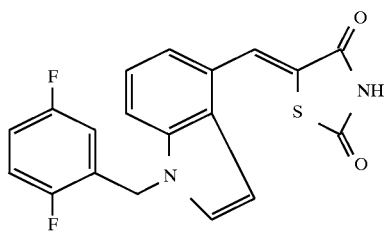

The same procedures used in Example 59 were repeated except for using 3.06 g of 2,5-difluorobenzyl bromide and 2.00 g of indole-4-carbaldehyde as a starting material to give 4.48 g of 5-[1-(2,5-difluorobenzyl)indol-4-yl]methylene-2,4-thiazolidinedione as yellow crystals. The yield thereof was found to be 88%.

IR (KBr) cm$^{-1}$: 1730, 1690, 1500, 1330, 1290; NMR (DMSO-d$_6$) δ: 5.54 (2H,s), .6.82 (1H,d,J=2,9 Hz), 6.8~7.0 (1H, m), 7.1~7.4 (4H,m), 7.6~7.7 (2H,m), 8.13 (1H,s), 12.60 (1H,bs)

EXAMPLE 62

Synthesis of 5-[1-(2,5-difluorobenzyl)indol-4-yl]-methyl-2,4-thiazolidinedione

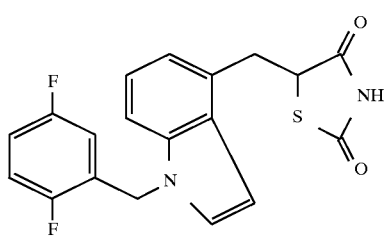

The same procedures used in Example 6 were repeated except for using 4.40 g of 5-[1-(2,5-difluorobenzyl)indol-4-yl]methylene-2,4-thiazolidinedione prepared in Example 61 to give 4.06 g of 5-[1-(2,5-difluorobenzyl)indol-4-yl]methyl-2,4-thiazolidinedione as colorless crystals. The yield thereof was found to be 92%.

IR (KBr) cm$^{-1}$: 1750, 1690, 1500, 1160, 750; NMR (DMSO-d$_6$) δ: 3.28 (1H,dd,J=14.1 Hz, 10.3 Hz), 3.78 (1H, dd,J=14.1 Hz, 4.0 Hz), 4.85 (1H,dd,J=10. 3 Hz, 4.0 Hz), 5.44 (2H,s), 6.60 (1H,d,J=2.9 Hz), 6.7~6.8 (1H,m), 6.93 (1H,d,J=7.5 Hz), 7.09 (1H,t,J=7.5 Hz), 7.1~7.3 (2H,m), 7.35 (1H,d,J=8.0 Hz), 7.42 (1H,d,J=2.9 Hz), 11.98 (1H,bs)

EXAMPLE 63

Synthesis of 1-(2,6-difluorobenzyl)indole-4-carbaldehyde

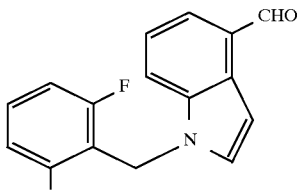

The same procedures used in Example 1 were repeated except for using 2.35 g of 2,6-difluorobenzyl chloride and 2.00 g of indole-4-carbaldehyde as a starting material to give 3.74 g of 1-(2,6-difluorobenzyl)indole-4-carbaldehyde as pale yellow crystals. The yield thereof was found to be 100%.

NMR (CDCl$_3$) δ: 5.41 (2H,s), 6.8~6.9 (2H,m), 7.2~7.5 (4H,m), 7.61 (1H,d,J=7.3 Hz), 7.82 (1H,d,J=8.1 Hz), 10.22 (1H,s)

EXAMPLE 64

Synthesis of 5-[1-(2,6-difluorobenzyl)indol-4-yl]-methylene-2,4-thiazolidinedione

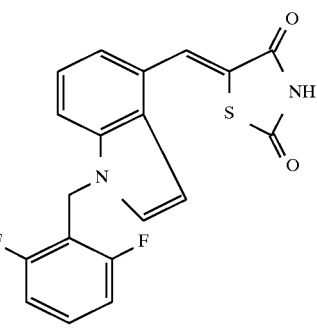

The same procedures used in Example 2 were repeated except for using 3.70 g of 1-(2,6-difluorobenzyl)indole-4-carbaldehyde prepared in Example 63 to give 4.98 g of 5-[1-(2,6-difluorobenzyl)indol-4-yl]methylene-2,4-thiazolidinedione as pale yellow crystals. The yield thereof was found to be 99%.

IR (KBr) cm$^{-1}$: 1730, 1690, 1470, 1330, 1280; NMR (DMSO-d$_6$) δ: 5.53 (2H,s), 6.77 (1H,d,J=3.3 Hz), 7.1~7.5 (6H, m), 7.66 (1H,d,J=8.1 Hz), 8.10 (1H,s), 12.59 (1H,bs)

EXAMPLE 65

Synthesis of 5-[1-(2,6-difluorobenzyl)indol-4-yl]-methyl-2,4-thiazolidinedione

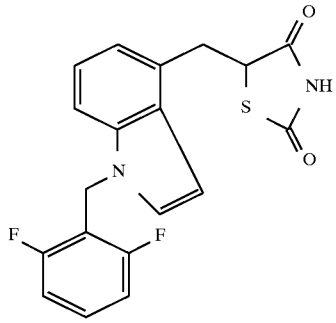

The same procedures used in Example 6 were repeated except for using 4.90 g of 5-[1-(2,6-difluorobenzyl)indol-4-yl]methylene-2,4-thiazolidinedione prepared in Example 64 to give 4.09 g of 5-[1-(2,6-difluorobenzyl)indol-4-yl]methyl-2,4-thiazolidinedione as colorless crystals. The yield thereof was found to be 83%.

IR (KBr) cm$^{-1}$: 1750, 1680, 1470, 1310, 750; NMR (DMSO-d$_6$) δ: 3.2~3.3 (1H,m), 3.66 (1H,dd,J=14.3 Hz, 4.0 Hz), 4.96 (1H,dd,J=10.3 Hz, 4.0 Hz), 5.45 (2H,s), 6.55 (1H,d,J=2.9 Hz), 6.90 (1H,d, J=7.0 Hz), 7.1~7.2 (3H,m), 7.3~7.5 (3H,m), 12.06 (1H,bs)

EXAMPLE 66

Synthesis of 1-(3,4-difluorobenzyl)indole-4-carbaldehyde

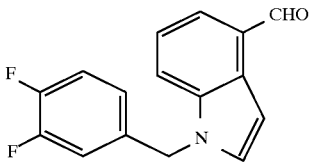

The same procedures used in Example 1 were repeated except for using 725 mg of indole-4-carbaldehyde and 1.14 g of 3,4-difluorobenzyl bromide in place of the benzyl bromide used in Example 1 to give 1.32 g of 1-(3,4-difluorobenzyl)indole-4-carbaldehyde as a yellow oily substance. The yield thereof was found to be 97%.

NMR (CDCl$_3$) δ: 5.35 (2H,s), 6.7~7.0 (2H,m), 7.07 (1H,dd,J=9.9 Hz, 8.0 Hz), 7.2~7.4 (3H,m), 7.50 (1H,d,J=8.4 Hz), 7.65 (1H,d,J=7.0 Hz), 10.26 (1H,s)

EXAMPLE 67

Synthesis of 5-[1-(3,4-difluorobenzyl)indol-4-yl]-methylene-2,4-thiazolidinedione

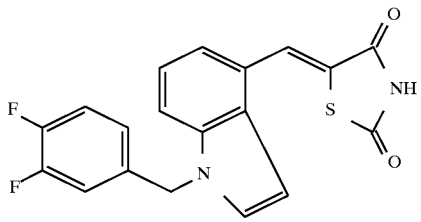

The same procedures used in Example 2 were repeated except for using 1.30 g of 1-(3,4-difluorobenzyl)indole-4-carbaldehyde prepared in Example 66 to give 1.57 g of 5-[1-(3,4-difluorobenzyl)indol-4-yl]methylene-2,4-thiazolidinedione as yellow crystals. The yield thereof was found to be 88%.

IR (KBr) cm$^{-1}$: 1730, 1680, 1520, 1290; NMR (DMSO-d$_6$) δ: 5.49 (2H,s), 6.82 (1H,d,J=3.0 Hz), 7.0~7.4 (5H,m), 7.68 (1H,d,J=7.7 Hz), 7.74 (1H,d,J=3.0 Hz), 8.13 (1H,s), 12.59 (1H,bs)

EXAMPLE 68

Synthesis of 5-[1-(3,4-difluorobenzyl)indol-4-yl]-methyl-2,4-thiazolidinedione

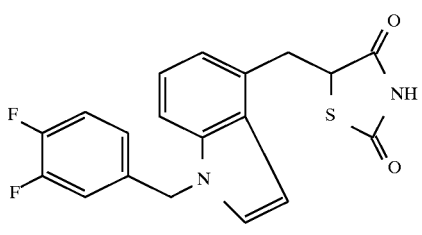

The same procedures used in Example 6 were repeated except for using 1.55 g of 5-[1-(3,4-difluorobenzyl)indol-4-yl]methylene-2,4-thiazolidinedione prepared in Example 67 to give 1.15 g of 5-[1-(3,4-difluorobenzyl)indol-4-yl]methyl-2,4-thiazolidinedione as colorless crystals. The yield thereof was found to be 74%.

IR (KBr) cm$^{-1}$: 1750, 1670, 1520, 1300; NMR (DMSO-d$_6$) δ: 3.31 (1H,dd,J=14.6 Hz, 10.2 Hz), 3.69 (1H,dd,J=14.6 Hz, 4.0 Hz), 4.99 (1H,dd,J=10.2 Hz, 4.0 Hz), 5.41 (2H,s), 6.59 (1H,dd,J=2.9 Hz), 6.90 (1H,d,J=7.3 Hz), 7.0~7.2 (2H,m), 7.2~7.4 (3H,m), 7.55 (1H,d,J=2.9 Hz), 12.06 (1H,bs)

EXAMPLE 69

Synthesis of 1-(3,5-difluorobenzyl)indole-4-carbaldehyde

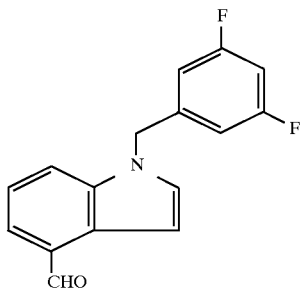

The same procedures used in Example 7 were repeated except for using 4.28 g of 3,5-difluorobenzyl bromide in place of the methyl 4-bromomethylbenzoate used in Example 7 to give 2.81 g of 1-(3,5-difluorobenzyl)indole-4-carbaldehyde as colorless crystals. The yield thereof was found to be 75%.

NMR (CDCl$_3$) δ: 5.37 (2H,s), 6.5~6.8 (3H,m), 7.2~7.5 (4H,m), 7. 66 (1H,d,J=7.0 Hz), 10.26 (1H,s)

EXAMPLE 70

Synthesis of 5-[1-(3,5-difluorobenzyl)indol-4-yl]-methylene-2,4-thiazolidinedione

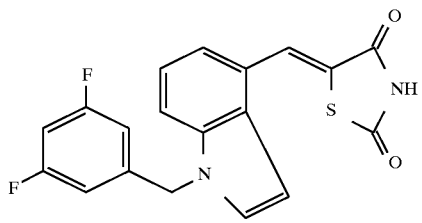

The same procedures used in Example 2 were repeated except for using 2.50 g of 1-(3,5-difluorobenzyl)indole-4-carbaldehyde prepared in Example 69 to give 2.15 g of 5-[1-(3,5-difluorobenzyl)indol-4-yl]methylene-2,4-thiazolidinedione as yellow crystals. The yield thereof was found to be 63%.

IR (KBr) cm$^{-1}$: 1730, 1690, 1590, 1320, 1300, 740; NMR (DMSO-d$_6$) δ: 5.53 (2H,s), 6.7~7.0 (3H,m), 7.0~7.5 (3H,m), 7.5~8.0 (2H,m), 8.14 (1H,s), 12.60 (1H,bs)

EXAMPLE 71

Synthesis of 5-[1-(3,5-difluorobenzyl)indol-4-yl]-methyl-2,4-thiazolidinedione

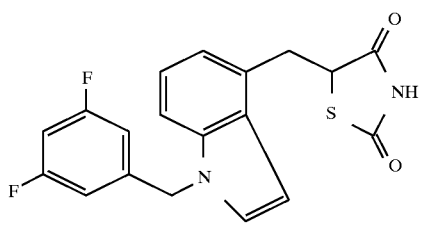

The same procedures used in Example 6 were repeated except for using 2.00 g of 5-[1-(3,5-difluorobenzyl)indol-4-yl]methylene-2,4-thiazolidinedione prepared in Example 70 to give 1.86 g of 5-[1-(3,5-difluorobenzyl)indol-4-yl]methyl-2,4-thiazolidinedione as colorless crystals. The yield thereof was found to be 92%.

IR (KBr) cm$^{-1}$: 1750, 1700, 1630, 1600, 1320, 1120, 750; NMR (DMSO-d$_6$) δ: 3.2~3.4 (1H,m), 3.6~3.8 (1H,m), 4.9~5.1 (1H,m), 5.44 (2H,s), 6.61 (1H,d,J=2.9 Hz), 6.8~7.3 (5H,m), 7.4~7.5 (1H,m), 7.56 (1H,d,J=2.9 Hz), 12.09 (1H, bs)

EXAMPLE 72

Synthesis of 1-(2-trifluoromethylbenzyl)indole-4-carbaldehyde

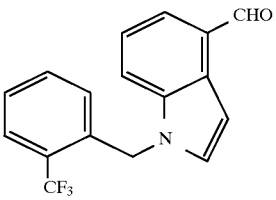

The same procedures used in Example 1 were repeated except for using 725 mg of indole-4-carbaldehyde and 2-trifluoromethylbenzyl methanesulfonate in place of the benzyl bromide used in Example 1 to give 1.44 g of 1-($^2$-trifluoromethylbenzyl)indole-4-carbaldehyde as a yellow oily substance. The yield thereof was found to be 95%.

NMR (CDCl$_3$) δ: 5.62 (2H,s), 6.52 (1H,d,J=6.2 Hz), 7.2~7.5 (6H,m), 7.66 (1H,dd,J=7.0 Hz, 1.0 Hz), 7.74 (1H, dd,J=6.2 Hz, 3.0 Hz), 10.28 (1H,s)

EXAMPLE 73

Synthesis of 5-[1-(2-trifluoromethylbenzyl)indol-4-yl]methylene-2,4-thiazolidinedione

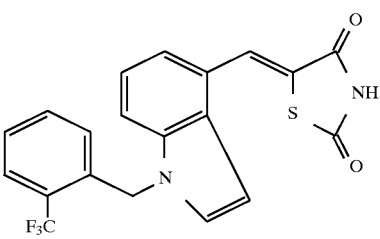

The same procedures used in Example 2 were repeated except for using 1.44 g of 1-(2-trifluoromethylbenzyl)indole-4-carbaldehyde prepared in Example 72 to give 769 mg of 5-[1-(2-trifluoromethylbenzyl) indol-4-yl]methylene-2,4-thiazolidinedione as orange-colored crystals. The yield thereof was found to be 40%.

IR (KBr) cm$^{-1}$: 1740, 1680, 1310, 1120; NMR (DMSO-d$_6$) δ: 5.71 (2H,s), 6.51 (1H,dd, J=5.1 Hz, 3.6 Hz), 6.89 (1H,d,J=3.3 Hz), 7.2~7.6 (5H,m), 7.66 (1H,d,J=3.3 Hz), 7.7~7.9 (1H,m), 8.17 (1H,s), 12.61 (1H,bs)

EXAMPLE 74

Synthesis of 5-[1-(2-trifluoromethylbenzyl)indol-4-yl]methyl-2,4-thiazolidinedione

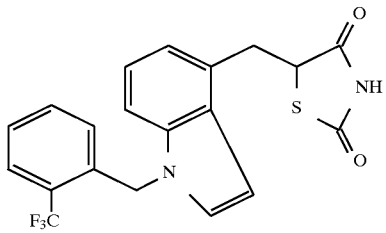

The same procedures used in Example 6 were repeated except for using 728 mg of 5-[1-(2-trifluoromethylbenzyl)indol-4-yl]methylene-2,4-thiazolidinedione prepared in Example 73 to give 586 mg of 5-[1-(2-trifluoromethylbenzyl)indol-4-yl]methyl-2,4-thiazolidinedione as colorless crystals. The yield thereof was found to be 80%.

IR (KBr) cm$^{-1}$: 1750, 1670, 1440, 1310; NMR (DMSO-d$_6$) δ: 3.37 (1H,dd,J=14.2 Hz, 10.2 Hz), 3.73 (1H,dd,J=14.2 Hz, 4.0 Hz), 5.01 (1H,dd,J=10.2 Hz, 4.0 Hz), 5.63 (2H,s), 6.51 (1H,dd,J=4.8 Hz, 3.6 Hz), 6.68 (1H,d,J=3.0 Hz), 6.93 (1H,d,J=6.6 Hz), 7.0~7.2 (2H,m), 7.4~7.6 (3H,m), 7.79 (1H,dd, J=4.8 Hz, 2.6 Hz), 12.08 (1H,bs)

EXAMPLE 75

Synthesis of 1-(3-trifluoromethylbenzyl)indole-4-carbaldehyde

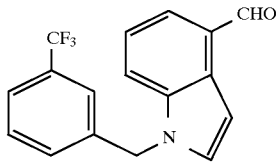

The same procedures used in Example 1 were repeated except for using 3.68 g of 3-trifluoromethylbenzyl methanesulfonate and 2.00 g of indole-4-carbaldehyde to give 4.12 g of 1-(3-trifluoromethylbenzyl) indole-4-carbaldehyde as yellow crystals. The yield thereof was found to be 99%.

NMR (CDCl$_3$) δ: 5.44 (2H,s), 7.15 (1H,d,J=8.1 Hz), 7.26 (1H,d,J=4.4 Hz), 7.3~7.7 (7H,m), 10.25 (1H,s)

EXAMPLE 76

Synthesis of 5-[1-(3-trifluoromethylbenzyl)indol-4-yl]methylene-2,4-thiazolidinedione

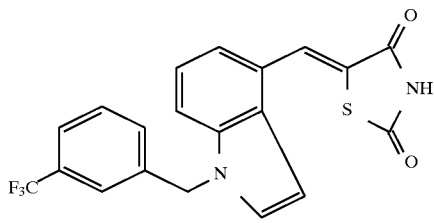

The same procedures used in Example 2 were repeated except for using 4.10 g of 1-(3-trifluoromethylbenzyl) indole-4-carbaldehyde prepared in Example 75 to give 3.98 g of 5-[1-(3-trifluoromethylbenzyl) indol-4-yl]methylene-2,4-thiazolidinedione as yellow crystals. The yield thereof was found to be 73%.

IR (KBr) cm$^{-1}$: 1740, 1700, 1330, 1280, 1110; NMR (DMSO-d$_6$) δ: 5.61 (2H,s), 6.83 (1H,d,J=2.9 Hz), 7.2~7.7 (7H, m), 7.77 (1H,d,J=2.9 Hz), 8.14 (1H,s), 12.60 (1H,bs)

EXAMPLE 77

Synthesis of 5-[1-(3-trifluoromethylbenzyl)indol-4-yl]methyl-2,4-thiazolidinedione

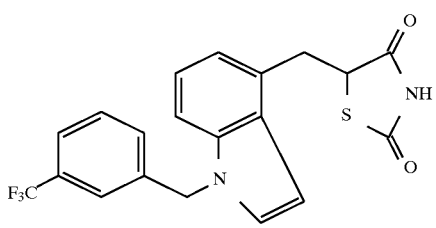

The same procedures used in Example 3 were repeated except for using 3.90 g of 5-[1-(3-trifluoromethylbenzyl) indol-4-yl]methylene-2,4-thiazolidinedione prepared in Example 76 to give 3.85 g of 5-[1-(3-trifluoromethylbenzyl) indol-4-yl]methyl-2,4-thiazolidinedione as yellow crystals. The yield thereof was found to be 98%.

IR (KBr) cm$^{-1}$: 1750, 1670, 1330, 1160, 1110; NMR (DMSO-d$_6$) δ: 3.2~3.4 (1H,m), 3.70 (1H,dd,J=14.1 Hz, 4,0 Hz), 5.00 (1H,dd,J=10.3 Hz, 4.0 Hz), 5.53 (2H,s), 6.62 (1H,d,J=2.9 Hz), 6.90 (1H,d,J=7.0 Hz), 7.07 (1H,t,J=7.9 Hz), 7.4~7.6 (6H,m), 12.37 (1H,bs)

EXAMPLE 78

Synthesis of 1-(4-trifluoromethylbenzyl)indole-4-carbaldehyde

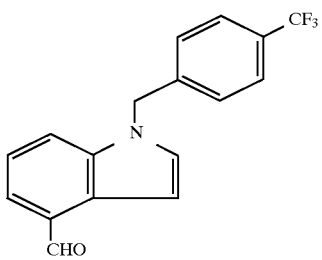

The same procedures used in Example 1 were repeated except for using 3.82 g of 4-trifluoromethylbenzyl methanesulfonate in place of the benzyl bromide used in Example 1 to give 2.77 g of 1-(4-trifluoromethylbenzyl)indole-4-carbaldehyde as yellow crystals. The yield thereof was found to be 66%.

NMR (CDCl$_3$) δ: 5.45 (2H,s), 7.0~7.7 (9H,m), 10.26 (1H,s)

EXAMPLE 79

Synthesis of 5-[1-(4-trifluoromethylbenzyl)indol-4-yl]methylene-2,4-thiazolidinedione

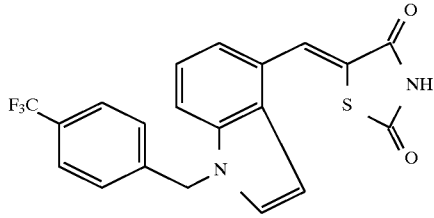

The same procedures used in Example 2 were repeated except for using 2.50 g of 1-(4-trifluoromethylbenzyl) indole-4-carbaldehyde prepared in Example 78 to give 1.54 g of 5-[1-(4-trifluoromethylbenzyl) indol-4-yl]methylene-2,4-thiazolidinedione as yellow crystals. The yield thereof was found to be 47%.

IR (KBr) cm$^{-1}$: 1740, 1690, 1330, 1290; NMR (DMSO-d$_6$) δ: 5.62 (2H,s), 6.84 (1H, d, J=2.9 Hz), 7.1~7.5 (5H,m), 7.5~7.8 (4H,m), 8.15 (1H,s), 12.60 (1H,bs)

EXAMPLE 80

Synthesis of 5-[1-(4-trifluoromethylbenzyl)indol-4-yl]methyl-2,4-thiazolidinedione

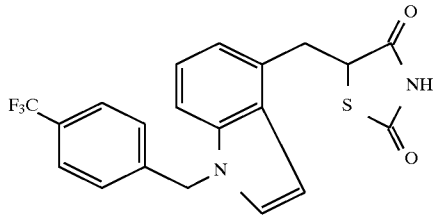

The same procedures used in Example 6 were repeated except for using 1.50 g of 5-[1-(4-trifluoromethylbenzyl) indol-4-yl]methylene-2,4-thiazolidinedione prepared in Example 79 to give 1.41 g of 5-[1-(4-trifluoromethylbenzyl) indol-4-yl]methyl-2,4-thiazolidinedione as colorless crystals. The yield thereof was found to be 94%.

IR (KBr) cm$^{-1}$: 1750, 1680, 1320, 750; NMR (DMSO-d$_3$) δ: 3.32 (1H,dd, J=10.3 Hz, 14.4 Hz), 3.71 (1H, dd,J=14.4 Hz, 4.0 Hz), 4.97 (1H,dd,J=4.0 Hz, 10.3 Hz), 5.54 (2H,s), 6.62 (1H,d,J=2.9 Hz,), 6.90 (1H,d,J=7.3 Hz), 7.06 (1H,dd, J=7.3 Hz, 7. 7 Hz), 7.2~7.4 (3H,m), 7.55 (1H,d,J=2.9 Hz), 7. 68 (2H,d,J=7.7 Hz)

EXAMPLE 81

Synthesis of 1-[2,4-bis(trifluoromethyl)benzyl]-indole-4-carbaldehyde

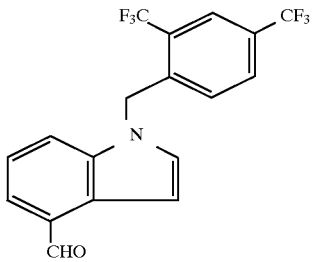

The same procedures used in Example 7 were repeated except for using 6.68 g of 2,4-bis(trifluoromethyl)benzyl bromide instead of the methyl 4-bromomethylbenzoate used in Example 7 to give 4.53 g of 1-[2,4-bis(trifluoromethyl) benzyl]indole-4-carbaldehyde as a colorless oily substance. The yield thereof was found to be 89%.

NMR (CDCl$_3$) δ: 5.67 (2H,s), 6.58 (1H,d,J=8.2 Hz), 7.3~7.5 (5H,m), 7.57 (1H,d,J=7.9 Hz), 7.67 (1H,d,J=5.5 Hz), 7.99 (1H,s), 10.27 (1H,s),

EXAMPLE 82

Synthesis of 5-{1-[2,4-bis(trifluoromethyl)-benzyl]indol-4-yl}methylene-2,4-thiazolidinedione

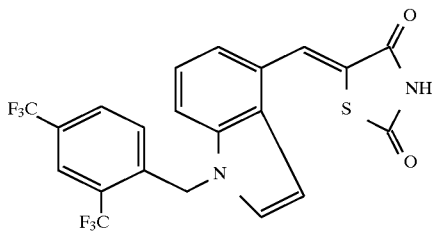

The same procedures used in Example 2 were repeated except for using 4.00 g of 1-[2,4-bis(trifluoromethyl)benzyl] indole-4-carbaldehyde prepared in Example 81 to give 2.89 g of 5-{1-[2,4-bis(trifluoromethyl)benzyl]indol-4-yl}methylene-2,4-thiazolidinedione as yellow crystals. The yield thereof was found to be 57%.

IR (KBr) cm$^{-1}$: 1740, 1680, 1350, 1300, 1130; NMR (DMSO-d$_6$) δ: 5.81 (2H,s), 6.62 (1H,d,J=8.4 Hz), 6.93 (1H, d,J=3 .3 Hz), 7.2~7.5 (3H,m) , 7.71 (1H,d,J=3.3 Hz), 7.92 (1H,d,J=8.4 Hz), 8.11 (1H,s), 8.18 (1H,s), 12.63 (1H,bs)

EXAMPLE 83

Synthesis of 5-{1-[2,4-bis(trifluoromethyl)-benzyl]indol-4-yl}methyl-2,4-thiazolidine-dione

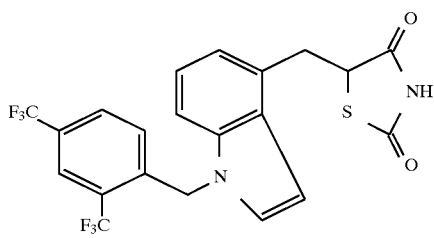

The same procedures used in Example 6 were repeated except for using 2.50 g of 5-{1-[2,4-bis(trifluoromethyl)benzyl]indol-4-yl}methylene-2,4-thiazolidinedione prepared in Example 82 to give 1.71 g of 5-{1-[2,4-bis(trifluoromethyl)benzyl]indol-4-yl}methyl-2,4-thiazolidinedione as a colorless amorphous substance. The yield thereof was found to be 68%.

IR (KBr) cm$^{-1}$: 1750, 1700, 1440, 1350, 1300, 1280, 750; NMR (DMSO-d$_6$) δ: 3.40 (1H,dd,J=10.0 Hz, 14.0 Hz), 3.79 (1H,dd,J=14.0 Hz , 3.8 Hz ), 5.00 (1H,dd,J=3.8 Hz, 10.0 Hz), 5.74 (2H,s), 6.5~6.8 (2H,m), 6.9~7.3 (3H,m), 7.55 (1H,s), 7.9~8.0 (1H,m), 8.10 (1H,s)

EXAMPLE 84

Synthesis of 1-(2-methoxybenzyl)indole-4-carbaldehyde

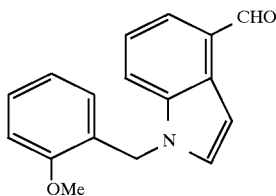

The same procedures used in Example 1 were repeated except for using 725 mg of indole-4-carbaldehyde and 2-methoxybenzyl methanesulfonate instead of the benzyl bromide used in Example 1 to give 906 mg of 1-(2-methoxybenzyl)indole-4-carbaldehyde as a yellow oily substance. The yield thereof was found to be 68%.

NMR (CDCl$_3$) δ: 3.87 (3H,s), 5.38 (2H,s), 6.7~7.0 (3H, m), 7.2~7.4 (4H,m), 7.5~7.7 (2H,m), 10.25 (1H, s)

EXAMPLE 85

Synthesis of 5-[1-(2-methoxybenzyl)indol-4-yl]-methylene-2,4-thiazolidinedione

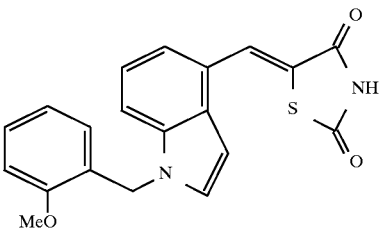

The same procedures used in Example 2 were repeated except for using 876 mg of 1-(2-methoxybenzyl)indole-4-carbaldehyde prepared in Example 84 to give 975 mg of 5-[1-(2-methoxybenzyl)indol-4-yl]methylene-2,4-thiazolidinedione as yellow crystals. The yield thereof was found to be 81%.

IR (KBr) cm$^{-1}$: 1730, 1680, 1580, 1330;

NMR (DMSO-d$_6$): 3.86 (3H,s), 5.41 (2H,s), 6.7~6.9 (3H,m), 7.03 (1H,d,J=8.4 Hz), 7.1~7.3 (3H,m), 7.60 (1H,S), 7.63 (1H,d,J=4.4 Hz), 8.13 (1H,s), 12.60 (1H,bs)

EXAMPLE 86

Synthesis of 5-[1-(2-methoxybenzyl)indol-4-yl]-methyl-2,4-thiazolidinedione

The same procedures used in Example 6 were repeated except for using 937 mg of 5-[1-(2-methoxybenzyl)indol-4-yl]methylene-2,4-thiazolidinedione prepared in Example 85 to give 821 mg of 5-[1-(2-methoxybenzyl)indol-4-yl]methyl-2,4-thiazolidinedione as pale yellow crystals. The yield thereof was found to be 87%.

IR (KBr) cm$^{-1}$: 1750, 1670, 1300, 1240; NMR (DMSO-d$_6$):3.30 (1H,dd,J=14.2 Hz, 10.4 Hz), 3.70 (1H,dd, J=14.2 Hz, 4.0 Hz), 3.86 (3H,s), 4.99 (1H,dd, J=10.4 Hz, 4.0 Hz), 5.34 (2H,s), 6.56 (1H,d, J=3.3 Hz), 6.7~6.9 (3H,m), 7.03 (1H,d,J=8.0 Hz), 7.07 (1H,d,J=7.3 Hz), 7.2~7.3 (1H,m), 7.34 (1H,d,J=8.4 Hz), 7.43 (1H,d,J=3.3 Hz), 12.06 (1H,bs)

EXAMPLE 87

Synthesis of 1-(3-methoxybenzyl)indole-4-carbaldehyde

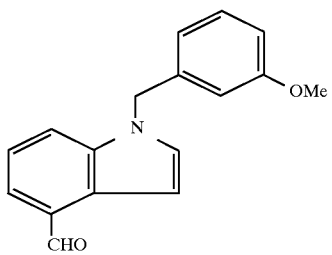

The same procedures used in Example 7 were repeated except for using 4.54 g of 3-methoxybenzyl chloride instead of the methyl 4-bromomethylbenzoate used in Example 7 to give 3.06 g of 1-(3-methoxybenzyl)indole-4-carbaldehyde as a colorless oily substance. The yield thereof was found to be 84%.

NMR (CDCl$_3$) δ: 3.71 (3H,s), 5.34 (2H,s), 6.5~6.7 (2H, m), 6.7~6.9 (1H,m), 7.1~7.4 (4H,m), 7.5~7.7 (2H,m), 10.24 (1H,s)

EXAMPLE 88

Synthesis of 5-[1-(3-methoxybenzyl)indol-4-yl]-methylene-2,4-thiazolidinedione

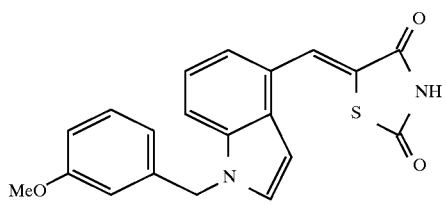

The same procedures used in Example 2 were repeated except for using 3.00 g of 1-(3-methoxybenzyl)indole-4-carbaldehyde prepared in Example 87 to give 2.33 g of 5-[1-(3-methoxybenzyl)indol-4-yl]methylene-2,4-thiazolidinedione as yellow crystals. The yield thereof was found to be 57%.

IR (KBr) cm$^{-1}$: 1740, 1690, 1590, 1330; NMR (DMSO-d$_6$) δ: 3.69 (3H,s), 5.45 (2H,s), 6.6~6.9 (4H,m) 7.1~7.4 (3H,m), 7.5~7.8 (2H,m), 8.14, (1H,s), 12.59 (1H,bs)

EXAMPLE 89

Synthesis of 5-[1-(3-methoxybenzyl)indol-4-yl]-methyl-2,4-thiazolidinedione

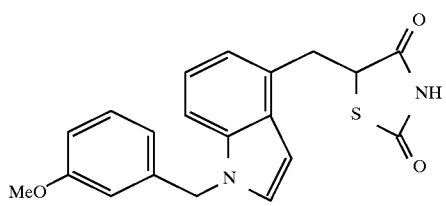

The same procedures used in Example 6 were repeated except for using 2.00 g of 5-[1-(3-methoxybenzyl)indol-4-yl]methylene-2,4-thiazolidinedione prepared in Example 88 to give 1.75 g of 5-[1-(3-methoxybenzyl)indol-4-yl]methyl-2,4-thiazolidinedione as colorless crystals. The yield thereof was found to be 87%.

IR (KBr) cm$^{-1}$: 1750, 1690, 1670, 750; NMR (DMSO-d$_6$) δ: 3.2~3.4 (1H,m), 3.6~3.8, 3.68 (total 4H,m,s), 4.9~5.1 (1H,m), 5.38 (2H,s), 6. 58 (1H,d,J=2.9 Hz), 6.7~6.9 (3H,m), 6.88 (1H,d,J=7.3 Hz), 7.0~7.1 (1H,m), 7.1~7.3 (1H,m), 7.36 (1H,d,J=7.3 Hz), 7.51 (1H,d,J=2.9 Hz)

EXAMPLE 90

Synthesis of 1-(3,4-dimethoxybenzyl)indole-4-carbaldehyde

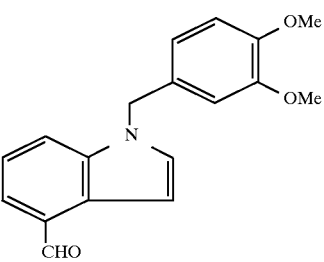

The same procedures used in Example 1 were repeated except for using 4.08 g of 3,4-dimethoxybenzyl methanesulfonate instead of the benzyl bromide used in Example 1 to give 2.03 g of 1-(3, 4-dimethoxybenzyl)indole-4-carbaldehyde as colorless crystals. The yield thereof was found to be 50%.

NMR (CDCl$_3$) δ: 3.77 (3H,s), 3.84 (3H,s), 5.32 8 (2H,s), 6.5~6.8 (3H, m), 7.2~7.4 (3H,m), 7.5~7.7 (2H, m), 10.25 (1H,s)

EXAMPLE 91

Synthesis of 5-[1-(3,4-dimethoxybenzyl)indol-4-yl] methylene-2,4-thiazolidinedione

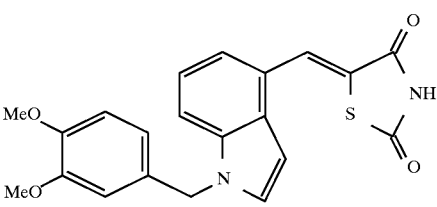

The same procedures used in Example 2 were repeated except for using 2.00 g of 1-(3,4-dimethoxybenzyl)indole-4-carbaldehyde prepared in Example 90 to give 1.98 g of 5-[1-(3,4-dimethoxybenzyl)indol-4-yl]methylene-2,4-thiazolidinedione as yellow crystals. The yield thereof was found to be 74%.

IR (KBr) cm$^{-1}$: 1740, 1700, 1520, 1290, 1260; NMR (DMSO-d$_6$) δ: 3.69 (3H,s), 3.70 (3H,s), 5.38 (2H,s), 6.6~7.0 (4H,m), 7.1~7.4 (2H,m), 7.6~7.8 (2H,m), 8.13 (1H,s), 12.57 (1H,bs)

EXAMPLE 92

Synthesis of 5-[1-(3,4-dimethoxybenzyl)indol-4-yl]methyl-2,4-thiazolidinedione

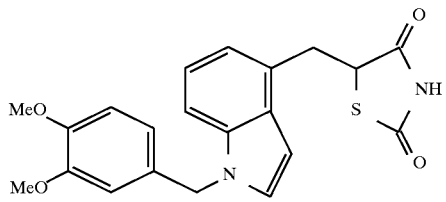

The same procedures used in Example 6 were repeated except for using 1.50 g of 5-[1-(3,4-dimethoxybenzyl)indol-4-yl]methylene-2,4-thiazolidinedione prepared in Example 91 to give 1.49 g of 5-[1-(3,4-dimethoxybenzyl)indol-4-yl]methyl-2,4-thiazolidinedione as colorless crystals. The yield thereof was found to be 99%.

IR (KBr) cm$^{-1}$: 1750, 1700, 1520, 1260, 1240; NMR (DMSO-d$_6$) δ: 3.2~3.4 (1H,m), 3.6~3.8, 3.68 (total 7H, m,s), 4.8~5.0 (1H,m), 5.31 (2H,s), 6.5~7.1 (6H,m), 7.3~7.6 (2H, m)

EXAMPLE 93

Synthesis of 1-(3,5-dimethoxybenzyl)indole-4-carbaldehyde

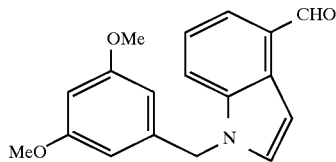

The same procedures used in Example 1 were repeated except for using 725 mg of indole-4-carbaldehyde and 3,5-dimethoxybenzyl methanesulfonate instead of the benzyl bromide used in Example 1 to give 1.29 g of 1-(3,5-dimethoxybenzyl)indole-4-carbaldehyde as a pale brown amorphous substance. The yield thereof was found to be 86%.

NMR (CDCl$_3$) δ: 3.70 (6H,s), 5.31 (2H,s), 6.22 (2H,d,J=2.2 Hz), 6.35 (1H,dd,J=2.2 Hz, 2.2 Hz), 7.2~7.4 (3H,m), 7.55 (1H,d,J=8.0 Hz), 7.62 (1H,d,J=7.3 Hz), 10.25 (1H,s)

EXAMPLE 94

Synthesis of 5-[1-(3,5-dimethoxybenzyl)indol-4-yl]methylene-2,4-thiazolidinedione

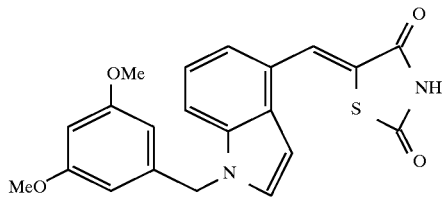

The same procedures used in Example 2 were repeated except for using 1.26 g of 1-(3,5-dimethoxybenzyl)indole-4-carbaldehyde prepared in Example 93 to give 1.60 g of 5-[1-(3,5-dimethoxybenzyl)indol-4-yl]methylene-2,4-thiazolidinedione as yellow crystals. The yield thereof was found to be 95%.

IR (KBr) cm$^{-1}$: 1730, 1680, 1600, 1290; NMR (DMSO-d$_6$) δ: 3.67 (6H,s), 5.40 (2H,s), 6.3~6.4 (3H,m), 6.79 (1H, d,J=3.0 Hz), 7.1~7.3 (2H,m), 7.64 (1H,d,J=7.7 Hz), 7.69 (1H,d,J=3.0 Hz), 8.13 (1H,s), 12.59 (1H,bs)

EXAMPLE 95

Synthesis of 5-[1-(3,5-dimethoxybenzyl)indol-4-yl]methyl-2,4-thiazolidinedione

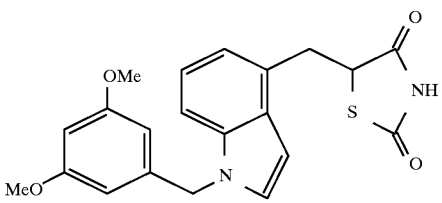

The same procedures used in Example 6 were repeated except for using 469 mg of 5-[1-(3,5-dimethoxybenzyl)indol-4-yl]methylene-2,4-thiazolidinedione prepared in Example 94 to give 400 mg of 5-[1-(3,5-dimethoxybenzyl)indol-4-yl]methyl-2,4-thiazolidinedione as colorless crystals. The yield thereof was found to be 85%.

IR (KBr) cm$^{-1}$: 1750, 1700, 1600, 1160; NMR (DMSO-d$_6$) δ: 3.32 (1H,dd,J=14.2 Hz, 10.3H), 3.66 (6H,s), 3.69 (1H,dd,J=14.2 Hz, 4.0 Hz), 4.98 (1H,dd, J=10.3 Hz, 4.0 Hz), 5.33 (2H,s), 6.2~6.4 (3H,m), 6.58 (1H,d,J=3.3 Hz), 6.89 (1H,d, J=7.0 Hz), 7.06 (1H,dd,J=7.0 Hz, 7.0 Hz), 7.36 (1H,d,J=7.0 Hz), 7.50 (1H,d,J=3.3 Hz), 12.04 (1H,bs)

EXAMPLE 96

Synthesis of 1-(2,5-dimethoxybenzyl)indole-4-carbaldehyde

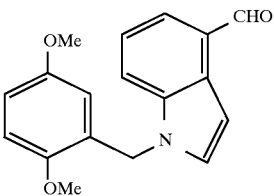

The same procedures used in Example 1 were repeated except for using 725 mg of indole-4-carbaldehyde and 2,5-dimethoxybenzyl methanesulfonate instead of the benzyl bromide used in Example 1 to give 940 mg of 1-(2,5-dimethoxybenzyl)indole-4-carbaldehyde as pale yellow crystals. The yield thereof was found to be 64%.

NMR (CDCl$_3$) δ: 3.60 (3H,s), 3.82 (3H,s), 5.34 (2H,s), 6.32 (1H,d,J=2.9 Hz), 6.75 (1H,dd,J=9.2 Hz, 2.9 Hz), 6.77 (1H,d,J=9.2 Hz), 7.2~7.4 (3H,m), 7.5~7.7 (2H,m), 10.25 (1H,s)

EXAMPLE 97

Synthesis of 5-[1-(2,5-dimethoxybenzyl)indol-4-yl]methylene-2,4-thiazolidinedione

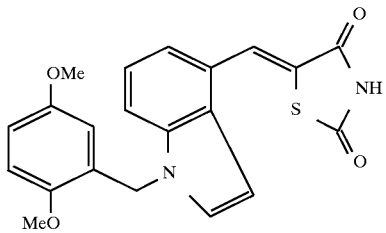

The same procedures used in Example 2 were repeated except for using 906 mg of 1-(2,5-dimethoxybenzyl)indole-4-carbaldehyde prepared in Example 96 to give 1.12 g of 5-[1-(2,5-dimethoxybenzyl)indol-4-yl]methylene-2,4-thiazolidinedione as yellow crystals. The yield thereof was found to be 93%.

IR (KBr) cm$^{-1}$: 1740, 1680, 1500, 1290; NMR (DMSO-d$_6$) δ: 3.59 (3H,s), 3.79 (3H,s), 5.38 (2H,s), 6.43 (1H,d,J=3.0 Hz), 6.7~6.9 (2H,m), 6.96 (1H,d,J=8.7 Hz), 7.1~7.3 (2H,m), 7.61 (1H, d,J=3.0 Hz), 7.64 (1H,d,J=7.0 Hz), 8.13 (1H, s), 12.54 (1H,bs)

EXAMPLE 98

Synthesis of 5-[1-(2,5-dimethoxybenzyl)indol-4-yl]methyl-2,4-thiazolidinedione

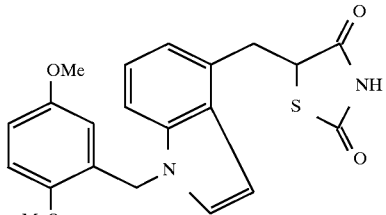

The same procedures used in Example 6 were repeated except for using 1.09 g of 5-[1-(2,5-dimethoxybenzyl)indol-4-yl]methylene-2,4-thiazolidinedione prepared in Example 97 to give 1.00 g of 5-[1-(2,5-dimethoxybenzyl)indol-4-yl]methyl-2,4-thiazolidinedione as pale yellow crystals. The yield thereof was found to be 91%.

IR (KBr) cm$^{-1}$: 1750, 1700, 1490, 1230; NMR (DMSO-d$_6$) δ: 3.32 (1H,dd,J=14.3 Hz, 10.3 Hz), 3.57 (3H,s), 3.69 (1H,dd,J=14.3 Hz, 4.4 Hz), 3.80 (3H,s), 4.99 (1H,dd,J=10.3 Hz, 4.4 Hz), 5.31 (2H,s), 6.35 (1H,dd,J=3.0 Hz,), 6.56 (1H,d,J=3.0 Hz), 6.79 (1H,dd,J=8.7 Hz, 3.0 Hz), 6.8~7.1 (3H,m), 7.35 (1H,d,J=8.0 Hz,), 7.43 (1H,d,J=3.0 Hz), 12.06 (1H,bs)

EXAMPLE 99

Synthesis of 1-(3-cyanobenzyl)indole-4-carbaldehyde

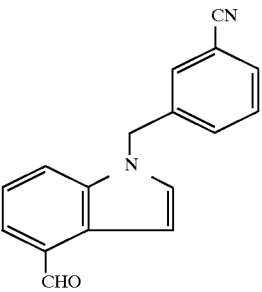

The same procedures used in Example 1 were repeated except for using 2.98 g of 3-cyanobenzyl bromide instead of the benzyl bromide used in Example 1 to give 1.89 g of 1-(3-cyanobenzyl)indole-4-carbaldehyde as colorless crystals. The yield thereof was found to be 53%.

NMR (CDC 1$_3$) δ: 5.44 (2H,s), 7.2~7.7 (9H,m), 10.26 (1H,s)

EXAMPLE 100

Synthesis of 5-[1-(3-cyanobenzyl)indol-4-yl]-methylene-2,4-thiazolidinedione

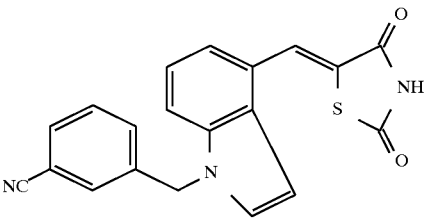

The same procedures used in Example 2 were repeated exceptfor using 1.50 g of 1-(3-cyanobenzyl)indole-4-carbaldehyde prepared in Example 99 to give 1.39 g of 5-[1-(3-cyanobenzyl)indol-4-yl]methylene-2,4-thiazolidinedione as yellow crystals. The yield thereof was found to be 67%.

IR (KBr) cm$^{-1}$: 1740, 1700, 1320, 1290; NMR (DMSO-d$_6$) δ: 5.56 (2H,s), 6.84 (1H,d,J=2.9 Hz), 7.1~7.4 (2H,m), 7.4~7.6 (2H,m), 7.6~7.8 (4H, m), 8.14 (1H,s), 12.60 (1H,bs)

EXAMPLE 101

Synthesis of 5-[1-(3-cyanobenzyl)indol-4-yl]-methyl-2,4-thiazolidinedione

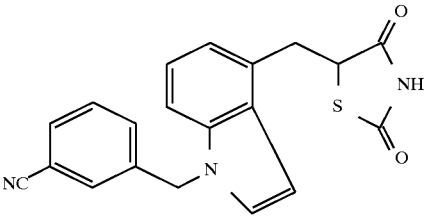

The same procedures used in Example 6 were repeated except for using 1.00 g of 5-[1-(3-cyanobenzyl)indol-4-yl]

methylene-2,4-thiazolidinedione prepared in Example 100 to give 0.96 g of 5-[1-(3-cyanobenzyl)indol-4-yl]methyl-2,4-thiazolidinedione as colorless crystals. The yield thereof was found to be 96%.

IR (KBr) cm$^{-1}$: 1750, 1690, 1670, 750; NMR (DMSO-d$_6$) δ: 3.34 (1H,dd,J=10.6 Hz, 14.0 Hz), 3.71 (1H,dd, J=14.0 Hz, 4.0 Hz), 4.98 (1H,dd,J=4.0 Hz, 10.6 Hz), 5.49 (2H,s), 6.62 (1H,dd,J=2.9 Hz), 6.90 (1H,d,J=7.0 Hz), 7.07 (1H,dd,J=7.3 Hz, 7.7 Hz), 7.39 (1H,d,J=8.1 Hz), 7.4~7.6 (3H, m), 7.7~7.8 (2H,m)

EXAMPLE 102

Synthesis of 1-(4-cyanobenzyl)indole-4-carbaldehyde

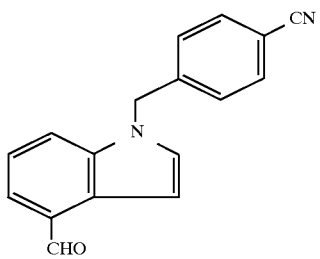

The same procedures used in Example 1 were repeated except for using 3.24 g of 4-cyanobenzyl bromide instead of the benzyl bromide used in Example 1 to give 2.67 g of 1-(4-cyanobenzyl)indole-4-carbaldehyde as yellow crystals. The yield thereof was found to be 74%.

NMR (CDCl$_3$) δ: 5.47 (2H,s), 7.0~7.8 (9H,m), 10.26 (1H,s)

EXAMPLE 103

Synthesis of 5-[1-(4-cyanobenzyl)indol-4-yl]-methylene-2,4-thiazolidinedione

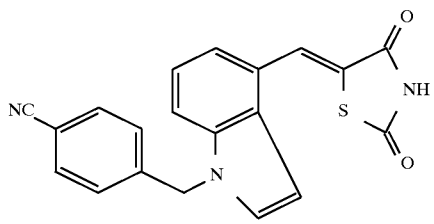

The same procedures used in Example 2 were repeated except for using 2.50 g of 1-(4-cyanobenzyl)indole-4-carbaldehyde prepared in Example 102 to give 1.88 g of 5-[1-(4-cyanobenzyl)indol-4-yl]methylene-2,4-thiazolidinedione as yellow crystals. The yield thereof was found to be 55%.

IR (KBr) cm$^{-1}$: 1740, 1680, 1320, 1280; NMR (DMSO-d$_6$) δ: 5.62 (2H,s), 6.84 (1H,d, J=3.3 Hz), 7.2~7.4 (4H,m), 7.60 (1H,d,J=7.7 Hz), 7.7~7.9 (3H,m), 8.14 (1H,s), 12.60 (1H,bs)

EXAMPLE 104

Synthesis of 5-[1-(4-cyanobenzyl)indol-4-yl]-methyl-2,4-thiazolidinedione

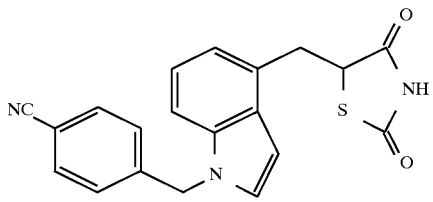

The same procedures used in Example 6 were repeated except for using 1.50 g of 5-[1-(4-cyanobenzyl)indol-4-yl]methylene-2,4-thiazolidinedione prepared in Example 103 to give 1.41 g of 5-[1-(4-cyanobenzyl)indol-4-yl]methyl-2,4-thiazolidinedione as colorless crystals. The yield thereof was found to be 93%.

IR (KBr) cm$^{-1}$: 1750, 1700, 1330, 1300, 750; NMR (DMSO-d$_6$) δ: 3.31 (1H,dd,J=10.3 Hz, 14.2 Hz), 3.70 (1H, dd, J=14.2 Hz, 4.0 Hz), 4.98 (1H,dd, J=4.0 Hz, 10.3 Hz), 5.54 (2H,s), 6.62 (1H,d,J=2.9 Hz), 6.90 (1H,d,J=7.0 Hz), 7.06 (1H,dd,J=7.7 Hz, 7.7 Hz), 7.2~7.4 (3H,m), 7.54 (1H, d,J=2.9 Hz), 7.7~7.9 (2H,m), 12.08 (1H,bs)

EXAMPLE 105

Synthesis of 1-(4-chlorobenzyl)indole-4-carbaldehyde

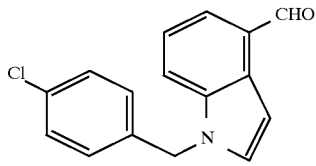

The same procedures used in Example 1 were repeated except for using 2.97 g of 4-chlorobenzyl bromide and 2.00 g of indole-4-carbaldehyde as a starting material to give 3.70 g of 1-(4-chlorobenzyl)indole-4-carbaldehyde as yellow crystals. The yield thereof was found to be 100%.

NMR (CDCl$_3$) δ: 5.35 (2H,s), 6.99 (2H,d,J=8.3 Hz), 7.2~7.4 (5H,m), 7.49 (1H,d,J=8.1 Hz), 7.6~7.7 (1H,m), 10.25 (1 H,s),

EXAMPLE 106

Synthesis of 5-[1-(4-chlorobenzyl)indol-4-yl]-methylene-2,4-thiazolidinedione

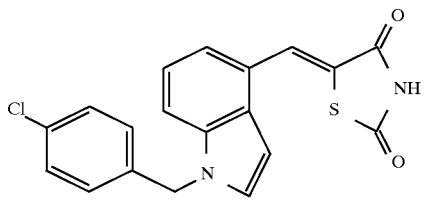

The same procedures used in Example 2 were repeated except for using 3.60 g of 1-(4-chlorobenzyl)indole-4-carbaldehyde prepared in Example 105 to give 4.31 g of 5-[1-(4-chlorobenzyl)indol-4-yl]methylene-2,4- thiazolidinedione as yellow crystals. The yield thereof was found to be 88%.

IR (KBr) cm$^{-1}$: 1740, 1690, 1290, 750, 620; NMR (DMSO-d$_6$) δ: 5.49 (2H,s), 6.8~6.9 (1H,m), 7.1~7.3 (3H,m), 7.3~7.4 (2H,m), 7.62 (1H,d,J=7.7 Hz), 7.7~7.8 (1H,m), 8.13 (1H,s), 12.59 (1H,s)

EXAMPLE 107

Synthesis of 5-[1-(4-chlorobenzyl)indol-4-yl]-methyl-2,4-thiazolidinedione

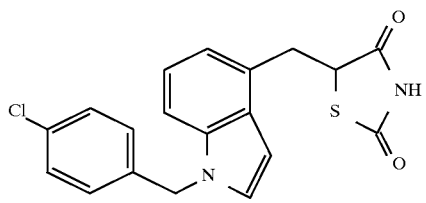

The same procedures used in Example 6 were repeated except for using 4.20 g of 5-[1-(4-chlorobenzyl)indol-4-yl]methylene-2,4-thiazolidinedione prepared in Example 106 to give 3.88 g of 5-[1-(4-chlorobenzyl)indol-4-yl]methyl-2,4-thiazolidinedione as colorless crystals. The yield thereof was found to be 92%.

IR (KBr) cm$^{-1}$: 1750, 1680, 1490, 1300, 750; NMR (DMSO-d$_6$) δ: 3.31 (1H,dd,J=14.3 Hz, 10.3 Hz), 3.70 (1H, dd, J=14.3 Hz, 4.0 Hz), 4.98 (1H,dd,J=10.3 Hz, 4.0 Hz), 5.42 (2H,s), 6.59 (1H,d,J=2.9 Hz), 6.89 (1H,d,J=7.0 Hz), 7.0~7.1 (1H,m), 7.20 (2H,d,J=8.4 Hz), 7.3~7.4 (1H,m), 7.37 (2H,d,J=8.4 Hz), 7.52 (1H,d,J=2.9 Hz), 12.06 (1H,bs)

EXAMPLE 108

Synthesis of 5-[1-(4-benzyloxybenzyl)indol-4-yl]-methylene-2,4-thiazolidinedione

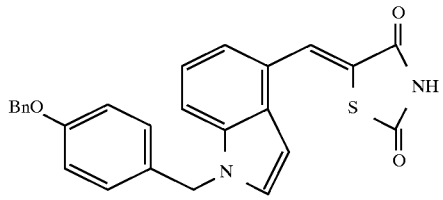

To 30 ml of dimethylformamide, there were added 2.00 g of indole-4-carbaldehyde, 8.06 g of 4-benzyloxybenzyl methanesulfonate and 9.52 g of potassium carbonate, followed by heating to 520° C. with stirring for 3 days. The reaction solution was poured into 300 ml of a 10% aqueous ammonium chloride solution, followed by extraction with ethyl acetate (150 ml×2). The resulting organic phase was washed with a saturated common salt solution, then dried over anhydrous sodium sulfate and the solvent was removed through evaporation under reduced pressure. The resulting crude product was purified by silica gel chromatography (hexane:ethyl acetate=5:1) to give 5.82 g of pale yellow crystals. The crystals were dissolved in 80 ml of ethyl alcohol, followed by addition of 289 mg of piperidine and 4.10 g of 2,4-thiazolidinedione and heating of the mixture under reflux over 16 hours. The reaction system was ice-cooled, then 160 ml of diethyl ether was added thereto, followed by stirring the system at that temperature for one hour, recovery of precipitated yellow crystals through filtration and washing with diethyl ether to give 3.74 g of 5-[1-(4-benzyloxybenzyl)indol-4-yl]methylene-2,4-thiazolidinedione as yellow crystals. The yield thereof was found to be 62%.

IR (KBr) cm$^{-1}$: 1740, 1690, 1510, 1330, 1290; NMR (DMSO-d$_6$): 5.04 (2H,s), 5.39 (2H,s), 6.77 (1H,d,J=3.3 Hz), 6.94 (2H,d,J=8.8 Hz), 7.1~7.4 (9H,m), 7.6~7.7 (2H,m), 8.13 (1H,s), 12.58 (1H,bs)

EXAMPLE 109

Synthesis of 5-[1-(4-benzyloxybenzyl)indol-4-yl]-methyl-2,4-thiazolidinedione

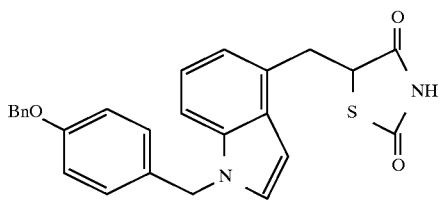

The same procedures used in Example 6 were repeated except for using 3.70 g of 5-[1-(4-benzyloxybenzyl)indol-4-yl]methylene-2,4-thiazolidinedione prepared in Example 108 to give 3.30 g of 5-[1-(4-benzyloxybenzyl)indol-4-yl]methyl-2,4-thiazolidinedione as colorless crystals. The yield thereof was found to be 89%.

IR (KBr) cm$^{-1}$: 1750, 1690, 1510, 1240, 750; NMR (DMSO-d$_6$) δ: 3.30 (1H,dd,J=14.1 Hz, 10.6 Hz), 3.69 (1H, dd, J=14.1 Hz, 4.0 Hz), 4.98 (1H,dd,J=10.6 Hz, 4.0 Hz), 5.04 (2H,s), 5.32 (2H,s), 6.55 (1H,d,J=2.9 Hz), 6.8~7.4 (12H,m), 7.49 (1H,d,J=2.9 Hz), 12.06 (1H,bs)

EXAMPLE 110

Synthesis of 1-piperonylindole-4-carbaldehyde

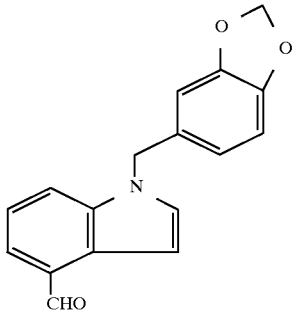

The same procedures used in Example 7 were repeated except for using 6.34 g of piperonyl methanesulfonate instead of the methyl 4-bromomethylbenzoate used in Example 7 to give 2.85 g of 1-piperonylindole-4-carbaldehyde as a yellow oily substance. The yield thereof was found to be 74%.

NMR (CDCl$_3$) δ: 5.24 (2H,s), 5.89 (2H,s), 6.5~6.8 (4H, m), 7.2~7.4 (3H,m), 7.5~7.7 (2H,m), 10.23 (1H,s),

EXAMPLE 111

Synthesis of 5-(1-piperonylindole-4-yl)-methyl-ene-2,4-thiazolidinedione

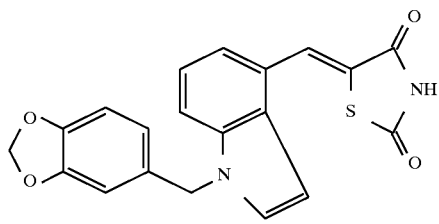

The same procedures used in Example 2 were repeated except for using 2.80 g of 1-piperonylindole-4-carbaldehyde prepared in Example 110 to give 1.76 g of 5-(1-piperonylindole-4-yl)methylene-2,4-thiazolidinedione as yellow crystals. The yield thereof was found to be 46%.

IR (KBr) cm$^{-1}$: 1740, 1700, 1600, 1500, 1320, 1280, 1250, 740; NMR (DMSO-d$_6$) δ: 5.36 (2H,s), 5.96 (2H,s), 6.8~66.9 4H,m), 7.1~7.4 (2H,m), 7.6~7.8 (2H,m), 8.13 (7H, s), 12.59 (7H,bs)

EXAMPLE 112

Synthesis of 5-(1-piperonylindole-4-yl)methyl-2,4-thiazolidinedione

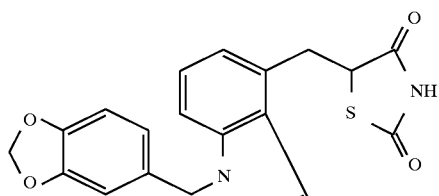

The same procedures used in Example 6 were repeated except for using 1.50 g of 5-(1-piperonylindole-4-yl) methylene-2,4-thiazolidinedione prepared in Example 111 to give 1.38 g of 5-(1-piperonylindole-4-yl)methyl-2,4-thiazolidinedione as colorless crystals. The yield thereof was found to be 92%.

IR (KBr) cm$^{-1}$: 1750, 1680, 1500, 1440, 1250, 1040, 750; NMR (DMSO-d$_6$) δ: 3.1~3.4 (1H,mn), 3.5~3.8 (1H,m), 4.8~5.0 (NH,m), 5.30 (2H,s), 5.98 (2H,s), 6.5~7.2 (6H,m), 7.34~7.6 (2H, m)

EXAMPLE 113

Synthesis of 1-(3-methylbenzyl)indole-4-carbaldehyde

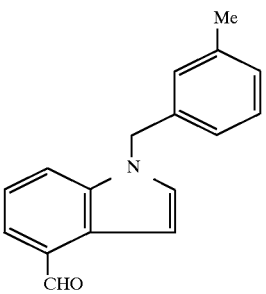

The same procedures used in Example 7 were repeated except for using 3.82 g of 3-methylbenzyl bromide instead of the methyl 4-bromomethylbenzoate used in Example 7 to give 2.02 g of 1-(3-methylbenzyl)indole-4-carbaldehyde as a brown oily substance. The yield thereof was found to be 59%.

NMR (CDCl$_3$) δ: 2.29 (3H,s), 5.34 (2H,s), 6.8~7.0 (2H, m), 7.0~7.4 (5H,m), 7.5~7.7 (2H,m), 10.26 (1H,s)

EXAMPLE 114

Synthesis of 5-[1-(3-methylbenzyl)indol-4-yl]-methylene-2,4-thiazolidinedione

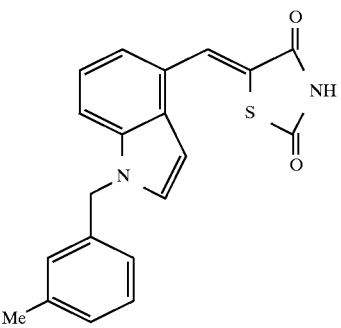

The same procedures used in Example 2 were repeated except for using 2.00 g of 1-(3-methylbenzyl)indole-4-carbaldehyde prepared in Example 113 to give 1.55 g of 5-[1-(3-methylbenzyl)indol-4-yl]methylene-2,4-thiazolidinedione as yellow crystals. The yield thereof was found to be 55%.

IR (KBr) cm$^{-1}$: 1740, 1690, 1580, 1330, 1290; NMR (DMSO-d$_6$) δ: 2.24 (3H,s), 5.44 (2H,s), 6.79 (1H,d,J=2.9 Hz), 6.9~7.4 (6H,m), 7.5~7.8 (2H,m), 8.14 (1H,s), 12.58 (1H,bs)

EXAMPLE 115

Synthesis of 5-[1-(3-methylbenzyl)indol-4-yl]-methyl-2,4-thiazolidinedione

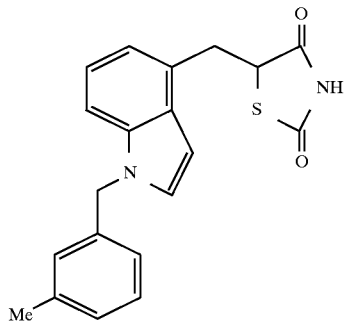

The same procedures used in Example 6 were repeated except for using 1.50 g of 5-[1-(3-methylbenzyl)indol-4-yl]methylene-2,4-thiazolidinedione prepared in Example 114 to give 1.46 g of 5-[1-(3-methylbenzyl)indol-4-yl]methyl-2,4-thiazolidinedione as colorless crystals. The yield thereof was found to be 97%.

IR (KBr) cm$^{-1}$: 1750, 1670, 1330, 1300, 750; NMR (DMSO-d$_6$) δ: 3.2~3.4 (1H,m), 3.6~3.8 (1H,m), 4.9~5.1 (1H,m), 5.36 (2H,s), 6.57 (1H,d,J=2.9 Hz), 6.88 (1H,d,J=7.0 Hz), 7.0~7.3 (5H,m), 7.36 (1H,d,J=8.1 Hz), 7.50 (1H,d,J=2.9 Hz)

EXAMPLE 116

Synthesis of 1-(2-phenylbenzyl)indole-4-carbaldehyde

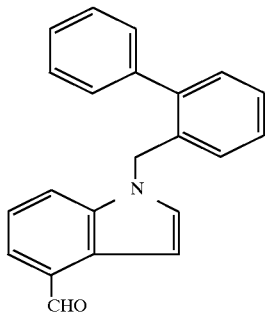

The same procedures used in Example 7 were repeated except for using 5.10 g of 2-phenylbenzyl bromide instead of the methyl 4-bromomethylbenzoate used in Example 7 to give 3.17 g of 1-(2-phenylbenzyl)indole-4-carbaldehyde as colorless crystals. The yield thereof was found to be 74%.

NMR (CDCl$_3$) δ: 5.30 (2H,s), 6.89 (1H,d,J=7.3 Hz), 7.1~7.5 (12H, m), 7.58 (1H,d,J=7.3 Hz), 10.23 (1H,s)

EXAMPLE 117

Synthesis of 5-[1-(2-phenylbenzyl)indol-4-yl]-methylene-2,4-thiazolidinedione

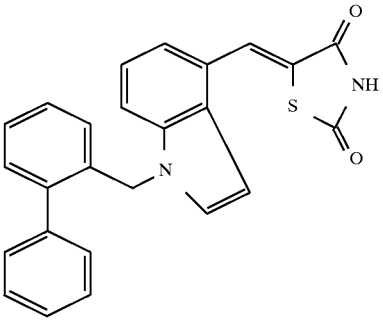

The same procedures used in Example 2 were repeated except for using 3.00 g of 1-(2-phenylbenzyl)indole-4-carbaldehyde prepared in Example 116 to give 3.30 g of 5-[1-(2-phenylbenzyl)indol-4-yl]methylene-2,4-thiazolidinedione as yellow crystals. The yield thereof was found to be 83%.

IR (KBr) cm$^{-1}$: 1730, 1680, 1330, 1290, 750; NMR (DMSO-d$_6$) δ: 5.43 (2H,s), 6.7~6.8 (1H,m), 7.1~7.6 (13H, m), 8.11 (1H,s), 12.60 (1H,bs)

EXAMPLE 118

Synthesis of 5-[1-(2-phenylbenzyl)indol-4-yl]-methyl-2,4-thiazolidinedione

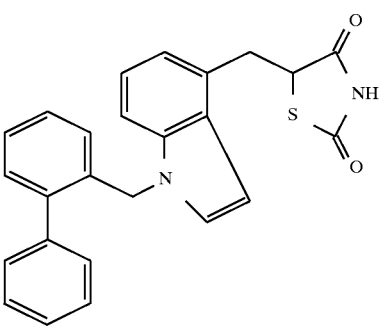

The same procedures used in Example 6 were repeated except for using 3.00 g of 5-(1-[2-phenylbenzyl)indol-4-yl]methylene-2,4-thiazolidinedione prepared in Example 117 to give 1.51 g of 5-[1-(2-phenylbenzyl)indol-4-yl]methyl-2,4-thiazolidinedione as a colorless amorphous substance. The yield thereof was found to be 50%.

IR (KBr) cm$^{-1}$: 1750, 1690, 1440, 1340, 1320, 1300, 750, 700; NMR (DMSO-d$_6$) δ: 3.2~3.4 (1H,m), 3.6~3.8 (1H,m), 4.8~5.0 (1H,m), 5.38 (2H,s), 6.5~6.6 (1H,m), 6.8~7.0 (4H, m), 7.2~7.6 (9H,m)

EXAMPLE 119

Synthesis of 1-phenethylindole-4-carbaldehyde

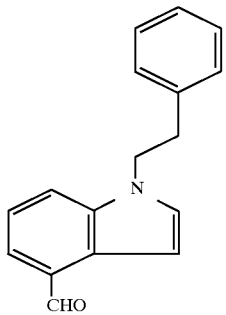

The same procedures used in Example 4 were repeated except for using 5.10 g of 2-phenethyl bromide instead of the 4-picolyl chloride hydrochloride used in Example 4 to give 1.94 g of 1-phenethylindole-4-carbaldehyde as a yellow oily substance. The yield thereof was found to be 56%.

NMR (CDCl$_3$) δ: 3.09 (2H,t,J=7.0 Hz), 4.39 (2H,t,J=7.0 Hz), 6.9~7.1 (3H,m), 7.2~7.4 (5H,m), 7.5~7.7 (2H,m), 10.22 (1H,s)

EXAMPLE 120

Synthesis of 5-(1-phenethylindol-4-yl)methylene-2,4-thiazolidinedione

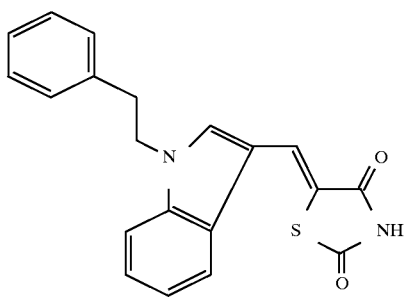

The same procedures used in Example 2 were repeated except for using 1.90 g of 1-phenethylindole-4-carbaldehyde prepared in Example 119 to give 2.05 g of 5-(1-phenethylindol-4-yl)methylene-2,4-thiazolidinedione as yellow crystals. The yield thereof was found to be 77%.

IR (KBr) cm$^{-1}$: 1740, 1690, 1590, 1330, 1290; NMR (DMSO-d$_6$) δ: 3.08 (2H,t,J=7.0 Hz), 4.49 (2H,t,J=7.0 Hz), 6.70 (1H,d,J=3.0 Hz), 7.0~7.4 (7H,m), 7.48 (1H,d,J=3.0 Hz), 7.6~7.8 (1H,m), 8.11 (1H,s), 12.60 (1H,bs)

EXAMPLE 121

Synthesis of 5-(1-phenethylindol-4-yl)methyl-2,4-thiazolidinedione

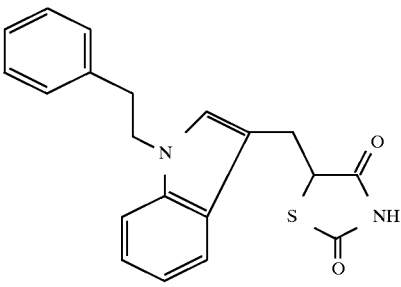

The same procedures used in Example 3 were repeated except for using 2.00 g of 5-(1-phenethylindol-4-yl) methylene-2,4-thiazolidinedione prepared in Example 120 to give 1.84 g of 5-(1-phenethylindol-4-yl)methyl-2,4-thiazolidinedione as a yellow amorphous substance. The yield thereof was found to be 92%.

IR (KBr) cm$^{-1}$: 1750, 1700, 1560, 1300, 1220, 750; NMR (CDCl$_3$) δ: 2.99 (2H,t,J=7.0 Hz), 3.15 (1H,dd,J=10.0 Hz, 14.0 Hz), 3.92 (1H,dd,J=14.0 Hz, 4.4 Hz), 4.20 (2H,t,J=7.0 Hz), 4.66 (1H,dd,J=4.4 Hz, 10.0 Hz), 6.47 (1H,d,J=3.0 Hz), 6.8~7.4 (9H,m)

EXAMPLE 122

Synthesis of 1-(4-fluorophenethyl)indole-4-carbaldehyde

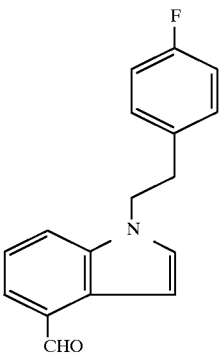

The same procedures used in Example 7 were repeated except for using 6.02 g of 4-fluorophenethyl methanesulfonate instead of the methyl 4-bromomethylbenzoate used in Example 7 to give 1.43 g of 1-(4-fluorophenethyl)indole-4-carbaldehyde as a yellow oily substance. The yield thereof was found to be 39%.

NMR (CDCl$_3$) δ: 3.06 (2H,t,J=6.8 Hz), 4.37 (2H,t,J=6.8 Hz), 6.8~7.4 (7H,m), 7.4~7.7 (2H,m), 10.23 (1H,s)

EXAMPLE 123

Synthesis of 5-[1-(4-fluorophenethyl)indol-4-yl]-methylene-2,4-thiazolidinedione

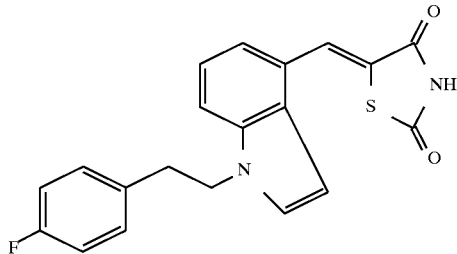

The same procedures used in Example 2 were repeated except for using 1.40 g of 1-(4-fluorophenethyl)indole-4-carbaldehyde prepared in Example 122 to give 1.05 g of 5-[1-(4-fluorophenethyl)indol-4-yl]methylene-2,4-thiazolidinedione as yellow crystals. The yield thereof was found to be 55%.

IR (KBr) cm$^{-1}$: 1740, 1680, 1600, 1510, 1330, 1300; NMR (DMSO-d$_6$) δ: 2.9~3.2 (2H,m), 4.2~4.6 (2H,m), 6.6~6.8 (1H,m), 6.9~7.8 (8H,m), 8.11 (1H,s), 12.59 (1H,bs)

EXAMPLE 124

Synthesis of 5-[1-(4-fluorophenethyl)indol-4-yl]-methyl-2,4-thiazolidinedione

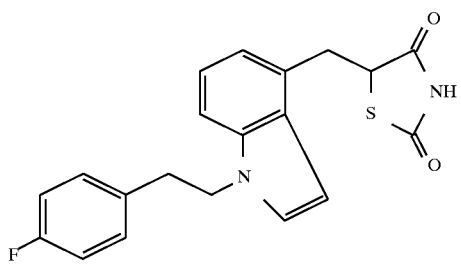

The same procedures used in Example 6 were repeated except for using 1.00 g of 5-[1-(4-fluorophenethyl)indol-4-yl]methylene-2,4-thiazolidinedione prepared in Example 123 to give 0.93 g of 5-[1-(4-fluorophenethyl)indol-4-yl]methyl-2,4-thiazolidinedione as colorless crystals. The yield thereof was found to be 93%.

IR (KBr) cm$^{-1}$: 1750, 1700, 1510, 750; NMR (DMSO-d$_6$) δ: 2.9~3.2 (2H,m), 3.2~3.4 (1H,m), 3.6~3.8 (1H,m), 4.2~4.5 (2H,m), 4.8~5.0 (1H,m), 6.4~6.5 (1H,m), 6.8~7.5 (8H,m)

EXAMPLE 125

Synthesis of 1-(3-phenylpropyl)indole-4-carbaldehyde

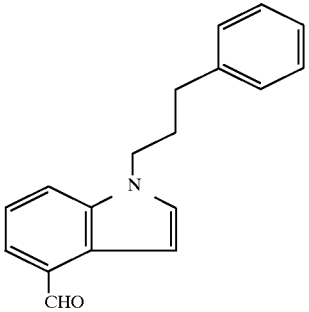

The same procedures used in Example 4 were repeated except for using 5.48 g of 3-phenylpropyl bromide instead of the 4-picolyl chloride hydrochloride used in Example 4 to give 3.04 g of 1-(3-phenylpropyl)indole-4-carbaldehyde as brown crystals. The yield thereof was found to be 84%.

NMR (CDCl$_3$) δ: 2.17 (2H,m,J=7.0 Hz), 2.61 (2H,t,J=7.0 Hz), 4.16 (2H,t,J=7.0 Hz), 7.1~7.4 (8H,m), 7.5~7.7 (2H, m), 10.24 (1H,s)

EXAMPLE 126

Synthesis of 5-[1-(3-phenylpropyl)indol-4-yl]-methylene-2,4-thiazolidinedione

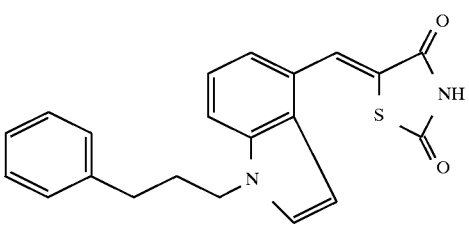

The same procedures used in Example 2 were repeated except for using 3.00 g of 1-(3-phenylpropyl)indole-4-carbaldehyde prepared in Example 125 to give 2.48 g of 5-[1-(3-phenylpropyl)indol-4-yl]methylene-2,4-thiazolidinedione as yellow crystals. The yield thereof was found to be 60%.

IR (KBr) cm$^{-1}$: 1740, 1690, 1590, 1340, 740; NMR (DMSO-d$_6$) δ: 2.0~2.2 (2H,m), 2.5~2.7 (2H,m), 4.26 (2H, t,J=7.0 Hz), 6.76 (1H,d,J=2.9 Hz), 7.1~7.4 (7H,m), 7.5~7.7 (2H,m), 8.14 (1H,s), 12.58 (1H,bs)

EXAMPLE 127

Synthesis of 5-[1-(3-phenylpropyl)indol-4-yl]-methyl-2,4-thiazolidinedione

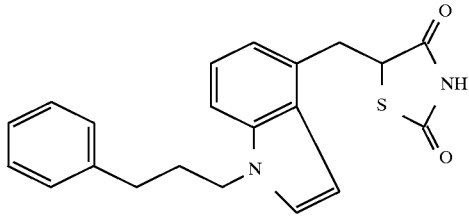

The same procedures used in Example 6 were repeated except for using 2.00 g of 5-[1-(3-phenylpropyl)indol-4-yl]methylene-2,4-thiazolidinedione prepared in Example 126 to give 1.65 g of 5-[1-(3-phenylpropyl)indol-4-yl]methyl-2,4-thiazolidinedione as colorless crystals. The yield thereof was found to be 82%.

IR (KBr) cm$^{-1}$: 1750, 1690, 1330, 1300, 750; NMR (DMSO-d$_6$) δ: 1.9~2.2 (2H,m), 2.5~2.7 (2H,m), 3.2~3.4 (1H,m), 3.6~3.8 (1H,m), 4.1~4.3 (2H,m), 4.9~5.1 (1H,m), 6.53 (1H,d,J=3.0 Hz), 6.8~7.0 (1H,m), 7.0~7.3 (7H,m), 7.41 (1H,d, J=3.0 Hz), 12.08 (1H,bs)

EXAMPLE 128

Synthesis of 1-(2-naphthylmethyl)indole-4-carbaldehyde

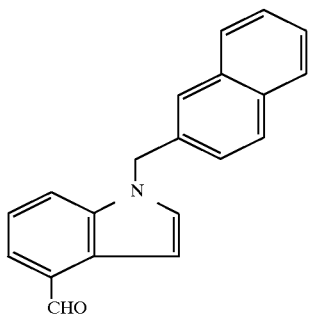

The same procedures used in Example 7 were repeated except for using 6.00 g of 2-(bromomethyl)naphthalene instead of the methyl 4-bromomethylbenzoate used in Example 7 to give 2.74 g of 1-(2-naphthylmethyl)indole-4-carbaldehyde as a colorless oily substance. The yield thereof was found to be 70%.

NMR (CDCl$_3$) δ: 5.47 (2H,s), 7.1~7.8 (12H,m), 10.24 (1H,s)

EXAMPLE 129

Synthesis of 5-[1-(2-naphthylmethyl)indol-4-yl]-methylene-2,4-thiazolidinedione

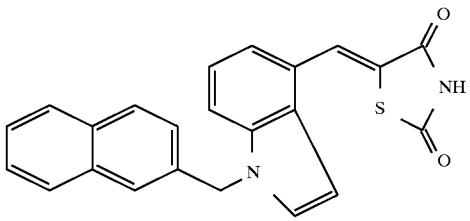

The same procedures used in Example 2 were repeated except for using 2.50 g of 1-(2-naphthylmethyl)indole-4-carbaldehyde prepared in Example 128 to give 2.29 g of 5-[1-(2-naphthylmethyl)indol-4-yl]methylene-2,4-thiazolidinedione as yellow crystals. The yield thereof was found to be 68%.

IR (KBr) cm$^{-1}$: 1740, 1680, 1330, 1290, 750; NMR (DMSO-d$_6$) δ: 5.65 (2H,s), 6.84 (1H,d, J=2.9 Hz), 7.1~8.0 (11H,m), 8.17 (1H,s), 12.60 (1H,bs)

EXAMPLE 130

Synthesis of 5-[1-(2-naphthylmethyl)indol-4-yl]-methyl-2,4-thiazolidinedione

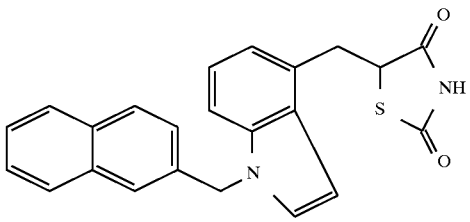

The same procedures used in Example 3 were repeated except for using 2.00 g of 5-[1-(2-naphthylmethyl)indol-4-yl]methylene-2,4-thiazolidinedione prepared in Example 129 to give 0.48 g of 5-[1-(2-naphthylmethyl)indol-4-yl]methyl-2,4-thiazolidinedione as a yellow amorphous substance. The yield thereof was found to be 24%.

IR (KBr) cm$^{-1}$: 1750, 1700, 1440, 1330, 1160, 750; NMR (CDCl$_3$+CD$_3$OD) δ: 3.25 (1H,dd,J=10.0 Hz, 14.0 Hz), 3.97 (1H,dd,J=14.0 Hz, 4.0 Hz), 4.68 (1H,dd, J=4.0 Hz, 10.0 Hz), 5.38 (2H,s), 6.5~6.7 (1H,m), 6.9~7.9 (11H,m)

EXAMPLE 131

Synthesis of 1-(2-picolyl)indole-4-carbaldehyde

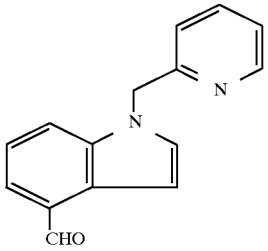

The same procedures used in Example 4 were repeated except for using 4.52 g of 2-picolyl chloride hydrochloride instead of the 4-picolyl chloride hydrochloride used in Example 4 to give 2.71 g of 1-(2-picolyl)indole-4-carbaldehyde as yellow crystals. The yield thereof was found to be 83%.

NMR (CDCl$_3$) δ: 5.50 (2H,s), 6.6~6.7 (1H,m), 7.1~7.7 (7H,m), 8.5~8.6 (1H,m), 10.28 (1H,s)

EXAPLE 132

Synthesis of 5-[1-(2-picolyl)indol-4-yl]methyl-ene-2,4-thiazolidinedione

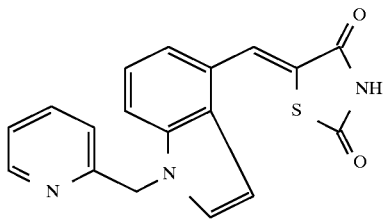

The same procedures used in Example 2 were repeated except for using 2.50 g of 1-(2-picolyl)indole-4-carbaldehyde prepared in Example 131 to give 2.78 g of 5-[1-(2-picolyl)indol-4-yl]methylene-2,4-thiazolidinedione as yellow crystals. The yield thereof was found to be 78%.

IR (KBr) cm$^{-1}$: 1740, 1690, 1590, 1330, 1290; NMR (DMSO-d$_6$) δ: 5.58 (2H,s), 6.81 (1H,d,J=3.3 Hz), 7.03 (1H, d,J=7.7 Hz), 7.2~7.4 (3H,m), 7.5~7.8 (3H,m), 8.14 (1H,s), 8.52 (1H,d,J=4.0 Hz), 12.60 (1H,bs)

EXAMPLE 133

Synthesis of 5-[1-2-picolyl)indol-4-yl]methyl-2,4-thiazolidinedione

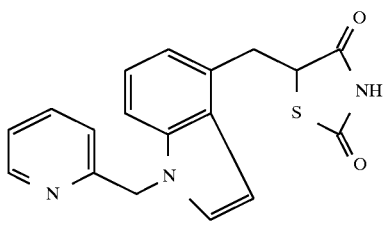

The same procedures used in Example 6 were repeated except for using 2.50 g of 5-[1-(2-picolyl)indol-4-yl]methylene-2,4-thiazolidinedione prepared in Example 132 to give 2.49 g of 5-[1-(2-picolyl)indol-4-yl]methyl-2,4-thiazolidinedione as colorless crystals. The yield thereof was found to be 99%.

IR (KBr) cm$^{-1}$: 1740, 1700, 1160, 750; NMR (DMSO-d$_6$) δ: 3.33 (1H,dd,J=10.6 Hz, 14.0 Hz), 3.70 (1H,dd,J=14.0 Hz, 4.0 Hz), 4.97 (1H,dd,J=4.0 Hz, 10.6 Hz), 5.50 (2H,s), 6.59 (1H,d,J=3.3 Hz), 6.8~7.1 (3H,m), 7.2~7.4 (2H,m), 7.52 (1H, d,J=3.3 Hz), 7.6~7.8 (1H,m), 8.53 (1H,d,J=4.8 Hz)

EXAMPLE 134

Synthesis of 1-(2-thienylmethyl)indole-4-carbaldehyde

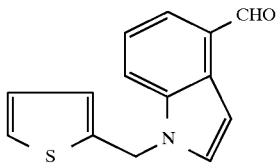

The same procedures used in Example 1 were repeated except for using 725 mg of indole-4-carbaldehyde and 2-thienylmethyl methanesulfonate instead of the benzyl bromide used in Example 1 to give 392 mg of 1-(2-thienylmethyl)indole-4-carbaldehyde as pale yellow crystals. The yield thereof was found to be 33%.

NMR (CDCl$_3$) δ: 5.53 (2H,s), 6.8~7.0 (2H,m), 7.2~7.4 (4H,m), 7.6~7.7 (2H,m), 10.24 (1H,s)

EXAMPLE 135

Synthesis of 5-[1-(2-thienylmethyl)indol-4-yl]-methylene-2,4-thiazolidinedione

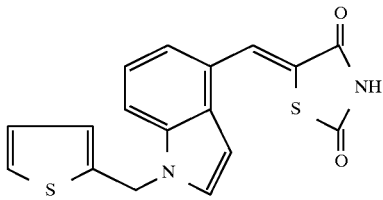

The same procedures used in Example 2 were repeated except for using 395 mg of 1-(2-thienylmethyl)indole-4-carbaldehyde prepared in Example 134 to give 379 mg of 5-[1-(2-thienylmethyl)indol-4-yl]methylene-2,4-thiazolidinedione as yellow crystals. The yield thereof was found to be 68%.

IR (KBr) cm–1: 1740, 1680, 1590, 1270; NMR (DMSO-d$_6$) δ: 5.68 (2H,s), 6.78 (1H,d,J=3.3 Hz), 6.96 (1H, dd,J=5.1 Hz, 3.3 Hz), 7.1~7.4 (3H,m), 7.41 (1H,dd, J=5.1 Hz, 1.1 Hz), 7.67 (1H,d,J=3.3 Hz), 8.12 (1H,s), 12.58 (1H, bs)

EXAMPLE 136

Synthesis of 5-[1-(2-thienylmethyl)indol-4-yl]-methyl-2,4-thiazolidinedione

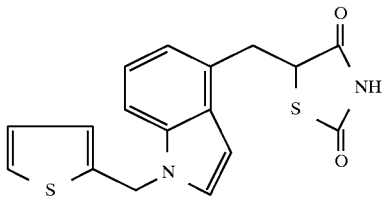

The same procedures used in Example 6 were repeated except for using 300 mg of 5-[1-(2-thienylmethyl)indol-4-yl]methylene-2,4-thiazolidinedione prepared in Example 135 to give 294 mg of 5-[1-(2-thienylmethyl)indol-4-yl]methyl-2,4-thiazolidinedione as pale yellow crystals. The yield thereof was found to be 97%.

IR (KBr) cm⁻¹: 1750, 1680, 1440, 1330; NMR (DMSO-d₆) δ: 3.28 (1H,dd,J=14.3 Hz, 10.6 Hz), 3.68 (1H,dd,J=14.3 Hz, 4.0 Hz), 4.97 (1H,dd,J=10.6 Hz, 4.0 Hz), 5.60 (2H,s), 6.56 (1H,d,J=3.0 Hz), 6.8~7.2 (4H,m), 7.39 (1H,dd,J=5.1 Hz, 1.0 Hz), 7.4~7.5 (2H,m), 12.08 (1H,bs)

EXAMPLE 137

Synthesis of 1-[2-(thien-2-yl)ethyl]indole-4-carbaldehyde

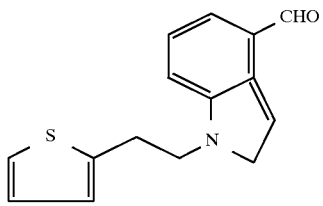

The same procedures used in Example 1 were repeated except for using 435 mg of indole-4-carbaldehyde and 680 mg of 2-(thien-2-yl)ethyl methanesulfonate instead of the benzyl bromide used in Example 1 to give 299 mg of 1-[2-(thien-2-yl)ethyl]indole-4-carbaldehyde as an orange-colored oily substance. The yield thereof was found to be 39%.

NMR (CDCl₃) δ: 3.31 (2H,t,J=7.0 Hz), 4.42 (2H,t,J=7.0 Hz), 6.62 (1H,d,J=3.3 Hz), 6.8~7.3 (4H,m), 7.32 (1H,d,J=7.7 Hz), 7.55 (1H,d,J=7.7 Hz), 7.61 (1H,d,J=7.7 Hz), 10.23 (1H,s)

EXAMPLE 138

Synthesis of 5-{1-[2-(thien-2-yl)ethyl]indol-4-yl}methylene-2,4-thiazolidinedione

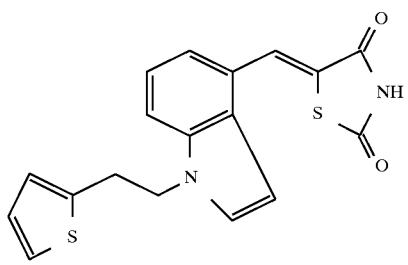

The same procedures used in Example 2 were repeated except for using 299 mg of 1-[2-(thien-2-yl)ethyl]indole-4-carbaldehyde prepared in Example 137 to give 330 mg of 5-{1-[2-(thien-2-yl)ethyl]indol-4-yl}methylene-2,4-thiazolidinedione as yellow crystals. The yield thereof was found to be 79%.

IR (KBr) cm⁻¹: 1730, 1680, 1590, 1330; NMR (DMSO-d₆) δ: 3.31 (2H,t,J=6.6 Hz), 4.49 (2H,t,J=6.6 Hz), 6.71 (1H,d,J=2.2 Hz), 6.8~7.0 (2H,m), 7.1~7.3 (3H,m), 7.51 (1H,dd, 3.0 Hz, 1.8 Hz), 7.64 (1H,d, 8.0 Hz), 8.11 (1H,s), 12.58 (1H,bs)

EXAMPLE 139

Synthesis of 5-{1-[2-(thien-2-yl)ethyl]indol-4-yl}methyl-2,4-thiazolidinedione

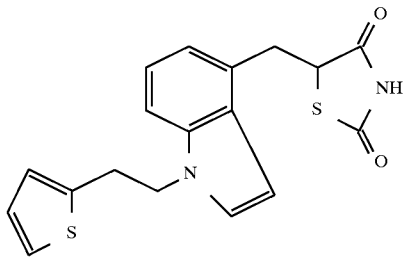

The same procedures used in Example 3 were repeated except for using 308 mg of 5-{1-[2-(thien-2-yl)ethyl]indol-4-yl}methylene-2,4-thiazolidinedione prepared in Example 138 to give 231 mg of 5-{1-[2-(thien-2-yl)ethy]indol-4-yl}methyl-2,4-thiazolidinedione as yellow crystals. The yield thereof was found to be 75%.

IR (KBr) cm⁻¹: 1750, 1700, 1300, 1170; NMR (CDCl₃) δ: 3.32 (2H,t,J=7.3 Hz), 3.35 (1H,dd,J=13.2 Hz, 11.0 Hz), 3.99 (1H,dd,J=13.2 Hz, 3.0 Hz), 4.38 (2H,t, J=7.3 Hz), 4.70 (1H,dd,J=11.0 Hz, 3.0 Hz), 6.52 (1H,d,J=3.3 Hz), 6.68 (1H,d,J=3.3 Hz), 6.8~7.3 (7H,m)

EXAMPLE 140

Synthesis of 1-[(2-methylthiazol-4-yl)methyl]-indole-4-carbaldehyde

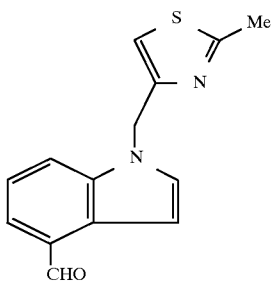

The same procedures used in Example 4 were repeated except for using 5.07 g of 4-chloromethyl-2-methylthiazole hydrochloride instead of the 4-picolyl chloride hydrochloride used in Example 4 to give 2.05 g of 1-[(2-methylthiazol-4-yl)methyl]indole-4-carbaldehyde as brown crystals. The yield thereof was found to be 58%.

NMR (CDCl₃) δ: 2.67 (3H,s), 5.43 (2H,s), 6.54 (1H,s), 7.2~7.4 (3H,m), 7.5~7.7 (2H,m), 10.23 (1H,s)

EXAMPLE 141

Synthesis of 5-{1-[(2-methylthiazol-4-yl)-methyl]indol-4-yl}methylene-2,4-thiazolidinedione

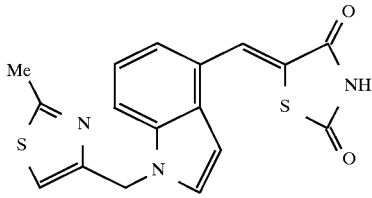

The same procedures used in Example 2 were repeated except for using 2.00 g of 1-[(2-methylthiazol-4-yl)methyl]indole-4-carbaldehyde prepared in Example 140 to give 2.14 g of 5-{1-[(2-methylthiazol-4-yl)methyl]indol-4-yl}methylene-2,4-thiazolidinedione as yellow crystals. The yield thereof was found to be 77%.

IR (KBr) cm$^{-1}$: 1740, 1690, 1590, 1330, 1290; NMR (DMSO-d$_6$) 0 2.58 (3H,s), 5.48 (2H,s), 6.76 (1H,d, J=2.9 Hz), 7.1~7.4 (3H,m), 7.63 (1H,d,J=2.9 Hz), 7.72 (1H,d,J=7.7 Hz), 8.13 (1H,s), 12.59 (1H,bs)

EXAMPLE 142

Synthesis of 5-{1-[(2-methylthiazol-4-yl)-methyl]indol-4-yl}methyl-2,4-thiazolidinedione

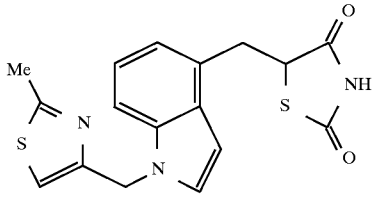

The same procedures used in Example 6 were repeated except for using 2.00 g of 5-{1-[(2-methylthiazol-4-yl)methyl]indol-4-yl}methylene-2,4-thiazolidinedione prepared in Example 141 to give 1.78 g of 5-{1-[(2-methylthiazol-4-yl)methyl]indol-4-yl}methyl-2,4-thiazolidinedione as a colorless amorphous substance. The yield thereof was found to be 89%.

IR (KBr) cm$^{-1}$: 1740, 1700, 1440, 1300, 1160; NMR (DMSO-d$_6$) δ: 2.58 (3H,s), 3.30 (1H,dd, J=10.6 Hz, 14.4 Hz), 3.73 (1H,dd,J=14.4 Hz, 4.0 Hz), 4.97 (1H,dd,J=4.0 Hz, 10.6 Hz), 5.41 (2H,s), 6.55 (1H,d,J=3.3 Hz), 6.89 (1H,d,J=7.0 Hz), 7.07 (1H,dd,J=7.2 Hz, 7.7 Hz), 7.28 (1H,s), 7.4~7.6 (2H,m)

EXAMPLE 143

Synthesis of 1-[2-(4-methylthiazol-5-yl)ethyl]-indole-4-carbaldehyde

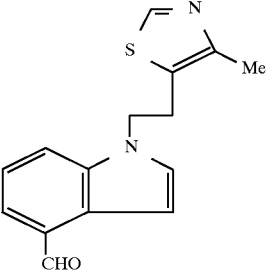

The same procedures used in Example 1 were repeated except for using 6.10 g of 5-(2-mesyloxyethyl)-4-methylthiazole instead of the benzyl bromide used in Example 1 to give 1.45 g of 1-[2-(4-methylthiazol-5-yl)ethyl]indole-4-carbaldehyde as a colorless amorphous substance. The yield thereof was found to be 39%.

NMR (CDCl$_3$) δ: 2.03 (3H,s), 3.28 (2H,t,J=7.0 Hz), 4.40 (2H,t,J=7.0 Hz), 7.0~7.7 (5H,m), 8.55 (1H,s), 10.22 (1H,s)

EXAMPLE 144

Synthesis of 5-{1-[2-(4-methylthiazol-5-yl)-ethyl]indol-4-yl}methylene-2,4-thiazolidinedione

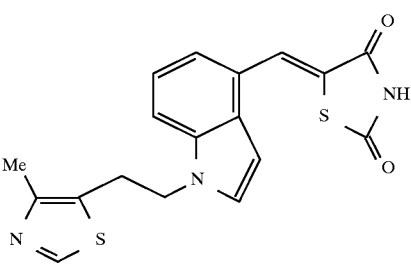

The same procedures used in Example 2 were repeated except for using 1.40 g of 1-[2-(4-methylthiazol-5-yl)ethyl]indole-4-carbaldehyde prepared in Example 143 to give 1.55 g of 5-{1-[2-(4-methylthiazol-5-yl) ethyl]indol-4-yl}methylene-2,4-thiazolidinedione as yellow crystals. The yield thereof was found to be 81%.

IR (KBr) cm$^{-1}$: 1740, 1700, 1320, 1290 740, 62, 620; NMR (DMSO-d$_6$) δ: 2.00 (3H,s), 3.28 (2H,t,J=7.0 Hz), 4.46 (2H, t,J=7.0 Hz), 6.72 (1H,d,J=3.0 Hz), 7.1~7.3 (2H,m), 7.43 (1H,d,J=3.0 Hz), 7.5~7.6 (1H,m), 8.11 (1H,s), 8.78 (1H,s), 12.57 (1H,bs)

EXAMPLE 145

Synthesis of 5-{1-[2-(4-methylthiazol- 5-yl)-ethyl]indol-4-yl}methyl-2, 4-thiazolidinedione

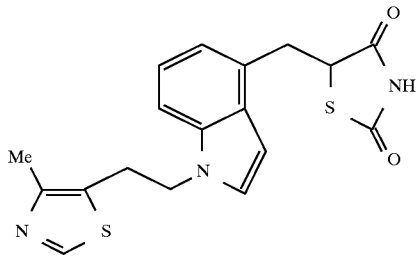

The same procedures used in Example 3 were repeated except for using 1.50 g of 5-{1-[2-(4-methylthiazol-5-yl)ethyl]indol-4-yl}methylene-2,4-thiazolidinedione prepared in Example 144 to give 0.80 g of 5-{1-[2-(4-methylthiazol-5-yl) ethyl]indol-4-yl}methyl-2,4-thiazolidinedione as a yellow amorphous substance. The yield thereof was found to be 53%.

IR (KBr) cm$^{-1}$: 1750, 1700, 1440, 1310, 1170, 750; NMR (DMSO-d$_6$) δ: 1.97 (3H,s), 3.1~3.3 (2H,m), 3.6~3.8 (1H,m), 4.0~4.5 (3H,m), 4.7~4.9 (1H,m), 6.4~6.6 (1H,m), 6.7~7.4 (4H,m), 8.77 (1H, s)

EXAMPLE 146

Synthesis of 1-[(quinol-2-yl)methyl]indole-4-carbaldehyde

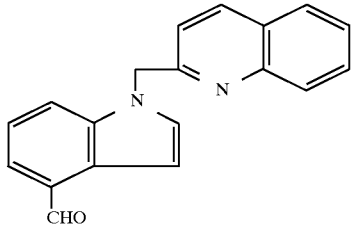

The same procedures used in Example 4 were repeated except for using 5.90 g of 2-(chloromethyl)quinoline hydrochloride instead of the 4-picolyl chloride hydrochloride used in Example 4 to give 2.08 g of 1-[(quinol-2-yl)methyl]indole-4-carbaldehyde as a colorless amorphous substance. The yield thereof was found to be 53%.

NMR (CDCl$_3$) δ: 5.66 (2H,s), 6.78 (1H,d,J=8.5 Hz), 7.2~7.8 (8H,m), 7.96 (1H,d,J=8.5 Hz), 8.10 (1H,d,J=8.6 Hz), 10.25 (1H,s)

EXAMPLE 147

Synthesis of 5-{1-[(quinol-2-yl)methyl]indol-4-yl}methylene-2,4-thiazolidinedione

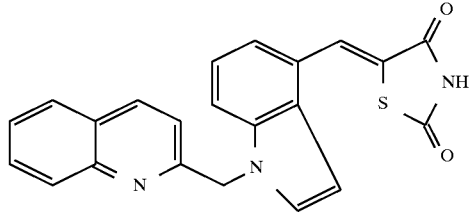

The same procedures used in Example 2 were repeated except for using 2.00 g of 1-[(quinol-2-yl)methyl]indole-4-carbaldehyde prepared in Example 146 to give 1.89 g of 5-{1-[(quinol-2-yl)methyl]indol-4-yl}methylene-2,4-thiazolidinedione as yellow crystals. The yield thereof was found to be 70%.

IR (KBr) cm$^{-1}$: 1740, 1680, 1600, 1510, 1330, 1290, 740; NMR (DMSO-d$_6$) δ: 5.79 (2H,s), 6.87 (1H,d,J=2.9 Hz), 7.09 (1H,d,J=8.4 Hz), 7.1~7.4 (2H,m), 7.5~8.1 (6H,m), 8.17 (1H,s), 8.27 (1H,d,J=8.4 Hz), 12.63 (1H,bs)

EXAMPLE 148

Synthesis of 5-{1-[(1,2,3,4-tetrahydroquinol-2-yl)methyl]indol-4-yl}methyl-2,4-thiazolidinedione

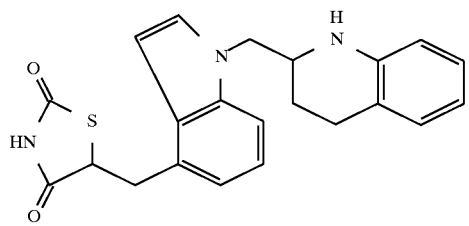

The same procedures used in Example 6 were repeated except for using 1.80 g of 5-{1-[(quinol-2-yl)methyl]indol-4-yl}methylene-2,4-thiazolidinedione prepared in Example 147 to give 1.49 g of 5-{1-[(1,2,3,4-tetrahydroquinol-2-yl)methyl]indol-4-yl}methyl-2,4-thiazolidinedione as a colorless amorphous substance. The yield thereof was found to be 82%.

IR (KBr) cm$^{-1}$: 1750, 1700, 1500, 1310, 1160, 750; NMR (DMSO-d$_6$) δ: 1.6~1.8 (2H,m), 2.5~2.7 (1H,m), 3.30 (1H, dd,J=10.2 Hz, 14.0 Hz), 3.5~3.8 (3H,m), 4.0~4.4 (2H,m), 4.97 (1H, dd, J=4.0 Hz, 10.2 Hz), 5.74 (1H,bs), 6.4~6.6 (3H,m), 6.7~7.0 (3H,m), 7.10 (1H,dd,J=7.3 Hz,J=7.7 Hz), 7.3~7.6 (2H,m)

EXAMPLE 149

Synthesis of 5-(indol-4-yl)methylene-2,4-thiazolidinedione

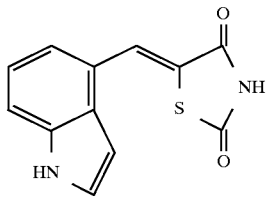

The same procedures used in Example 2 were repeated except for using 2.00 g of indole-4-carbaldehyde instead of the 1-benzylindole-4-carbaldehyde used in Example 2 to give 2.38 g of 5-(indol-4-yl) methylene-2,4-thiazolidinedione as yellow crystals. The yield thereof was found to be 71%.

IR (KBr) cm$^{-1}$: 1710, 1690, 1590, 1330, 1280; NMR (DMSO-d$_6$) δ: 6.6~6.9 (1H,m), 7.0~7.4 (2H,m), 7.5~7.7 (2H,m), 8.16 (1H,s), 11.51 (1H,bs) TLC : Rf=0.41 (chloroform-methanol=12:1)

EXAMPLE 150

Synthesis of 5-(indol-4-yl)methyl-2,4-thiazolidinedione

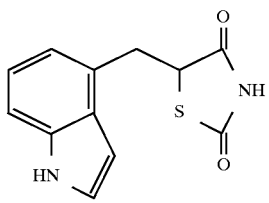

The same procedures used in Example 3 were repeated except for using 2.00 g of 5-(indol-4-yl)methylene-24-thiazolidinedione prepared in Example 149 to give 0.69 g of 5-(indol-4-yl)methyl-2,4-thiazolidinedione as colorless crystals. The yield thereof was found to be 34%.

IR (KBr) cm$^{-1}$: 1750, 1680, 1330, 1170, 750; NMR (CDCl$_3$) δ: 3.23 (1H,dd,J=10.2 Hz, 14.0 Hz) 3.75 (1H,d,J= 14.0 Hz, 4.0 Hz), 4.90 (1 H,dd,J=4.0 Hz, 10.2 Hz), 6.4~6.6 (1H,m), 6.8~7.4 (4H,m), 11.15 (1H, bs)

EXAMPLE 151

Synthesis of 1-methylindole-4-carbaldehyde

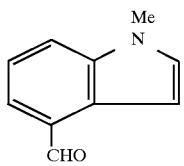

The same procedures used in Example 1 were repeated except for using 2.16 g of methyl iodide instead of the benzyl bromide used in Example 1 to give 2.15 g of 1-methylindole-4-carbaldehyde as a brown oily substance. The yield thereof was found to be 98%.

NMR (CDCl$_3$) δ: 3.85 (3H,s), 7.2~7.4 (3H,m), 7.5~7.7 (2H,m), 10.24 (1H,s)

EXAMPLE 152

Synthesis of 5-(1-methylindol-4-yl)methylene-2,4-thiazolidinedione

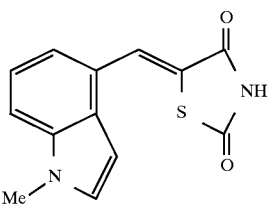

The same procedures used in Example 2 were repeated except for using 2.00 g of 1-methylindole-4-carbaldehyde prepared in Example 151 to give 0.72 g of 5-(1-methylindol-4-yl)methylene-2,4-thiazolidinedione as yellow crystals. The yield thereof was found to be 22%.

IR (KBr) cm$^{-1}$: 1730, 1690, 1580, 1340, 1290; NMR (DMSO-d$_6$) δ: 3.85 (3H,s), 6.72 (1H,d,J=2.9 Hz), 7.22 (1H,d,J=7.0 Hz ), 7.32 (1H, dd,J=7.7 Hz, 7.7 Hz), 7.52 (1H,d,J=2.9 Hz), 7.61 (1H,d,J=7.0 Hz), 8.13 (1H,s), 12.57 (1H,bs)

EXAMPLE 153

Synthesis of 5-(1-methylindol-4-yl)methyl-2,4-thiazolidinedione

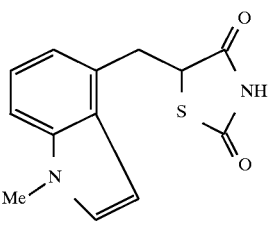

The same procedures used in Example 6 were repeated except for using 0.70 g of 5-(1-methylindol-4-yl)methylene-2,4-thiazolidinedione prepared in Example 152 to give 0.67 g of 5-(1-methylindol-4-yl)methyl-2,4-thiazolidinedione as yellow crystals. The yield thereof was found to be 95%.

IR (KBr) cm$^{-1}$: 1750, 1700, 1330, 1300, 750; NMR (DMSO-d$_6$) δ: 3.2~3.4 (1H,m), 3.6~3.8, 3.78 (total 4H, m,s), 4.8~5.0 (1H,m), 6.4~6.6 (1H,m), 6.8~7.0 (1H,m), 7.0~7.2 (1H,m), 7.2~7.5 (2H,m)

EXAMPLE 154

Synthesis of 1-hexylindole-4-carbaldehyde

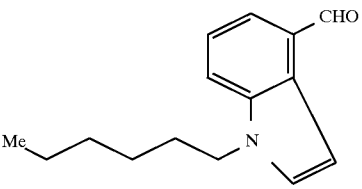

There were dissolved, in 26 ml of dimethylformamide, 2.00 g of indole-4-carbaldehyde and 4.64 g of n-hexyl bromide, followed by addition of 9.52 g of potassium carbonate and heating the reaction solution to 55° C. with stirring for 12.5 hours. The reaction solution was poured into 500 ml of a 10% aqueous solution of ammonium chloride followed by extraction with ethyl acetate (150 ml×3). The resulting organic phase was washed with a saturated common salt solution, dried over anhydrous sodium sulfate, followed by removal of the solvent through evaporation under reduced pressure. The resulting crude product was purified by silica gel column chromatography (hexane:ethyl acetate=10:1) to give 1.91 g of 1-hexylindole-4-carbaldehyde as a yellow oily substance. The yield thereof was found to be 61%.

NMR (CDCl$_3$) δ: 0.86 (3H,t,J=6.6 Hz), 1.29~1.33 (6H, m), 1.79~1.82 (2H,m), 4.15 (2H,t,J=7.1 Hz), 7.25~7.36 (3H, m), 7.59~7.63 (2H,m), 10.24 (1H,s)

EXAMPLE 155

Synthesis of 5-(1-hexylindol-4-yl)methylene-2,4-thiazo idinedione

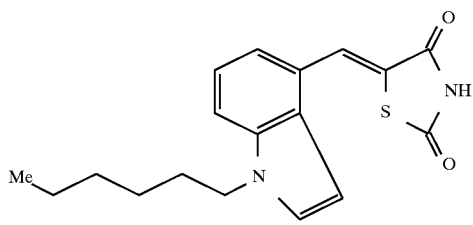

The same procedures used in Example 2 were repeated except for using 1.90 g of 1-hexylindole-4-carbaldehyde prepared in Example 154 to give 2.25 g of 5-(1-hexylindol-4-yl)methylene-2,4-thiazolidinedione as yellow crystals. The yield thereof was found to be 83%.

IR (KBr) cm$^{-1}$: 1740, 1690, 1590, 1330, 740; NMR (CDCl$_6$) δ: 0.7~0.9 (3H, m), 1.219 1.33 (6H,m), 1.6~1.8 (2H,m), 4.1~4.3 (2H,m), 6.7~6.8 (1H,m), 7.1~7.3 (2H,m), 7.5~7.7 (2H,m), 8.12 (1H,s), 12.58 (1H, bs)

EXAMPLE 156

Synthesis of 5-(1-hexylindol-4-yl)methyl-2,4-thiazolidinedione

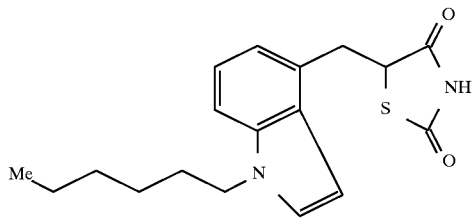

The same procedures used in Example 3 were repeated except for using 2.20 g of 5-(1-hexylindol-4-yl)methylene-2,4-thiazolidinedione prepared in Example 155 to give 2.05 g of 5-(1-hexylindol-4-yl)methyl-2,4-thiazolidinedione as yellow crystals. The yield thereof was found to be 93%.

IR (KBr) cm$^{-1}$: 1750, 1700, 1330, 1300, 750; NMR (CDCl$_3$) δ: 0.8~0.9 (3H,m), 1.2~1.4 (6H,m), 1.7~1.9 (2H, m), 3.2~3.3 (1H, m), 3.9~4.05 (1H,m), 4.10 (2H,t,J=7.1 Hz), 4.6~4.8 (1H,m), 6.5~6.6 (1H,m), 6.9~7.0 (1H,m), 7.1~7.3 (3H,m)

EXAMPLE 157

Synthesis of 1-(2-ethylbutyl)indole-4-carbaldehyde

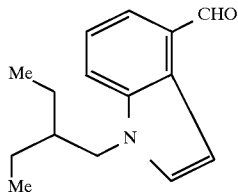

The same procedures used in Example 1 were repeated except for using 4.55 g of 1-bromo-2-ethylbutane and 2.00 g of indole-4-carbaldehyde as a starting material to give 1.92 g of 1-(2-ethylbutyl) indole-4-carbaldehyde as a yellow oily substance. The yield thereof was found to be 61%.

NMR (CDCl$_3$) δ: 0.89 (6H,t,J=7.3 Hz), 1.2~1.4 (4H,m), 1.7~1.9 (1H,m), 4.03 (2H,d,J=7.3 Hz), 7.25~7.35 (3H,m), 7.5~7.6 (2H,m), 10.24 (1H,s)

EXAMPLE 158

Synthesis of 5-[1-(2-ethylbutyl)indol-4-yl]-methylene-2,4-thiazolidinedione

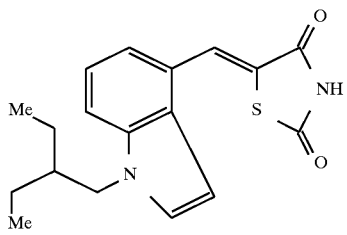

The same procedures used in Example 2 were repeated except for using 1.9 g of 1-(2-ethylbutyl)indole-4-carbaldehyde prepared in Example 157 to give 2.34 g of 5-[1-(2-ethylbutyl)indol-4-yl]methylene-2,4-thiazolidinedione as yellow crystals. The yield thereof was found to be 86%.

IR (KBr) cm$^{-1}$: 1730, 1680, 1580, 1330, 1290, 740; NMR (DMSO-d$_6$) δ: 0.8~0.9 (6H,m), 1.2~1.4 (4H,m), 1.6~1.8 (1H,m), 4.0~4.1 (2H,m), 6.6~6.8 (1H,m), 7.1~7.3 (2H,m), 7.4~7.6 (2H,m), 8.13 (1H,s), 12.5 (1H,bs)

EXAMPLE 159

Synthesis of 5-[1-(2-ethylbutyl)indol-4-yl]-methyl-2,4-thiazolidinedione

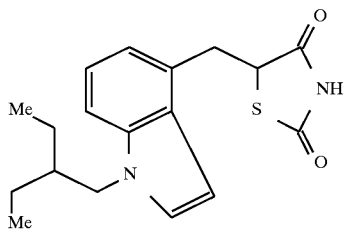

The same procedures used in Example 3 were repeated except for using 2.3 g of 5-[1-(2-ethylbutyl)indol-4-yl] methylene-2,4-thiazolidinedione prepared in Example 158 to give 1.61 g of 5-[1-(2-ethylbutyl)indol-4-yl]methyl-2,4-thiazolidinedione as yellow crystals. The yield thereof was found to be 70%.

IR (KBr) cm$^{-1}$: 1750, 1670, 1440, 1300, 1140, 750; NMR (CDCl$_3$) δ: 0.90 (6H,t,J=7.3 Hz), 1.2~1.4 (4H,m), 1.8~1.9 (1H,m), 3.2~3.4 (1H,m), 3.6~3.8 (1H,m), 4.0 (2H,d,J=7.3 Hz), 4.7~4.8 (1H,m), 6.55 (1H,m), 6.9~7.0 (1H,m), 7.1~7.2 (2H,m), 7.2~7.3 (1H,m)

EXAMPLE 160

Synthesis of 1-cyclohexylmethylindole-4-carbaldehyde

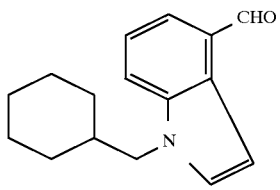

The same procedures used in Example 1 were repeated except for using 4.93 g of cyclohexylmethyl bromide and 2.00 g of indole-4-carbaldehyde as a starting material to give 2.82 g of 1-cyclohexylmethylindole-4-carbaldehyde as a yellow oily substance. The yield thereof was found to be 85%.

NMR (CDCl$_3$) δ: 1.0~1.3 (5H,m), 1.5~1.7 (6H,m), 3.97 (2H,d, J=7.3 Hz), 7.2~7.4 (3H,m), 7.60 (2H,d,J=7.7 Hz), 10.24 (1H,s)

EXAMPLE 161

Synthesis of 5-(1-cyclohexylmethylindol-4-yl)-methylene-2,4-thiazolidinedione

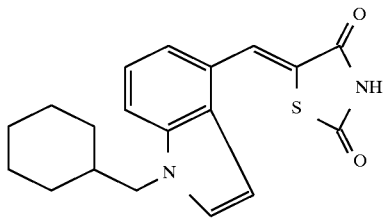

The same procedures used in Example 2 were repeated except for using 2.80 g of 1-cyclohexylmethylindole-4-carbaldehyde prepared in Example 160 to give 2.78 g of 5-(1-cyclohexylmethyl-indol-4-yl) methylene-2,4-thiazolidinedione as yellow crystals. The yield thereof was found to be 71%.

IR (KBr) cm$^{-1}$: 2930, 1720, 1700, 1660, 1290; NMR (DMSO-d$_6$) δ: 0.9~1.2 (5H,m), 1.4~1.8 (6H,m), 4.06 (2H, d,J=7.0 Hz), 6.72 (1H,d,J=2.9 Hz), 7.2~7.3 (2H,m), 7.52 (1H,d,J=2.9 Hz), 7.65 (1H,d, J=7.7 Hz), 8.14 (1H,s), 13.27 (1H,bs)

EXAMPLE 162

Synthesis of 5-(1-cyclohexylmethylindol-4-yl)-methyl-2,4-thiazolidinedione

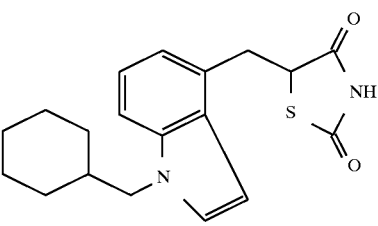

The same procedures used in Example 3 were repeated except for using 2.70 g of 5-(1-cyclohexylmethylindol-4-yl) methylene-2,4-thiazolidinedione prepared in Example 161 to give 2.54 g of 5-(1-cyclohexylmethylindol-4-yl)methyl-2,4-thiazolidinedione as a yellow amorphous substance. The yield thereof was found to be 94%.

IR (KBr) cm$^{-1}$: 2930, 1750, 1680, 1320, 750; NMR (DMSO-d$_6$) δ: 0.9~1.3 (5H,m), 1.6~1.8 (6H,m), 3.26 (1H, dd,J=14.1 Hz, 11.2 Hz), 3.9~4.0 (1H,m), 3.93 (2H,d,J=7.3 Hz), 4.72 (1H,dd, J=11.2 Hz, 3.5 Hz), 6.54 (1H,d,J=3.3 Hz), 6.94 (1H,d,J=7.0 Hz), 7.0~7.2 (2H,m), 7.28 (1H,d, J=8.4 Hz), 9.15 (1H,bs)

EXAMPLE 163

Synthesis of 1-(4-methyl-3-pentenyl)indole-4-carbaldehyde

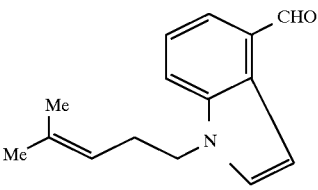

The same procedures used in Example 7 were repeated except for using 4.59 g of 5-bromo-2-methyl-2-pentene and 2.00 g of indole-4-carbaldehyde as a starting material to give 2.72 g of 1-(4-methyl-3-pentenyl)indole-4-carbaldehyde as a brown oily substance. The yield thereof was found to be 87%.

NMR (CDCl$_3$) δ: 1.39 (3H,s), 1.64 (3H,s), 2.4~2.6 (2H, m), 4.14 (2H,t,J=7.0 Hz), 5.0~5.2 (1H,m), 7.2~7.3 (3H,m) 7.5~7.6 (2H,m), 10.23 (1H,s)

EXAMPLE 164

Synthesis of 5-[1-(4-methyl-3-pentenyl)indol-4-yl] methylene-2,4-thiazolidinedione

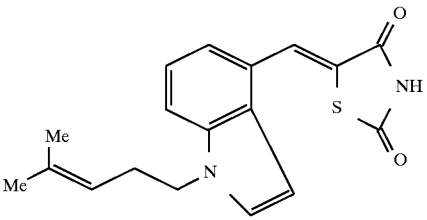

The same procedures used in Example 2 were repeated except for using 2.70 g of 1-(4-methyl-3-pentenyl)indole-4- carbaldehyde prepared in Example 163 to give 1.80 g of 5-[1-(4-methyl-3-pentenyl)indol-4-yl]methylene-2,4-thiazolidinedione as yellow crystals. The yield thereof was found to be 46%.

IR (KBr) cm$^{-1}$: 1740, 1680, 1580, 1310, 1300; NMR (DMSO-d$_6$) δ: 1.36 (3H,s), 1.58 (3H,s), 2.4~2.5 (2H,m), 4.21 (2H,t,J=7.0 Hz), 5.0~5.2 (1H,m), 6.72 (1H,d,J=2.9 Hz), 7.2~7.3 (2H,m), 7.54 (1H, d,J=2.9HZ), 7.65 (1H,d,J=8.1 Hz), 8.13 (1H,s), 12.58 (1H,bs)

EXAMPLE 165

Synthesis of 5-[1-(4-methyl-3-pentenyl)indol-4-yl]methyl-2,4-thiazolidinedione

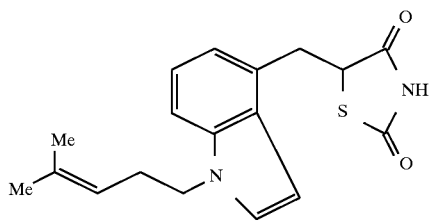

The same procedures used in Example 3 were repeated except for using 1.75 g of 5-[1-(4-methyl-3-pentenyl)indol-4-yl]methylene-2,4-thiazolidinedione prepared in Example 164 to give 1.37 g of 5-[1-(4-methyl-3-pentenyl)indol-4-yl]methyl-2,4-thiazolidinedione as yellow crystals. The yield thereof was found to be 78%.

IR (KBr) cm$^{-1}$: 1750, 1690, 1680, 1300, 750; NMR (DMSO-d$_6$) δ: 1.38 (3H,s), 1.59 (3H,s), 2.4~2.5 (2H,m), 3.23 (1H,dd,J=14.3 Hz, 10.3 Hz), 3.6~3.7 (1H,m), 4.13 (2H,t,J=7.0 Hz), 4.88 (1H,dd,J=10.3 Hz, 3.7 Hz), 5.0~5.2 (1H,m), 6.49 (1H,d,J=2.9 Hz), 6.87 (1H,d,J=7.3 Hz), 7.0~7.1 (1H,m), 7.3~7.4 (2H,m)

EXAMPLE 166

Synthesis of 1-(2-butynyl)indole-4-carbaldehyde

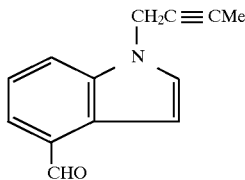

The same procedures used in Example 7 were repeated except for using 4.08 g of 2-butynylmethanesulfonate instead of the methyl 4-bromomethylbenzoate to give 1.99 g of 1-(2-butynyl)indole- 4-carbaldehyde as brown crystals. The yield thereof was found to be 73%.

NMR (CDCl$_3$) δ: 1.81 (3H,s), 4.86 (2H,s), 7.26~7.5 (3H,m), 7.5~7.8 (2H,m), 10.23 (1H,s)

EXAMPLE 167

Synthesis of 5-[1-(2-butynyl)indol-4-yl]methyl-ene-2,4-thiazolidinedione

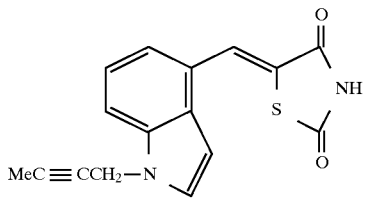

The same procedures used in Example 2 were repeated except for using 1.50 g of 1-(2-butynyl)indole-4-carbaldehyde prepared in Example 166 to give 1.26 g of 5-[1-(2-butynyl)indol-4-yl]methylene-2,4-thiazolidinedione as yellow crystals. The yield thereof was found to be 59%.

IR (KBr) cm$^{-1}$: 1740, 1690, 1590, 1330, 1290; NMR (DMSO-d$_6$) δ: 1.80 (3H,s), 5.10 (2H,s), 6.76 (1H,d,J=2.9 Hz), 7.2~7.5 (2H,m), 7.5~7.8 (2H,m), 8.13 (1H,s), 12.60 (1H,bs)

EXAMPLE 168

Synthesis of 5-[1-(2-butynyl)indol-4-yl]methyl-2,4-thiazolidinedione

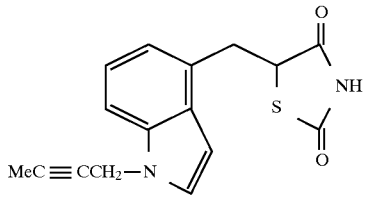

The same procedures used in Example 3 were repeated except for using 1.00 g of 5-[1-(2-butynyl)indol-4-yl]methylene-2,4-thiazolidinedione prepared in Example 167 to give 0.94 g of 5-[1-(2-butynyl)indol-4-yl]methyl-2,4-thiazolidinedione as yellow crystals. The yield thereof was found to be 93%.

IR (KBr) cm$^{-1}$: 1750, 1680, 1330, 1300, 750; NMR (DMSO-d$_6$) δ: 1.79 (3H,s), 3.32 (1H,dd,J=10.0 Hz, 14.2 Hz), 3.69 (1H,dd,J=14.2 Hz, 4.0 Hz), 4.9~5.1, 5.00 (total 3H,m,s), 6.54 (1H,d,J=2.9 Hz), 6.92 (1H,d,J=7.3 Hz), 7.12 (1H,dd,J=7.3 Hz, 7.7 Hz), 7.3~7.5 (2H,m), 12.08 (1H,bs)

EXAMPLE 169

Synthesis of 1-[2-(pyrrolidin-1-yl)ethyl]indole-4-carbaldehyde

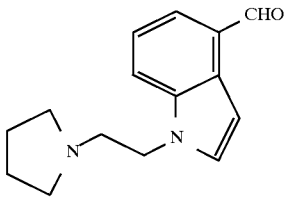

The same procedures used in Example 154 were repeated except for using 5.32 g of N-(2-methanesulfonyloxyethyl)

pyrrolidine and 2.00 g of indole-4-carbaldehyde as a starting material to give 1.08 g of 1-[2-(pyrrolidin-1-yl)ethyl]indole-4-carbaldehyde as a yellow oily substance. The yield thereof was found to be 33%.

NMR (CDCl₃) δ: 1.7~1.8 (4H,m), 2.5~2.6 (4H,m), 2.87 (2H,t, J=7.3 Hz), 4.31 (2H,t,J=7.3 Hz), 7.2~7.4 (3H,m), 7.6~7.7 (2H,m), 10.23 (1H,s)

EXAMPLE 170

Synthesis of 5-{1-[2-(pyrrolidin-1-yl)ethyl]-indol-4-yl}methylene-2,4-thiazolidinedione

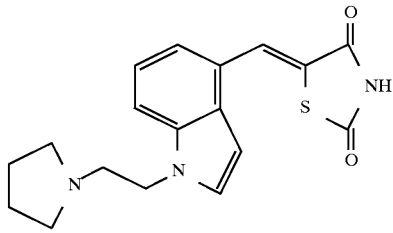

The same procedures used in Example 2 were repeated except for using 1.00 g of 1-[2-(pyrrolidin-1-yl)ethyl]indole-4-carbaldehyde prepared in Example 169 to give 899 mg of 5-{1-[2-(pyrrolidin-1-yl) ethyl]indol-4-yl}methylene-2,4-thiazolidinedione as brown crystals. The yield thereof was found to be 64%.

IR (KBr) cm⁻¹: 3450, 1700, 1620, 1570, 1290, 1210; NMR (DMSO-d₆) δ: 1.7~1.8 (4H,m), 2.7~2.8 (4H,m), 3.07 (2H,t,J=6.2 Hz), 4.42 (2H,t,J=6.2 Hz), 6.72 (1H,d,J=2.6 Hz), 7.2~7.3 (2H,m), 7.5~7.6 (2H,m), 7.99 (1H,s)

EXAMPLE 171

Synthesis of 5-{1-[2-(pyrrolidin-1-yl)ethyl]-indol-4-yl}methyl-2,4-thiazolidinedione

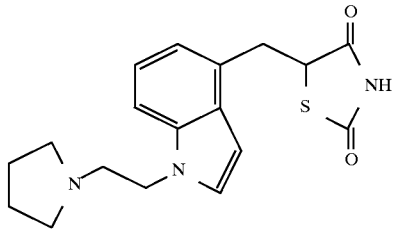

The same procedures used in Example 3 were repeated except for using 890 mg of 5-{1-[2-(pyrrolidin-1-yl)ethyl]indol-4-yl}methylene-2,4-thiazolidinedione prepared in Example 170 to give 807 mg of 5-{1-[2-(pyrrolidin-1-yl) ethyl]indol-4-yl}methyl-2,4-thiazolidinedione as brown crystals. The yield thereof was found to be 90%.

IR (KBr) cm⁻¹: 3430, 1700, 1600, 1570, 1300, 1220; NMR (DMMO-d₆) δ: 1.6~1.7 (4H,m), 2.5~2.6 (4H,m), 2.86 (2H,t,J=6.6 Hz), 3.26 (1H,dd,J=14.3 Hz, 10.3 Hz) 3.70 (1H,dd,J=14.3 Hz, 4.0 Hz), 4.29 (2H,t,J=6.6 Hz), 4.92 (1H,dd,J=10.3 Hz, 4.0 Hz), 6.51 (1H,d,J=2.9 Hz), 6.88 (1H,d,J=7.3 Hz), 7.0~7.1 (1H,m), 7.3~7.4 (2H,m)

EXAMPLE 172

Synthesis of 1-(α-methylbenzyl)indole-4-carbaldehyde

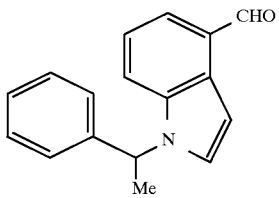

The same procedures used in Example 4 were repeated except for using 703 mg of indole-4-carbaldehyde and 987 mg of α-phenylethyl bromide instead of the 4-picolyl chloride hydrochloride to give 845 mg of 1-(α-methylbenzyl) indole-4-carbaldehyde as an orange-colored oily substance. The yield thereof was found to be 70%.

NMR (CDCl₃) δ: 1.85 (3H,d,J=7.0 Hz), 5.64 (1H,q,J=7.0 Hz), 7.0~7.7 (10H,m), 10.91 (1H,s)

EXAMPLE 173

Synthesis of 5-[1-(α-methylbenzyl)indol-4-yl]-methylene-2,4-thiazolidinedione

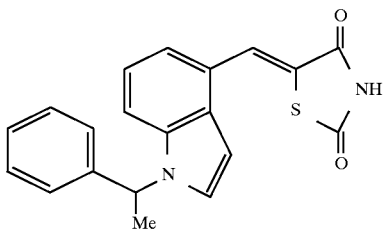

The same procedures used in Example 2 were repeated except for using 845 mg of 1-(α-methylbenzyl)indole-4-carbaldehyde prepared in Example 172 to give 540 mg of 5-[1-(α-methylbenzyl)indol-4-yl]methylene-2,4-thiazolidinedione as yellow crystals. The yield thereof was found to be 46%.

IR (KBr) cm⁻¹: 1730, 1680, 1320, 1280; NMR (CDCl₃) δ: 1.90 (3H,d,J=7.0 Hz), 5.88 (1H,q,J=7.0 Hz), 6.82 (1H,d, J=3.3 Hz), 7.1~7.4 (7H,m), 7.58 (1H,d, J=7.2 Hz), 7.85 (1H,d,J=3.3 Hz), 8.15 (1H,s), 12.50 (1H,bs)

EXAMPLE 174

Synthesis of 5-[1-(α-methylbenzyl)indol-4-yl]-methyl-2,4-thiazolidinedione

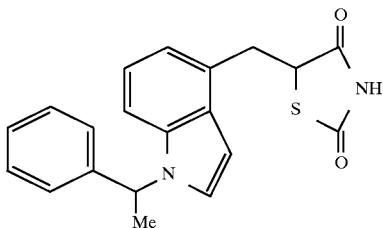

The same procedures used in Example 3 were repeated except for using 300 mg of 5-[1-(α-methylbenzyl)indol-4- yl]methylene-2,4-thiazolidinedione prepared in Example 173 to give 186 mg of 5-[1-(α-methylbenzyl)indol-4-yl]methyl-2,4-thiazolidinedione as a yellow amorphous substance. The yield thereof was found to be 62%.

IR (KBr) cm⁻¹: 1750, 1690, 1320, 1160; NMR (CDCl₃) δ: 1.82 (3H,d,J=7.0 Hz), 3.20 (1H,dd,J=13.2 Hz, 11.0 Hz), 3.94 (1H,dd,J=13.2 Hz, 3.0 Hz), 4.57 (1H,dd, J=11.0 Hz, 3.0 Hz), 5.60 (1H,q,J=7.0 Hz), 6.6~7.5 (10H,m)

EXAMPLE 175

Synthesis of 1-benzhydrylindole-4-carbaldehyde

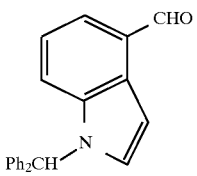

The same procedures used in Example 1 were repeated except for using 870 mg of indole-4-carbaldehyde and benzhydryl chloride instead of the benzyl bromide used in Example 1 to give 1.14 g of 1-benzhydrylindole-4-carbaldehyde as an orange-colored oily substance. The yield thereof was found to be 61%.

NMR (CDCl₃) δ: 6.89 (1H,s), 7.0~7.4 (13H,m), 7.50 (1H,d,J=8.0 Hz), 7.62 (1H,dd,J=7.1 Hz, 1.0 Hz), 10.25 (1H,s)

EXAMPLE 176

Synthesis of 5-[1-(benzhydryl)indol-4-yl]-methylene-2,4-thiazolidinedione

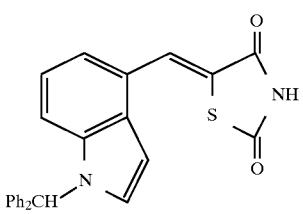

The same procedures used in Example 2 were repeated except for using 1.10 g of 1-benzhydrylindole-4-carbaldehyde prepared in Example 175 to give 962 mg of 5-[1-(benzhydryl)indol-4-yl]methylene-2,4-thiazolidinedione as orange-colored crystals. The yield thereof was found to be 66%.

IR (KBr) cm⁻¹: 1740, 1680, 1580, 1330; NMR (DMSO-d₆) δ: 6.81 (1H,d,J=3.3 Hz), 7.1~7.5 (14H,m), 7.61 (1H,d, J=6.0 Hz), 8.13 (1H,s), 12.57 (1H,bs)

EXAMPLE 177

Synthesis of 5-[1-(benzhydryl)indol-4-yl]methyl-2,4-thiazolidinedione

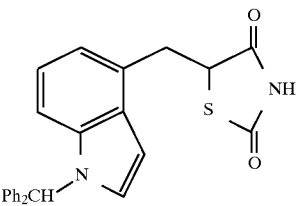

The same procedures used in Example 3 were repeated except for using 400 mg of 5-[1-(benzhydryl)indol-4-yl]methylene-2,4-thiazolidinedione prepared in Example 176 to give 305 mg of 5-[1-(benzhydryl)indol-4-yl]methyl-2,4-thiazolidinedione as a yellow amorphous substance. The yield thereof was found to be 76%.

IR (KBr) cm⁻¹: 1750, 1700, 1320, 1160; NMR (CDCl₃) δ: 3.28 (1H,dd,J=14.3 Hz, 11.4 Hz), 3.98 (1H, dd, J=14 .3 Hz, 3.8 Hz), 4.72 (1H, dd,J=11.4 Hz, 3.8 Hz), 6.55 (1H,d, J=3.3 Hz), 6.8~7.4 (15H,m), 8.4 (1H,bs)

EXAMPLE 178

Synthesis of 1-(2-cyclohexenyl)indole-4-carbaldehyde

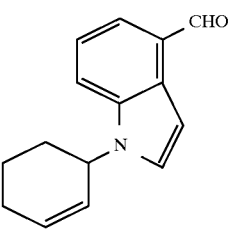

The same procedures used in Example 1 were repeated except for using 2.44 g of 3-bromocyclohexene and 2.00 g of indole-4-carbaldehyde as a starting material to give 556 mg of 1-(2-cyclohexenyl)indole-4-carbaldehyde as a yellow-colored oily substance. The yield thereof was found to be 18%.

NMR (CDCl₃) δ: 1.6~2.3 (6H,m), 5.0~5.1 (1H,m), 5.8~5.9 (1H,m), 6.1~6.2 (1H,m), 7.2~7.4 (3H,m), 7.6~7.7 (1H,m), 10.25 (1H,s)

EXAMPLE 179

Synthesis of 5-[1-(2-cyclohexenyl)indol-4-yl]-methylene-2,4-thiazolidinedione

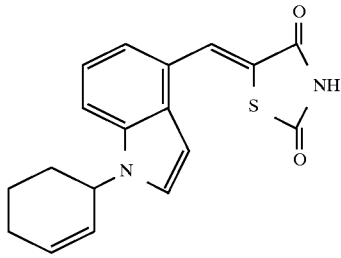

The same procedures used in Example 2 were repeated except for using 540 mg of 1-(2-cyclohexenyl)indole-4-carbaldehyde prepared in Example 178 to give 568 mg of 5-[1-(2-cyclohexenyl)indol-4-yl]methylene-2,4-thiazolidinedione as yellow crystals. The yield thereof was found to be 73%.

IR (KBr) cm$^{-1}$: 1740, 1690, 1590, 1330, 1300, 1270; NMR (DMSO-d$_6$) δ: 1.6~2.2 (6H,m), 5.2~5.3 (1H,m), 5.7~5.8 (1H,m), 6.1~6.2 (1H,m), 6.74 (1H,d, J=3.3 Hz), 7.22 (1H,d,J=7.7 Hz), 7.31 (1H,t, J=7.7 Hz), 7.49 (1H,d,J= 3.3 Hz), 7.72 (1H,d, J=7.7 Hz), 8.12 (1H,s), 12.54 (1H,bs)

EXAMPLE 180

Synthesis of 5-(1-cyclohexylindol-4-yl)-methyl-2,4-thiazolidinedione

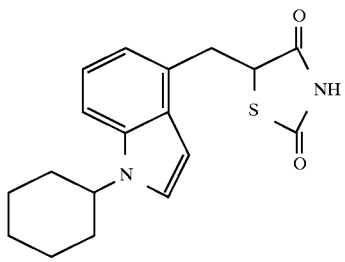

The same procedures used in Example 6 were repeated except for using 550 mg of 5-[1-(2-cyclohexenyl)indol-4-yl]methylene-2,4-thiazolidinedione prepared in Example 179 to give 425 mg of 5-(1-cyclohexylindol-4-yl)methyl-2,4-thiazolidinedione as pale yellow crystals. The yield thereof was found to be 76%.

IR (KBr) cm$^{-1}$: 1750, 1700, 1670, 1450, 1300, 1170, 750; NMR (DMSO-d$_6$) δ: 1.1~2.0 (10H,m), 3.2~3.4 (1H,m), 3.69 (1H,dd,J=14.1 Hz, 4.0 Hz), 4.2~4.4 (1H,m), 4.97 (1H,dd,J= 10.4 Hz, 4.0 Hz), 6.52 (1H,d,J=2.9 Hz), 6.87 (1H,d,J=7.0 Hz), 7.07 (1H, t,J=7.0 Hz), 7.3~7.5 (2H,m), 12.05 (1H,bs)

EXAMPLE 181

Synthesis of 5-[1-(4-cyanophenyl)indol-4-yl]-methylene-2,4-thiazolidinedione

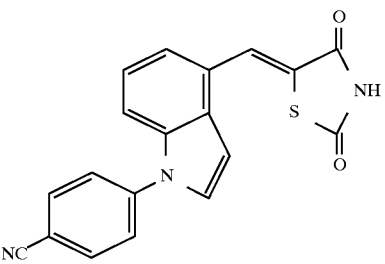

The same procedures used in Examples 1 and 2 were repeated except for using 2.08 g of 4-chlorobenzonitrile instead of the benzyl bromide used therein to give 0.31 g of 5-[1-(4-cyanophenyl)indol-4-yl]methylene-2,4-thiazolidinedione as yellow crystals. The yield thereof was found to be 10%.

IR (KBr) cm$^{-1}$: 1740, 1710, 1600, 1520, 1340; NMR (DMSO-d$_6$) δ: 7.11 (1H,d,J=3.0 Hz), 7.3~7.5 (2H,m), 7.7~8.1 (6H,m), 8.17 (1H,s), 12.65 (1H,bs)

EXAMPLE 182

Synthesis of 5-[1-(4-cyanophenyl)indol-4-yl]-methyl-2,4-thiazolidinedione

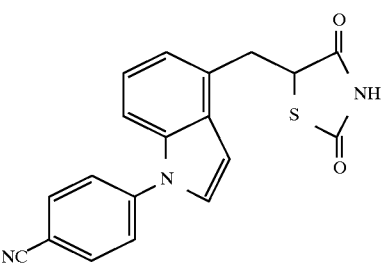

The same procedures used in Example 6 were repeated except for using 0.30 g of 5-[1-(4-cyanophenyl)indol-4-yl] methylene-2,4-thiazolidinedione prepared in Example 181 to give 0.26 g of 5-[1-(4-cyanophenyl)indol-4-yl]methyl-2, 4-thiazolidinedione as colorless crystals. The yield thereof was found to be 86%.

IR (KBr) cm$^{-1}$: 1750, 1700, 1520, 1510, 750; NMR (DMSO-d$_6$) δ: 3.2~3.4 (1H,m), 3.6~3.8 (1H,m), 4.9~5.1 (1H,m), 6.8~7.3 (3H,m), 7.5~8.2 (6H,m)

EXAMPLE 183

Synthesis of 1-(4-nitrophenyl)indole-4-carbaldehyde,

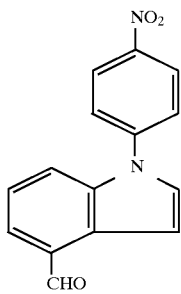

The same procedures used in Example 1 were repeated except for using 2.41 g of 4-chloronitrobenzene instead of the benzyl bromide used therein to give 2.15 g of 1-(4-nitrophenyl)indole-4-carbaldehyde as yellow crystals. The yield thereof was found to be 59%.

NMR (CDCl$_3$) δ: 7.4~7.9 (7H,m), 8.45 (2H,d,J=7.8 Hz), 10.30 (1H,s)

EXAMPLE 184

Synthesis of 5-[1-(4-aminophenyl)indol-4-yl]-methyl-2,4-thiazolidinedione

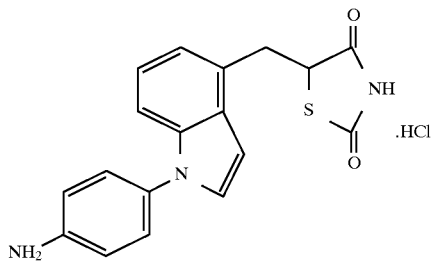

The same procedures used in Examples 2 and 6 were repeated except for using 2.00 g of 1-(4-nitrophenyl)indole-4-carbaldehyde prepared in Example 183 to give 1.76 g of a residue. To this residue, there was added 5 ml of ethyl acetate, followed by stirring, addition of 5 ml of 4N hydrochloric acid (a solution in ethyl acetate) and recovery of the precipitated crystals through filtration. The crystals were washed with ethyl acetate and dried under reduced pressure at room temperature to give 1.77 g of 5-[1-(4-aminophenyl) indol-4-yl]methyl- 2,4-thiazolidinedione as pink-colored crystals. The yield thereof was found to be 65%.

IR (KBr) cm$^{-1}$: 1700, 1520, 1440, 750; NMR (DMSO-d$_6$) δ: 3.42 (1H,dd,J=10.3 Hz, 14.1 Hz), 5.04 (1H,dd, J=4.2 Hz, 10.3 Hz), 6.84 (1H,d,J=3.3 Hz), 7.03 (1H,d,J=7.3 Hz), 7.18 (1H,dd,J=7.3 Hz, 7.8 Hz), 7.4~7.6 (3H,m), 7.6~7.8 (3H,m)

EXAMPLE 185

Synthesis of 1-phenacylindole-4-carbaldehyde

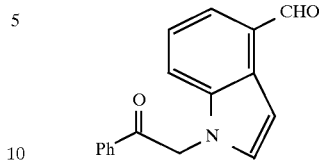

The same procedures used in Example 7 were repeated except for using 5.49 g of bromoacetophenone and 2.00 g of indole-4-carbaldehyde as a starting material to give 494 mg of 1-phenacylindole-4-carbaldehyde as yellow crystals. The yield thereof was found to be 14%.

NMR (DMSO-d$_6$) δ: 6.06 (2H,s), 7.18 (1H,d,J=2.9 Hz), 7.32 (1H, t,J=7.8 Hz), 7.6~7.8 (6H,m), 8.0~8.1 (2H,m), 10.23 (1H,s)

EXAMPLE 186

Synthesis of 5-(1-phenacylindol-4-yl)methylene-2,4-thiazolidinedione

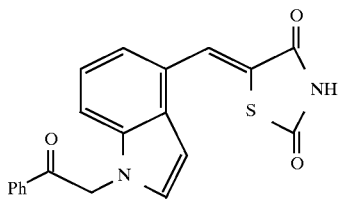

The same procedures used in Example 2 were repeated except for using 480 mg of 1-phenacylindole-4-carbaldehyde prepared in Example 185 to give 519 mg of 5-(1-phenacylindol-4-yl)methylene-2,4-thiazolidinedione as yellow crystals. The yield thereof was found to be 79%.

IR (KBr) cm$^{-1}$: 1730, 1710, 1680, 1330, 1290; NMR (DMSO-d$_6$) δ: 6.00 (2H,s), 6.81 (1H,d,J=2.9 Hz), 7.2~7.3 (2H,m), 7.5~7.8 (5H,m), 8.0~8.1 (2H,m), 12.60 (1H,bs)

EXAMPLE 187

Synthesis of 5-(1-phenacylindol-4-yl)methyl-2,4-thiazolidinedione

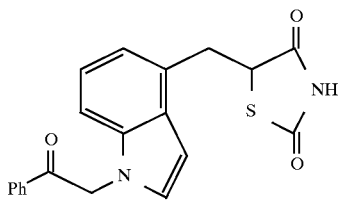

The same procedures used in Example 6 were repeated except for using 500 mg of 5-(1-phenacylindol-4-yl) methylene-2,4-thiazolidinedione prepared in Example 186 to give 439 mg of 5-(1-phenacylindol-4-yl) methyl-2,4-thiazolidinedione as pale yellow crystals. The yield thereof was found to be 87%.

IR (KBr) cm$^{-1}$: 1750, 1690, 1330, 1300, 1220; NMR (DMSO-d$_6$) δ: 3.33 (1H,dd,J=14.1 Hz, 10.6 Hz), 3.73 (1H, dd,J=14.1 Hz, 4.0 Hz), 5.01 (1H,dd,J=10.6 Hz, 4.0 Hz), 5.91

(2H,s), 6.59 (1H,d,J=2.9 Hz), 6.90 (1H,d,J=7.3 Hz), 7.0~7.1 (1H,m), 7.28 (1H,d,J=8.1 Hz), 7.35 (1H,d,J=2.9 Hz), 7.5~7.8 (3H, m), 8.0~8.1 (2H,m), 12.05 (1H,bs)

EXAMPLE 188

Synthesis of 1-(4-nitrobenzyl)indole-4-carbaldehyde

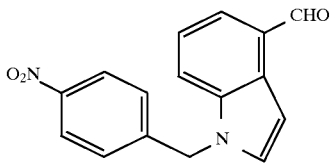

The same procedures used in Example 7 were repeated except for using 4.46 g of 4-nitrobenzyl bromide and 2.00 g of indole-4-carbaldehyde as a starting material to give 2.14 g of 1-(4-nitrobenzyl) indole-4-carbaldehyde as an orange-colored oily substance. The yield thereof was found to be 59%.

NMR (CDCl$_3$) δ: 5.51 (2H,s), 7.18 (2H,d,J=8.8 Hz), 7.2~7.5 (4H,m), 7.65 (1H,d,J=8.1 Hz), 8.13 (2H,d,J=8.8 Hz), 10.25 (1H,s)

EXAMPLE 189

Synthesis of 5-[1-(4-nitrobenzyl)indol-4-yl]-methylene-2,4-thiazolidinedione

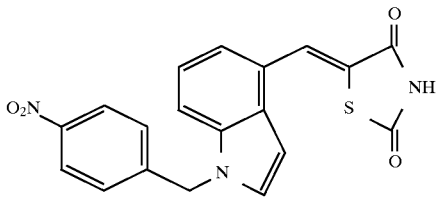

The same procedures used in Example 2 were repeated except for using 2.10 g of 1-(4-nitrobenzyl)indole-4-carbaldehyde prepared in Example 188 to give 1.55 g of 5-[1-(4-nitrobenzyl)indol-4-yl]methylene-2,4-thiazolidinedione as yellow crystals. The yield thereof was found to be 51%.

IR (KBr) cm$^{-1}$: 1740, 1690, 1670, 1520, 1350, 1280; NMR (DMSO-d$_6$) δ: 5.68 (2H,s), 6.85 (1H,d,J=2.9 Hz), 7.2~7.3 (2H,m), 7.39 (2H,d,J=8.8 Hz) 7.60 (1H,d,J=7.7 Hz), 7.75 (1H,d,J=2.9 Hz), 8.14 (1H,s), 8.18 (2H,d,J=8.8 Hz), 12.60 (1H,bs)

EXAMPLE 190

Synthesis of 5-[1-(4-aminobenzyl)indol-4-yl]-methyl-2,4-thiazolidinedione

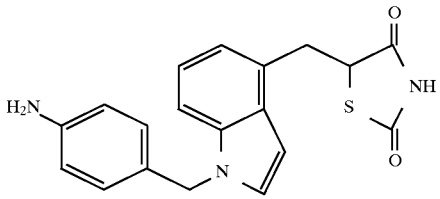

The same procedures used in Example 6 were repeated except for using 750 mg of 5-[1-(4-nitrobenzyl)indol-4-yl] methylene- 2,4-thiazolidinedione prepared in Example 189 to give 429 mg of 5-[1-(4-aminobenzyl)indol-4-yl]methyl-2,4-thiazolidinedione as colorless crystals. The yield thereof was found to be 62%.

IR (KBr) cm$^{-1}$: 1750, 1690, 1630, 1520, 1160, 750; NMR (DMSO-d$_6$) δ: 3.29 (1H,dd,J=14.3 Hz, 10.6 Hz), 3.69 (1H, dd, J=14.3 Hz, 4.0 Hz), 4.97 (1H,dd,J=10.6 Hz, 4.0 Hz), 5.17 (2H,s), 6.48 (2H,d,J=8.3 Hz), 6.52 (1H, d,J=2.9 Hz), 6.87 (1H,d,J=7.0 Hz), 6.96 (2H, d,J=8.3 Hz), 7.04 (1H,t,J=7.7 Hz), 7.3~7.4 (2H,m)

EXAMPLE 191

Synthesis of 1-[(1S, 5S, 2-pinen-10-yl)methyl]-indole-4-carbaldehyde

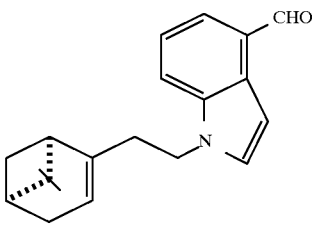

The same procedures used in Example 1 were repeated except for using 3.54 g of (1S, 5S, 2-pinen-10-yl)methyl methanesulfonate and 2.00 g of indole-4-carbaldehyde as a starting material to give 3.20 g of 1-[(1S, 5S, 2-pinen-10-yl)methyl]indole-4-carbaldehyde as a pale yellow oily substance. The yield thereof was found to be 79%.

NMR (CDCl$_3$) δ: 0.84 (3H,s), 1.13 (1H,d,J=8.4 Hz), 1.30 (3,s), 2.08 (2H,d,J=5.5 Hz), 2.2~2.3 (2H,m), 2.3~2.6 (3H, m), 4.19 (2H,t,J=7.7 Hz), 5.2~5.3 (1H,m), 7.2~7.4 (3H,m), 7.6~7.7 (2H,m), 10.24 (1H, s)

EXAMPLE 192

Synthesis of 5-{1-[(1S, 5S, 2-pinen-10-yl)methyl]-indol-4-yl}methylene-2,4-thiazolidinedione

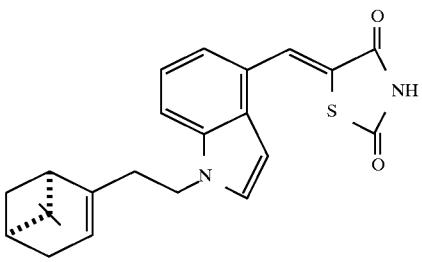

The same procedures used in Example 2 were repeated except for using 3.10 g of 1-[(1S, 5S, 2-pinen-10-yl)methyl] indole-4-carbaldehyde prepared in Example 191 to give 3.02 g of 5-{1-[(1S, 5S, 2-pinen-10-yl) methyl]indol-4-yl}methylene-2,4-thiazolidinedione as yellow crystals. The yield thereof was found to be 73%.

IR (KBr) cm$^{-1}$: 1740, 1680, 1590, 1330, 1290, 1160, 750; NMR (DMSO-d$_6$) δ: 0.76 (3H,s), 1.00 (1H,d,J=8.4 Hz), 1.26 (3H, s), 2.0~2.2 (4H,m), 2.3~2.5 (3H,m), 4.24 (2H,t,J=7.3 Hz), 5.2~5.3 (1H,m), 6.71 (1H, d,J=2.9 Hz), 7.20 (1H,d,J=7.7 Hz), 7.30 (1H,t,J=7.7 Hz), 7.56 (1H,d,J=2.9 Hz), 7.63 (1H,d,J=7.7 Hz), 8.12 (1H,s), 12.55 (1H,bs)

EXAMPLE 193

Synthesis of 5-{1-[(1S, 5S, 2-pinen-10-yl)methyl]-indol-4-yl}methyl-2,4-thiazolidinedione

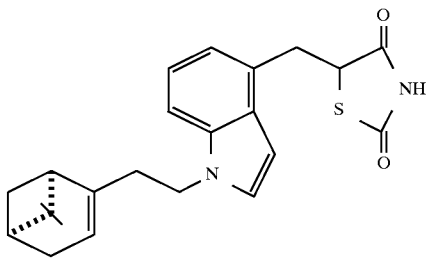

The same procedures used in Example 3 were repeated except for using 3.00 g of 5-{1-[(1S, 5S, 2-pinen-10-yl)methyl]indol-4-yl}methylene-2,4-thiazolidinedione prepared in Example 192 to give 2.98 g of 5-{1-[(1S, 5S, 2-pinen-10-yl)methyl]indol-4-yl}methyl-2,4-thiazolidinedione as a yellow amorphous substance. The yield thereof was found to be 99%.

IR (KBr) cm$^{-1}$: 1750, 1700, 1440, 1330, 1300, 1160, 750; NMR (DMSO-d$_6$) δ: 0.77 (3H,s), 1.06 (1H,d,J=8.4 Hz), 1.26 (3H,s), 2.0~2.2 (4H,m), 2.3~2.5 (3H,m), 3.2~3.3 (1H,m), 3.68 (1H,dd,J=14.1 Hz, 4.0 Hz), 4.17 (2H,t,J=7.5 Hz), 4.97 (1H,dd,J=10.3 Hz, 4.0 Hz), 5.2~5.3 (1H,m), 6.50 (1H,d,J=2.9 Hz), 6.88 (1H,d,J=7.0 Hz), 7.08 (1H,t,J=7.6 Hz), 7.3~7.4 (2H,m), 12.04 (1H,bs)

EXAMPLE 194

Synthesis of 1-(2,4-dimethoxybenzyl)indole-4-carbaldehyde

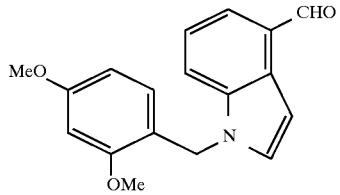

The same procedures used in Example 1 were repeated except for using 2.03 g of 2,4-dimethoxybenzyl methanesulfonate and 2.00 g of indole-4-carbaldehyde as a starting material to give 602 mg of 1-(2,4-dimethoxybenzyl)indole-4-carbaldehyde as a yellow oily substance. The yield thereof was found to be 15%.

NMR (CDCl$_3$) δ: 3.72 (3H,s), 3.82 (3H,s), 5.28 (2H,s), 6.3~6.5 (2H,m), 7.2~7.4 (4H,m), 7.6~7.7 (2H,m), 10.24 (1H,s)

EXAMPLE 195

Synthesis of 5-[1-(2,4-dimethoxybenzyl)indol-4-yl]methylene-2,4-thiazolidinedione

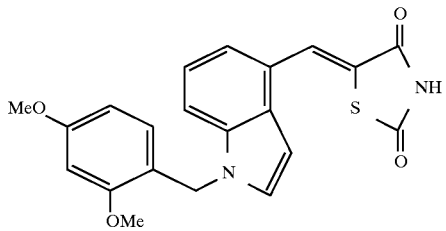

The same procedures used in Example 2 were repeated except for using 550 mg of 1-(2,4-dimethoxybenzyl)indole-4-carbaldehyde prepared in Example 194 to give 173 mg of 5-[1-(2,4-dimethoxybenzyl)indol-4-yl]methylene-2,4-thiazolidinedione as yellow crystals. The yield thereof was found to be 24%.

IR (KBr) cm$^{-1}$: 1730, 1690, 1590, 1510, 1330, 1290, 750; NMR (DMSO-d$_6$) δ: 3.71 (3H,s), 3.82 (3H,s), 5.31 (2H,s), 6.43 (1H,dd,J=8.1 Hz, 2.2 Hz), 6.58 (1H,d,J=2.2 Hz), 6.73 (1H,d,J=2.9 Hz), 6.93 (1H,d,J=8.4 Hz), 7.2~7.3 (2H,m), 7.56 (1H,d,J=2.9 Hz), 7.65 (1H,d,J=8.1 Hz), 8.12 (1H,s), 12.56 (1H,bs)

EXAMPLE 196

Synthesis of 5-[1-(2,4-dimethoxybenzyl)indol-4-yl]methyl-2,4-thiazolidinedione

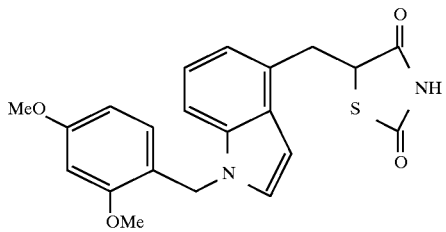

The same procedures used in Example 6 were repeated except for using 160 mg of 5-[1-(2,4-dimethoxybenzyl)indol-4-yl]methylene-2,4-thiazolidinedione prepared in Example 195 to give 45.2 mg of 5-[1-(2,4-dimethoxybenzyl)indol-4-yl]methyl-2,4-thiazolidinedione as a yellow amorphous substance. The yield thereof was found to be 28%.

IR (KBr) cm$^{-1}$: 1750, 1700, 1610, 1510, 1200, 1160, 750; NMR (CDCl$_3$) δ: 3.26 (1H,dd,J=14.1 Hz, 11.0 Hz), 3.76 (3H,s), 3.84 (3H,s), 3.98 (1H,dd,J=14.1 Hz, 3.7 Hz), 4.73 (1H,dd,J=11.0 Hz, 3.7 Hz), 5.24 (2H,s), 6.36 (1H,dd,J=8.4 Hz, 2.6 Hz), 6.47 (1H,d,J=2.2 Hz), 6.55 (1H,d,J=2.9 Hz)6.77 (1H,d,J=8.4 Hz), 6.94 (1H, d,J=7.0 Hz), 7.1~7.4 (3H,m)

EXAMPLE 197

Synthesis of 1-(1S, 5S, 2-pinen-10-yl)indole-4-carbaldehyde

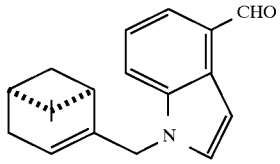

The same procedures used in Example 1 were repeated except for using 4.45 g of (1S, 5S, 2-pinen-10-yl) bromide and 2.00 g of indole-4-carbaldehyde as a starting material to give 1.76 g of 1-(1S, 5S, 2-pinen-10-yl)indole-4-carbaldehyde as a yellow oily substance. The yield thereof was found to be 46%.

NMR (CDCl$_3$) δ: 0.73 (3H,s), 1.12 (1H,d, J=8.8 Hz), 1.20 (3H,s), 1.9~2.0 (1H,m), 2.0~2.2 (1H,m), 2.2~2.4 (3H,m), 4.6~4.7 (2H,m), 5.2~5.4 (1H,m), 7.2~7.4 (3H,m), 7.5~7.7 (2H,m), 10.24 (1H,s)

EXAMPLE 198

Synthesis of 5-[1-(1S, 5S, 2-pinen-10-yl)indol-4-yl]methylene-2,4-thiazolidinedione

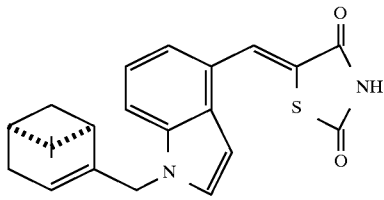

The same procedures used in Example 2 were repeated except for using 1.75 g of 1-(1S, 5S, 2-pinen-10-yl)indole-4-carbaldehyde prepared in Example 197 to give 1.47 g of 5-[1-(1S, 5S, 2-pinen-10-yl)indol-4-yl]methylene-2,4-thiazolidinedione as yellow crystals. The yield thereof was found to be 62%.

IR (KBr) cm$^{-1}$: 1740, 1680, 1590, 1330, 1290, 750; NMR (DMSO-d$_6$) δ: 0.60 (3H,s), 1.02 (1H,d,J=8.4 Hz), 1.15 (3H, s), 1.9~2.1 (2H,m), 2.1~2.4 (3H,m), 4.76 (2H,s), 5.3~5.4 (1H,m), 6.73 (1H,d,J=2.9 Hz), 7.20 (1H,d,J=7.7 Hz), 7.29 (1H,t,J=7.7 Hz), 7.51 (1H,d,J=2.9 Hz), 7.60 (1H,d,J=7.7 Hz), 8.13 (1H,s), 12.56 (1H,bs)

EXAMPLE 199

Synthesis of 5-[1-(1S, 5S, 2-pinen-10-yl)indol-4-yl]methyl-2,4-thiazolidinedione

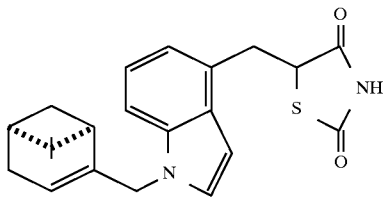

The same procedures used in Example 3 were repeated except for using 1.45 g of 5-[1-(1S, 5S, 2-pinen-10-yl)indol-4-yl]methylene-2,4-thiazolidinedione prepared in Example 198 to give 1.44 g of 5-[1-(1S, 5S, 2-pinen-10-yl)indol-4-yl]methyl-2,4-thiazolidinedione as a yellow amorphous substance. The yield thereof was found to be 99%.

IR (KBr) cm$^{-1}$: 1750, 1700, 1440, 1330, 1300, 1160, 750; NMR (DMSO-d$_6$) δ: 0.61 (3H,s), 1.03 (1H,d,J=8.4 Hz), 1.15 (3H, s), 1.9~2.1 (2H,m), 2.1~2.3 (3H,m), 3.2~3.4 (1H,m), 3.6~3.8 (1H,m), 4.68 (2H,s), 4.98 (1H,dd,J=10.4 Hz, 4.0 Hz), 5.2~5.4 (1H, m), 6.51 (1H,d,J=3.3 Hz), 6.87 (1H,d,J=7.0 Hz), 7.06 (1H,t,J=7.7 Hz), 7.2~7.4 (2H,m), 12.05 (1H, bs)

EXAMPLE 200

Synthesis of 1-(2-benzodioxanylmethyl)indole-4-carbaldehyde

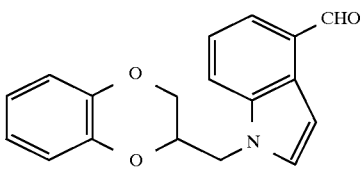

The same procedures used in Example 1 were repeated except for using 870 mg of indole-4-carbaldehyde and 2-benzodioxanylmethyl methanesulfonate instead of the benzyl bromide used in Example 1 to give 699 mg of 1-(2-benzodioxanylmethyl)indole-4-carbaldehyde as a pale yellow oily substance. The yield thereof was found to be 40%.

NMR (CDCl$_3$) δ: 3.87 (1H,dd,J=11.3 Hz, 5.1 Hz), 4.20 (1H,dd,J=11.3 Hz, 2.2 Hz), 4.3~4.6 (3H,m), 6.88 (4H,s), 7.3~7.5 (3H,m), 7.65 (2H,d), 10.25 (1H,s)

EXAMPLE 201

Synthesis of 5-[1-(2-benzodioxanylmethyl)indol-4-yl]methylene-2,4-thiazolidinedione

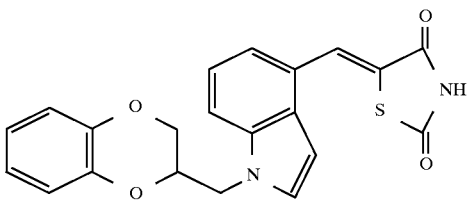

The same procedures used in Example 2 were repeated except for using 660 mg of 1-(2-benzodioxanylmethyl)indole-4-carbaldehyde prepared in Example 200 to give 616 mg of 5-[1-(2-benzodioxanylmethyl)indol-4-yl]methylene-2,4-thiazolidinedione as orange-colored crystals. The yield thereof was found to be 70%.

IR (KBr) cm$^{-1}$: 1740, 1680, 1590, 1490; NMR (DMSO-d$_6$) δ: 3.91 (1H,dd,J=11.3 Hz, 5.8 Hz), 4.36 (1H,dd, J=11.3 Hz, 1.8 Hz), 4.4~4.7 (3H,m), 6.7~7.0 (5H,m), 7.2~7.4 (2H,m), 7.56 (1H,d,J=2.9 Hz), 7.72 (1H,d,J=8.1 Hz), 8.14 (1H,s), 12.58 (1H,bs)

EXAMPLE 202

Synthesis of 5-[1-(2-benzodioxanylmethyl)indol-4-yl]methyl-2,4-thiazolidinedione

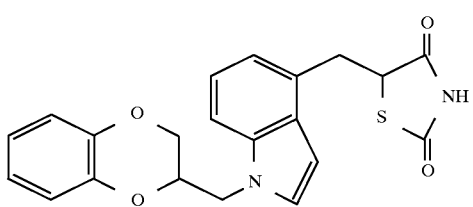

The same procedures used in Example 6 were repeated except for using 571 mg of 5-[1-(2-benzodioxanylmethyl) indol-4-yl]methylene-2,4-thiazolidinedione prepared in Example 201 to give 494 mg of 5-[1-(2-benzodioxanylmethyl)indol-4-yl]methyl-2,4-thiazolidinedione as colorless crystals. The yield thereof was found to be 86%.

IR (KBr) $cm^{-1}$: 1750, 1680, 1450, 1270; NMR (DMSO-$d_6$) δ: 3.32 (1H,dd,J=14.2 Hz, 10.2 Hz), 3.70 (1H, dd, J=14.2 Hz, 4.0 Hz), 3.90 (1H,dd,J=11.3 Hz, 5.8 Hz), 4.3~4.6 (4H,m), 4.99 (1H,dd,J=10.2 Hz, 4.0 Hz), 6.58 (1H,d,J=3.3 Hz), 6.7~7.0 (5H,m), 7.11 (1H,dd,J=8.0 Hz, 8.0 Hz), 7.38 (1H,d,J=3.3 Hz), 7.45 (1H,d,J=8.0 Hz), 12.06 (1H,bs)

EXAMPLE 203

Synthesis of 1-(2-methyl-2-hepten-6-yl)indole-4-carbaldehyde

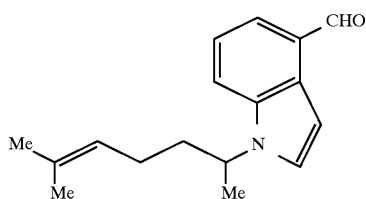

The same procedures used in Example 1 were repeated except for using 1.02 g of indole-4-carbaldehyde and (2-methyl-2-hepten-6-yl) methanesulfonate instead of the benzyl bromide used in Example 1 to give 1.36 g of 1-(2-methyl-2-hepten-6-yl)indole-4-carbaldehyde as a yellow oily substance. The yield thereof was found to be 76%.

NMR (CDCl$_3$) δ:1.33 (3H,s), 1.52 (3H,d,J=6.6 Hz), 1.64 (3H,s), 1.8~2.1 (4H,m), 4.54 (1H,bq), 5.02 (1H,bt), 7.2~7.4 (3H,m), 7.5~7.7 (2H,m), 10.25 (1H,s)

EXAMPLE 204

Synthesis of 5-[1-(2-methyl-2-hepten-6-yl)indol-4-yl]methylene-2,4-thiazolidinedione

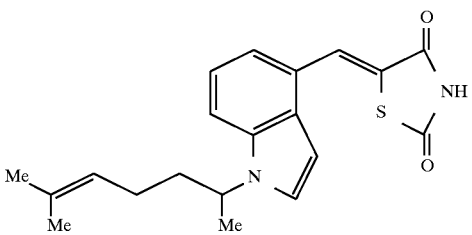

The same procedures used in Example 2 were repeated except for using 1.28 g of 1-(2-methyl-2-hepten-6-yl)indole-4-carbaldehyde prepared in Example 203 to give 1.21 g of 5-[1-(2-methyl-2-hepten-6-yl) indol-4-yl]methylene-2,4-thiazolidinedione as yellow crystals. The yield thereof was found to be 68%.

IR (KBr) $cm^{-1}$: 1740, 1680, 1580, 1320; NMR (DMSO-$d_6$) δ: 1.28 (3H,s), 1.46 (3H,d,J=6.6 Hz), 1.58 (3H, s), 1.6~2.0 (4H,m), 4.62 (1H,bq), 5.04 (1H,bt), 6.78 (1H,d,J= 2.9 Hz), 7.2~7.4 (2H,m), 7.6~7.8 (2H,m), 8.14 (1H,s), 12.57 (1H,bs)

EXAMPLE 205

Synthesis of 5-[1-(2-methyl-2-hepten-6-yl)indol-4-yl]methyl-2,4-thiazolidinedione

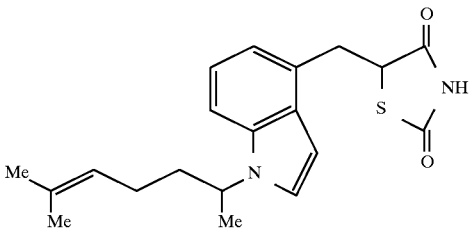

The same procedures used in Example 3 were repeated except for using 600 mg of 5-[1-(2-methyl-2-hepten-6-yl) indol-4-yl]methylene-2,4-thiazolidinedione prepared in Example 204 to give 492 mg of 5-[1-(2-methyl-2-hepten-6-yl)indol-4-yl]methyl-2,4-thiazolidinedione as an orange-colored oily substance. The yield thereof was found to be 82%.

IR (KBr) $cm^{-1}$: 1750, 1700, 1440, 1320; NMR (CDCl$_3$) δ: 1.35 (3H,s), 1.49, 1.50 (total 3H,d,J=6.6 Hz, d, J=6.6 Hz), 1.64 (3H,s), 1.7~2.1 (4H,m), 3.26 (1H,d,J=13.9 Hz, 11.0 Hz, 3.99 (1H,d,J=13.9 Hz, 3.6 Hz), 4.46 (1H,bq), 4.6~4.8 (1H, m), 5.08 (1H,bt), 6.59 (1H,d,J=3.3 Hz), 6.94 (1H,d,J=7.0 Hz), 7.1~7.3 (4H,m), 8.71 (1H,bs)

EXAMPLE 206

Synthesis of 1-(4S-p-mentha-1,8-dien-7-yl)indole-4-carbaldehyde

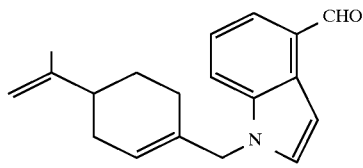

The same procedures used in Example 1 were repeated except for using 3.31 g of (4S-p-mentha-1,8-dien-7-yl) methanesulfonate and 2.00 g of indole-4-carbaldehyde as a starting material to give 1.46 g of 1-(4S-p-mentha-1,8-dien-7-yl)indole-4-carbaldehyde as a yellow oily substance. The yield thereof was found to be 38%.

NMR (CDCl$_3$) δ: 1.3~1.5 (1H,m), 1.26 (3H,s), 1.8~2.2 (6H,m), 4.6~4.7 (4H,m), 5.5~5.6 (1H,m), 7.2~7.4 (3H, m), 7.6~7.7 (2H,m), 10.25 (1H, s)

EXAMPLE 207

Synthesis of 5-[1-(4S-p-mentha-1,8-dien-7-yl)-indol-4-yl]methylene-2,4-thiazolidinedione

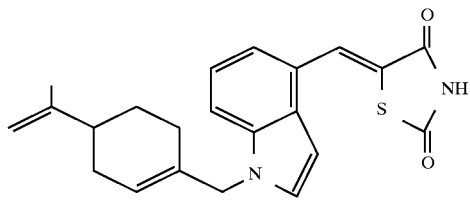

The same procedures used in Example 2 were repeated except for using 1.40 g of 1-(4S-p-mentha-1,8-dien-7-yl) indole-4-carbaldehyde prepared in Example 206 to give 0.97 g of 5-[1-(4S-p-mentha-1,8-dien-7-yl)indol-4-yl]methylene-2,4-thiazolidinedione as yellow crystals. The yield thereof was found to be 51%.

IR (KBr) cm$^{-1}$: 1740, 1690, 1590, 1330, 1290, 750; NMR (DMSO-d$_6$) δ: 1.2~1.4 (1H,m), 1.66 (3H,s), 1.7~2.2 (6H,m), 4.66 (2H,s), 4.77 (2H,s), 5.5~5.6 (1H,m), 6.74 (1H,d,J=2.9 Hz), 7.21 (1H,d,J=7.7 Hz), 7.30 (1H,t,J=7.7 Hz), 7.51 (1H, d,J=2.9 Hz), 7.61 (1H,d,J=7.7 Hz), 8.13 (1H,s), 12.55 (1H, bs)

EXAMPLE 208

Synthesis of 5-[1-(4S-p-mentha-1,8-dien-7-yl)-indol-4-yl]methyl-2,4-thiazolidinedione

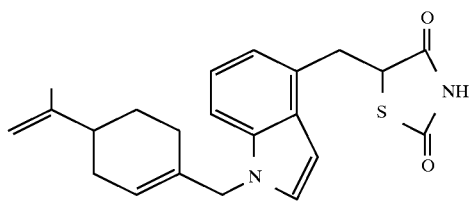

The same procedures used in Example 3 were repeated except for using 950 mg of 5-[1-(4S-p-mentha-1,8-dien-7-yl)indol-4-yl]methylene-2,4-thiazolidinedione prepared in Example 207 to give 950 mg of 5-[1-(4S-p-mentha-1,8-dien-7-yl)indol-4-yl]methyl-2,4-thiazolidinedione as yellow crystals. The yield thereof was found to be 100%.

IR (KBr) cm$^{-1}$: 1750, 1680, 1440, 1330, 1310, 1160, 750; NMR (DMSO-d$_6$) δ: 1.2~1.5 (1H,m), 1.66 (3H,s), 1.7~2.1 (6 H,m), 3.2~3.4 (1H,m), 3.70(1H,dd,J=14.1 Hz, 4.0 Hz) , 4.67 (4H,s), 4.98 (1H,dd,J=10.3 Hz, 4.0 Hz), 5.5~5.6 (1H, m), 6.53 (1H,d,J=2.9 Hz), 6.88 (1H,d,J=7.0 Hz), 7.07 (1H, t,J=7.7 Hz), 7.2~7.4 (2H,m), 12.06 (1H,bs)

EXAMPLE 209

Synthesis of 1-(1S, 2S, 5S-pinan-10-yl)indole-4-carbaldehyde

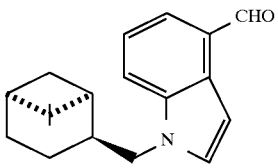

The same procedures used in Example 1 were repeated except for using 3.85 g of (1S, 2S, 5S-pinan-10-yl) methanesulfonate and 2.00 g of indole-4-carbaldehyde as a starting material to give 3.42 g of 1-(1S, 2S,5S-pinan-10-yl)indole-4-carbaldehyde as a yellow oily substance. The yield thereof was found to be 88%.

NMR (CDCl$_3$) δ: 0.77 (3H,s), 1.14 (3H,s), 1.3~1.9 (7H, m), 2.0~2.2 (1H,m), 2.4~2.6 (1H,m), 3.99 (2H,d,J=7.7 Hz), 7.2~7.4 (3H,m), 7.5~7.7 (2H,m), 10.25 (1H,s)

EXAMPLE 210

Synthesis of 5-[1-(1S, 2S, 5S-pinan-10-yl)indol-4-yl]methylene-2,4-thiazolidinedione

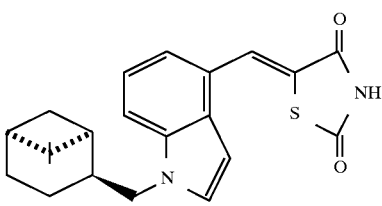

The same procedures used in Example 2 were repeated except for using 3.40 g of 1-(1S, 2S, 5S-pinan-10-yl)indole-4-carbaldehyde prepared in Example 209 to give 2.87 g of 5-[1-(1S, 2S, 5S-pinan-10-yl)indol-4-yl]methylene-2,4-thiazolidinedione as yellow crystals. The yield thereof was found to be 63%.

IR (KBr) cm$^{-1}$: 1740, 1680, 1600, 1330, 1280, 750; NMR (DMSO-d$_6$) δ: 0.73 (1H,s), 1.10 (3H,s), 1.2~1.8 (7H,m), 1.9~2.1 (1H,m), 2.3~2.5 (1H,m), 4.05 (2H,d,J=7.3 Hz), 6.71 (1H,d,J=2.9 Hz), 7.20 (1H,d,J=7.6 Hz), 7.30 (1H,t,J=7.6 Hz), 7.54 (1H,d,J=2.9 Hz), 7.61 (1H,d,J=7.6 Hz), 8.12 (1H,s), 12.56 (1H,bs)

EXAMPLE 211

Synthesis of 5-[1-(1S, 2S, 5S-pinan-10-yl)indol-4-yl]methyl-2,4-thiazolidinedione

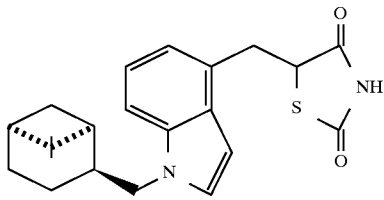

The same procedures used in Example 6 were repeated except for using 2.80 g of 5-[1-(1S, 2S, 5S-pinan-10-yl)indol-4-yl]methylene-2,4-thiazolidinedione prepared in Example 210 to give 2.62 g of 5-[1-(1S, 2S,5S-pinan-10-yl)indol-4-yl]methyl-2,4-thiazolidinedione as a colorless amorphous substance. The yield thereof was found to be 93%.

IR (KBr) cm$^{-1}$: 1750, 1700, 1690, 1340, 750; NMR (DMSO-d$_6$) δ: 0.74 (3H,s), 1.11 (3H,s), 1.3~1.9 (8H,m), 1.9~2.1 (1H,m), 3.2~3.4 (1H,m), 3.69 (1H, dd,J=14.3 Hz, 4.0 Hz), 3.98 (2H,d,J=7.7 Hz), 4.98 (1H,dd, J=10.3 Hz, 4.0 Hz), 6.49 (1H,d,J=2.9 Hz), 6.87 (1H,d,J=7.3 Hz), 7.0~7.2 (1H,m), 7.33 (1H,d,J=8.1 Hz), 7.34 (1H,d,J=2.9 Hz), 12.05 (1H,bs)

EXAMPLE 212

Synthesis of 1-[3,5-bis(trifluoromethyl)benzyl]-indole-4-carbaldehyde

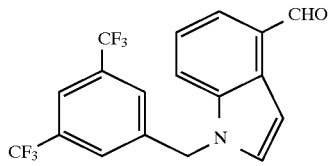

The same procedures used in Example 1 were repeated except for using 4.80 g of [3,5-bis(trifluoromethyl)benzyl] methanesulfonate and 2.00 g of indole-4-carbaldehyde as a starting material to give 4.24 g of 1-[3,5-bis(trifluoromethyl) benzyl]indole-4-carbaldehyde as pale yellow crystals. The yield thereof was found to be 83%.

NMR (CDCl$_3$) δ: 5.51 (2H,s), 7.2~7.6 (6H,m), 7.6~7.7 (1H,m), 7.81 (1H,s), 10.27 (1H,s)

EXAMPLE 213

Synthesis of 5-{1-[3,5-bis(trifluoromethyl)-benzyl]indol-4-yl}methylene-2,4-thiazolidinedione

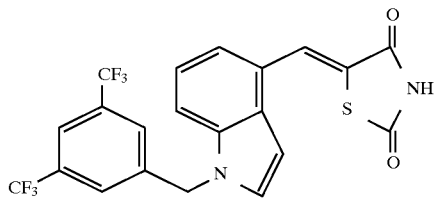

The same procedures used in Example 2 were repeated except for using 4.20 g of 1-[3,5-bis(trifluoromethyl)benzyl] indole-4-carbaldehyde prepared in Example 212 to give 3.33 g of 5-{1-[3,5-bis(trifluoromethyl)benzyl]indol-4-yl}methylene-2,4-thiazolidinedione as yellow crystals. The yield thereof was found to be 63%.

IR (KBr) cm$^{-1}$: 1740, 1690, 1330, 1280, 1170, 1130; NMR (DMSO-d$_6$) δ: 5.71 (2H,s), 6.86 (1H,d,J=3.3 Hz), 7.23 (1H, d,J=7.7 Hz), 7.32 (1H,t,J=7.7 Hz), 7.73 (1H,d,J=7.7 Hz), 7.83 (1H,d,J=3.3 Hz), 7.93 (2H,s), 8.02 (1H,s), 8.14 (1H,s), 12.58 (1H,bs)

EXAMPLE 214

Synthesis of 5-{1-[3,5-bis(trifluoromethyl)-benzyl]indol-4-yl}methyl-2,4-thiazolidinedione

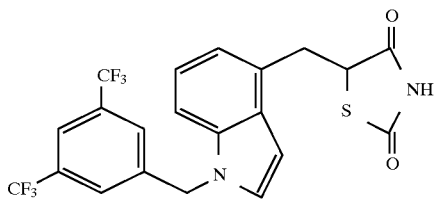

The same procedures used in Example 6 were repeated except for using 3.30 g of 5-{1-[3,5-bis(trifluoromethyl) benzyl]indol-4-yl}methylene-2,4-thiazolidinedione prepared in Example 213 to give 3.31 g of 5-{1-[3,5-bis(trifluoromethyl)benzyl]indol-4-yl}methyl-2,4-thiazolidinedione as colorless crystals. The yield thereof was found to be 100%.

IR (KBr) cm$^{-1}$: 1750, 1690, 1280, 1170, 1130, 750; NMR (DMSO-d$_6$) δ: 3.2~3.4 (1H,m), 3.71 (1H,dd,J=14.3 Hz, 4.0 Hz), 5.00 (1H,dd,J=10.3 Hz, 4.0 Hz), 5.65 (2H,s), 6.66 (1H,d,J=3.3 Hz), 6.92 (1H,d,J=7.7 Hz), 7.09 (1H,t,J=7.7 Hz), 7.46 (1H,d,J=7.7 Hz), 7.69 (1H,d,J=3.3 Hz), 7.89 (2H,s), 8.01 (1H, s), 12.07 (1H,bs)

EXAMPLE 215

Synthesis of 1-(3-methyl-2-butenyl)indole-4-carbaldehyde

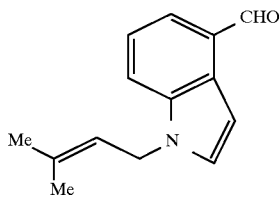

The same procedures used in Example 1 were repeated except for using 725 mg of indole-4-carbaldehyde and 1-chloro-3-methyl-2-butene instead of the benzyl bromide used in Example 1 to give 554 mg of 1-(3-methyl-2-butenyl) indole-4-carbaldehyde as an orange-colored oily substance. The yield thereof was found to be 52%.

NMR (CDCl$_3$) δ: 1.78 (6H,s), 5.15 (1H,d,J=17.6 Hz), 5.25 (1H,d,J=10.6 Hz), 6.15 (1H,dd,J=17.6 Hz, 10.6 Hz), 7.2~7.4 (2H,m), 7.50 (1H,d,J=3.3 Hz), 7.59 (1H,d,J=7.3 Hz), 7.81 (1H,d,J=8.4 Hz), 10.23 (1H,s)

EXAMPLE 216

Synthesis of 5-[1-(3-methyl-2-butenyl)indol-4-yl]methylene-2,4-thiazolidinedione

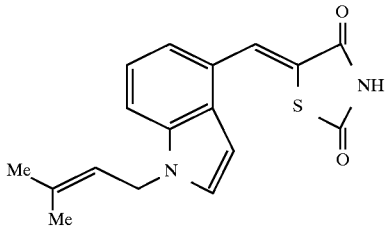

The same procedures used in Example 2 were repeated except for using 426 mg of 1-(3-methyl-2-butenyl)indole-4-carbaldehyde prepared in Example 215 to give 387 mg of 5-[1-(3-methyl-2-butenyl)indol-4-yl]methylene-2,4-thiazolidinedione as orange-colored crystals. The yield thereof was found to be 62%.

IR (KBr) cm$^{-1}$: 1730, 1680, 1580, 1270; NMR (DMSO-d$_6$) δ: 1.78 (6H,s), 5.14 (1H,d,J=17.5 Hz), 5.23 (1H,d,J=10.6 Hz), 6.15 (1H,dd,J=17.5 Hz, 10.6 Hz), 6.73 (1H,d,J=3.3 Hz), 7.1~7.3 (2H,m), 7.5~7.7 (2H,m), 8.07 (1H,s)

EXAMPLE 217

Synthesis of 5-[1-(3-methyl-2-butenyl)indol-4-yl]methyl-2,4-thiazolidinedione

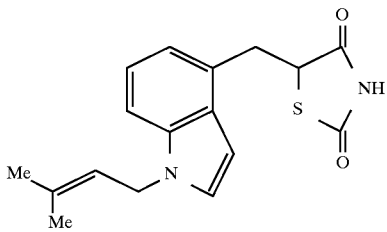

The same procedures used in Example 3 were repeated except for using 312 mg of 5-[1-(3-methyl-2-butenyl)indol-4-yl]methylene-2,4-thiazolidinedione prepared in Example 216 to give 226 mg of 5-[1-(3-methyl-2-butenyl)indol-4-yl]methyl-2,4-thiazolidinedione as a pale yellow amorphous substance. The yield thereof was found to be 72%.

IR (KBr) cm$^{-1}$: 1750, 1700, 1440, 1320; NMR (CDCl$_3$) δ: 1.76 (6H,s), 3.25 (1H,dd,J=13.9 Hz, 11.4 Hz), 3.99 (1H,dd,J=13.9 Hz, 3.7 Hz), 4.73 (1H,dd,J=11.4 Hz, 3.7 Hz), 5.17 (1H,d,J=17.6 Hz), 5.23 (1H,d,J=10.6 Hz), 6.15 (1H,dd,J=17.6 Hz, 10.6 Hz), 6.55 (1H,d,J=3.5 Hz), 6.93 (1H,d, J=7.0 Hz), 7.07 (1H,dd,J=8.0 Hz, 7.0 Hz), 7.35 (1H,d,J=3.5 Hz), 7.48 (1H,d,J=8.0 Hz)8.34 (1H,bs)

EXAMPLE 218

Synthesis of (2-bromobenzyl)indole-4-carbaldehyde

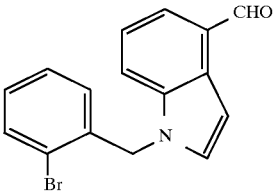

The same procedures used in Example 1 were repeated except for using 3.78 g of o-bromobenzyl bromide and 2.00 g of indole-4-carbaldehyde as a starting material to give 4.18 g of (2-bromobenzyl) indole-4-carbaldehyde as pale yellow crystals. The yield thereof was found to be 97%.

NMR (CDCl$_3$) δ: 5.45 (2H,s), 6.4~6.6 (1H,m), 7.1~7.2 (2H,m), 7.2~7.4 (3H,m), 7.5~7.7 (3H,m), 10.27 (1H,s)

EXAMPLE 219

Synthesis of 5-[1-(2-bromobenzyl)indol-4-yl]-methylene-2,4-thiazolidinedione

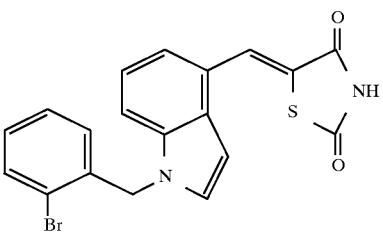

The same procedures used in Example 2 were repeated except for using 4.10 g of (2-bromobenzyl)indole-4-carbaldehyde prepared in Example 218 to give 4.51 g of 5-[1-(2-bromobenzyl)indol-4-yl]methylene-2,4-thiazolidinedione as yellow crystals. The yield thereof was found to be 84%.

IR (KBr) cm$^{-1}$: 1740, 1680, 1330, 1290, 750; NMR (DMSO-d$_6$) δ: 5.55 (2H,s), 6.5~6.6 (1H,m), 6.85 (1H,d,J= 3.3 Hz), 7.1~7.3 (4H,m), 7.55 (1H,d,J=7.3 Hz), 7.6~7.8 (2H,m), 8.16 (1H,s), 12.60 (1H,bs)

EXAMPLE 220

Synthesis of 5-[1-(2-bromobenzyl)indol-4-yl]-methyl-2,4-thiazolidinedione

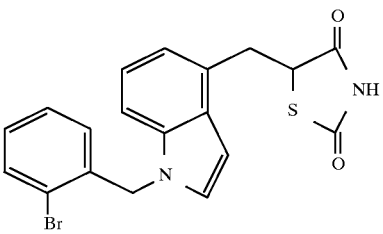

The same procedures used in Example 3 were repeated except for using 4.50 g of 5-[1-(2-bromobenzyl)indol-4-yl]methylene-2,4-thiazolidinedione prepared in Example 219 to give 2.74 g of 5-[1-( 2-bromobenzyl)indol-4-yl]methyl- 2,4-thiazolidinedione as yellow crystals. The yield thereof was found to be 61%.

IR (KBr) cm$^{-1}$: 1750, 1690, 1330, 1160, 750; NMR (DMSO-d$_6$) δ: 3.2~3.4 (1H,m), 3.6~3.8 (1H,m), 4.9~5.1 (1H,m), 5.47 (2H,s), 6.5~6.6 (1H,m), 6.64 (1H,d,J=2.9 Hz), 6.8~7.0 (1H,m), 7.0~7.4 (3H,m), 7.46 (1H,d,J=2.9 Hz), 7.6~7.7 (2H,m), 12.08 (1H,bs)

EXAMPLE 221

Synthesis of 1-(α-methylbenzyl)indole-3-carbaldehyde

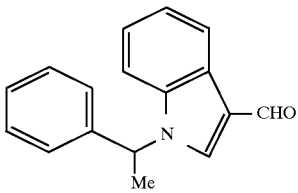

The same procedures used in Example 1 were repeated except for using 870 mg of indole-3-carbaldehyde and α-phenylethyl bromide in place of the benzyl bromide used in Example 1 to give 1.42 g of 1-(α-methylbenzyl)indole-3-carbaldehyde as an orange-colored oily substance. The yield thereof was found to be 95%.

NMR (CDCl$_3$) δ: 1.96 (3H,d,J=7.3 Hz), 5.69 (1H,q,J=7.3 Hz), 7.1~7.4 (8H,m), 7.88 (1H,s), 8.2~8.4 (1H,m), 10.03 (1H,s)

EXAMPLE 222

Synthesis of 5-[1-(α-methylbenzyl)indol-3-yl]-methylene-2,4-thiazolidinedione

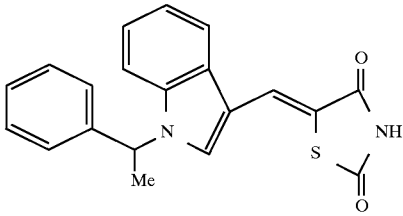

The same procedures used in Example 2 were repeated except for using 1.42 g of 1-(α-methylbenzyl)indole-3-carbaldehyde prepared in Example 221 to give 1.86 g of 5-[1-(α-methylbenzyl)indol-3-yl]methylene-2,4-thiazolidinedione as yellow crystals. The yield thereof was found to be 85%.

IR (KBr) cm$^{-1}$: 1740, 1680, 1590, 1520; NMR (DMSO-d$_6$) δ: 1.95 (3H,d,J=7.0 Hz), 5.99 (1H,q,J=7.0 Hz), 7.1~7.4 (7H,m), 7.4~7.6 (1H,m), 7.8~8.0 (1H,m), 7.85 (1H,s), 8.06 (1H,s), 12.31 (1H,bs)

EXAMPLE 223

Synthesis of 5-[1-(α-methylbenzyl)indol-3-yl]-methyl-2,4-thiazolidinedione

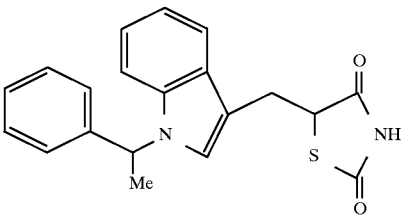

The same procedures used in Example 3 were repeated except for using 400 mg of 5-[1-(α-methylbenzyl)indol-3-yl]methylene-2,4-thiazolidinedione prepared in Example 222 to give 300 mg of 5-[1-(α-methylbenzyl)indol-3-yl] methyl-2,4-thiazolidinedione as a pale yellow amorphous substance. The yield thereof was found to be 74%.

IR (KBr) cm$^{-1}$: 1750, 1700, 1460, 1330; NMR (CDCl$_3$) δ: 1.90 (3H,d,J=7.3 Hz), 3.2~3.4 (1H,m), 3.6~3.8 (1H,m), 4.5~4.7 (1H,m), 5.64 (1H,q,J=7.3 Hz), 7.0~7.4 (9H,m), 7.5~7.7 (1H,m), 8.40 (1H,bs)

EXAMPLE 224

Synthesis of 1-(3,4-difluorobenzyl)indole-3-carbaldehyde

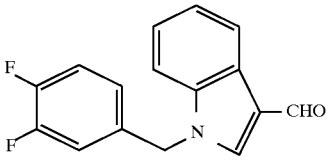

The same procedures used in Example 1 were repeated except for using 870 mg of indole-3-carbaldehyde and 3,4-difluorobenzyl bromide in place of the benzyl bromide used in Example 1 to give 1.59 g of 1-(3,4-difluorobenzyl) indole-3-carbaldehyde as pale brown crystals. The yield thereof was found to be 98%.

NMR (CDCl$_3$) δ: 5.33 (2H,s), 6.8~7.4 (6H,m), 7.72 (1H,s), 8.3~8.4 (1H,m), 10.03 (1H,s)

EXAMPLE 225

Synthesis of 5-[1-(3,4-difluorobenzyl)indol-3-yl] methylene-2,4-thiazolidinedione

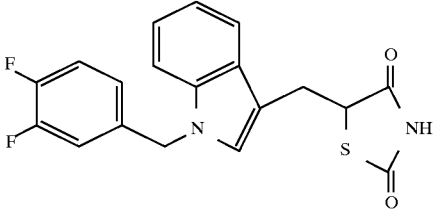

The same procedures used in Example 2 were repeated except for using 1.36 g of 1-(3,4-difluorobenzyl)indole-3-carbaldehyde prepared in Example 224 to give 1.74 g of 5-[1-(3,4-difluorobenzyl)indol-3-yl]methylene-2,4- thiazolidinedione as yellow crystals. The yield thereof was found to be 94%.

IR (KBr) cm$^{-1}$: 1740, 1680, 1600, 1520; NMR (DMSO-d$_6$) δ: 5.58 (2H,s), 7.0~7.5 (5H,m), 7.60 (1H,dd,J=6.9 Hz, 1.8 Hz), 7.93 (1H,dd,J=8.4 Hz, 1.8 Hz), 8.03 (1H,s), 8.04 (1H,s), 12.33 (1H,bs)

EXAMPLE 226

Synthesis of 5-[1-(3,4-difluorobenzyl)indol-3-yl]methyl-2,4-thiazolidinedione

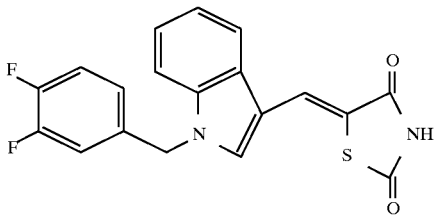

The same procedures used in Example 3 were repeated except for using 400 mg of 5-[1-(3,4-difluorobenzyl)indol-3-yl]methylene-2,4-thiazolidinedione prepared in Example 225 to give 220 mg of 5-[1-(3,4-difluorobenzyl)indol-3-yl]methyl-2,4-thiazolidinedione as pale yellow crystals. The yield thereof was found to be 55%.

IR (KBr) cm$^{-1}$: 1740, 1690, 1520, 1440; NMR (CDCl$_3$) δ: 3.34 (1H,dd,J=15.0 Hz, 9.1 Hz), 3.69 (1H,dd,J=15.0 Hz, 3.6 Hz), 4.64 (1H,dd,J=9.1 Hz, 3.6 Hz), 5.24 (2H,s), 6.7~7.0 (2H,m), 7.0~7.3 (5H,m), 7.5~7.7 (1H,m), 8.52 (1H,bs)

EXAMPLE 227

Synthesis of 1-(2-fluorobenzyl)indole-3-carbaldehyde

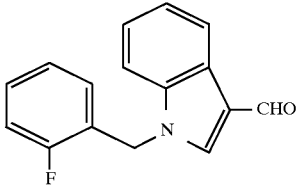

The same procedures used in Example 1 were repeated except for using 870 mg of indole-3-carbaldehyde and 2-fluorobenzyl bromide in place of the benzyl bromide used in Example 1 to give 1.46 g of 1-(2-fluorobenzyl)indole-3-carbaldehyde as yellowish brown crystals. The yield thereof was found to be 96%.

NMR (CDCl$_3$) δ: 5.40 (2H,s), 7.0~7.2 (3H,m), 7.2~7.5 (4H,m), 7.76 (1H,s), 8.2~8.4 (1H,m), 10.01 (1H,s)

EXAMPLE 228

Synthesis of 5-[1-(2-fluorobenzyl)indol-3-yl]-methylene-2,4-thiazolidinedione

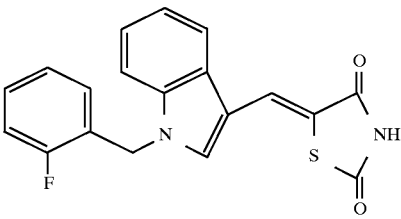

The same procedures used in Example 2 were repeated except for using 1.27 g of 1-(2-fluorobenzyl)indole-3-carbaldehyde prepared in Example 227 to give 1.65 g of 5-[1-(2-fluorobenzyl)indol-3-yl]methylene-2,4-thiazolidinedione as yellow crystals. The yield thereof was found to be 94%.

IR (KBr) cm$^{-1}$: 1740, 1680, 1600, 1520; NMR (DMSO-d$_6$) δ: 5.65 (2H,s), 7.0~7.4 (6H,m), 7.57 (1H,d, J=6.9 Hz), 7.8~8.0 (1H,m), 7.92 (1H,s), 8.05 (1H,s), 12.32 (1H,bs)

EXAMPLE 229

Synthesis of 5-[1-(2-fluorobenzyl)indol-3-yl]-methyl-2,4-thiazolidinedione

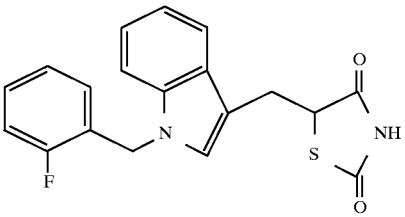

The same procedures used in Example 3 were repeated except for using 400 mg of 5-[1-(2-fluorobenzyl)indol-3-yl]methylene-2,4-thiazolidinedione prepared in Example 228 to give 244 mg of 5-[1-(2-fluorobenzyl)indol-3-yl]methyl-2,4-thiazolidinedione as pale yellow crystals. The yield thereof was found to be 61%.

IR (KBr) cm$^{-1}$: 1740, 1700, 1460, 1340; NMR (CDCl$_3$) δ: 3.33 (1H,dd,J=15.0 Hz, 9.5 Hz), 3.69 (1H,dd,J=15.0 Hz, 4.0 Hz), 4.64 (1H,dd,J=9.5 Hz, 4.0 Hz), 5.34 (2H,s), 6.7~6.9 (1H,m), 6.9~7.4 (7H,m), 7.63 (1H,dd,J=6.7 Hz, 1.4 Hz), 8.31 (1H,bs)

EXAMPLE 230

Synthesis of 1-[2-(trifluoromethyl)benzyl]indole-3-carbaldehyde

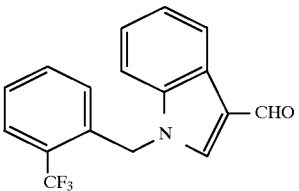

The same procedures used in Example 1 were repeated except for using 870 mg of indole-3-carbaldehyde and (2-trifluoromethyl)benzyl methanesulfonate instead of the benzyl bromide used in Example 1 to give 1.78 g of 1-[2-(trifluoromethyl)benzyl]indole-3-carbaldehyde as yellowish brown crystals. The yield thereof was found to be 97%.

NMR (CDCl$_3$) δ: 5.59 (2H,s), 6.6~6.8 (1H,m), 7.1~7.5 (5H,m), 7.7~7.9 (1H,m), 7.73 (1H,s), 8.36 (1H,dd,J=6.2 Hz, 2.6 Hz), 10.05 (1H,s)

EXAMPLE 231

Synthesis of 5-{1-[2-(trifluoromethyl)benzyl]-indol-3-yl}methylene-2,4-thiazolidinedione

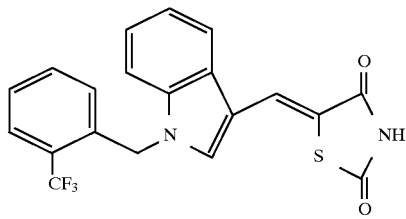

The same procedures used in Example 2 were repeated except for using 1.52 g of 1-[2-(trifluoromethyl)benzyl]indole-3-carbaldehyde prepared in Example 230 to give 1.81 g of 5-{1-[2-(trifluoromethyl) benzyl]indol-3-yl}methylene-2,4-thiazolidinedione as yellow crystals. The yield thereof was found to be 90%.

IR (KBr) cm$^{-1}$: 1730, 1680, 1590, 1310; NMR (DMSO-d$_6$) δ: 5.81 (2H,s), 6.5~6.7 (1H,m), 7.1~7.3 (3H,m), 7.4~7.6 (2H,m), 7.7~7.9 (1H,m), 7.9~8.1 (1H,m), 7.96 (1H,s), 8.09 (1H,s), 12.34 (1H,bs)

EXAMPLE 232

Synthesis of 5-{1-[2-(trifluoromethyl)benzyl]-indol-3-yl}methyl-2,4-thiazolidinedione

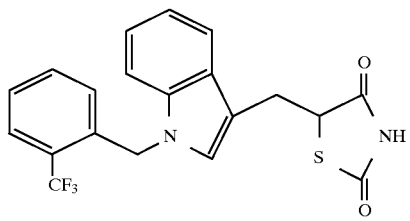

The same procedures used in Example 3 were repeated except for using 400 mg of 5-{1-[2-(trifluoromethyl)benzyl] indol-3-yl}methylene-2,4-thiazolidinedione prepared in Example 231 to give 242 mg of 5-{1-[2-(trifluoromethyl) benzyl]indol-3-yl}methyl-2,4-thiazolidinedione as pale yellow crystals. The yield thereof was found to be 60%.

IR (KBr) cm$^{-1}$: 1750, 1690, 1470, 1320; NMR (DMSO-d$_6$) δ: 3.31 (1H,dd,J=8.3 Hz, 7.0 Hz), 3.45 (1H,dd,J=7.0 Hz,4.3 Hz), 4.95 (1H,dd,J=8.3 Hz, 4.3 Hz), 5.61 (2H,s), 6.3~6.5 (1H,m), 7.0~7.2 (3H,m), 7.36 (1H,s), 7.4~7.6 (2H,m), 7.6~7.7 (1H,m), 7.7~7.8 (1H,m), 11.95 (1H,bs)

EXAMPLE 233

Synthesis of 1-(2-methoxybenzyl)indole-3-carbaldehyde

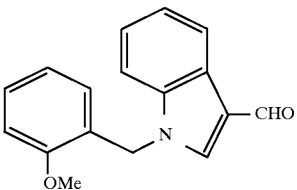

The same procedures used in Example 1 were repeated except for using 870 mg of indole-3-carbaldehyde and 2-methoxybenzyl methanesulfonate in place of the benzyl bromide used in Example 1 to give 926 mg of 1-(2-methoxybenzyl)indole-3-carbaldehyde as pale yellow crystals. The yield thereof was found to be 58%.

NMR (CDCl$_3$) δ: 3.86 (3H,s), 5.34 (2H,s), 6.8~7.0 (3H, m), 7.2~7.5 (4H,m), 7.72 (1H,s), 8.2~8.4 (1H,m), 9.98 (1H,s)

EXAMPLE 234

Synthesis of 5-[1-(2-methoxybenzyl) indol-3-yl]-methylene-2,4-thiazolidinedione

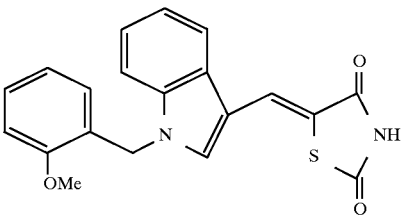

The same procedures used in Example 2 were repeated except for using 795 mg of 1-(2-methoxybenzyl)indole-3-carbaldehyde prepared in Example 233 to give 1.04 g of 5-[1-(2-methoxybenzyl)indol-3-yl]methylene-2,4-thiazolidinedione as yellow crystals. The yield thereof was found to be 95%.

IR (KBr) cm$^{-1}$: 1740, 1680, 1600, 1320; NMR (DMSO-d$_6$) δ: 3.87 (3H,s), 5.50 (2H,s), 6.88 (1H,dd, J=7.4 Hz, 7.4 Hz), 7.06 (1H,dd,J=7.4 Hz, 2.6 Hz), 7.1~7.4 (3H,m), 7.59 (1H,dd,J=7.0 Hz, 1.6 Hz), 7.85 (1H,s), 7.90 (1H,dd,J=7.0 Hz, 2.0 Hz), 8.04 (1H,s), 12.31 (1H,bs)

EXAMPLE 235

Synthesis of 5-[1-(2-methoxybenzyl)indol-3-yl]-methyl-2,4-thiazolidinedione

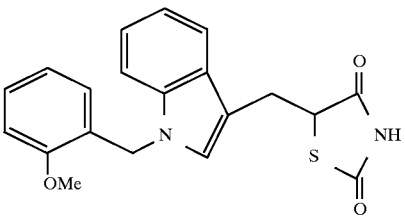

The same procedures used in Example 3 were repeated except for using 400 mg of 5-[1-(2-methoxybenzyl)indol- 3-yl]methylene-2,4-thiazolidinedione prepared in Example 234 to give 320 mg of 5-[1-(2-methoxybenzyl)indol-3-yl]methyl-2,4-thiazolidinedione as yellow crystals. The yield thereof was found to be 80%.

IR (KBr) cm$^{-1}$: 1740, 1700, 1460, 1340; NMR (DMSO-d$_6$) δ: 3.34 (1H,dd,J=8.3 Hz, 7.0 Hz), 3.45 (1H,dd,J=7.0 Hz, 4.3 Hz), 3.86 (3H,s), 4.92 (1H,dd,J=8.3 Hz, 4.3 Hz), 5.31 (2H,s), 6.66 (1H, d,J=7.3 Hz), 6.79 (1H,dd,J=7.3 Hz, 7.3 Hz), 6.9~7.2 (3H,m), 7.2~7.3 (1H,m), 7.29 (1H,s), 7.37 (1H,d,J=7.3 Hz), 7.57 (1H,d,J=7.3 Hz), 11.94 (1H,bs)

EXAMPLE 236

Synthesis of 1-(1S, 5S, 2-pinen-10-yl)indole-3-carbaldehyde

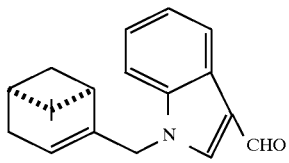

The same procedures used in Example 1 were repeated except for using 3.50 g of (1S, 5S, 2-pinen-10-yl) methanesulfonate and 2.00 g of indole-3-carbaldehyde as a starting material to give 3.06 g of 1-(1S, 5S, 2-pinen-10-yl)indole-3-carbaldehyde as pale yellow crystals. The yield thereof was found to be 80%.

NMR (CDCl$_3$) δ: 0.77 (3H,s), 1.17 (1H,d,J=8.8 Hz), 1.24 (3H,s), 2.0~2.2 (2H,m), 2.2~2.5 (3H,m), 4.6~4.7 (2H,m), 5.4~5.5 (1H,m), 7.2~7.4 (3H,m), 7.71 (1H,s), 8.2~8.4 (1H,m), 10.01 (1H,s)

EXAMPLE 237

Synthesis of 5-[1-(1S, 5S, 2-pinen-10-yl)indol-3-yl]methylene-2,4-thiazolidinedione

The same procedures used in Example 2 were repeated except for using 3.00 g of 1-(1S, 5S, 2-pinen-10-yl)indole-3-carbaldehyde prepared in Example 236 to give 2.56 g of 5-[1-(1S, 5S, 2-pinen-10-yl)indol-3-yl]methylene-2,4-thiazolidinedione as yellow crystals. The yield thereof was found to be 63%.

IR (KBr) cm$^{-1}$: 1720, 1670, 1590, 1340, 1320, 1190, 1160; NMR (DMSO-d$_6$) δ: 0.60 (3 H,s), 1.04 (1H,d,J=8.8 Hz), 1.15 (3H,s), 1.9~2.1 (2H,m), 2.2~2.4 (3H,m), 4.87 (2H,s) , 5.4~5.5 (1H,m) , 7.1~7.4 (2H,m), 7.57 (1H,d,J=7.7 Hz), 7.75 (1H,s), 7.90 (1H,d,J=7.0 Hz), 8.03 (1H,s), 12.31 (1H,bs)

EXAMPLE 238

Synthesis of 5-[1-(1S, 5S, 2-pinen-10-yl)indol-3-yl]methyl-2,4-thiazolidinedione

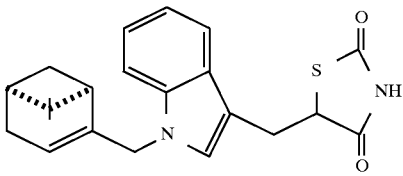

The same procedures used in Example 3 were repeated except for using 2.50 g of 5-[1-(1S, 5S, 2-pinen-10-yl)indol-3-yl]methylene-2,4-thiazolidinedione prepared in Example 237 to give 2.10 g of 5-[1-(1S, 5S, 2-pinen-10-yl)indol-3-yl]methyl-2,4-thiazolidinedione as a yellow amorphous substance. The yield thereof was found to be 83%.

IR (KBr) cm$^{-1}$: 1750, 1690, 1460, 1330, 1150, 740; NMR (DMSO-d$_6$) δ: 0.5~0.7 (3H,m), 1.0~1.1 (1H,m), 1.16 (3H,s), 1.9~2.1 (2H,m), 2.1~2.4 (3H,m), 3.2~3.5 (2H,m), 4.64 (2H,s), 4.8~5.0 (1H,m), 5.2~5.3 (1H,m), 7.00 (1H,t,J=7.0 Hz), 7.11 (1H,t,J=7.0 Hz), 7.17 (1H,s), 7.39 (1H,d,J=7.0 Hz), 7.55 (1H,d,J=7.0 Hz), 11.92 (1H,bs)

EXAMPLE 239

Synthesis of 1-(4-methyl-3-pentenyl)indole-3-carbaldehyde

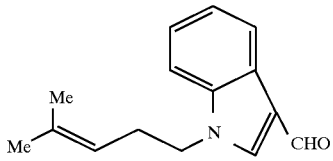

The same procedures used in Example 1 were repeated except for using 2.52 g of 5-bromo-2-methyl-2-pentene and 2.00 g of indole-3-carbaldehyde as a starting material to give 3.06 g of 1-(4-methyl-3-pentenyl)indole-3-carbaldehyde as colorless crystals. The yield thereof was found to be 98%.

NMR (CDCl$_3$) δ: 1.40 (3H,s), 1.67 (3H,s), 2.55 (2H,q,J=7.0 Hz), 4.15 (2H,t,J=7.0 Hz), 5.0~5.2 (1H,m), 7.2~7.4 (3H,m), 7.67 (1H,s), 8.2~8.4 (1H,m), 9.99 (1H,s)

EXAMPLE 240

Synthesis of 5-[1-(4-methyl-3-pentenyl)indol-3-yl]methylene-2,4-thiazolidinedione

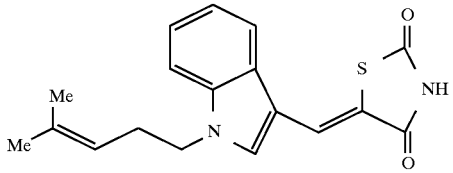

The same procedures used in Example 2 were repeated except for using 3.00 g of 1-(4-methyl-3-pentenyl)indole-3-carbaldehyde prepared in Example 239 to give 3.80 g of 5-[1-(4-methyl-3-pentenyl)indol-3-yl]methylene-2,4-thiazolidinedione as yellow crystals. The yield thereof was found to be 88%.

IR (KBr) cm$^{-1}$: 1740, 1680, 1600, 1340, 1320, 1160, 740; NMR (DMSO-d$_6$) δ: 1.29 (3H,s), 1.59 (3H,s), 2.49 (2H,g, J=7.0 Hz), 4.30 (2H,t,J=7.0 Hz), 5.1~5.2 (1H,m), 7.1~7.4 (2H,m), 7.6 (1H,d,J=8.1 Hz), 7.72 (1H,s), 7.89 (1H,d,J=7.3 Hz), 8.03 (1H,s), 12.30 (1H,bs)

EXAMPLE 241

Synthesis of 5-[1-(4-methyl-3-pentenyl)indol-3-yl]methyl-2,4-thiazolidinedione

The same procedures used in Example 3 were repeated except for using 3.75 g of 5-[1-(4-methyl-3-pentenyl)indol-3-yl]methylene-2,4-thiazolidinedione prepared in Example 240 to give 3.28 g of 5-[1-(4-methyl-3-pentenyl)indol-3-yl]methyl-2,4-thiazolidinedione as a yellow oily substance. The yield thereof was found to be 87%.

IR (KBr) cm$^{-1}$: 1750, 1690, 1470, 1330, 1150, 740; NMR (DMSO-d$_6$) δ: 1.37 (3H,s), 1.60 (3H,s), 2.37 (2H,q,J=7.0 Hz), 3.26 (1H,dd,J=15.0 Hz, 9.2 Hz), 3.47 (1H,dd,J=15.0 Hz, 4.0 Hz) 4.11 (2H,t,J=7.0 Hz), 4.90 (1H,dd,J=9.2 Hz, 4.0 Hz), 5.0~5.2 (1H,m), 7.01 (1H,t,J=7.0 Hz), 7.13 (1H,t,J=7.7 Hz), 7.20 (1H,s), 7.42 (1H,d,J=7.7 Hz ), 7.55 (1H,d,J=7.0 Hz), 11.95 (1H,bs)

EXAMPLE 242

Synthesis of 1-(3-trifluoromethylbenzyl)indole-3-carbaldehyde

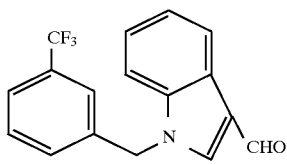

The same procedures used in Example 1 were repeated except for using 3.68 g of (3-trifluoromethylbenzyl) methanesulfonate and 2.00 g of indole-3-carbaldehyde as a starting material to give 3.98 g of 1-(3-trifluoromethylbenzyl)indole-3-carbaldehyde as pale yellow crystals. The yield thereof was found to be 95%.

NMR (CDCl$_3$) δ: 5.42 (2H,s), 7.2~7.4 (4H,m), 7.4~7.7 (3H,m), 7.73 (1H,s), 8.3~8.4 (1H,m), 10.03 (1H,s)

EXAMPLE 243

Synthesis of 5-[1-(3-trifluoromethylbenzyl)indol-3-yl]methylene-2,4-thiazolidinedione

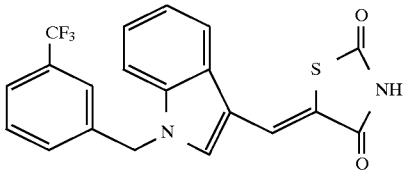

The same procedures used in Example 2 were repeated except for using 3.90 g of 1-(3-trifluoromethylbenzyl) indole-3-carbaldehyde prepared in Example 242 to give 4.60 g of 5-[1-(3-trifluoromethylbenzyl) indol-3-yl]methylene-2,4-thiazolidinedione as yellow crystals. The yield thereof was found to be 89%.

IR (KBr) cm$^{-1}$: 1730, 1680, 1590, 1520, 1320, 1160, 1120, 740; NMR (DMSO-d$_6$) δ: 5.70 (2H,s), 7.2~7.3 (2H,m), 7.5~7.7 (4H,m), 7.76 (1H,s), 7.93 (1H,d,J=6.6 Hz), 8.05 (2H,s), 12.33 (1H,bs)

EXAMPLE 244

Synthesis of 5-[1-(3-trifluoromethylbenzyl)indol-3-yl]methyl-2,4-thiazolidinedione

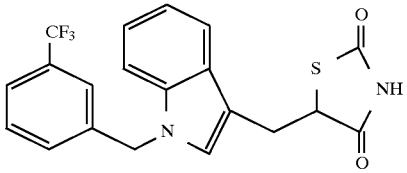

The same procedures used in Example 3 were repeated except for using 4.50 g of 5-[1-(3-trifluoromethylbenzyl) indol-3-yl]methylene-2,4-thiazolidinedione prepared in Example 243 to give 3.80 g of 5-[1-(3-trifluoromethylbenzyl)indol-3-yl]methyl-2,4-thiazolidinedione as yellow crystasls. The yield thereof was found to be 84%.

IR (KBr) cm$^{-1}$: 1750, 1690, 1470, 1330, 1160, 1120, 740; NMR (DMSO-d$_6$) δ: 3.3~3.6 (2H,m), 4.94 (1H,dd,J=8.4 Hz, 4.4 Hz), 5.52 (2H,s), 7.0~7.2 (2H,m), 7.3~7.6 (7H,m), 11.98 (1H,bs)

EXAMPLE 245

Synthesis of (4-fluorobenzyl)indole-3-carbaldehyde

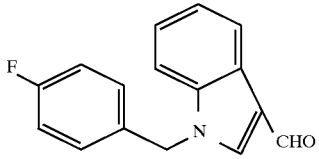

The same procedures used in Example 1 were repeated except for using 2.74 g of 4-fluorobenzyl bromide and 2.00 g of indole-3-carbaldehyde as a starting material to give 3.18 g of (4-fluorobenzyl) indole-3-carbaldehyde as colorless crystals. The yield thereof was found to be 91%.

NMR (CDCl$_3$) δ: 5.33 (2H,s), 7.0~7.2 (4H,m), 7.2~7.4 (3H,m), 7.69 (1H,s), 8.3~8.4 (1H,m), 10.00 (1H,s)

EXAMPLE 246

Synthesis of 5-[1-(4-fluorobenzyl)indol-3-yl]-methylene-2,4-thiazolidinedione

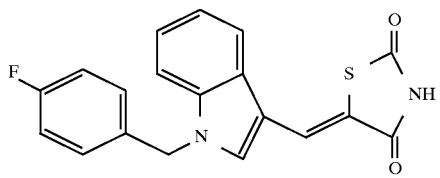

The same procedures used in Example 2 were repeated except for using 3.10 g of (4-fluorobenzyl)indole-3-carbaldehyde prepared in Example 245 to give 4.22 g of 5-[1-(4-fluorobenzyl)indol-3-yl]methylene-2,4-thiazolidinedione as yellow crystals. The yield thereof was found to be 98%.

IR (KBr) cm$^{-1}$: 1730, 1680, 1600, 1520, 1340, 1310, 1180, 740; NMR (DMSO-d$_6$) δ: 5.58 (2H,s), 7.1~7.4 (6H, m), 7.57 (1H,d,J=6.6 Hz), 7.9~8.0 (1H,m), 8.01 (1H,s), 8.05 (1H,s), 12.33 (1H,bs)

EXAMPLE 247

Synthesis of 5-[1-(4-fluorobenzyl)indol-3-yl]-methyl-2,4-thiazolidinedione

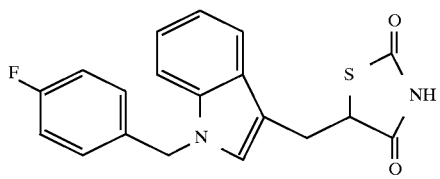

The same procedures used in Example 3 were repeated except for using 4.20 g of 5-[1-(4-fluorobenzyl)indol-3-yl] methylene-2,4-thiazolidinedione prepared in Example 246 to give 2.75 g of 5-[1-(4-fluorobenzyl)indol-3-yl]methyl-2,4-thiazolidinedione as yellow crystals. The yield thereof was found to be 65%.

IR (KBr) cm$^{-1}$: 1750, 1690, 1510, 1470, 1340, 1160, 740; NMR (DMSO-d$_6$) δ: 3.3~3.4 (1H,m), 3.47 (1H,dd,J=14.7 Hz, 4.4 Hz), 4.92 (1H,dd,J=8.4 Hz, 4.4 Hz), 5.38 (2H, s), 7.0~7.3 (6H,m), 7.3~7.4 (2H,m), 7.58 (1H,d,J=7.0 Hz), 11.94 (1H,bs)

EXAMPLE 248

Synthesis of 1-(2,5-difluorobenzyl)indole-3-carbaldehyde

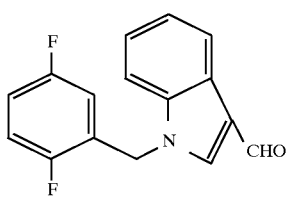

The same procedures used in Example 1 were repeated except for using 3.06 g of 2,5-difluorobenzyl bromide and 2.00 g of indole-3-carbaldehyde as a starting material to give 3.46 g of 1-(2,5-difluorobenzyl)indole-3-carbaldehyde as pale yellow crystals. The yield thereof was found to be 93%.

NMR (CDCl$_3$) δ: 5.37 (2H,s), 6.6~6.7 (1H,m), 6.9~7.2 (2H,m), 7.3~7.4 (3H,m), 7.76 (1H,s), 8.3~8.4 (1H,m), 10.02 (1H,s)

EXAMPLE 249

Synthesis of 5-[1-(2,5-difluorobenzyl)indol-3-yl] methylene-2,4-thiazolidinedione

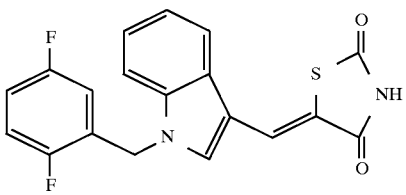

The same procedures used in Example 2 were repeated except for using 3.40 g of 1-(2,5-difluorobenzyl)indole-3-carbaldehyde prepared in Example 248 to give 4.41 g of 5-[1-(2,5-difluorobenzyl)indol-3yl]methylene-2,4-thiazolidinedione as yellow crystals. The yield thereof was found to be 95%.

IR (KBr) cm$^{-1}$: 1740, 1690, 1590, 1340, 1320, 1180, 740; NMR (DMSO-d$_6$) δ: 5,65 (2H,s), 7.0~7.1 (1H,m), 7.1~7.4 (4H,m), 7.60 (1H,d,J=7.3 Hz), 7.9~8.0 (1H,m), 7.95 (1H,s), 8.05 (1H,s), 12.37 (1H,bs)

EXAMPLE 250

Synthesis of 5-[1-(2,5-difluorobenzyl) indol-3-yl] methyl-2,4-thiazolidinedione

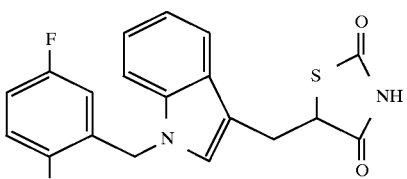

The same procedures used in Example 3 were repeated except for using 4.40 g of 5-[1-(2,5-difluorobenzyl)indol-3-yl]methylene-2,4-thiazolidinedione prepared in Example 249 to give 2.92 g of 5-[1-(2,5-difluorobenzyl)indol-3-yl] methyl-2,4-thiazolidione as yellow crystals. The yield therefore was found to be 66%.

IR (KBr) cm$^{-1}$: 1740, 1690, 1490, 1330, 1160, 740; NMR (DMSO-d$_6$) δ: 3.2~3.4 (1H,m), 3.49 (1H,dd,J=14.6 Hz, 4.4 Hz), 4.93 (1H,dd,J=8.8 Hz), 5.45 (2H,s), 6.6~6.8 (1H,m), 7.0~7.3 (4H,m), 7.35 (1H,s), 7.44 (1H,d,J=7.7 Hz), 7.69 (1H,d,J=7.7 Hz), 11.96 (1H,bs)

EXAMPLE 251

Synthesis of 1-(4-chlorobenzyl)indole-3-carbaldehyde

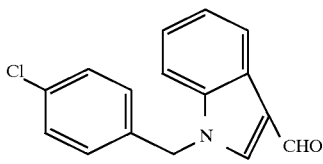

The same procedures used in Example 1 were repeated except for using 2.98 g of 4-chlorobenzyl bromide and 2.00 g of indole-3-carbaldehyde as a starting material to give 3.42 g of 1-(4-chlorobenzyl)indole-3-carbaldehyde as pale yellow crystals. The yield thereof was found to be 92%.

NMR (CDCl$_3$) δ: 5.32 (2H,s), 7.09 (2H,d,J=8.4 Hz), 7.2~7.4 (5H,m), 7.69 (1H,s), 8.3~8.4 (1H,m), 10.05 (1H,s)

EXAMPLE 252

Synthesis of 5-[1-(4-chlorobenzyl)indol-3-yl]-methylene-2,4-thiazolidinedione

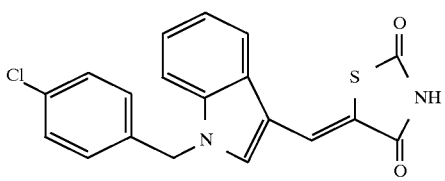

The same procedures used in Example 2 were repeated except for using 3.40 g of 1-(4-chlorobenzyl)indole-3-carbaldehyde prepared in Example 251 to give 4.57 g of 5-[1-(4-chlorobenzyl)indol-3-yl]methylene-2,4-thiazolidinedione as yellow crystals. The yield thereof was found to be 98%.

IR (KBr) cm$^{-1}$: 1730, 1680, 1590, 1520, 1340, 1320, 1170; NMR (DMSO-d$_6$) δ: 5.59 (2H,s), 7.2~7.4 (6H,m), 7.5~7.6 (1H,m), 7.9~8.0 (1H,m), 8.01 (1H,s), 8.05 (1H,s), 12.33 (1H, bs)

EXAMPLE 253

Synthesis of 5-[1-(4-chlorobenzyl)indol-3-yl]-methyl-2,4-thiazolidinedione

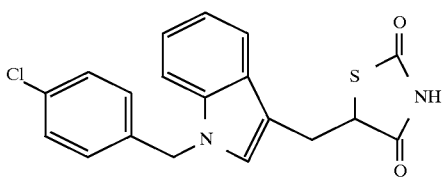

The same procedures used in Example 3 were repeated except for using 4.50 g of 5-[1-(4-chlorobenzyl)indol-3-yl]methylene- 2,4-thiazolidinedione prepared in Example 252 to give 2.95 g of 5-[1-(4-chlorobenzyl)indol-3-yl]methyl-2, 4-thiazolidinedione as yellow crystals. The yield thereof was found to be 65%.

IR (KBr) cm$^{-1}$: 1750, 1690, 1490, 1460, 1330, 1150, 740; NMR (DMSO-d$_6$) δ: 3.3~3.5 (2H,m), 4.93 (1H,dd,J=7.9 Hz, 4.0 Hz), 5.40 (2H,s), 7.0~7.2 (4H,m), 7.3~7.4 (4H,m), 7.59 (1H,d,J=7.3 Hz), 11.97 (1H,bs)

EXAMPLE 254

Synthesis of 1-(4-nitrobenzyl)indole-3-carbaldehyde

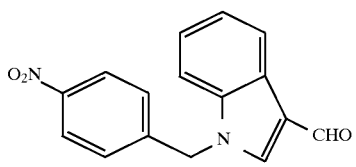

The same procedures used in Example 7 were repeated except for using 5.96 g of 4-nitrobenzyl bromide and 2.00 g of indole-3-carbaldehyde as a starting material to give 2.38 g of 1-(4-nitrobenzyl) indole-3-carbaldehyde as pale brown crystals. The yield thereof was found to be 62%.

NMR (CDCl$_3$) δ: 5.50 (2H,s), 7.1~7.4 (3H,m), 7.28 (2H,s,J=8.8 Hz) 7.77 (1H,s), 8.19 (2H,d,J=8.8 Hz), 8.3~8.4 (1H,m), 10.05 (1H,s)

EXAMPLE 255

Synthesis of 5-[1-(4-nitrobenzyl)indol-3-yl]-methylene-2,4-thiazolidinedione

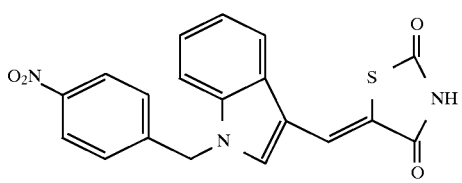

The same procedures used in Example 2 were repeated except for using 2.30 g of 1-(4-nitrobenzyl)indole-3-carbaldehyde prepared in Example 254 to give 2.92 g of 5-[1-(4-nitrobenzyl)indol-3-yl]methylene-2,4-thiazolidinedione as yellow crystals. The yield thereof was found to be 94%.

IR (KBr) cm$^{-1}$: 1730, 1680, 1600, 1520, 1340, 1170, 740; NMR (DMSO-d$_6$) δ: 5.78 (2H,s), 7.1~7.3 (2H,m), 7.47 (2H,d,J=8.8 Hz), 7.5~7.6 (1H,m), 7.9~8.0 (1H,m), 8.07 (1H,s), 8.08 (1H,s), 8.20 (2H,d,J=8.8 Hz), 12.36 (1H,bs)

EXAMPLE 256

Synthesis of 5-[1-(4-aminobenzyl)indol-3-yl]-methyl-2,4-thiazolidinedione

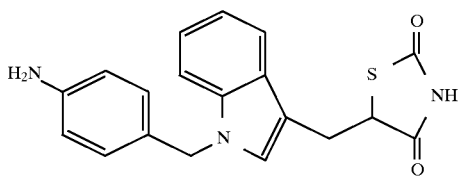

The same procedures used in Example 6 were repeated except for using 2.90 g of 5-[1-(4-nitrobenzyl)indol-3-yl] methylene-2,4-thiazolidinedione prepared in Example 255 to give 1.98 g of 5-[1-(4-aminobenzyl)indol-3-yl]methyl-2, 4-thiazolidinedione as yellow crystals. The yield thereof was found to be 74%.

IR (KBr) cm$^{-1}$: 1690, 1620, 1510, 1330, 1160, 740; NMR (DMSO-d$_6$) δ: 3.28 (1H,dd,J=14.7 Hz, 8.8 Hz), 3.45 (1H, dd,J=14.7 Hz, 4.0 Hz), 4.90 (1H,dd,J=8.8 Hz, 4.0 Hz), 5.14

(2H,s), 6.46 (2H,d,J=8.2 Hz), 6.88 (2H,d,J=8.2 Hz), 6.9~7.1 (2H,m), 7.28 (1H, s), 7.40 (1H,d,J=8.1 Hz), 7.55 (1H,d,J= 7.7 Hz)

EXAMPLE 257

Synthesis of 1-phenacylindole-3-carbaldehyde

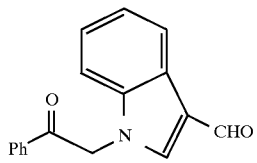

The same procedures used in Example 1 were repeated except for using 2.88 g of bromoacetophenone and 2.00 g of indole-3-carbaldehyde as a starting material to give 2.06 g of 1-phenacylindole-3-carbaldehyde as pale yellow crystals. The yield thereof was found to be 57%.

NMR (DMSO-d₆) δ: 6.09 (2H,s), 7.2~7.3 (2H,m), 7.5~7.8 (4H,m), 8.0~8.2 (3H,m), 8.26 (1H,s), 9.96 (1H,s)

EXAMPLE 258

Synthesis of 5-(1-phenacylindol-3-yl)methylene-2, 4-thiazolidinedione

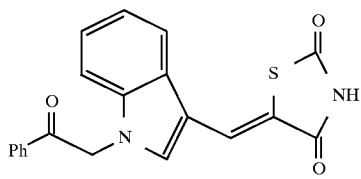

The same procedures used in Example 2 were repeated except for using 2.00 g of 1-phenacylindole-3-carbaldehyde prepared in Example 257 to give 2.28 g of 5-(1-phenacylindol-3-yl)methylene-2,4-thiazolidinedione as yellow crystals. The yield thereof was found to be 83%.

IR (KBr) cm⁻¹: 1710, 1670, 1580, 1520, 1340, 1320, 1190, 740; NMR (DMSO-d₆) δ: 6.10 (2H,s), 7.1~7.3 (2H, m), 7.5~7.8 (4H,m), 7.86 (1H,s), 7.9~8.0 (1H,m), 8.0~8.2 (3H,m), 12.28 (1H,bs)

EXAMPLE 259

Synthesis of 5-(1-phenacylindol-3-yl)methyl-2,4-thiazolidinedione

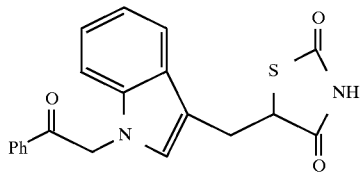

The same procedures used in Example 6 were repeated except for using 2.20 g of 5-(1-phenacylindol-3-yl) methylene-2,4-thiazolidinedione prepared in Example 258 to give 1.56 g of 5-(1-phenacylindol-3-yl)methyl-2,4-thiazolidinedione as yellow crystals. The yield thereof was found to be 71%.

IR (KBr) cm⁻¹: 1750, 1700, 1650, 1460, 1340, 1220, 1160, 750; NMR (DMSO-d₆) δ: 3.30 (1H,dd,J=14.7 Hz, 9.2 Hz), 3.52 (1H,dd,J=14.7 Hz, 4.0 Hz), 4.93 (1H,dd,J=9.2 Hz, 4.0 Hz), 5.87 (2H,s), 7.0~7.2 (2H,m), 7.22 (1H, s), 7.3~7.4 (1H,m), 7.5~7.8 (3H,m), 8.0~8.2 (2H,m), 11.98 (1H,bs)

EXAMPLE 260

Synthesis of 1-benzhydrylindole-3-carbaldehyde

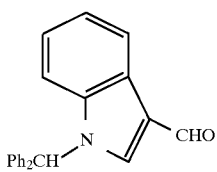

The same procedures used in Example 1 were repeated except for using 870 mg of indole-3-carbaldehyde and benzhydryl chloride in place of the benzyl bromide used in Example 1 to give 852 mg of 1-benzhydrylindole-3-carbaldehyde as brown crystals. The yield thereof was found to be 46%.

NMR (CDCl₃) δ: 6.84 (1H,s), 7.0~7.4 (14H,m), 8.33 (1H,dd,J=7.3 Hz, 1.4 Hz), 9.91 (1H,s)

EXAMPLE 261

Synthesis of 5-[1-(benzhydryl)indol-3-yl]methylene-2,4-thiazolidinedione

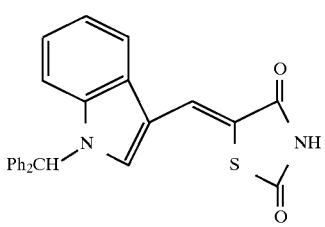

The same procedures used in Example 2 were repeated except for using 827 mg of 1-benzhydrylindole-3-carbaldehyde prepared in Example 260 to give 694 mg of 5-[1-(benzhydryl)indol-3-yl]methylene-2,4-thiazolidinedione as yellow crystals. The yield thereof was found to be 64%.

IR (KBr) cm⁻¹: 1730, 1680, 1590, 1520; NMR (DMSO-d₆) δ: 7.1~7.5 (15H,m), 7.96 (1H,dd,J=6.2 Hz, 2.9 Hz), 8.04 (1H,s), 12.32 (1H,bs)

EXAMPLE 262

Synthesis of 5-[1-(benzhydryl)indol-3-yl]methyl-2, 4-thiazolidinedione

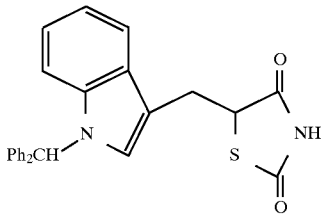

The same procedures used in Example 3 were repeated except for using 411 mg of 5-[1-(benzhydryl)indol-3-yl]

methylene-2,4-thiazolidinedione prepared in Example 261 to give 335 mg of 5-[1-(benzhydryl)indol-3-yl]methyl-2,4-thiazolidinedione as a yellow amorphous substance. The yield thereof was found to be 81%.

IR (KBr) cm⁻¹: 1750, 1690, 1460, 1310; NMR (CDCl₃) δ: 3.25 (1H,dd,J=14.6 Hz, 9.5 Hz), 3.63 (1H,dd,J=14.6 Hz, 3.7 Hz), 4.60 (1H,dd,J=9.5 Hz, 3.7 Hz), 6.74 (1H,s), 6.80 (1H,s), 7.0~7.4 (13H,m), 7.62 (1H,dd,J=6.0 Hz, 2.8 Hz), 8.20 (1H,bs)

EXAMPLE 263

Synthesis of 1-(4-benzyloxybenzyl)indole-3-carbaldehyde

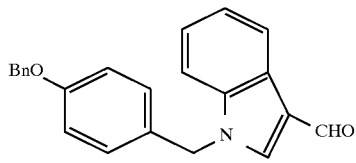

The same procedures used in Example 1 were repeated except for using 435 mg of indole-3-carbaldehyde and 4-benzyloxybenzyl methanesulfonate in place of the benzyl bromide used in Example 1 to give 626 mg of 1-(4-benzyloxybenzyl)indole-3-carbaldehyde as colorless crystals. The yield thereof was found to be 61%.

NMR (CDCl₃) δ: 5.04 (2H,s), 5.27 (2H,s), 6.95 (2H,d,J=8.4 Hz), 7.14 (2H,d,J=8.4 Hz), 7.2~7.5 (8H,m), 7.66 (1H,s), 8.2~8.4 (1H,m), 9.98 (1H,s)

EXAMPLE 264

Synthesis of 5-[1-(4-benzyloxybenzyl)indol-3-yl]-methylene-2,4-thiazolidinedione

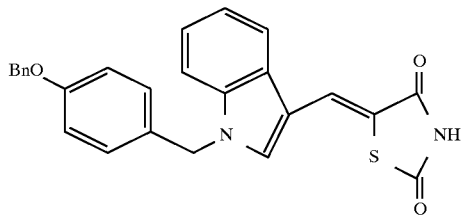

The same procedures used in Example 2 were repeated except for using 612 mg of 1-(4-benzyloxybenzyl)indole-3-carbaldehyde prepared in Example 263 to give 492 mg of 5-[1-(4-benzyloxybenzyl)indol-3-yl]methylene-2,4-thiazolidinedione as yellow crystals. The yield thereof was found to be 62%.

IR (KBr) cm⁻¹: 1740, 1680, 1590, 1520; NMR (DMSO-d₆) δ: 5.05 (2H,s), 5.49 (2H,s), 6.97 (2H,d,J=8.4 Hz), 7.1~7.5 (9H,m), 7.58 (1H,dd,J=7.0 Hz, 1.5 Hz), 7.91 (1H,dd,J=7.0 Hz, 1.5 Hz), 7.97 (1H,s), 8.04 (1H,s), 12.31 (1H,bs)

EXAMPLE 265

Synthesis of 5-[1-(4-benzyloxybenzyl)indol-3-yl]-methyl-2,4-thiazolidinedione

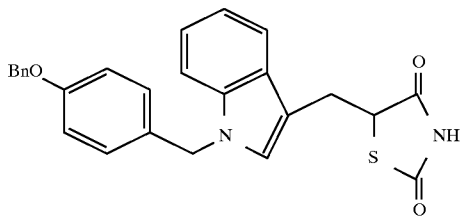

The same procedures used in Example 6 were repeated except for using 478 mg of 5-[1-(4-benzyloxybenzyl)indol-3-yl]methylene-2,4-thiazolidinedione prepared in Example 264 to give 288 mg of 5-[1-(4-benzyloxybenzyl)indol-3-yl]methyl-2,4-thiazolidinedione as pale yellow crystals. The yield thereof was found to be 60%.

IR (KBr) cm⁻¹: 1740, 1680, 1510, 1240; NMR (DMSO-d₆) δ: 3.31 (1H,dd,J=14.6 Hz, 8.4 Hz), 3.47 (1H,dd,J=14.6 Hz, 4.0 Hz), 4.92 (1H,dd,J=8.4 Hz, 4.0 Hz), 5.03 (2H,S), 5.30 (2H,s), 6.92 (2H,d,J=8.8 Hz), 7.0~7.2 (4H,m), 7.2~7.4 (7H,m), 7.57 (1H,d, J=7.3 Hz), 11.94 (1H,bs)

EXAMPLE 266

Synthesis of 5-[1-(2-butynyl)indol-3-yl]methyl-ene-2,4-thiazolidinedione

The same procedures used in Example 1 were repeated except for using 2.00 g of indole-3-carbaldehyde and 2.44 g of 2-butynyl methanesulfonate instead of the indole-4-carbaldehyde and the benzyl bromide used in Example 1 respectively to give 4.18 g of a residue.

The same procedures used in Example 2 were repeated except that the residue prepared above was used to give 2.47 g of 5-[1-(2-butynyl)indol-3-yl]methylene-2,4-thiazolidinedione as yellow crystals. The yield thereof was found to be 64%.

IR (KBr) cm⁻¹: 1740, 1680, 1590, 1520, 1340; NMR (DMSO-d₆) δ: 1.81 (3H,s), 5.20 (2H,s), 7.2~7.4 (2H,m), 7.6~7.7 (1H,m), 7.84, 7.9~8.0 (total 3H,s,m), 8.02 (1H,s), 12.33 (1H,bs)

EXAMPLE 267

Synthesis of 5-[1-(2-butynyl)indol-3-yl]methyl-2,4-thiazolidinedione

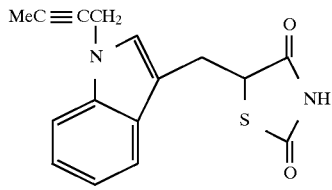

The same procedures used in Example 3 were repeated except for using 2.00 g of 5-[1-(2-butynyl)indol-3-yl]methylene-2,4-thiazolidinedione prepared in Example 266 to give 1.82 g of 5-[1-(2-butynyl)indol-3-yl]methyl-2,4-thiazolidinedione as pale yellow crystals. The yield thereof was found to be 90%.

IR (KBr) cm$^{-1}$: 1750, 1710, 1680, 740; NMR (DMSO-d$_6$) δ: 1.78 (3H,s), 3.2~3.6 (2H,m), 4.8~5.0, 4.98 (total 3H,m,s), 7.0~7.2 (2H,m), 7.27 (1H,s), 7.4~7.7 (2H,m), 11.98 (1H,bs)

EXAMPLE 268

Synthesis of 5-[1-(3-methoxybenzyl)indol-3-yl]-methylene-2,4-thiazolidinedione

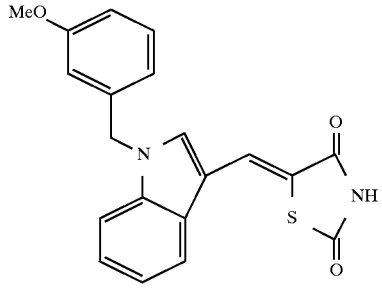

The same procedures used in Examples 1 and 2 were repeated except for using 2.00 g of indole-3-carbaldehyde and 2.72 g of 3-methoxybenzyl chloride instead of the indole-4-carbaldehyde and benzyl bromide used in Examples 1 and 2 to give 3.82 g of 5-[1-(3-methoxybenzyl)indol-3-yl]methylene-2,4-thiazolidinedione as yellow crystals. The yield thereof was found to be 76%.

IR (KBr) cm$^{-1}$: 1730, 1680, 1590, 1340, 1310, 740; NMR (DMSO-d$_6$) δ: 3.71 (3H,s), 5.55 (2H,s), 6.7~6.9 (3H,m), 7.2~7.4 (3H,m), 7.5~7.6 (1H,m), 7.9~8.0 (1H,m), 7.99 (1H, s), 8.05 (1H,s), 12.31 (1H,bs)

EXAMPLE 269

Synthesis of 5-[1-(3-methoxybenzyl)indol-3-yl]-methyl-2,4-thiazolidinedione

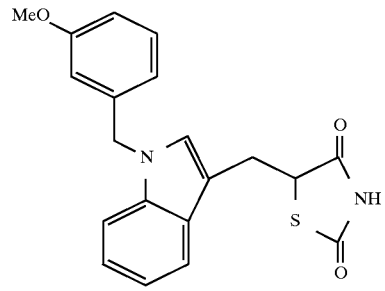

The same procedures used in Example 3 were repeated except for using 2.00 g of 5-[1-(3-methoxybenzyl)indol-3-yl]methylene-2,4-thiazolidinedione prepared in Example 268 to give 1.52 g of 5-[1-(3-methoxybenzyl)indol-3-yl]methyl-2,4-thiazolidinedione as pale yellow crystals. The yield thereof was found to be 76%.

IR (KBr) cm$^{-1}$: 1750, 1690, 1460, 740; NMR (DMSO-d$_6$) δ: 3.2~3.6 (2H,m), 3.68 (3H,s), 4.93 (1H,dd, J=4.0 Hz, 8.6 Hz), 5.35 (2H,s), 6.6~6.9 (3H,m), 7.0~7.3 (4H,m), 7.3~7.5, 7.37 (total 2H,m,s), 7.5~7.7 (1H,m), 11.95 (1H,bs)

EXAMPLE 270

Synthesis of 5-{1-[4-(trifluoromethyl)benzyl]-indol-3-yl}methylene-2,4-thiazolidinedione

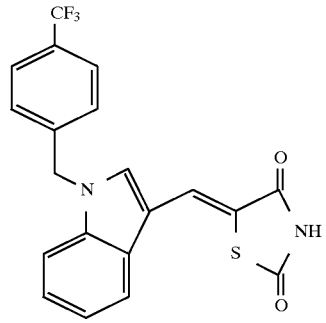

The same procedures used in Examples 1 and 2 were repeated except for using 2.00 g of indole-3-carbaldehyde and 4.16 g of 4-(trifluoromethyl)benzyl methanesulfonate instead of the indole-4-carbaldehyde and benzyl bromide used in Examples 1 and 2 to give 2.57 g of 5-{1-[4-(trifluoromethyl)benzyl]indol-3-yl}methylene-2,4-thiazolidinedione as yellow crystals. The yield thereof was found to be 46%.

IR (KBr) cm$^{-1}$: 1740, 1680, 1600, 1320; NMR (DMSO-d$_6$) δ: 5.72 (2H,s), 7.2~7.3 (2H,m), 7.4~7.6 (3H,m), 7.71 (2H,dd,J=8.1 Hz, 8.1 Hz), 7.9~8.0 (1H,m), 8.04, 8.05 (total 2H,s,s)

EXAMPLE 271

Synthesis of 5-{1-[4-(trifluoromethyl)benzyl]-indol-3-yl}methyl-2,4-thiazolidinedione

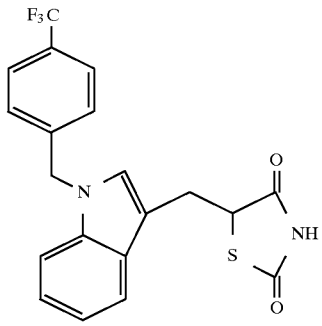

The same procedures used in Example 3 were repeated except for using 2.00 g of 5-{1-[4-(trifluoromethyl)benzyl]indol-3-yl}methylene-2,4-thiazolidinedione prepared in Example 270 to give 1.21 g of 5-{1-[4-(trifluoromethyl)benzyl]indol-3-yl}methyl-2,4-thiazolidinedione as yellow crystals. The yield thereof was found to be 60%.

IR (KBr) cm$^{-1}$: 1750, 1690, 1330, 1160, 1120, 1060, 740; NMR (DMSO-d$_6$) δ: 3.2~3.5 (2H,m), 4.8~5.0 (1H,m), 5.55 (2H,s), 7.0~7.2 (2H,m), 7.2~7.5 (4H,m), 7.6~7.8 (3H,m), 11.95 (1H,bs)

EXAMPLE 272

Synthesis of 5-[1-(3-fluorobenzyl)indol-3-yl]-methylene-2,4-thiazolidinedione

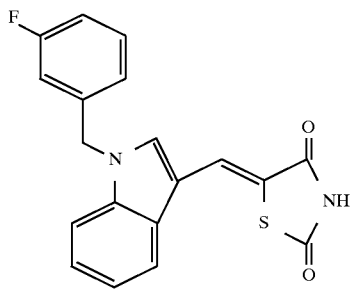

The same procedures used in Examples 1 and 2 were repeated except for using 2.00 g of indole-3-carbaldehyde and 3.12 g of 3-fluorobenzyl bromide instead of the indole-4-carbaldehyde and benzyl bromide used in these Examples to give 3.57 g of 5-[1-(3-fluorobenzyl)indol-3-yl]methylene-2,4-thiazolidinedione as yellow crystals. The yield thereof was found to be 74%.

IR (KBr) cm$^{-1}$: 1730, 1680, 1590, 1340, 1320, 740; NMR (DMSO-d$_6$) δ: 5.61 (2H,s), 7.0~7.4 (6H,m), 7.5~7.6 (1H,m), 7.9~8.0 (1H,m), 8.02 (1H,s), 8.04 (1H,s)

EXAMPLE 273

Synthesis of 5-[1-(3-fluorobenzyl)indol-3-yl]-methyl-2,4-thiazolidinedione

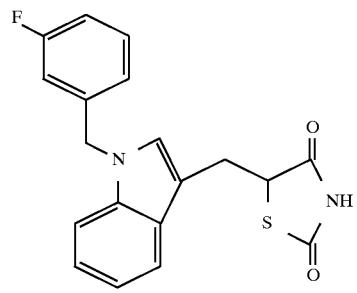

The same procedures used in Example 3 were repeated except for using 2.00 g of 5-[1-(3-fluorobenzyl)indol-3-yl]methylene-2,4-thiazolidinedione prepared in Example 272 to give 1.19 g of 5-[1-(3-fluorobenzyl)indol-3-yl]methyl-2,4-thiazolidinedione as pale yellow crystals. The yield thereof was found to be 59%.

IR (KBr) cm$^{-1}$: 1750, 1690, 1330, 740; NMR (DMSO-d$_6$) δ: 3.2~3.6 (2H,m), 4.94 (1H,dd,J=4.4 Hz, 8.4 Hz), 5.42 (2H,s), 6.8~7.2 (5H,m), 7.2~7.5 (3H,m), 7.59 (1H,d,J=7.3 Hz), 11.97 (1H,bs)

EXAMPLE 274

Synthesis of 5-[1-(3,5-difluorobenzyl)indol-3-yl]methylene-2,4-thiazolidinedione

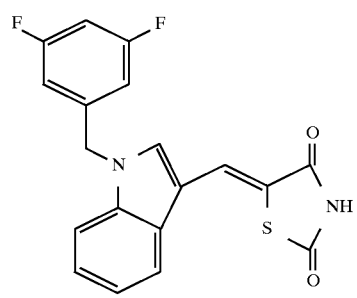

The same procedures used in Examples 1 and 2 were repeated except for using 2.00 g of indole-3-carbaldehyde and 3.42 g of 3,5-difluorobenzyl bromide instead of the indole-4-carbaldehyde and benzyl bromide used in these Examples to give 3.00 g of 5-[1-(3,5-difluorobenzyl)indol-3-yl]methylene-2,4-thiazolidinedione as yellow crystals. The yield thereof was found to be 59%.

IR (KBr) cm$^{-1}$: 1730, 1680, 1600, 740; NMR (DMSO-d$_6$) δ: 5.63 (2H,s), 6.9~7.4 (5H,m), 7.5~7.7 (1H,m), 7.9~8.0 (1H,m), 8.05 (2H,s), 12.31 (1H,bs)

EXAMPLE 275

Synthesis of 5-[1-(3,5-difluorobenzyl)indol-3-yl]methyl-2,4-thiazolidinedione

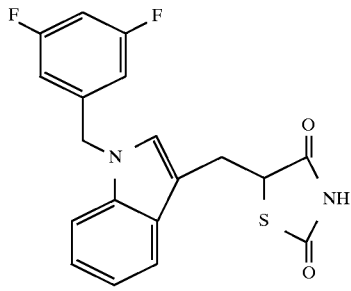

The same procedures used in Example 3 were repeated except for using 2.00 g of 5-[1-(3,5-difluorobenzyl)indol-3-yl]methylene-2,4-thiazolidinedione prepared in Example 274 to give 1.00 g of 5-[1-(3,5-difluorobenzyl)indol-3-yl]methyl-2,4-thiazolidinedione as a yellow amorphous substance. The yield thereof was found to be 50%.

IR (KBr) cm$^{-1}$: 1750, 1700, 1620, 1600, 1120; NMR (DMSO-d$_6$) δ: 3.2~3.7 (2H,m), 4.8~5.1 (1H,m), 5.48 (2H,s), 6.7~7.7 (8H,m), 11.95 (1H,bs)

EXAMPLE 276

Synthesis of 5-{1-[2,4-bis(trifluoromethyl)-benzyl]indol-3-yl}methylene-2,4-thiazolidinedione

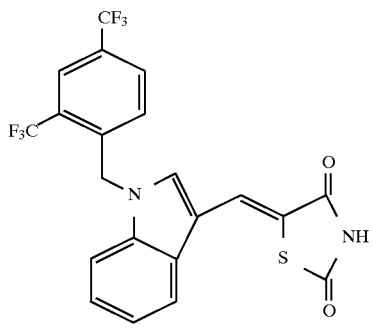

The same procedures used in Examples 1 and 2 were repeated except for using 2.00 g of indole-3-carbaldehyde and 4.90 g of 2,4-bis(trifluoromethyl)benzyl bromide instead of the indole-4-carbaldehyde and benzyl bromide used in Examples 1 and 2 to give 3.88 g of 5-{1-[2,4-bis(trifluoromethyl)benzyl]indol-3-yl}methylene-2,4-thiazolidinedione as yellow crystals. The yield thereof was found to be 60%.

IR (KBr) cm$^{-1}$: 1740, 1680, 1600, 1340, 1130, 740; NMR (DMSO-d$_6$) δ: 5.92 (2H,s), 6.68 (1H,d,J=8.4 Hz), 7.26, 7.28 (total 3H,s,s), 7.9~8.2, 8.05, 8.10 (total 5H,m,s,s), 12.39 (1H,bs)

EXAMPLE 277

Synthesis of 5-{1-[2,4-bis(trifluoromethyl)-benzyl]indol-3-yl}methyl-2,4-thiazolidinedione

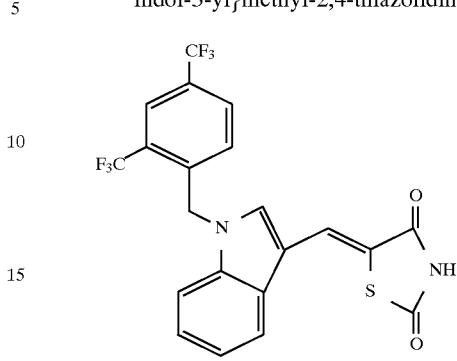

The same procedures used in Example 6 were repeated except for using 2.00 g of 5-{$^1$-[2,4-bis(trifluoromethyl)benzyl]indol-3-yl}methylene-2,4-thiazolidinedione prepared in Example 276 to give 1.45 g of 5-{1-[2,4-bis(trifluoromethyl)benzyl]indol-3-yl}methyl-2,4-thiazolidinedione as colorless crystals. The yield thereof was found to be 72%.

IR (KBr) cm$^{-1}$: 1760, 1680, 1340, 1280, 1180, 1170, 1130, 750; NMR (DMSO-d$_6$) δ: 3.3~3.6 (2H,m), 4.95 (1H, dd,J=4.8 Hz, 7.3 Hz), 5.72 (2H,s), 6.47 (1H,d,J=8.1 Hz), 7.0~7.3 (3H, m), 7.40 (1H,s), 7.6~7.7 (1H,m), 7.85 (1H,d, J=8.1 Hz), 8.09 (1H,s), 11.93 (1H,bs)

EXAMPLE 278

Synthesis of 5-[1-(2-picolyl)indol-3-yl]-methylene-2,4-thiazolidinedione

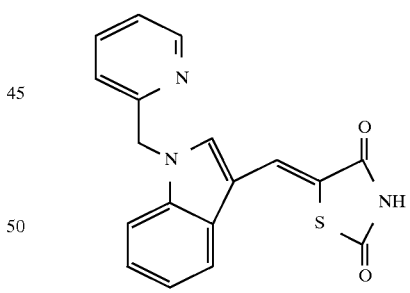

The same procedures used in Examples 4 and 2 were repeated except for using 2.00 g of indole-3-carbaldehyde instead of the indole-4-carbaldehyde used in these Examples and 2.72 g of 2-picolyl chloride hydrochloride to give 3.94 g of 5-[1-(2-picolyl)indol-3-yl]methylene-2,4-thiazolidinedione as pale yellow crystals. The yield thereof was found to be 85%.

IR (KBr) cm$^{-1}$: 1690, 1600, 1340, 1180; NMR (DMSO-d$_6$) δ: 5.68 (2H,s), 7.1~7.3 (4H,m), 7.4~7.6 (1H,m), 7.7~7.8 (1H,m), 7.9~8.0 (1H,m), 7.99 (1H,s), 8.06 (1H,s), 8.5~8.6 (1H,m), 12.32 (1H,bs)

EXAMPLE 279

Synthesis of 5-[1-(2-picolyl)indol-3-yl]methyl-2,4-thiazolidinedione

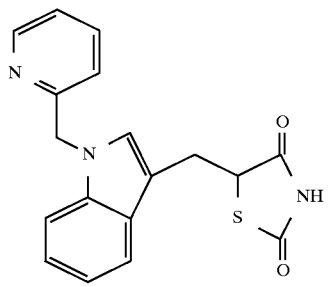

The same procedures used in Example 6 were repeated except for using 2.00 g of 5-[1-(2-picolyl)indol-3-yl]methylene-2,4-thiazolidinedione prepared in Example 278 to give 1.37 g of 5-[1-(2-picolyl)indol-3-yl]methyl-2,4-thiazolidinedione as colorless crystals. The yield thereof was found to be 68%.

IR (KBr) cm$^{-1}$: 1700, 1600, 1460, 1330, 1160, 740; NMR (DMSO-d$_6$) δ: 3.2~3.4 (H,m), 3.48 (1H,dd,J=12.5 Hz, 4.4 Hz), 4.92 (1H,dd,J=4.4 Hz, 8.4HZ), 5.48 (2H,S), 6.80 (1H, d,J=7.7 Hz), 7.0~7.2 (2H,m), 7.2~7.3 (1H,m), 7.3~7.5, 7.38 (total 2H,m,s), 7.5~7.8 (2H,m), 8.5~8.6 (1H,m), 11.95 (1H, bs)

EXAMPLE 280

Synthesis of 5-[1-(3-methylbenzyl)indol-3-yl]-methylene-2,4-thiazolidinedione

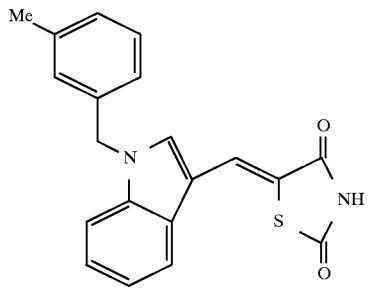

The same procedures used in Examples 1 and 2 were repeated except for using 2.00 g of indole-3-carbaldehyde and 3.06 g of 3-methylbenzyl bromide instead of the indole-4-carbaldehyde and benzyl bromide used in these Examples to give 3.45 g of 5-[1-(3-methylbenzyl)indol-3-yl]methylene-2,4-thiazolidinedione as yellow crystals. The yield thereof was found to be 72%.

IR (KBr) cm$^{-1}$: 1730, 1680, 1600, 1340, 1320; NMR (DMSO-d$_6$) δ: 2.25 (3H,s), 5.54 (2H,s), 7.0~7.4 (6H,m), 7.5~7.6 (1H,m), 7.9~8.0 (1H,m), 7.98 (1H,s), 8.05 (1H,s), 12.31 (1H,bs)

EXAMPLE 281

Synthesis of 5-[1-(3-methylbenzyl)indol-3-yl]-methyl-2,4-thiazolidinedione

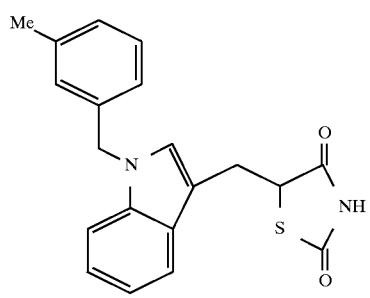

The same procedures used in Example 6 were repeated except for using 2.00 g of 5-[1-(3-methylbenzyl)indol-3-yl]methylene-2,4-thiazolidinedione prepared in Example 280 to give 0.88 g of 5-[1-(3-methylbenzyl)indol-3-yl]methyl-2,4-thiazolidinedione as a pale yellow amorphous substance. The yield thereof was found to be 44%.

IR (KBr) cm$^{-1}$: 1750, 1690, 1460, 740; NMR (CDCl$_3$) δ: 2.29 (3H,s), 3.30 (1H,dd,J=9.5 Hz, 14.6 Hz), 3.69 (1H,dd, J=14.6 Hz, 3.7 Hz), 4.62 (1H,dd,J=3.7 Hz, 9.5 Hz), 5.23 (2H,s), 6.8~7.0 (2H,m), 7.0~7.3 (6H,m), 7.5~7.7 (1H,m), 8.53 (1H,bs)

EXAMPLE 282

Synthesis of 5-[1-(3-cyanobenzyl)indol-3-yl]-methylene-2,4-thiazolidinedione

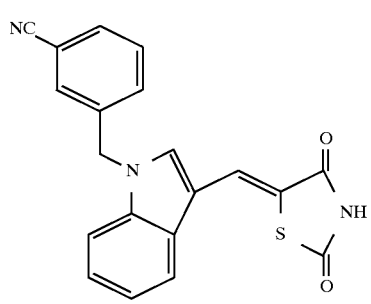

The same procedures used in Examples 1 and 2 were repeated except for using 2.00 g of indole-3-carbaldehyde and 3.24 g of 3-cyanobenzyl bromide instead of the indole-4-carbaldehyde and benzyl bromide used in these Examples to give 3.95 g of 5-[1-(3-cyanobenzyl)indol-3-yl]methylene-2,4-thiazolidinedione as orange-colored crystals. The yield thereof was found to be 80%.

IR (KBr) cm$^{-1}$: 1730, 1680, 1600, 1520, 1350, 740; NMR (DMSO-d$_6$) δ: 5.66 (2H,s), 7.2~7.4 (2H,m), 7.5~7.7 (3H,m), 7.7~8.0 (3H,m), 8.06, 8.06 (total 2H,s,s), 12.35 (1H,bs)

EXAMPLE 283

Synthesis of 5-[1-(3-cyanobenzyl)indol-3-yl]-methyl-2,4-thiazolidinedione

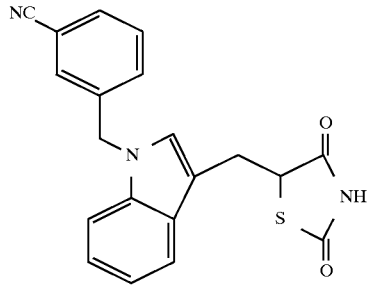

The same procedures used in Example 6 were repeated except for using 2.00 g of 5-[1-(3-cyanobenzyl)indol-3-yl] methylene-2,4-thiazolidinedione prepared in Example 282 to give 0.90 g of 5-[1-(3-cyanobenzyl)indol-3-yl]methyl-2,4-thiazolidinedione as a pale yellow amorphous substance. The yield thereof was found to be 45%.

IR (KBr) cm$^{-1}$: 1750, 1700, 1330, 740; NMR (CDCl$_3$) δ: 3.37 (1H,dd,J=9.2 Hz, 14.6 Hz), 3.68 (1H,dd,J=14.6 Hz, 3.4 Hz), 4.65 (1H,dd,J=3.4 Hz, 9.2 Hz), 5.33 (2H,s), 7.05 (1H,s), 7.1~7.3 (4H,m), 7.3~7.5 (2H,m), 7.5~7.7 (2H,m), 8.28 (1H,bs)

EXAMPLE 284

Synthesis of 5-[1-(4-cyanobenzyl)indol-3-yl]-methylene-2,4-thiazolidinedione

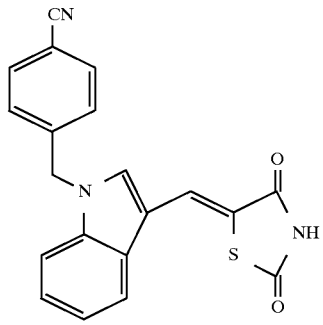

The same procedures used in Examples 1 and 2 were repeated except for using 2.00 g of indole-3-carbaldehyde and 3.24 g of 4-cyanobenzyl bromide instead of the indole-4-carbaldehyde and benzyl bromide used in these Examples to give 3.31 g of 5-[1-(4-cyanobenzyl)indol-3-yl]methylene-2,4-thiazolidinedione as orange-colored crystals. The yield thereof was found to be 67%.

IR (KBr) cm$^{-1}$: 1730, 1680, 1590, 1520, 1340, 1320, 740; NMR (DMSO-d$_6$) δ: 5.71 (2H,s), 7.2~7.6 (5H,m), 7.7~8.0 (3H,m), 8.05, 8.05 (total 2H,s,s), 12.32 (1H,bs)

EXAMPLE 285

Synthesis of 5-[1-(4-cyanobenzyl)indol-3-yl]-methyl-2,4-thiazolidinedione

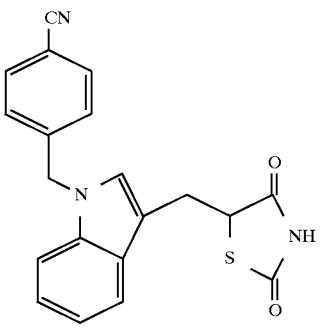

The same procedures used in Example 6 were repeated except for using 2.00 g of 5-[1-(4-cyanobenzyl)indol-3-yl] methylene-2,4-thiazolidinedione prepared in Example 284 to give 1.02 g of 5-[1-(4-cyanobenzyl)indol-3-yl]methyl-2,4-thiazolidinedione as a pale yellow amorphous substance. The yield thereof was found to be 51%.

IR (KBr) cm$^{-1}$: 1750, 1700, 1460, 740; NMR (CDCl$_3$) δ: 3.38 (1H,dd,J=9.2 Hz, 14.8 Hz), 3.67 (1H,dd,J=14.8 Hz, 4.0 Hz), 4.65 (1H,dd,J=4.0 Hz, 9.2 Hz), 5.36 (2H,s), 7.0~7.3 (6H,m), 7.5~7.7 (3H, m), 8.27 (1H,bs)

EXAMPLE 286

Synthesis of 1-benzylindole-3-carbaldehyde

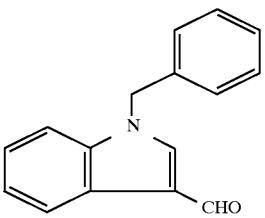

The same procedures used in Example 1 were repeated except for using 2.00 g of indole-3-carbaldehyde instead of the indole-4-carbaldehyde used in Example 1 to give 3.04 g of 1-benzylindole-3-carbaldehyde as brown crystals. The yield thereof was found to be 94%.

NMR (CDCl$_3$) δ: 5.31 (2H,s), 7.0~7.4 (4H,m), 7.66 (1H,s), 8.2~8.4 (1H,m), 9.96 (1H,s)

EXAMPLE 287

Synthesis of 5-(1-benzylindol-3-yl)methylene-2,4-thiazolidinedione

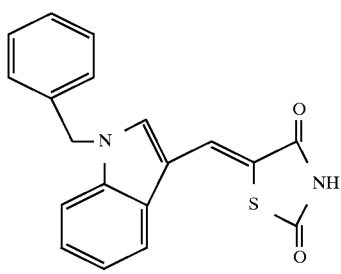

The same procedures used in Example 2 were repeated except for using 3.00 g of 1-benzylindole-3-carbaldehyde prepared in Example 286 to give 3.91 g of 5-(1-benzylindol-3-yl)methylene-2,4-thiazolidinedione as yellow crystals. The yield thereof was found to be 92%.

IR (KBr) cm$^{-1}$: 1720, 1670, 1600, 1520, 1340, 1320, 1300, 1170, 1150; NMR (DMSO-d$_6$) δ: 5.59 (2H,s), 7.1~7.4 (7H,m), 7.5~7.6 (1H,m), 7.8~7.9 (1H,m), 8.00 (1H,s), 8.06 (1H,s), 12.35 (1H,bs)

EXAMPLE 288

Synthesis of 5-(1-benzylindol-3-yl)methyl-2,4-thiazolidinedione

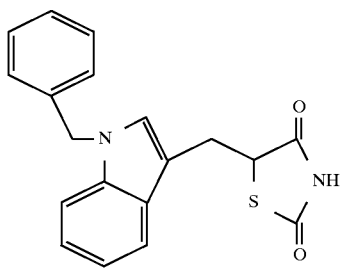

The same procedures used in Example 3 were repeated except for using 3.00 g of 5-(1-benzylindol-3-yl)methylene-2,4-thiazolidinedione prepared in Example 287 to give 1.88 g of 5-(1-benzylindol-3-yl)methyl-2,4-thiazolidinedione as a yellow amorphous substance. The yield thereof was found to be 62%.

IR (KBr) cm$^{-1}$: 1750, 1690, 1330, 1150, 740; NMR (CDCl$_3$) δ: 3.19 (1H,dd,J=9.9 Hz, 14.7 Hz), 3.64 (1H,dd, J=14.7 Hz, 4.8 Hz), 4.53 (1H,dd,J=4.8 Hz, 9.9 Hz), 5.16 (2H,s), 6.8~7.4 (8H,m), 7.59 (2H,d,J=6.6 Hz)

EXAMPLE 289

Synthesis of 1-phenethylindole-3-carbaldehyde

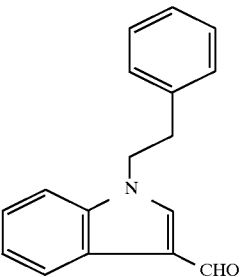

The same procedures used in Example 7 were repeated except for using 2.00 g of indole-3-carbaldehyde instead of the indole-4-carbaldehyde used in Example 7 and 2.35 g of 2-phenethyl bromide to give 3.34 g of 1-phenethylindole-3-carbaldehyde as a brown oily substance. The yield thereof was found to be 97%.

NMR (CDCl$_3$) δ: 3.12 (2H,t,J=7.0 Hz), 4.36 (2H,t,J=7.0 Hz), 6.9~7.1 (2H,m), 7.2~7.4 (7H,m), 8.2~8.4 (1H,m), 9.85 (1H,s)

EXAMPLE 290

Synthesis of 5-(1-phenethylindol-3-yl)methylene-2,4-thiazolidinedione

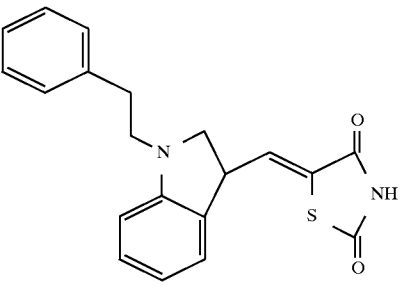

The same procedures used in Example 2 were repeated except for using 3.00 g of 1-phenethylindole-3-carbaldehyde prepared in Example 289 to give 3.73 g of 5-(1-phenethylindol-3-yl)methylene-2,4-thiazolidinedione as yellow crystals. The yield thereof was found to be 89%.

IR (KBr) cm$^{-1}$: 1740, 1680, 1590, 1520, 1350, 1320, 1230, 1170, 740; NMR (DMSO-d$_6$) δ: 3.10 (2H,t,J=7.0 Hz), 4.52 (2H,t,J=7.0 Hz), 7.1~7.4 (7H,m), 7.61 (1H,s), 7.64 (1H,d,J=7.3 Hz), 7.88 (1H,d,J=7.3 Hz), 8.00 (1H,s), 12.30 (1H,bs)

EXAMPLE 291

Synthesis of 5-(1-phenethylindol-3-yl)methyl-2,4-thiazolidinedione

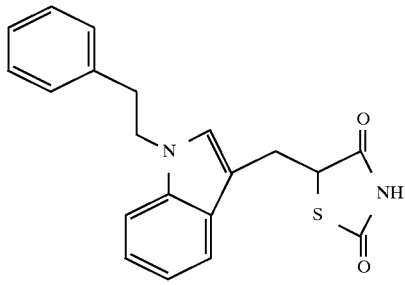

The same procedures used in Example 3 were repeated except for using 3.00 g of 5-(1-phenethylindol-3-yl)methylene-2,4-thiazolidinedione prepared in Example 290 to give 2.79 g of 5-(1-phenethylindol-3-yl)methyl-2,4-thiazolidinedione as yellow crystals. The yield thereof was found to be 92%.

IR (KBr) cm$^{-1}$: 1750, 1700, 1460, 1340, 1160, 740, 700; NMR (DMSO-d$_6$) δ: 3.00 (2H,t,J=7.0 Hz), 3.16 (1H,dd,J=10.0 Hz, 14.4 Hz), 3.48 (1H,dd,J=14.4 Hz, 4.0 Hz), 4.36 (2H,t,J=7.0 Hz), 4.76 (1H,dd,J=4.0 Hz, 10.0 Hz), 6.9~7.7 (10H,m)

EXAMPLE 292

Synthesis of 1-benzenesulfonylindole-3-carbaldehyde

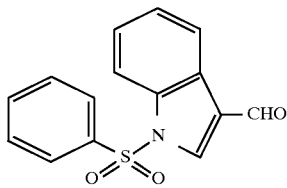

The same procedures used in Example 17 were repeated except for using 870 mg of indole-3-carbaldehyde to give 1.63 g of 1-benzenesulfonylindole-3-carbaldehyde as pale brown crystals. The yield thereof was found to be 95%.

NMR (CDCl$_3$) δ: 7.3~7.7 (5H,m), 7.9~8.1 (3H,m), 8.2~8.3 (1H,m), 8.24 (1H,s), 10.10 (1H,s)

EXAMPLE 293

Synthesis of 5-[1-(benzenesulfonyl)indol-3-yl]-methylene-2,4-thiazolidinedione

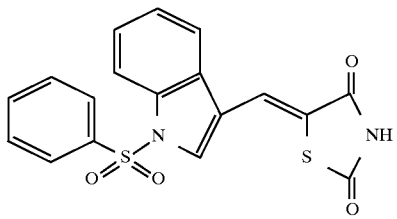

The same procedures used in Example 2 were repeated except for using 1.43 g of 1-benzenesulfonylindole-3-carbaldehyde prepared in Example 292 to give 1.80 g of 5-[1-(benzenesulfonyl)indol-3-yl]methylene-2,4-thiazolidinedione as pale yellow crystals. The yield thereof was found to be 94%.

IR (KBr) cm$^{-1}$: 1740, 1680, 1610, 1450; NMR (DMSO-d$_6$) δ: 7.3~7.5 (2H,m), 7.6~7.8 (3H,m), 7.8~8.1 (4H,m), 8.1~8.2 (2H,m), 12.6 (1H,bs)

EXAMPLE 294

Synthesis of 5-[1-(benzenesulfonyl)indol-3-yl]-methyl-2,4-thiazolidinedione

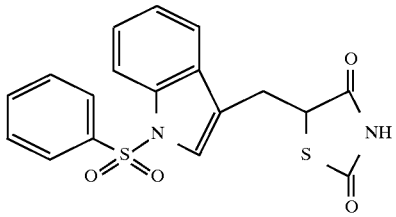

The same procedures used in Example 6 were repeated except for using 400 mg of 5-[1-(benzenesulfonyl)indol-3-yl]methylene-2,4-thiazolidinedione prepared in Example 293 to give 300 mg of 5-[1-(benzenesulfonyl)indol-3-yl]methyl-2,4-thiazolidinedione as pale yellow crystals. The yield thereof was found to be 75%.

IR (KBr) cm$^{-1}$: 1760, 1700, 1690, 1450; NMR (CDCl$_3$) δ: 3.28 (1H,dd,J=15.0 Hz, 9.1 Hz), 3.58 (1H,dd,J=15.0 Hz, 3.8 Hz), 4.59 (1H,dd,J=9.1 Hz, 3.8 Hz), 7.2~7.6 (7H,m), 7.7~7.9 (2H,m), 7.99 (1H,d,J=7.7 Hz), 8.37 (1H,bs)

EXAMPLE 295

Synthesis of 1-(4-fluorobenzenesulfonyl)indole-3-carbaldehyde

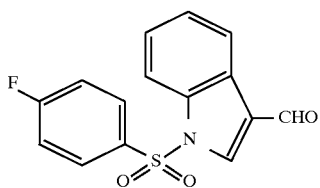

The same procedures used in Example 17 were repeated except for using 870 mg of indole-3-carbaldehyde and 4-fluorobenzenesulfonyl chloride instead of the benzenesulfonyl chloride used in Example 17 to give 1.73 g of 1-(4-fluorobenzenesulfonyl)indole-3-carbaldehyde as brown crystals. The yield thereof was found to be 95%.

NMR (CDCl$_3$) δ: 7.1~7.3 (2H,m), 7.3~7.5 (2H,m), 7.9~8.1 (3H,m), 8.2~8.3 (1H,m), 8.21 (1H,s), 10.10 (1H,s)

EXAMPLE 296

Synthesis of 5-[1-(4-fluorobenzenesulfonyl)indol-3-yl]methylene-2,4-thiazolidinedione

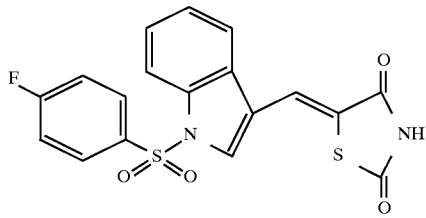

The same procedures used in Example 2 were repeated except for using 1.52 g of 1-(4-fluorobenzenesulfonyl) indole-3-carbaldehyde prepared in Example 295 to give 1.35 g of 5-[1-(4-fluorobenzenesulfonyl) indol-3-yl]methylene-2,4-thiazolidinedione as pale yellow crystals. The yield thereof was found to be 66%.

IR (KBr) cm$^{-1}$: 1740, 1690, 1610, 1180; NMR (DMSO-$d_6$) δ: 7.3~7.6 (4H,m), 7.8~8.1 (4H,m), 8.1~8.3 (2H,m), 12.66 (1H,bs)

EXAMPLE 297

Synthesis of 5-[1-(4-fluorobenzenesulfonyl)indol-3-yl]methyl-2,4-thiazolidinedione

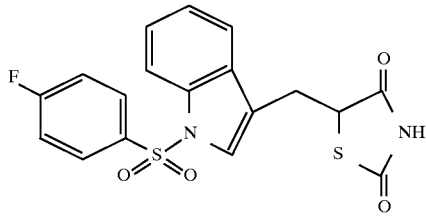

The same procedures used in Example 6 were repeated except for using 500 mg of 5-[1-(4-fluorobenzenesulfonyl) indol-3-yl]methylene-2,4-thiazolidinedione prepared in Example 296 to give 370 mg of 5-[1-(4-fluorobenzenesulfonyl)indol-3-yl]methyl-2,4-thiazolidinedione as pale yellow crystals. The yield thereof was found to be 74%.

IR (KBr) cm$^{-1}$: 1750, 1690, 1380, 1180; NMR (DMSO-$d_6$) δ: 3.32 (1H,dd,J=7.7 Hz, 7.0 Hz), 3.45 (1H,dd,J=7.0 Hz, 5.1 Hz), 5.01 (1H,dd,J=7.7 Hz, 5.1 Hz), 7.2~7.5 (4H,m), 7.5~7.7 (2H,m), 7.8~8.1 (3H,m), 12.01 (1H,bs)

EXAMPLE 298

Synthesis of ethyl 1-phenethylindole-2-carboxylate

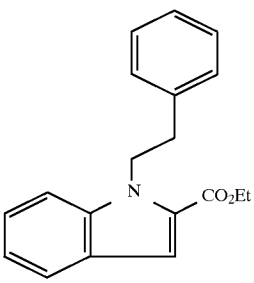

To a mixture of 2.00 g of ethyl indole-2-carboxylate and 3.51 g of potassium carbonate, there was added 40 ml of acetonitrile, followed by stirring the resulting mixture. To the mixed solution, there was added 2.35 g of 2-phenethyl bromide and the mixture was then stirred at 80° C. for 24 hours.

The reaction solution was filtered and the solvent was removed through evaporation under reduced pressure to give 3.75 g of a residue. The residue was purified by silica gel chromatography (hexane:ethyl acetate=24:1→19:1) to give 1.60 g of ethyl 1-phenethylindole-2-carboxylate as colorless crystals. The yield thereof was found to be 52%.

NMR (CDCl$_3$) δ: 1.40 (3H,t,J=7.1 Hz), 3.06 (2H,t,J=7.8 Hz), 4.36 (2H,q,J=7.1 Hz), 4.77 (2H,t,J=7.8 Hz), 7.1~7.4 (9H,m), 7.67 (1H,d,J=8.1 Hz)

EXAMPLE 299

Synthesis of 2-(hydroxymethyl)-1-phenethylindole

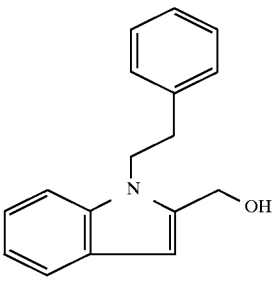

Lithium aluminum hydride (0.41 g) was added to and suspended in 16 ml of tetrahydrofuran in an argon gas atmosphere and the resulting suspension was stirred while cooling the same to a temperature ranging from 0° to 10° C. To the mixed solution, there was dropwise added a solution of the ethyl 1-phenethylindole-2-carboxylate (1.50 g) prepared in Example 298 in tetrahydrofuran (16 ml) over 15 minutes.

To this reaction solution, there were added, in order, 32 ml of water-containing ether and 3 ml of water and then the resulting precipitates were filtered off. The resulting filtrate was dried over anhydrous sodium sulfate and the solvent was removed through evaporation under reduced pressure to give 1.17 g of 2-(hydroxymethyl)-1-phenethylindole as colorless crystals. The yield thereof was found to be 91%.

NMR (CDCl$_3$) δ: 1.37 (1H,t,J=6.1 Hz), 3.10 (2H,t,J=7.6 Hz), 4.43, 4.49 (total 4H,t,d,J=7.6 Hz, 6.1 Hz), 6.40 (1H,s), 7.0~7.4 (8H,m), 7.60 (1H,d,J=7.6 Hz)

EXAMPLE 300

Synthesis of 1-phenethylindole-2-carbaldehyde

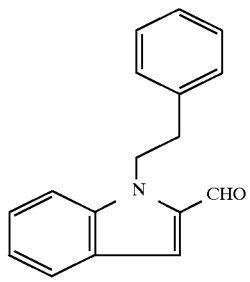

The same procedures used in Example 35 were repeated except for using 1.00 g of the 2-(hydroxymethyl)-1-phenethylindole prepared in Example 299 to give 0.97 g of 1-phenethylindole-2-carbaldehyde as a brown oily substance. The yield thereof was found to be 98%.

NMR (CDCl$_3$) δ: 3.04 (2H,t,J=7.6 Hz), 4.75 (2H,t,J=7.6 Hz), 7.0~7.4 (9H,m), 7.72 (1H,d,J=7.9 Hz), 9.86 (1H,s)

EXAMPLE 301

Synthesis of 5-(1-phenethylindol-2-yl)methylene-2,4-thiazolidinedione

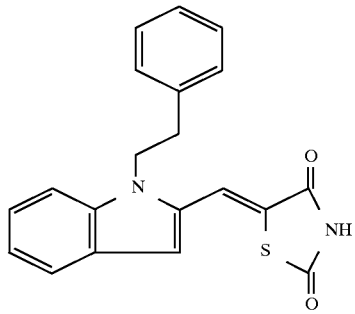

The same procedures used in Example 2 were repeated except for using 0.90 g of 1-phenethylindole-2-carbaldehyde prepared in Example 300 to give 0.89 g of 5-(1-phenethylindol-2-yl)methylene- 2,4-thiazolidinedione as yellow crystals. The yield thereof was found to be 71%.

IR (KBr) cm$^{-1}$: 1730, 1670, 1600, 1320, 1300; NMR (DMSO-d$_6$) δ: 2.95 (2H,t,J=6.6 Hz), 4.60 (2H,t,J=6.6 Hz), 6.76 (1H,s), 6.9~7.4 (8H,m), 7.54 (1H,s), 7.67 (1H,d,J=8.1 Hz), 12.50 (1H,bs)

EXAMPLE 302

Synthesis of 5-(1-phenethylindol-2-yl)methyl-2,4-thiazolidinedione

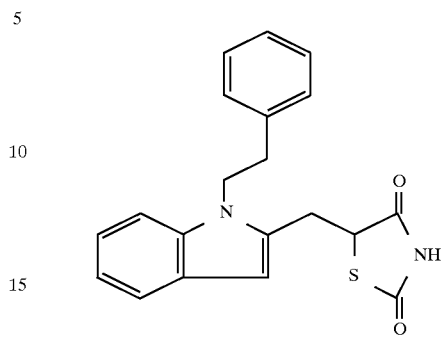

The same procedures used in Example 6 were repeated except for using 0.80 g of 5-(1-phenethylindol-2-yl) methylene-2,4-thiazolidinedione prepared in Example 301 to give 0.64 g of 5-(1-phenethylindol-2-yl)methyl-2,4-thiazolidinedione as a yellow amorphous substance. The yield thereof was found to be 80%.

IR (KBr) cm$^{-1}$: 1750, 1690, 1460, 1320, 750; NMR (DMSO-d$_6$) δ: 2.8~3.0 (2H,m), 3.2~3.4 (1H,m), 3.4~3.6 (1H,m), 4.2~4.4 (2H,m), 4.8~5.0 (1H,m), 6.21 (1H,s), 6.9~7.4 (8H,m), 7.4~7.6 (2H,m)

EXAMPLE 303

Synthesis of methyl 1-phenethylindole-5-carboxylate

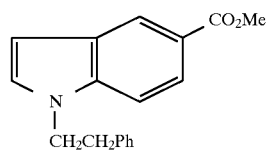

The same procedures used in Example 298 were repeated except for using 1.40 g of methyl indole-5-carboxylate to give 1.74 g of methyl 1-phenethylindole-5-carboxylate as pale yellow crystals. The yield thereof was found to be 78%.

NMR (CDCl$_3$) δ: 3.08 (2H,t,J=7.3 Hz), 3.92 (3H,s), 4.34 (2H,t,J=7.3 Hz), 6.52 (1H,d,J=3.3 Hz), 6.95 (1H,d,J=3.3 Hz), 7.0~7.1 (2H,m), 7.1~7.3 4H,m), 7.88 (1H,dd,J=8.7 Hz, 1.5 Hz), 8.38 (1H,s)

EXAMPLE 304

Synthesis of 5-(1-phenethylindol-5-yl)methylene-2,4-thiazolidinedione

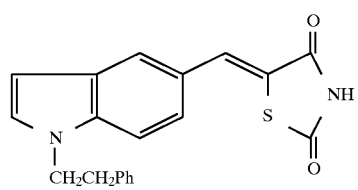

The same procedures used in Examples 299, 30 and 2 were repeated except for using 1.63 g of methyl 1-phenethylindole-5-carboxylate prepared in Example 303 to give 948 mg of 5-(1-phenethylindol-5-yl) methylene-2,4-thiazolidinedione as yellow crystals. The yield thereof was found to be 47%.

IR (KBr) cm$^{-1}$: 1720, 1680, 1590, 1320; NMR (DMSO-d$_6$) δ: 3.07 (2H,t,J=7.3 Hz), 4.45 (2H,t,J=7.3 Hz), 6.54 (1H,d,J=3.3 Hz), 7.1~7.4 (7H,m), 7.64 (1H,d,J=8.4 Hz), 7.82 (1H,d,J=1.0 Hz), 7.90 (1H,s) 12.46 (1H,bs)

EXAMPLE 305

Synthesis of 5-(1-phenethylindol-5-yl)methyl-2,4-thiazolidinedione

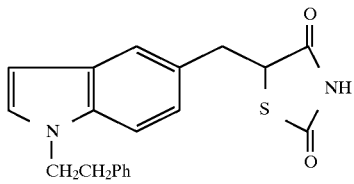

The same procedures used in Example 3 were repeated except for using 522 mg of 5-(1-phenethylindol-5-yl) methylene-2,4-thiazolidinedione prepared in Example 304 to give 422 mg of 5-(1-phenethylindol-5-yl)methyl-2,4-thiazolidinedione as pale yellow crystals. The yield thereof was found to be 80%.

IR (KBr) cm$^{-1}$: 1750, 1680, 1340, 1160; NMR (DMSO-d$_6$) δ: 3.04 (2H,t,J=7.3 Hz), 3.14 (1H,dd,J=14.3 Hz, 9.5 Hz), 3.46 (1H,dd,J=14.3 Hz, 4.4 Hz), 4.37 (2H,t,J=7.3 Hz), 4.92 (1H,dd,J=9.5 Hz, 4.4 Hz), 6.34 (1H,d,J=3.0 Hz), 6.99 (1H, dd,J=8.4 Hz, 1.5 Hz), 7.1~7.3 (6H,m), 7.3~7.5 (2H,m), 11.99 (1H,bs)

EXAMPLE 306

Synthesis of methyl 1-benzylindole-5-carboxylate

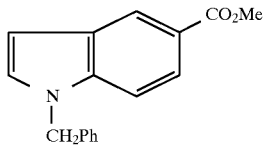

Methyl indole-5-carboxylate (1.40 g) was dissolved in 10 ml of dimethylformamide, followed by addition of 212 mg of sodium hydride (content: 95%) under ice-cooling and stirring for one hour. To the mixture, there was added 1.51 g of benzyl bromide, followed by stirring the mixture for 2 hours, pouring the reaction solution into 140 ml of a 5% ammonium chloride aqueous solution and extraction with ethyl acetate (50 ml×2). The resulting organic phase was washed with water (50 ml×2), dried over anhydrous sodium sulfate and the solvent was removed through evaporation under reduced pressure to give 2.09 g of methyl 1-benzylindole-5-carboxylate as orange-colored crystals. The yield thereof was found to be 99%.

NMR (CDCl$_3$) δ:3.91 (3H,s), 5.31 (2H,s), 6.63 (1H,d,J= 3.3 Hz), 7.0~7.4 (7H,m), 7.87 (1H,dd,J=8.4 Hz, 1.5 Hz ), 8.41 (1H,d,J=1.5 Hz)

EXAMPLE 307

Synthesis of 5-(1-benzylindol-5-yl)methylene-2,4-thiazolidinedione

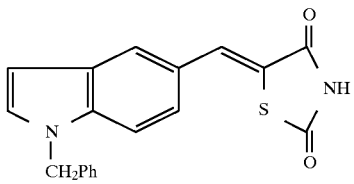

The same procedures used in Examples 299, 30 and 2 were repeated except for using 1.59 g of methyl 1-benzylindole-5-carboxylate prepared in Example 306 to give 750 mg of 5-(1-benzylindol-5-yl)methylene-2,4-thiazolidinedione as yellow crystals. The yield thereof was found to be 37%.

IR (KBr) cm$^{-1}$: 1730, 1680, 1580, 1310; NMR (DMSO-d$_6$) δ: 5.47 (2H,s), 6.64 (1H,d,J=3.0 Hz), 7.1~7.4 (6H,m), 7.5~7.7 (2H,m), 7.86 (1H,d,J=3.0 Hz), 7.88 (1H,s), 12.44 (1H,bs)

EXAMPLE 308

Synthesis of 5-(1-benzylindol-5-yl)methyl-2,4-thiazolidinedione

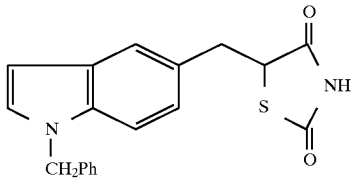

The same procedures used in Example 3 were repeated except for using 300 mg of 5-(1-benzylindol-5-yl) methylene-2,4-thiazolidinedione prepared in Example 307 to give 218 mg of 5-(1-benzylindol-5-yl)methyl-2,4-thiazolidinedione as pale yellow crystals. The yield thereof was found to be 72%.

IR (KBr) cm$^{-1}$: 1750, 1690, 1340, 1160; NMR (DMSO-d$_6$) δ: 3.12 (1H,dd,J=14.0 Hz, 9.2 Hz), 3.44 (1H,dd, J=14.0 Hz, 4.0 Hz), 4.90 (1H,dd,J=9.2 Hz, 4.0 Hz), 5.39 (2H,s), 6.44 (1H,d,J=3.0 Hz), 7.00 (1H,dd,J=8.0 Hz, 1.9 Hz), 7.1~7.4 (7H,m), 7.48 (1H,d,J=3.0 Hz), 11.98 (1H,bs)

EXAMPLE 309

Synthesis of 1-benzyl-2-(hydroxymethyl)indole

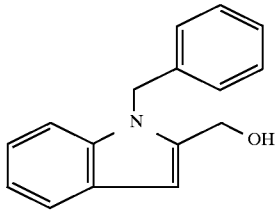

The same procedures used in Examples 1 and 299 were repeated except for using 2.00 g of ethyl indole-2-carboxylate instead of the indole-4-carbaldehyde used in these Examples to give 2.40 g of 1-benzyl-2-(hydroxymethyl)indole as a brown oily substance. The yield thereof was found to be 97%.

NMR (CDCl$_3$+CD$_3$OD) δ: 4.69 (2H,s), 5.48 (2H,s), 6.9~7.3 (9H,m), 7.5~7.7 (1H,m)

EXAMPLE 310

Synthesis of 1-benzylindole-2-carbaldehyde

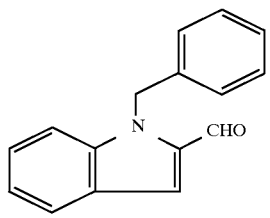

The same procedures used in Example 35 were repeated except for using 2.00 g of 1-benzyl-2-(hydroxymethyl)indole prepared in Example 309 to give 1.69 g of 1-benzylindole-2-carbaldehyde as brown crystals. The yield thereof was found to be 85%.

NMR (CDCl$_3$) δ: 5.80 (2H,s), 7.0~7.4 (9H,m), 7.7~7.8 (1H, m), 9.89 (1H,s)

EXAMPLE 311

Synthesis of 5-(1-benzylindol-2-yl)methylene-2,4-thiazolidinedione

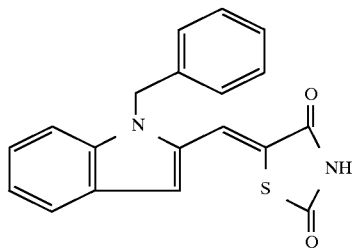

The same procedures used in Example 2 were repeated except for using 1.50 g of 1-benzylindole-2-carbaldehyde prepared in Example 310 to give 1.57 g of 5-(1-benzylindol-2-yl)methylene-2,4-thiazolidinedione as brown crystals. The yield thereof was found to be 74%.

IR (KBr) cm$^{-1}$: 1740, 1690, 1600, 1340, 1320; NMR (DMSO-d$_6$) δ: 5.71 (2H,s), 6.9~7.4 (8H,m), 7.5~7.8 (2H,m), 7.80 (1H,s), 12.60 (1H,bs)

EXAMPLE 312

Synthesis of 5-(1-benzylindol-2-yl)methyl-2,4-thiazolidinedione

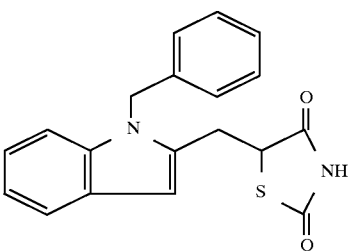

The same procedures used in Example 3 were repeated except for using 1.50 g of 5-(1-benzylindol-2-yl)methylene-2,4-thiazolidinedione prepared in Example 311 to give 1.19 g of 5-(1-benzylindol-2-yl)methyl-2,4-thiazolidinedione as colorless crystals. The yield thereof was found to be 79%.

IR (KBr) cm$^{-1}$: 1740, 1700, 1450, 1320, 1170, 730; NMR (DMSO-d$_6$) δ: 3.2~3.5 (2H,m), 4.9~5.1 (1H,m), 5.48 (2H,s), 6.34 (1H,s), 6.9~7.6 (9H,m), 12.12 (1H,bs)

EXAMPLE 313

Synthesis of methyl 1-benzylindole-6-carboxylate

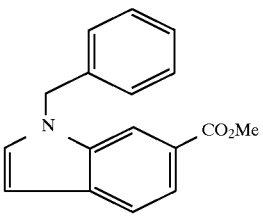

The same procedures used in Example 1 were repeated except for using 2.00 g of methyl indole-6-carboxylate instead of the indole-4-carbaldehyde used therein to give 3.00 g of methyl 1-benzylindole-6-carboxylate as a brown oily substance. The yield thereof was found to be 99%.

NMR (CDCl$_3$) δ: 3.90 (3H,s), 5.40 (2H,s), 6.58 (1H,d,J=3.0 Hz), 7.0~7.2 (2H,m), 7.2~7.4 (4H,m), 7.65 (1H,d,J=7.6 Hz), 7.80 (1H,d,J=7.6 Hz), 8.10 (1H,s)

EXAMPLE 314

Synthesis of 1-benzylindole-6-carbaldehyde

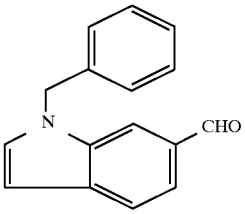

The same procedures used in Examples 299 and 35 were repeated except for using 2.50 g of the methyl 1-benzylindole-6-carboxylate prepared in Example 313 to give 1.65 g of 1-benzylindole-6-carbaldehyde as brown crystals. The yield thereof was found to be 75%.

NMR (CDCl$_3$) δ: 5.40 (2H,s), 6.62 (1H,d,J=3.1 Hz), 7.0~7.2 (2H,m), 7.2~7.4 (4H,m), 7.64 (1H,d,J=8.2 Hz), 7.74 (1H,d,J=8.2 Hz), 7.85 (1H,s), 10.00 (1H,s)

EXAMPLE 315

Synthesis of 5-(1-benzylindol-6-yl)methylene-2,4-thiazolidinedione

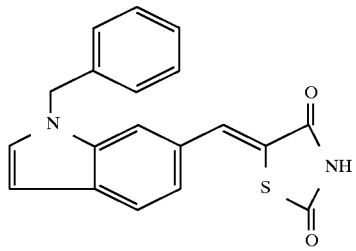

The same procedures used in Example 2 were repeated except for using 1.50 g of 1-benzylindole-6-carbaldehyde prepared in Example 314 to give 1.77 g of 5-(1-benzylindol-6-yl)methylene-2,4-thiazolidinedione as yellow crystals. The yield thereof was found to be 83%.

IR (KBr) cm$^{-1}$: 1740, 1690, 1590, 1320; NMR (DMSO-d$_6$) δ: 5.48 (2H,s), 6.58 (1H,d,J=2.9 Hz), 7.0~7.4 (6H,m), 7.6~7.8 (3H,m), 7.87 (1H,s), 12.48 (1H,bs)

EXAMPLE 316

Synthesis of 5-(1-benzylindol-6-yl)methyl-2,4-thiazolidinedione

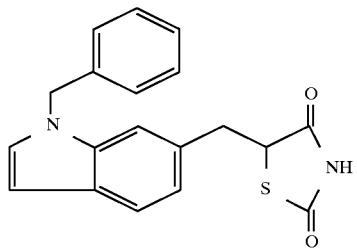

The same procedures used in Example 6 were repeated except for using 1.50 g of 5-(1-benzylindol-6-yl)methylene-2,4-thiazolidinedione prepared in Example 315 to give 0.98 g of 5-(1-benzylindol-6-yl)methyl-2,4-thiazolidinedione as a colorless amorphous substance. The yield thereof was found to be 65%.

IR (KBr) cm$^{-1}$: 1750, 1690, 1320, 1150; NMR (DMSO-d$_6$) δ: 3.0~3.2 (1H,m), 3.4~3.6 (1H,m), 4.8~5.0 (1H,m), 5.38 (2H,s), 6.44 (1H,d,J=2.9 Hz), 6.92 (1H,d,J=8.1 Hz), 7.1~7.6 (8H,m)

EXAMPLE 317

Synthesis of 5-[1-(4-hydroxybenzyl)indol-3-yl]-methyl-2,4-thiazolidinedione

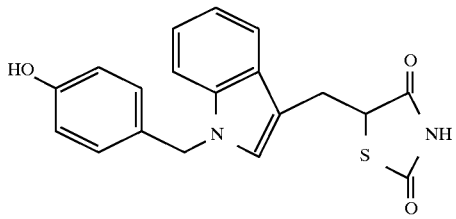

There was dissolved, in 30 ml of methylene chloride, 259 mg of 5-[1-(4-benzyloxybenzyl)indol-3-yl]methyl-2,4-thiazolidinedione prepared in Example 265 and the resulting solution was cooled to −78° C. After dropwise addition of a solution of boron tribromide (1.0M) in methylene chloride (10.17 ml), the temperature of the mixture was slowly raised up to room temperature. After stirring the mixture for 2 hours, a saturated sodium hydrogen carbonate aqueous solution was added followed by extraction with ethyl acetate. The resulting organic phase was washed with a saturated common salt solution, dried over anhydrous sodium sulfate and the solvent was removed by evaporation under reduced pressure to give 105 mg of 5-[1-(4-hydroxybenzyl)indol-3-yl]methyl-2,4-thiazolidinedione as a yellow amorphous substance. The yield thereof was found to be 51%.

IR (KBr) cm$^{-1}$: 1740, 1680, 1510, 1330; NMR (DMSO-d$_6$) δ: 3.31 (1H,dd,J=14.6 Hz, 8.4 Hz), 3.46 (1H,dd, J=14.6 Hz, 4.0 Hz), 4.92 (1H,dd,J=8.4 Hz, 4.0 Hz), 5.24 (2H,s), 6.65 (2H,d,J=7.6 Hz), 6.9~7.3 (4H,m), 7.33 (1H,s), 7.40 (1H,d, J=8.0 Hz), 7.56 (1H,d,J=7.3 Hz), 9.35 (1H,s), 11.96 (1H,bs)

EXAMPLE 318

Synthesis of 5-[1-(4-hydroxybenzyl)indol-4-yl]-methyl-2,4-thiazolidinedione

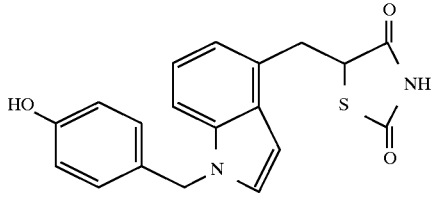

The same procedures used in Example 317 were repeated except for using 1.50 g of 5-[1-(4-benzyloxybenzyl)indol-4-yl]methyl-2,4-thiazolidinedione prepared in Example 109 to give 1.19 g of 5-[1-(4-hydroxybenzyl)indol-4-yl]methyl-2,4-thiazolidinedione as pale brown crystals. The yield thereof was found to be 100%.

IR (KBr) cm$^{-1}$: 1750, 1690 1510, 1180, 750; NMR (DMSO-d$_6$) δ: 3.30 (1H,dd,J=14.1 Hz, 10.3 Hz), 3.69 (1H, dd, J=14 .1 Hz, 4 .0 Hz ), 4.98 (1H,dd,J=10.3 Hz, 4.0 Hz), 5.26 (2H,s), 6.54 (1H,d,J=3.3 Hz), 6.68 (2H,d,J=8.4 Hz), 6.87 (1H,d,J=7.0 Hz), 7.05 (1H,t,J=7.0 Hz), 7.08 (2H,d,J= 8.4 Hz), 7.38 (1H,d,J=7.0 Hz), 7.46 (1H,d,J=3.3 Hz), 9.33 (1H,bs), 12.06 (1H,bs)

EXAMPLE 319

Synthesis of 1-(2-hydroxy-2-phenylethyl)indole-4-carboxylic acid

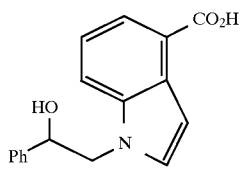

The same procedures used in Example 1 were repeated except for using 4.53 g of styrene oxide and 6.00 g of methyl indole-4-carboxylate as a starting material to give 5.48 g of 1-(2-hydroxy-2-phenylethyl) indole-4-carboxylic acid as a yellow amorphous substance. The yield thereof was found to be 57%.

NMR (CDCl$_3$) δ: 4.37 (2H,d,J=5.5 Hz), 5.04 (1H,t,J=5.5 Hz), 7.1~7.4 (8H,m), 7.5~7.6 (1H,m), 8.0~8.1 (1H,m)

EXAMPLE 320

Synthesis of methyl 1-(2-hydroxy-2-phenylethyl)-indole-4-carboxylate

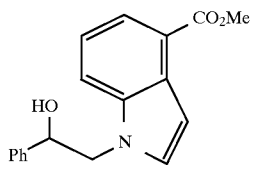

There were dissolved, in 80 ml of dimethylformamide, 5.39 g of 1-(2-hydroxy-2-phenylethyl)indole-4-carboxylic acid prepared in Example 319 and 3.05 g of methyl iodide, followed by further addition of 2.91 g of potassium carbonate and stirring at room temperature for 30 minutes. The reaction system was poured into 300 ml of a 10% ammonium chloride aqueous solution and extracted with ethyl acetate (100 ml×3). The resulting organic phase was washed, in order, with a 10% citric acid aqueous solution and a saturated common salt solution, dried over anhydrous sodium sulfate and the solvent was removed by evaporation under reduced pressure to give a crude product. The crude product was purified by silica gel column chromatography (hexane:ethyl acetate=5:1) to give 5.14 g of methyl 1-(2-hydroxy-2-phenylethyl)indole-4-carboxylate as a yellow oily substance. The yield thereof was found to be 91%.

NMR (CDCl$_3$) δ: 3.91 (3H,s), 4.28 (2H,d,J=5.9 Hz), 4.9~5.0 (1H,m), 7.0~7.4 (8H,m), 7.48 (1H,d,J=7.7 Hz), 7.85 (1H,d,J=7.3 Hz)

EXAMPLE 321

Synthesis of 1-(2-hydroxy-2-phenylethyl)indole-4-carbaldehyde

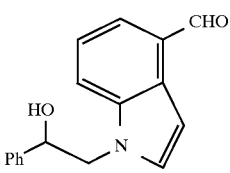

There were dissolved, in 40 ml of dimethylformamide, 5.14 g of 1-(2-hydroxy-2-phenylethyl)indole-4-carboxylate prepared in Example 320, 2.37 g of imidazole and 4.50 g of t-butyldimethylsilyl chloride and the resulting solution was stirred at room temperature for 21 hours. The solution was then poured into 100 ml of water and extracted with ethyl acetate (100 ml×2). The extract was washed in order with a 10% citric acid aqueous solution, a saturated sodium hydrogen carbonate aqueous solution and a saturated common salt solution, then dried over anhydrous sodium sulfate and the solvent was removed by evaporation under reduced pressure. The resulting crude product was purified by silica gel column chromatography (hexane:ethyl acetate=10:1) to give 6.97 g of a pale yellow oily substance. The substance was dissolved in 20 ml of tetrahydrofuran and then dropwise added to a suspension of lithium aluminum hydride (516 mg) in tetrahydrofuran (40 ml) with ice-cooling. After stirring at room temperature for 1.5 hour, 0.52 ml of water, 0.52 ml of a 15% aqueous sodium hydroxide solution and 1.56 ml of water were, in order, added to the mixture, followed by drying over potassium carbonate, filtration and removal of the solvent through evaporation under reduced pressure to give 6.42 g of a colorless oily substance. This substance was dissolved in 70 ml of methylene chloride, followed by addition of 37.5 g of manganese dioxide, stirring at room temperature for 17 hours, filtration through a Celite layer, removal of the solvent through evaporation under reduced pressure to give 5.1 g of a pale yellow oily substance. The substance was dissolved in 40 ml of tetrahydrofuran, followed by addition of 25.8 ml of a 1.0M tetrabutylammonium fluoride solution and stirring at room temperature for 3.5 hours. water (50 ml) was added to the solution, extracted with ethyl acetate (100 ml×2), followed by washing of the extract with, in order, 5% hydrochloric acid, a saturated sodium hydrogen carbonate aqueous solution and a saturated common salt solution, drying over anhydrous sodium sulfate and removal of the solvent through evaporation under reduced pressure to give a crude product. The crude product was purified by silica gel column chromatography to give 3.55 g of 1-(2-hydroxy-2-phenylethyl)indole-4-carbaldehyde as a yellow oily substance. The yield thereof was found to be 75%.

NMR (CDCl$_3$) δ: 4.3~4.4 (2H,m), 5.05 (1H,dd,J=6.6 Hz, 5.1 Hz) 7.1~7.4 (8H,m), 7.6~7.7 (2H,m), 10.22 (1H,s)

EXAMPLE 322

Synthesis of 5-[1-(2-hydroxy-2-phenylethyl)indol-4-yl]methylene-2,4-thiazolidinedione

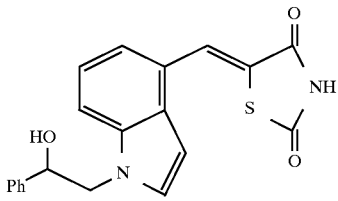

The same procedures used in Example 2 were repeated except for using 1.00 g of 1-(2-hydroxy-2-phenylethyl) indole-4-carbaldehyde prepared in Example 321 to give 544 mg of 5-[1-(2-hydroxy-2-phenylethyl) indol-4-yl] methylene-2,4-thiazolidinedione as yellow crystals. The yield thereof was found to be 40%.

IR (KBr) cm$^{-1}$: 1730, 1690, 1590, 1330, 1290, 1160, 750; NMR (DMSO-d$_6$) δ: 4.3~4.4 (2H,m), 4.9~5.0 (1H,m), 6.69 (1H,d,J=2.9 Hz), 7.1~7.4 (7H,m), 7.47 (1H,d,J=2.9 Hz), 7.63 (1H,d,J=7.7 Hz), 8.12 (1H,s), 12.53 (1H,bs)

EXAMPLE 323

Synthesis of 5-[1-(2-hydroxy-2-phenylethyl)indol-4-yl]methyl-2,4-thiazolidinedione

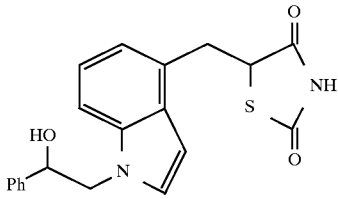

The same procedures used in Example 3 were repeated except for using 540 mg of 5-[1-(2-hydroxy-2-phenylethyl) indol-4-yl)methylene-2,4-thiazolidinedione prepared in Example 322 to give 538 mg of 5-[1-(2-hydroxy-2-phenylethyl)indol-4-yl]methyl-2,4-thiazolidinedione as a yellow amorphous substance. The yield thereof was found to be 99%.

IR (KBr) cm$^{-1}$: 1750, 1690, 1330, 1160, 750; NMR (CDCl$_3$) δ: 3.25 (1H,dd,J=13.9 Hz, 11.0 Hz), 3.93 (1H,dd, J=13.9 Hz, 3.7 Hz), 4.2~4.4 (2H,m), 4.68 (1H,dd,J=11.0 Hz, 3.7 Hz), 5.0~5.1 (1H,m), 6.54 (1H,d,J=3.3 Hz), 6.95 (1H, d,J=7.0 Hz), 7.1~7.4 (8H,m)

EXAMPLE 324

Synthesis of 1-(2-benzyloxy-2-phenylethyl)indole-4-carbaldehyde

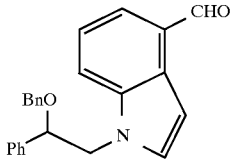

There was suspended 26.4 mg of 60% sodium hydride in 5 ml of dimethylformamide, followed by addition of a solution of 1-(2-hydroxy-2-phenylethyl)indole-4-carbaldehyde (160 mg) in dimethylformamide (2 ml) with ice-cooling. After stirring at room temperature for 15 minutes, the mixture was ice-cooled, then a solution of benzyl bromide (115.2 mg) in dimethylformamide (2 ml) was added thereto and stirred at room temperature for 3 hours. The reaction system was poured into 50 ml of a 10% ammonium chloride aqueous solution and extracted with ethyl acetate (50 ml×2). The resulting organic phase was washed with, in order, a 10% citric acid aqueous solution, a saturated sodium hydrogen carbonate aqueous solution and a saturated common salt solution, dried over anhydrous sodium sulfate and the solvent was removed through evaporation under reduced pressure to give a crude product. The crude product was purified by silica gel column chromatography (hexane:ethyl acetate=10:1) to give 170 mg of 1-(2-benzyloxy-2-phenylethyl)indole-4-carbaldehyde as a yellow oily substance. The yield thereof was found to be 80%.

NMR (CDCl$_3$) δ: 4.1~4.5 (4H,m), 4.64 (1H,dd,J=7.3 Hz, 4.4 Hz) 6.9~7.0 (2H,m), 7.1~7.4 (11H,m), 7.5~7.7 (2H,m), 10.26 (1H,s)

EXAMPLE 325

Synthesis of 5-[1-(2-benzyloxy-2-phenylethyl)-indol-4-yl]methylene-2,4-thiazolidinedione

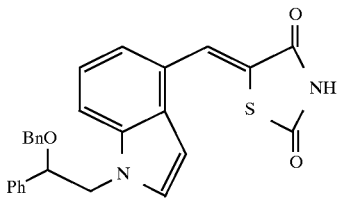

The same procedures used in Example 2 were repeated except for using 165 mg of 1-(2-benzyloxy-2-phenylethyl) indole-4-carbaldehyde prepared in Example 324 to give 164 mg of 5-[1-(2-benzyloxy-2-phenylethyl)indol-4-yl] methylene-2,4-thiazolidinedione as a yellow amorphous substance. The yield thereof was found to be 78%.

IR (KBr) cm$^{-1}$: 1750, 1680, 1590, 1330, 1290, 750; NMR (DMSO-d$_6$) δ: 4.15 (1H,d,J=12.3 Hz), 4.34 (1H,d,J=12.3 Hz), 4.4~4.6 (2H,m), 4.78 (1H,dd,J=7.5 Hz, 4.4 Hz), 6.74 (1H,d,J=3.3 Hz), 6.9~7.0 (2H,m), 7.1~7.5 (10H,m), 7.51 (1H,d,J=3.3 Hz), 7.6~7.7 (1H,m), 8.15 (1H,s), 12.57 (1H,bs)

EXAMPLE 326

Synthesis of 5-[1-(2-benzyloxy-2-phenylethyl)-indol-4-yl]methyl-2,4-thiazolidinedione

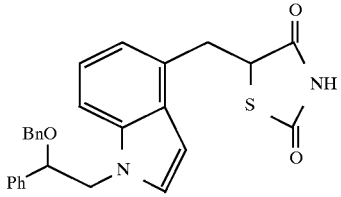

The same procedures used in Example 3 were repeated except for using 160 mg of 5-[1-(2-benzyloxy-2-phenylethyl)indol-4-yl]methylene-2,4-thiazolidinedione prepared in Example 325 to give 139 mg of 5-[1-(2-benzyloxy-2-phenylethyl)indol-4-yl]methyl-2,4- thiazolidinedione as a yellow amorphous substance. The yield thereof was found to be 87%.

IR (KBr) cm$^{-1}$: 1750, 1690, 1330, 1290, 1090, 740; NMR (DMSO-d$_6$) δ: 3.32 (1H,dd,J=14.1 Hz, 10.3 Hz), 3.71 (1H, dd,J=14.1 Hz, 4.0 Hz), 4.14 (1H,d,J=12.8 Hz), 4.34 (1H,d, J=12.8 Hz), 4.3~4.5 (2H,m), 4.76 (1H,dd,J=7.3 Hz, 4.0 Hz), 5.00 (1H,dd, J=10.3 Hz, 4.0 Hz), 6.53 (1H,d,J=3.3 Hz), 6.8~7.5 (14H,m), 12.06 (1H,bs)

EXAMPLE 327

Synthesis of 5-[1-(2-fluoro-2-phenylethyl)indol-4-yl]methyl-2,4-thiazolidinedione

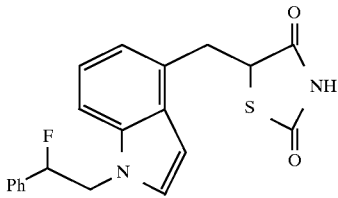

To 10 ml of methylene chloride, there was dissolved 134 mg of 5-[1-(2-hydroxy-2-phenylethyl)indol-4-yl]methyl-2, 4-thiazolidinedione prepared in Example 323 under an argon gas atmosphere and the resulting solution was then cooled to −34° C. After addition of 88 mg of diethylaminosulfur trifluoride to the solution and stirring it for 5 minutes and the solution was then stirred at room temperature for additional 30 minutes. After addition of 10 ml of methanol, the solution was poured into 50 ml of water and extracted with ethyl acetate. The resulting extract was dried over anhydrous sodium sulfate and the solvent was removed through evaporation under reduced pressure to give a crude product. The product was purified by preparatory silica gel thin layer chromatography (hexane:ethyl acetate=10:1) to give 98 mg of 5-[1-(2-fluoro-2-phenylethyl)indol-4-yl]methyl-2,4-thiazolidinedione as a yellow amorphous substance. The yield thereof was found to be 73%.

IR (KBr) cm$^{-1}$: 1750, 1700, 1440, 1330, 1300, 1600, 750; NMR (CDCl$_3$) δ: 3.27 (1H,dd,J=13.9 Hz, 11.0 Hz), 3.96 (1H,dd,J=13.9 Hz, 3.7 Hz), 4.4~4.6 (2H,m), 4.71 (1H,dd,J= 11.0 Hz, 3.7 Hz), 5.6~5.8 (1H,m), 6.57 (1H,d,J=2.9 Hz), 6.97 (1H,d,J=6.6 Hz), 7.1~7.4 (8H,m), 8.90 (1H,bs)

EXAMPLE 328

Synthesis of 5-[1-(2-chloro-2-phenylethyl)indol-4-yl]methyl-2,4-thiazolidinedione

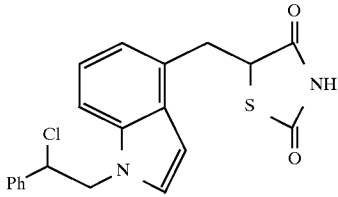

To 10 ml of methylene chloride, there were dissolved 150 mg of 5-[1-(2-hydroxy-2-phenylethyl)indol-4-yl]methyl-2, 4-thiazolidinedione prepared in Example 323 and 45 mg of triethylamine under an argon gas atmosphere and then 51 mg of methanesulfonyl chloride was added to the solution under ice-cooling. After stirring at room temperature for 30 minutes, 30 ml of ethyl acetate was added to the solution, the mixture was in order washed with a 10% citric acid aqueous solution, a saturated sodium hydrogen carbonate aqueous solution and a saturated common salt solution, dried over anhydrous sodium sulfate and then the solvent was removed by evaporation under reduced pressure. The resulting residue was dissolved in 10 ml of dimethylformamide, followed by addition of 21 mg of lithium chloride and heating to 70° C. with stirring for 20 hours. The solution was poured into a 10% ammonium chloride aqueous solution and extracted with ethyl acetate (20 ml×3). The resulting extract was in order washed with a 10% citric acid aqueous solution, a saturated sodium hydrogen carbonate aqueous solution and a saturated common salt solution, dried over anhydrous sodium sulfate and the solvent was removed through evaporation under reduced pressure to give a crude product. The product was purified by preparatory silica gel thin layer chromatography (hexane:ethyl acetate=10:1) to give 35 mg of 5-[1-(2-chloro-2-phenylethyl)indol-4-yl]methyl-2,4-thiazolidinedione as a yellow amorphous substance. The yield thereof was found to be 22%.

IR (KBr) cm$^{-1}$: 1750, 1690, 1440, 1330, 1300, 1600, 750; NMR (CDCl$_3$) δ: 3.1~3.3 (1H,m), 3.8~4.0 (1H,m), 4.5~4.7 (3H, m), 5.16 (1H,t,J=7.0 Hz), 6.47 (1H,d,J=3.3 Hz), 6.9~7.0 (2H,m), 7.1~7.4 (7H,m), 8.48 (1H,bs)

EXAMPLE 329

Synthesis of 1-(2-azido-2-phenylethyl)indole-4-carbaldehyde

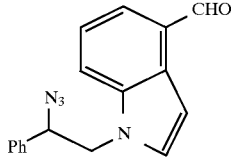

To 10 ml of methylene chloride, there were dissolved 200 mg of 1-(2-hydroxy-2-phenylethyl)indole-4-carbaldehyde prepared in Example 321 and 152 mg of triethylamine and then the resulting solution was ice-cooled, under an argon gas atmosphere. To the solution there was added 103 mg of methanesulfonyl chloride and the mixture was stirred at room temperature for 10 minutes. Ethyl acetate (30 ml) was added to the solution, the mixture was in order washed with a 2% hydrochloric acid aqueous solution, a saturated sodium hydrogen carbonate aqueous solution and a saturated common salt solution, dried over anhydrous sodium sulfate and then the solvent was removed by evaporation under reduced pressure. The resulting residue was dissolved in 5 ml of dimethylformamide, followed by addition of 78 mg of sodium azide, heating to 45° C. with stirring for 30 minutes. The reaction system was poured into 20 ml of water and then extracted with ethyl acetate. The resulting extract was in order washed with a 2% hydrochloric acid aqueous solution, a saturated sodium hydrogen carbonate aqueous solution and a saturated common salt solution, dried over anhydrous sodium sulfate and then the solvent was removed by evaporation under reduced pressure to give a crude product. The crude product was purified by silica gel column chromatography (hexane:ethyl acetate=10:1) to give 162 mg of 1-(2-azido-2-phenylethyl)indole-4-carbaldehyde as a yellow oily substance. The yield thereof was found to be 98%.

NMR (CDCl$_3$) δ: 4.36 (2H,d,J=6.6 Hz), 4.87 (1H,t,J=6.6 Hz), 7.1~7.4 (8H,m), 7.54 (1H,d,J=8.5 Hz), 7.6~7.7 (1H,m), 10.24 (1H,s)

EXAMPLE 330

Synthesis of 5-[1-(2-azido-2-phenylethyl)indol-4-yl]methylene-2,4-thiazolidinedione

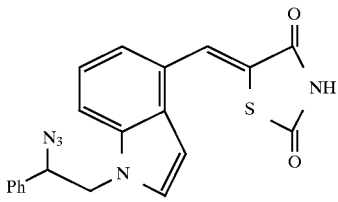

The same procedures used in Example 2 were repeated except for using 160 mg of 1-(2-azido-2-phenylethyl)indole-4-carbaldehyde prepared in Example 329 to give 108 mg of 5-[1-(2-azido-2-phenylethyl)indol-4-yl]methylene-2,4-thiazolidinedione as a yellow amorphous substance. The yield thereof was found to be 50%.

IR (KBr) cm$^{-1}$: 1730, 1690, 1500, 1310, 1160; NMR (CDCl$_3$) δ: 4.34 (2H,d,J=6.6 Hz), 4.88 (1H,t,J=6.6 Hz), 6.75 (1H,d,J=3.3 Hz), 7.0~7.2 (2H,m), 7.2~7.5 (7H,m), 8.34 (1H,s), 9.12 (1H,bs)

EXAMPLE 331

Synthesis of 5-[1-(2-amino-2-phenylethyl)indol-4-yl]methyl-2,4-thiazolidinedione

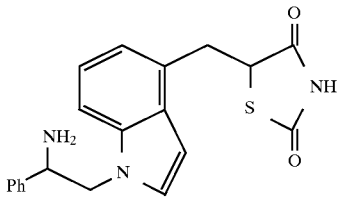

The same procedures used in Example 6 were repeated except for using 100 mg of 5-[1-(2-azido-2-phenylethyl)indol-4-yl]methylene-2,4-thiazolidinedione prepared in Example 330 to give 55 mg of 5-(1-(2-amino-2-phenylethyl)indol-4-yl]methyl-2,4-thiazolidinedione as a yellow amorphous substance. The yield thereof was found to be 58%.

IR (KBr) cm$^{-1}$: 1690, 1560, 1290, 1220, 750; NMR (CDCl$_3$) δ: 3.29 (1H,dd,J=14.8 Hz, 11.4 Hz), 3.98 (1H,dd, J=18 Hz, 3.7 Hz), 4.2~4.5 (3H,m), 4.72 (1H, dd,J=11.4 Hz, 3.7 Hz), 6.5~6.6 (1H,m), 6.9~7.0 (1H,m), 7.1~7.4 (8H,m)

EXAMPLE 332

Synthesis of 5-{1-[2-(N,N-dimethylamino)-2-phenylethyl]indol-4-yl}methyl-2,4-thiazolidinedione

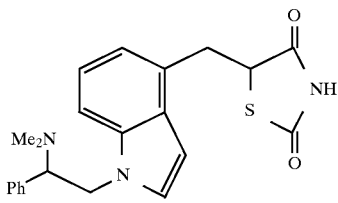

To 5 ml of ethanol, there were added 40 mg of 5-[1-(2-amino-2-phenylethyl)indol-4-yl]methyl-2,4-thiazolidinedione prepared in Example 331, 36 mg of 37% formalin and 28 mg of sodium cyanoborohydride, followed by addition of a drop of acetic acid and heating under reflux for 2.5 hours. The reaction system was poured into 20 ml of water and extracted with ethyl acetate. The resulting extract was, in order, washed with a 10% citric acid aqueous solution, a saturated sodium hydrogen carbonate aqueous solution and a saturated common salt solution, dried over anhydrous sodium sulfate and the solvent was removed through evaporation under reduced pressure to give a crude product. The product was purified by preparatory silica gel thin layer chromatography (chloroform:methanol=10:1) to give 25 mg of 5-{1-[2-(N,N-dimethylamino)-2-phenylethyl]indol-4-yl}methyl-2,4-thiazolidinedione as a yellow amorphous substance. The yield thereof was found to be 58%.

IR (KBr) cm$^{-1}$: 1690, 1610, 1290, 1160, 750; NMR (DMSO-d$_6$) δ:2.15 (6H,s), 3.28 (1H,dd,J=14.3 Hz, 9.9 Hz), 3.64 (1H,dd,J=14.3 Hz, 4.0 Hz), 3.92 (2H,t,J=7.0 Hz), 4.4~4.6 (1H,m), 6.5~6.6 (1H,m), 6.8~6.9 (1H,m), 7.0~7.1 (1H,m), 7.2~7.4 (7H,m)

EXAMPLE 333

Synthesis of 1-(2-methoxy-2-phenylethyl)indole-4-carbaldehyde

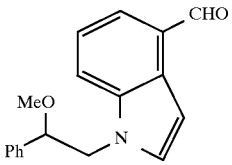

The same procedures used in Example 324 were repeated except for using 113 mg of methyl iodide and 189 mg of 1-(2-hydroxy-2-phenylethyl)indole-4-carbaldehyde prepared in Example 321 as a starting material to give 185 mg of 1-(2-methoxy-2-phenylethyl)indole-4-carbaldehyde as a yellow oily substance. The yield thereof was found to be 93%.

NMR (CDCl$_3$) δ: 3.17 (3H,s), 4.2~4.5 (3H,m), 7.1~7.4 (8H,m 7.54 (1H,d,J=8.1 Hz), 7.60 (1H,d,J=7.3 Hz), 10.24 (1H,s)

EXAMPLE 334

Synthesis of 5-[1-(2-methoxy-2-phenylethyl)indol-4-yl]methylene-2,4-thiazolidinedione

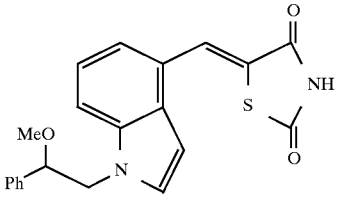

The same procedures used in Example 2 were repeated except for using 180 mg of 1-(2-methoxy-2-phenylethyl)indole-4-carbaldehyde prepared in Example 333 to give 241 mg of 5-[1-(2-methoxy-2-phenylethyl) indol-4-yl]methylene-2,4-thiazolidinedione as yellow crystals. The yield thereof was found to be 99%.

IR (KBr) cm$^{-1}$: 1740, 1690, 1300, 1100, 750; NMR (CDCl$_3$) δ: 3.19 (3H,s), 4.2~4.5 (3H,m), 6.70 (1H,d,J=2.9 Hz), 7.1~7.4 (9H,m), 8.35 (1H,s), 9.03 (1H, bs)

EXAMPLE 335

Synthesis of 5-[1-(2-methoxy-2-phenylethyl)indol-4-yl]methyl-2,4-thiazolidinedione

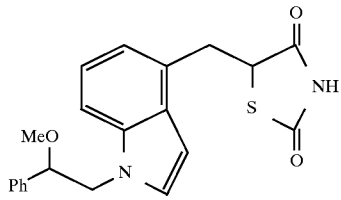

The same procedures used in Example 3 were repeated except for using 230 mg of 5-[1-(2-methoxy-2-phenylethyl)indol-4-yl]methylene-2,4-thiazolidinedione prepared in Example 334 to give 182 mg of 5-[1-(2-methoxy-2-phenylethyl)indol-4-yl]methyl-2,4-thiazolidinedione as a yellow amorphous substance. The yield thereof was found to be 79%.

IR (KBr) cm$^{-1}$: 1750, 1690, 1330, 1160, 750; NMR (DMSO-d$_6$) δ: 3.05 (3H,s), 3.31 (1H,dd,J=14.3 Hz, 10.3 Hz), 3.68 (1H,dd,J=14.3 Hz, 4.0 Hz), 4.2~4.4 (2H,m), 4.59 (1H,dd,J=7.3 Hz, 4.4 Hz), 4.98 (1H,dd,J=10.3 Hz, 4.0 Hz), 6.49 (1H,d,J=3.3 Hz), 6.87 (1H,d,J=7.3 Hz), 7.05 (1H,t,J=7.3 Hz), 7.2~7.4 (7H,m), 12.05 (1H,bs)

EXAMPLE 336

Synthesis of 5-[1-(N,N-dimethylaminobenzyl)indol-4-yl]methyl-2,4-thiazolidinedione

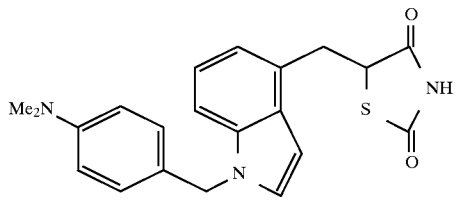

To 150 ml of ethanol, there was dissolved 750 mg of 5-[1-(4-nitrobenzyl)indol-4-yl]methylene-2,4-thiazolidinedione prepared in Example 189, followed by addition of 0.4 ml of 37% formalin and 750 mg of 10% palladium/carbon and stirring at room temperature and a hydrogen gas pressure (6 kg/cm$^2$) for 13 hours. The catalyst was filtered off through a Celite layer and the solvent was removed through evaporation under reduced pressure. Hexane was added to the residue obtained to crystallize it and to thus give 409 mg of 5-[1-(N,N-dimethylaminobenzyl)indol-4-yl]methyl-2,4-thiazolidinedione as pale brown crystals. The yield thereof was found to be 55%.

IR (KBr) cm$^{-1}$: 1740, 1690, 1620, 1520, 1350, 1160, 750; NMR (DMSO-d$_6$) δ: 2.83 (6H,s), 3.1~3.3 (1H,m), 3.76 (1H, dd, J=14 .3 Hz, 4.0 Hz), 5.05 (1H,dd,J=10.6 Hz, 4.0 Hz), 5.24 (2H,s), 6.53 (1H,d,J=2.9 Hz), 6.64 (2H,d,J=8.8 Hz), 6.88 (1H,d,J=7.3 Hz), 7.0~7.2 (1H,m), 7.11 (2H,d, J=8.8 Hz), 7.40 (1H,d,J=8.1 Hz), 7.47 (1H,d,J=2.9 Hz)

EXAMPLE 337

Synthesis of 5-[1-(2-picolyl)indol-4-yl]methyl-2,4-thiazolidinedione hydrochloride

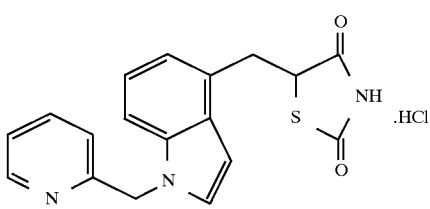

Ethyl acetate (50 ml) was added to 1.00 g of 5-[1-(2-picolyl) indol-4-]methyl-2,4-thiazolidinedione prepared in Example 133, followed by stirring the mixture, addition of 5 ml of 4N hydrochloric acid (a solution in ethyl acetate) and recovery of the separated crystals through filtration. The crystals were washed with ethyl acetate and then dried at room temperature under reduced pressure to give 1.07 g of 5-[1-(2-picolyl)indol-4-yl]methyl-2,4-thiazolidinedione hydrochloride as colorless crystals. The yield thereof was found to be 96%.

IR (KBr) cm$^{-1}$: 1700, 1640, 1620, 760; NMR (DMSO-d$_6$) δ: 3.34 (1H,dd,J=10.6 Hz, 14.5 Hz), 3.70 (1H,dd,J=14.5 Hz, 3.7 Hz), 5.00 (1H,dd,J=3.7 Hz, 10.6 Hz), 5.73 (2H,s), 6.66 (1H,d,J=3.3 Hz), 6.93 (1H,d,J=7.3 Hz), 7.08 (1H, dd,J=7.3 Hz, 7.7 Hz), 7.18 (1H,d,J=8.1 Hz), 7.43 (1H,d,J=8.1 Hz), 7.5~7.7 (2H,m), 8.0~8.2 (1H,m), 8.74 (1H,d,J=4.8 Hz), 12.08 (1H,bs)

EXAMPLE 338

Synthesis of methyl 1-phenethylindole-6-carboxylate

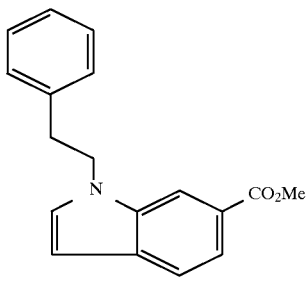

The same procedures used in Example 1 were repeated except for using 2.00 g of methyl indole-6-carboxylate and 2.54 g of phenethyl bromide instead of the indole-4-carbaldehyde and benzyl bromide used in Example 1 to give 0.61 g of methyl 1-phenethylindole-6-carboxylate as a yellow oily substance. The yield thereof was found to be 19%.

NMR (CDCl$_3$) δ: 3.12 (2H,t,J=7.1 Hz), 3.95 (3H,s), 4.41 (2H,t,J=7.1 Hz), 6.45 (1H,d,J=2.9 Hz), 6.9~7.4 (6H,m), 7.62 (1H,d,j=8.3 Hz), 7.79 (1H,d,j=8.3 Hz), 8.10 (1H,s)

EXAMPLE 339

Synthesis of 6-(hydroxymethyl)-1-phenethylindole

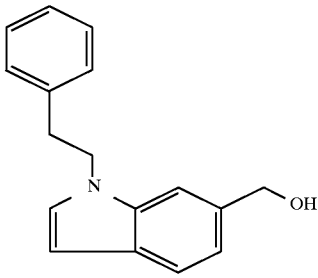

The same procedures used in Example 299 were repeated except for using 0.60 g of methyl 1-phenethylindole-6-carboxylate prepared in Example 338 to give 0.50 g of 6-(hydroxymethyl)-1-phenethylindole as colorless crystals. The yield thereof was found to be 93%.

NMR (CDCl$_3$) δ: 3.10 (2H,t,J=7.0 Hz), 4.38 (2H,t,J=7.0 Hz), 4.80 (2H,s), 6.42 (1H,d,J=3.0 Hz), 6.9~7.4 (8H, m), 7.61 (1H,d,J=8.0 Hz)

EXAMPLE 340

Synthesis of 1-phenethylindole-6-carbaldehyde

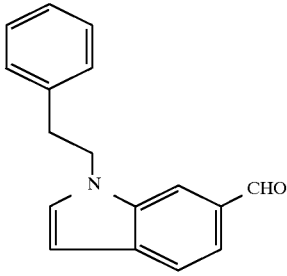

The same procedures used in Example 35 were repeated except for using 0.50 g of 6-(hydroxymethyl)-1-phenethylindole prepared in Example 339 to give 0.49 g of 1-phenethylindole-6-carbaldehyde as a brown oily substance. The yield thereof was found to be 98%.

NMR (CDCl$_3$) δ: 3.12 (2H,t,J=7.2 Hz), 4.46 (2H,t,J=7.2 Hz), 6.50 (1H,d,j=2.9 Hz), 7.0~7.4 (6H,m), 7.5~7.9 (3H,m), 10.05 (1H,s)

EXAMPLE 341

Synthesis of 5-(1-phenethylindol-6-yl)methylene-2,4-thiazolidinedione

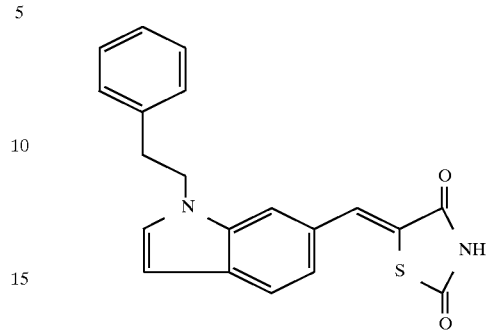

The same procedures used in Example 2 were repeated except for using 0.45 g of 1-phenethylindole-6-carbaldehyde prepared in Example 340 to give 0.46 g of 5-(1-phenethylindol-6-yl)methylene-2,4-thiazolidinedione as yellow crystals. The yield thereof was found to be 74%.

IR (KBr) cm$^{-1}$: 1740, 1680, 1580, 1350, 1320; NMR (DMSO-d$_6$) δ: 3.10 (2H,t,J=7.1 Hz), 4.47 (2H,t,J=7.1 Hz), 6.48 (1H,d,J=3.3 Hz), 7.1~7.3 (6H,m), 7.50 (1H,d,J=3.3 Hz), 7.67 (1H,d,J=8.4 Hz), 7.81 (1H,s), 7.94 (1H,s), 12.48 (1H,bs)

EXAMPLE 342

Synthesis of 5-(1-phenethylindol-6-yl)methyl-2,4-thiazolidinedione

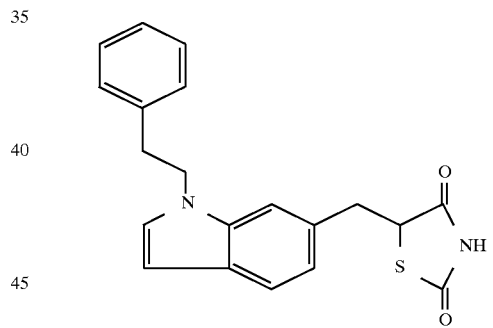

The same procedures used in Example 6 were repeated except for using 0.40 g of 5-(1-phenethylindol-6-yl)methylene-2,4-thiazolidinedione prepared in Example 341 to give 0.32 g of 5-(1-phenethylindol-6-yl)methyl-2,4-thiazolidinedione as a yellow oily substance. The yield thereof was found to be 80%.

IR (KBr) cm$^{-1}$: 1750, 1700, 1680, 1340, 1320; NMR (DMSO-d$_6$) δ:3.05 (2H,t,J=7.0 Hz), 3.1~3.3 (1H,m), 3.5~3.7 (1H,m), 4.37 (2H,t,J=7.0 Hz), 4.7~4.9 (1H,m), 6.33 (1H,d,J=2.9 Hz), 6.90 (1H,d,J=8.8 Hz), 7.1~7.5 (8H,m)

Preparation of Tablet

| | |
|---|---|
| (1) Compound (the compound prepared in Example 3) | 20 mg |
| (2) lactose | 142 mg |
| (3) corn starch | 30 mg |
| (4) hydroxypropyl cellulose | 7.4 mg |
| (5) water | (0.03 ml) |

-continued

Preparation of Tablet

| | | |
|---|---|---|
| (6) magnesium stearate | | 0.6 mg |
| | total | 200 mg |

The foregoing components were weighed out, followed by mixing Components (1) to (4), kneading them after addition of water (5), drying in vacuo at 40° C. for 16 hours, pulverization in a mortar and classification through a sieve of 16 mesh size to thus give granules. Component (6) was added to the granules, followed by admixing them and forming them into tablets (200 mg each) using a rotary tablet machine.

TEST EXAMPLE

Glucose-uptake tests as a means for screening compounds for the effect of reducing the blood sugar level were carried out according to the following procedures.

Materials

1) Cell: The following cells were used.
   3T3-L1 (purchased from Dainippon Pharmaceutical Co. Ltd.)
2) Reagents: The following reagents were used.
   DMEM (GIBCO); FBS (GIBCO); PBS (Nippon Suisan Kaisha, Ltd.); 2-DOG: 2-deoxyglucose (SIGMA); 2-H$^3$-DOG: 2-H$^3$-deoxyglucose (Amersham); DMSO: dimethylsulfoxide (Wako Pure Chemical Co., Ltd.); ACS2 (Amersham); urea (Wako Pure Chemical Co., Ltd.); protein-determining kit (Bio Rad Code No.).
3) Instrument: The following instrument was used in the test.
   24-well plate (Falcon)

Method

3T3-L1 cells were dispersed in a 10% FBS-containing DME medium in a cell concentration of 10000 cells/ml, the resulting cell suspension was dispensed into a 24-well plate in an amount of 1 ml per well and the cells were cultivated in a 5% CO$_2$-incubator at 37° C. for 5 days. After soaking up the medium in the wells, the plate was washed once with PBS in an amount of 2 ml/well. Each sample compound was dissolved in DMSO and then diluted with a 10% FBS-containing DME medium to a concentration of 50, 25, 12.5, 6.25 or 0 μg/ml. The cells were cultivated in a sample compound-containing medium at 37° C. for 24 hours in a 5%-CO$_2$-incubator. After the cultivation, the medium was soaked up and the plate was washed three times with 2 ml/well each of PBS. After soaking up the PBS, PBS containing 2-H$^3$-DOG (0.2 μCi) and 20 nM of 2-DOG (20mM for non specific bound) was added in an amount of 0.5 ml per well, followed by incubation at 37° C. for 7 minutes, transferring the plate on ice and immediate removal of the supernatant through soaking up. After washing with 2 ml/well of PBS, the PBS was sufficiently soaked up. The cells were lysed by addition of 1 ml/well of 4M urea, followed by taking 0.7 ml of the lysate, addition of 15 ml of ACS2 and determination of the amount of the 2-H$^3$-DOG taken in the cells using a scintillation counter. The lysate was also inspected for the amount of proteins using 0.2 ml out of the rest of the lysate, according to the microassay method using a protein-determining kit. Each cpm value determined was divided by the amount of proteins and the value thus obtained was defined to be 2-DOG uptake (%).

RESULTS

Experimental Results on Glucose-Uptake [2-DOG Uptake (%) at a concentration of 50 μg/ml]

| Ex. No. | % | Ex. No. | % | Ex. No. | % | Ex. No. | % |
|---|---|---|---|---|---|---|---|
| 2 | 182 | 3 | 217 | 5 | 227 | 6 | 166 |
| 8 | 172 | 9 | 180 | 13 | 150 | 21 | 162 |
| 24 | 186 | 31 | 208 | 32 | 215 | 50 | 201 |
| 52 | 280 | 55 | 180 | 62 | 192 | 68 | 202 |
| 71 | 250 | 74 | 210 | 77 | 185 | 80 | 210 |
| 83 | 199 | 86 | 161 | 89 | 185 | 92 | 190 |
| 98 | 180 | 101 | 240 | 104 | 290 | 112 | 155 |
| 115 | 162 | 121 | 218 | 133 | 240 | 139 | 153 |
| 142 | 160 | 147 | 156 | 148 | 153 | 150 | 191 |
| 155 | 233 | 158 | 221 | 165 | 285 | 168 | 172 |
| 173 | 153 | 174 | 252 | 177 | 159 | 180 | 232 |
| 187 | 174 | 190 | 164 | 199 | 206 | 208 | 189 |
| 214 | 185 | 250 | 209 | 253 | 203 | 256 | 172 |
| 271 | 165 | 273 | 215 | 275 | 185 | 281 | 244 |
| 283 | 232 | 285 | 225 | 288 | 209 | 305 | 215 |
| 312 | 164 | 317 | 169 | 337 | 181 | | |
| Comp. Ex. | | | | | | | |
| CS-045* | 172 | | | | | | |

CS-045*: (±)-5-[4-(6-hydroxy-2,5,7,8-tetramethylchroman-2-yl-methoxy)benzyl]-2,4-thiazolidinedione Acute Toxicity Test The acute toxicity was determined by an acute toxicity test wherein each sample compound was orally administered to rats. The results (LD$_{50}$ values) thus obtained are listed below:

| Compound (Ex. No.) | LD$_{50}$ value |
|---|---|
| 3 | not less than 2 g/kg |
| 52 | not less than 2 g/kg |

The compounds of the present invention exhibit excellent effects of reducing the blood sugar level and of reducing the lipid concentration in blood and are useful as therapeutic agents for treating illness mellitus, which are almost free of any side effect.

What is claimed is:

1. A thiazolidinedione derivative represented by the following general formula (I) or a pharmaceutically acceptable salt thereof:

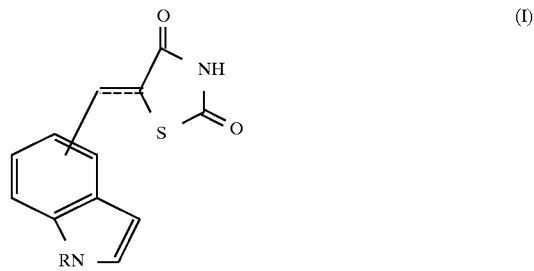

(I)

wherein the dotted line represents a single bond or a double bond, the thiazolidinedione ring residue is linked to either of 2-, 3-, 4-, 5- and 6-positions on the indole ring and R represents a group selected from the group consisting of alkyl, alkenyl, alkynyl, phenyl, aralkyl, heterocycloalkyl, arylsulfonyl and arylaminocarbonyl groups.

2. A thiazolidinedione derivative or a pharmaceutically acceptable salt thereof as set forth in claim 1 wherein the alkyl group is an unsubstituted alkyl group or a linear, cyclic or branched alkyl group substituted with an alkoxycarbonyl or carboxyl group; the alkenyl group is a linear, cyclic or branched alkenyl group; the alkynyl group is a linear or branched alkynyl group; the phenyl group may be substituted with an amino group or a cyano group;

the aryl or heterocyclic group constituting the aralkyl, heterocyclic alkyl, arylsulfonyl or arylaminocarbonyl group is a member selected from the group consisting of phenyl, naphthyl, pyridyl, thienyl, quinolyl, tetrahydroquinolyl, oxazolyl, thiazolyl, pyrrolidinyl and benzdioxanyl groups, provided that these groups may be unsubstituted or substituted with a halogen atom, an alkyl group, a trihalomethyl group, an alkoxy group, a benzyloxy group, a methylenedioxy group, a cyano group, a carboxyl group, an alkoxycarbonyl group, a hydroxyl group, an amino group, a dialkylamino group, a phenyl group and/or a nitro group and that if these groups each has at least two substituents, the substituents may be the same or different, the alkylene group constituting the aralkyl or heterocyclic alkyl group is represented by the formula: $(CH_2)_n$ (n is an integer ranging from 1 to 3) and a hydrogen atom thereof may be substituted with a halogen atom or an alkyl, hydroxy, alkoxy, benzyloxy, phenyl, azido, amino or dialkylamino group or two hydrogen atoms bonded to the same carbon atom may be substituted with an oxygen atom.

3. A thiazolidinedione derivative or a pharmaceutically acceptable salt thereof as set forth in claim 1 wherein the dotted line represents a single bond.

4. A thiazolidinedione derivative or a pharmaceutically acceptable salt thereof as set forth in claim 1 wherein the thiazolidinedione ring residue is linked to the 3- or 4-position on the indole ring.

5. A thiazolidinedione derivative or a pharmaceutically acceptable salt thereof as set forth in claim 1 wherein the aryl group constituting the aralkyl group is an unsubstituted phenyl group or a phenyl group substituted with a fluorine atom, a cyano group or a trifluoromethyl group; and the alkylene group is a group represented by $(CH_2)_n$ (n is 1 or 2).

6. A thiazolidinedione derivative of claim 1 wherein it is selected from the group consisting of 5-(1-benzylindol-4-yl)methyl-2,4-thiazolidinedione, 5-(1-benzylindol-3-yl)methyl-2,4-thiazolidinedione, 5-[1-(2-fluorobenzyl)indol-4-yl]methyl-2,4-thiazolidinedione, 5-[1-(3-fluorobenzyl)indol-4-yl]methyl-2,4-thiazolidinedione, 5-[1-(4-fluorobenzyl)indol-4-yl]methyl-2,4-thiazolidinedione, 5-[1-(2-fluorobenzyl)indol-3-yl]methyl-2,4-thiazolidinedione, 5-[1-(3-fluorobenzyl)indol-3-yl]methyl-2,4-thiazolidinedione, 5-[1-(4-fluorobenzyl)indol-3-yl]methyl-2,4-thiazolidinedione, 5-[1-(2-trifluoromethylbenzyl)indol-4-yl]methyl-2,4-thiazolidinedione, 5-[1-(3-trifluoromethylbenzyl)indol-4-yl]methyl-2,4-thiazolidinedione, 5-[1-(4-trifluoromethylbenzyl)indol-4-yl]methyl-2,4-thiazolidinedione, 5-[1-(2-trifluoromethylbenzyl)indol-3-yl]methyl-2,4-thiazolidinedione, 5-[1-(3-trifluoromethylbenzyl)indol-3-yl]methyl-2,4-thiazolidinedione, 5-[1-(4-trifluoromethylbenzyl)indol-3-yl]methyl-2,4-thiazolidinedione, 5-[1-(3-cyanobenzyl)indol-4-yl]methyl-2,4-thiazolidinedione, 5-[1-(4-cyanobenzyl)indol-4-yl]methyl-2,4-thiazolidinedione, 5-[1-(3-cyanobenzyl)indol-3-yl]methyl-2,4-thiazolidinedione, 5-[1-(4-cyanobenzyl)indol-3-yl]methyl-2,4-thiazolidinedione, 5-[1-(2,3-difluorobenzyl)indol-4-yl]methyl-2,4-thiazolidinedione, 5-[1-(2,4-difluorobenzyl)indol-4-yl]methyl-2,4-thiazolidinedione, 5-[1-(2,5-difluorobenzyl)indol-4-yl]methyl-2,4-thiazolidinedione, 5-[1-(2,6-difluorobenzyl)indol-4-yl]methyl-2,4-thiazolidinedione, 5-[1-(3,4-difluorobenzyl)indol-4-yl]methyl-2,4-thiazolidinedione, 5-[1-(3,5-difluorobenzyl)indol-4-yl]methyl-2,4-thiazolidinedione, 5-[1-(2,5-difluorobenzyl)indol-3-yl]methyl-2,4-thiazolidinedione, 5-[1-(3,4-difluorobenzyl)indol-3-yl]methyl-2,4-thiazolidinedione, 5-[1-(3,5-difluorobenzyl)indol-3-yl]methyl-2,4-thiazolidinedione or 5-[1-(4S-p-mentha-1,8-dien-7-yl)indol-4-yl]methyl-2,4-thiazolidinedione.

7. A pharmaceutical composition comprising, as an effective component, a thiazolidinedione derivative represented by the following general formula (I) or a pharmaceutically acceptable salt thereof:

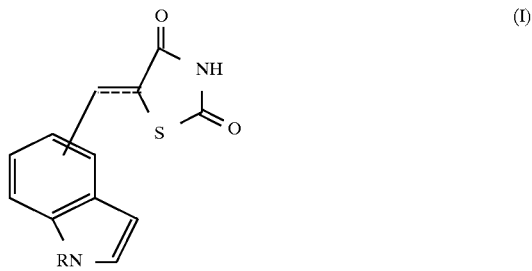

(I)

wherein the dotted line represents a single bond or a double bond, the thiazolidinedione ring residue is linked to either of 2-, 3-, 4-, 5- and 6-positions on the indole ring and R represents a group selected from the group consisting of alkyl, alkenyl, alkynyl, phenyl, aralkyl, heterocycloalkyl, arylsulfonyl and arylaminocarbonyl groups.

8. The pharmaceutical composition of claim 7 as a therapeutic agent for treating diabates mellitus.

9. A method for preparing a thiazolidinedione derivative represented by the following general formula (III):

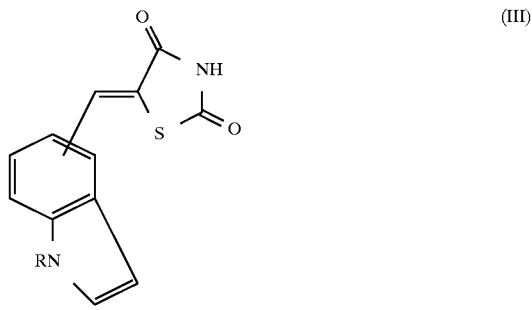

(III)

(wherein the thiazolidinedione ring residue is linked to either of 2-, 3-, 4-, 5- and 6-positions on the indole ring and R represents a group selected from the group consisting of hydrogen atom and alkyl, alkenyl, alkynyl, phenyl, aralkyl, heterocycloalkyl, arylsulfonyl and arylaminocarbonyl groups), comprising the step of condensing an indole carbaldehyde derivative represented by the following general formula (II):

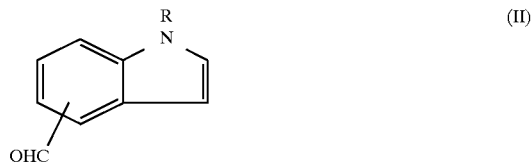

(II)

(wherein the aldehyde group is linked to either of 2-, 3-, 4-, 5- and 6-positions on the indole ring and R represents a group selected from the group consisting of alkyl, alkenyl, alkynyl, phenyl, aralkyl, heterocycloalkyl, arylsulfonyl and arylaminocarbonyl groups) with 2,4-thiazolidinedione.

10. A method for preparing a thiazolidinedione derivative represented by the following general formula (IV):

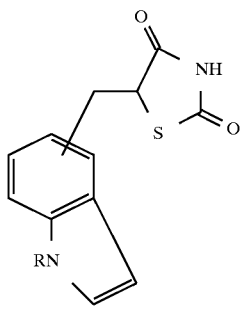

(IV)

(wherein the thiazolidinedione ring residue is linked to either of 2-, 3-, 4-, 5- and 6-positions on the indole ring and R represents a group selected from the group consisting of hydrogen atom and alkyl, alkenyl, alkynyl, phenyl, aralkyl, heterocycloalkyl, arylsulfonyl and arylaminocarbonyl groups), comprising the step of subjecting, to a reducing reaction, a thiazolidinedione derivative represented by the following general formula (III):

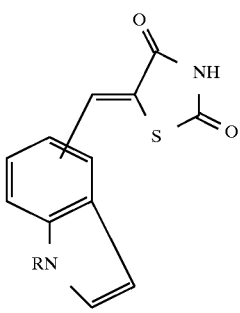

(III)

(wherein the thiazolidinedione ring residue is linked to either of 2-, 3-, 4-, 5- and 6- positions on the indole ring and R represents a group selected from the group consisting of alkyl, alkenyl, alkynyl, phenyl, aralkyl, heterocycloalkyl, arylsulfonyl and arylaminocarbonyl groups).

11. A method of treating diabetes mellitus comprising administering to a patient in need thereof an effective amount of the thiazolidinedione derivative of claim 1.

* * * * *